(12) United States Patent
Leamon et al.

(10) Patent No.: US 7,575,865 B2
(45) Date of Patent: Aug. 18, 2009

(54) METHODS OF AMPLIFYING AND SEQUENCING NUCLEIC ACIDS

(75) Inventors: John H. Leamon, Guilford, CT (US); Keith E. McDade, Higganum, CT (US); Joseph M. Fierro, New Haven, CT (US); James R. Knight, Marlobrough, CT (US); Jaran Charumilind, New Haven, CT (US); Eugene W. Myers, Jr., Washington, DC (US); John W. Simpson, Madison, CT (US); Greg A. Volkmer, Bosque Farms, NM (US)

(73) Assignee: 454 Life Sciences Corporation, Branford, CT (US)

( * ) Notice: Subject to any disclaimer, the term of this patent is extended or adjusted under 35 U.S.C. 154(b) by 396 days.

(21) Appl. No.: 11/195,254

(22) Filed: Aug. 1, 2005

(65) Prior Publication Data

US 2006/0040297 A1 Feb. 23, 2006

Related U.S. Application Data

(63) Continuation-in-part of application No. 10/767,779, filed on Sep. 22, 2004.

(60) Provisional application No. 60/497,985, filed on Aug. 25, 2003, provisional application No. 60/476,602, filed on Jun. 6, 2003, provisional application No. 60/476,592, filed on Jun. 6, 2003, provisional application No. 60/476,504, filed on Jun. 6, 2003, provisional application No. 60/476,313, filed on Jun. 6, 2003, provisional application No. 60/465,071, filed on Apr. 23, 2003, provisional application No. 60/443,471, filed on Jan. 29, 2003.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/22.1; 536/23.1

(58) Field of Classification Search .................. 435/6, 435/91.2; 536/24.33, 22.1, 23.1
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,811,218 A | 3/1989 | Hunkapiller et al. |
| 4,822,746 A | 4/1989 | Walt |
| 4,863,849 A | 9/1989 | Melamede |
| 4,965,188 A | 10/1990 | Mullis et al. |
| 4,971,903 A | 11/1990 | Hyman |
| 5,114,984 A | 5/1992 | Branch et al. |
| 5,143,853 A | 9/1992 | Walt |
| 5,171,534 A | 12/1992 | Smith et al. |
| 5,244,636 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,320,814 A | 6/1994 | Walt et al. |
| 5,405,746 A | 4/1995 | Uhlen |
| 5,429,807 A | 7/1995 | Matson et al. |
| 5,436,327 A | 7/1995 | Southern et al. |
| 5,445,934 A | 8/1995 | Fodor et al. |
| 5,445,971 A | 8/1995 | Rohr |
| 5,506,100 A | 4/1996 | Surzycki et al. |
| 5,508,169 A | 4/1996 | Deugau et al. |
| 5,512,490 A | 4/1996 | Walt et al. |
| 5,525,464 A | 6/1996 | Drmanac et al. |
| 5,534,424 A | 7/1996 | Uhlen et al. |
| 5,602,509 A | 2/1997 | Kimura |
| 5,604,097 A | 2/1997 | Brenner |
| 5,610,010 A | 3/1997 | Surzycki et al. |
| 5,633,972 A | 5/1997 | Walt et al. |
| 5,648,245 A | 7/1997 | Fire et al. |
| 5,700,637 A | 12/1997 | Southern |
| 5,714,320 A | 2/1998 | Kool |
| 5,716,785 A | 2/1998 | Van Gelder et al. |
| 5,728,524 A | 3/1998 | Sibson |
| 5,728,529 A | 3/1998 | Metzker et al. |
| 5,744,305 A | 4/1998 | Fodor et al. |
| 5,750,341 A | 5/1998 | Macevicz |

(Continued)

FOREIGN PATENT DOCUMENTS

EP 0 373 203 8/1994

(Continued)

OTHER PUBLICATIONS

Baner et al. (1998). *Nuc. Acids Res.* 26: 5073-5078.

(Continued)

*Primary Examiner*—Suryaprabha Chunduru
(74) *Attorney, Agent, or Firm*—Ivor R. Elrifi; Mintz Levin Cohn Ferris Glovsky and Popeo PC

(57) ABSTRACT

An apparatus and method for performing rapid DNA sequencing, such as genomic sequencing, is provided herein. The method includes the steps of preparing a sample DNA for genomic sequencing, amplifying the prepared DNA in a representative manner, and performing multiple sequencing reaction on the amplified DNA with only one primer hybridization step.

11 Claims, 65 Drawing Sheets

U.S. PATENT DOCUMENTS

| | | |
|---|---|---|
| 5,770,367 A | 6/1998 | Southern et al. |
| 5,780,231 A | 7/1998 | Brenner |
| 5,795,716 A | 8/1998 | Chee et al. |
| 5,800,992 A | 9/1998 | Fodor et al. |
| 5,814,524 A | 9/1998 | Walt et al. |
| 5,821,058 A | 10/1998 | Smith et al. |
| 5,830,662 A | 11/1998 | Soares et al. |
| 5,834,252 A | 11/1998 | Stemmer et al. |
| 5,846,721 A | 12/1998 | Soares et al. |
| 5,846,727 A | 12/1998 | Soper et al. |
| 5,851,772 A | 12/1998 | Mirzabekov et al. |
| 5,854,033 A | 12/1998 | Lizardi |
| 5,863,722 A | 1/1999 | Brenner |
| 5,871,697 A | 2/1999 | Rothberg et al. |
| 5,871,928 A | 2/1999 | Fodor et al. |
| 5,882,874 A | 3/1999 | Fisher |
| 5,891,636 A | 4/1999 | Van Gelder et al. |
| 5,900,481 A | 5/1999 | Lough et al. |
| 5,919,673 A | 7/1999 | Wong et al. |
| 5,928,905 A | 7/1999 | Stemmer et al. |
| 5,962,228 A | 10/1999 | Brenner |
| 5,989,892 A | 11/1999 | Nishimaki et al. |
| 6,013,445 A | 1/2000 | Albrecht et al. |
| 6,023,540 A | 2/2000 | Walt et al. |
| 6,040,193 A | 3/2000 | Winkler et al. |
| 6,054,270 A | 4/2000 | Southern |
| 6,080,585 A | 6/2000 | Southern et al. |
| 6,114,114 A | 9/2000 | Seilhamer et al. |
| 6,133,436 A | 10/2000 | Koster et al. |
| 6,136,543 A | 10/2000 | Anazawa et al. |
| 6,146,593 A | 11/2000 | Pinkel et al. |
| 6,150,095 A | 11/2000 | Southern et al. |
| 6,184,012 B1 | 2/2001 | Neri et al. |
| 6,200,737 B1 | 3/2001 | Walt et al. |
| 6,210,891 B1 | 4/2001 | Nyren et al. |
| 6,210,896 B1 | 4/2001 | Chan |
| 6,210,910 B1 | 4/2001 | Walt et al. |
| 6,218,111 B1 | 4/2001 | Southern et al. |
| 6,221,653 B1 | 4/2001 | Caren et al. |
| 6,225,061 B1 | 5/2001 | Becker et al. |
| 6,255,476 B1 | 7/2001 | Vinayak et al. |
| 6,258,568 B1 | 7/2001 | Nyren |
| 6,263,286 B1 | 7/2001 | Gilmanshin et al. |
| 6,266,459 B1 | 7/2001 | Walt et al. |
| 6,284,465 B1 | 9/2001 | Wolber |
| 6,306,597 B1 | 10/2001 | Macevicz |
| 6,307,039 B1 | 10/2001 | Southern et al. |
| 6,333,155 B1 | 12/2001 | Lockhart et al. |
| 6,355,420 B1 | 3/2002 | Chan |
| 6,355,431 B1 | 3/2002 | Chee et al. |
| 6,468,748 B1 | 10/2002 | Monforte et al. |
| 6,489,103 B1 | 12/2002 | Griffiths et al. |
| 7,323,305 B2 | 1/2008 | Leamon et al. |
| 2001/0006630 A1 | 7/2001 | Yacoby-Zeevi |
| 2001/0024790 A1 | 9/2001 | Kambara et al. |
| 2001/0041335 A1 | 11/2001 | Goldberg et al. |
| 2002/0009729 A1 | 1/2002 | McGall et al. |
| 2002/0022721 A1 | 2/2002 | Trulson et al. |
| 2002/0051971 A1 | 5/2002 | Stuelpnagel et al. |
| 2002/0150909 A1* | 10/2002 | Stuelpnagel et al. ........... 435/6 |
| 2002/0172965 A1 | 11/2002 | Kamb et al. |
| 2003/0068629 A1 | 4/2003 | Rothberg et al. |
| 2003/0096268 A1 | 5/2003 | Weiner et al. |
| 2003/0108867 A1 | 6/2003 | Chee et al. |
| 2005/0009022 A1 | 1/2005 | Weiner et al. |
| 2005/0037392 A1 | 2/2005 | Griffiths et al. |

FOREIGN PATENT DOCUMENTS

| | | |
|---|---|---|
| EP | 0 619 321 | 1/1999 |
| WO | 89/10977 | 11/1989 |
| WO | 97/19193 | 5/1997 |
| WO | 97/27326 | 7/1997 |
| WO | 97/40141 | 10/1997 |
| WO | 97/41260 | 11/1997 |
| WO | 98/08973 | 3/1998 |
| WO | 98/13523 | 4/1998 |
| WO | 98/20019 | 5/1998 |
| WO | 98/28440 | 7/1998 |
| WO | 98/35012 | 8/1998 |
| WO | 98/44151 | 10/1998 |
| WO | 98/44152 | 10/1998 |
| WO | 98/50782 | 11/1998 |
| WO | 98/53300 | 11/1998 |
| WO | 99/02671 | 1/1999 |
| WO | 99/05315 | 2/1999 |
| WO | 99/07896 | 2/1999 |
| WO | 99/15702 | 4/1999 |
| WO | 99/28494 | 6/1999 |
| WO | 99/30823 | 6/1999 |
| WO | 99/36576 | 7/1999 |
| WO | 99/53102 | 10/1999 |
| WO | 99/60007 | 11/1999 |
| WO | 99/61662 | 12/1999 |
| WO | 99/66313 | 12/1999 |
| WO | 99/67641 | 12/1999 |
| WO | 00/06770 | 2/2000 |
| WO | 00/27521 | 5/2000 |
| WO | 00/39587 | 7/2000 |
| WO | 00/40712 | 7/2000 |
| WO | 00/43540 | 7/2000 |
| WO | 00/44491 | 8/2000 |
| WO | 00/47996 | 8/2000 |
| WO | 00/48000 | 8/2000 |
| WO | 00/56455 | 9/2000 |
| WO | 00/58507 | 10/2000 |
| WO | 00/60072 | 10/2000 |
| WO | 00/60114 | 10/2000 |
| WO | 00/63437 | 10/2000 |
| WO | 00/71243 | 11/2000 |
| WO | 00/71992 | 11/2000 |
| WO | 00/71995 | 11/2000 |
| WO | 00/75373 | 12/2000 |
| WO | 01/18244 | 3/2001 |
| WO | 01/18524 | 3/2001 |
| WO | 01/24937 | 4/2001 |
| WO | 01/25480 | 4/2001 |
| WO | 01/42496 | 6/2001 |
| WO | 01/46675 | 6/2001 |
| WO | 01/57268 | 8/2001 |
| WO | 01/57269 | 8/2001 |
| WO | 01/59432 | 8/2001 |
| WO | 01/61043 | 8/2001 |
| WO | 01/85341 | 11/2001 |
| WO | 02/00336 | 1/2002 |
| WO | 02/12897 | 2/2002 |
| WO | 02/16649 | 2/2002 |
| WO | 02/20836 | 3/2002 |
| WO | 02/20837 | 3/2002 |
| WO | 02/21128 | 3/2002 |
| WO | 02/22869 | 3/2002 |
| WO | 02/103363 | 12/2002 |
| WO | 03/044187 | 3/2003 |
| WO | 07/086935 | 8/2007 |

OTHER PUBLICATIONS

Bankier et al. (1987). *Methods in Enzymol.* 155: 51-93.
Barshop et al. (1991). *Anal Biochem.* 197: 266-272.
Bauer, Johann (1999). *J. Chromatography* 722: 55-69.
Brandis et al. (1996). *Biochem.* 35: 2189-2200.
Brody & Quake (1999). *Applied Physics Letters* 74: 144-146.
Bronk et al. (1995). *Anal.Chem.* 67: 2750-2757.
Burns et al. (1996). *Proc. Natl. Acad. Sci. USA* 93: 5556-5561.

Burns et al. (1998). *Science* 282: 484-487.
Chan and Nie (1998). *Science* 281: 2016-2018.
Chee et al. (1996). *Science* 274: 610-614.
Chiou et al. (2001). *Anal. Chem.* 73: 2018-2021.
Chiu and Christopoulos (1996). *Anal Chem.* 68: 2304-2308.
Connell et al. (1998). *Plant Mol. Biol. Rptr.* 16: 341-349.
Costa and Weiner (1994). *Nucl. Acids Res.* 22: 2423.
Costa and Weiner (1994). *PCR Methods and Appls.* 3: S95-S106.
Costa and Weiner (1994). *PCR Methods and Appls.* 3: 338-345.
Curcio and Roeraade (2003). *Anal. Chem.* 75: 1-7.
Daubendiek and Kool (1997). *Nature Biotechnol.* 15: 273-277.
Dickson et al. (1996). *Science* 274: 966-968.
Dickson et al. (1997). *Nature* 388: 355-358.
Dressman et al. (2003). *PNAS* 100: 8817-8822.
Ferguson et al. (1996). *Nature Biotechnol.* 14: 1681-1684.
Fire and Xu (1995). *Proc. Natl. Acad. Sci. USA* 92: 4641-4645.
Ghadessy et al. (2001). *PNAS* 99: 4552-4557.
Giordano et al. (2001). *Anal. Biochem.* 291: 124-132.
Griffiths & Tawfik (2003). *EMBO J.* 22: 24-35.
Ha et al. (1996). *Proc. Natl. Acad. Sci. USA* 93: 6264-6268.
Hacia, Joseph (1999). *Nature Genetics Suppl.* 21: 42-47.
Hamilton et al. (2001). *BioTechniques* 31: 370-383.
Hatch et al. (1999). *Genetic Analysis: Biomolecular Engineering* 15: 35-40.
Healey and Walt (1997). *Anal. Chem.* 69: 2213-2216.
Healey et al. (1995). *Science* 269: 1078-1080.
Hengsakul and Cass (1996). *Bioconjugate Chem.* 7: 249-254.
Hoheisel, Jorg (1997). *Trends in BioTechnol.* 15: 465-469.
Huhmer and Landers (2000). *Anal. Chem.* 72: 5507-5512.
Hyman, Edward (1988). *Anal. Biochem.* 174: 423-436.
Ishijima et al. (1998). *Cell* 92: 161-171.
Ito et al. (1994). *FEBS Letters* 351: 231-236.
Izawa et al. (1998). *J. Biol. Chem.* 273: 14242-14246.
Kalinina et al. (1997). *Nucl. Acids Res.* 25: 1999-2004.
Karamohamed et al. (1999). *Protein Expression and Purification* 15: 381-388.
Karamohamed et al. (1999). *Anal. Biochem.* 271: 81-85.
Keller et al. (1996). *Applied Spectroscopy* 50: 12A-32A.
Kievits et al. (1991). *J. Virological Methods* 35: 273-286.
Kopp et al. (1998). *Science* 280: 1046-1048.
Kricka, Larry (1998). *Clinical Chem.* 44: 2008-2014.
Lagally et al. (2001). *Anal. Chem.* 73: 565-570.
Lander (1996). *Science* 274: 536-539.
Liu et al. (1996). *J. Am. Chem. Soc.* 118: 1587-1594.
Lizardi et al. (1998). *Nature Genetics* 19: 225-232.
Melgar and Goldthwait (1968). *J. Biol. Chem.* 243: 4409-4416.
Metzker et al. *BioTechniques* 25: 814-817.
Metzker et al. (1998). *BioTechniques* 25: 446-462.
Michael et al. (1998). *Anal Chem.* 70: 1242-1248.
Mitra and Church (1999). *Nuc. Acids Res.* 27(e34): i-vi.
Mooney et al. (1996). *Proc. Natl. Acad. Sci. USA* 93: 12287-12291.
Munkholm and Walt (1986). *Anal. Chem.* 58: 1427-1430.
Nagai et al. (2001). *Anal. Chem.* 73: 1043-1047.
Nagai et al. (2001). *Biosensors & Bioelectronics* 16: 1015-1019.
Narang et al. (1997). *Biosensors & Bioelectronics* 12: 937-945.
Nie et al. (1994). *Science* 266: 1018-1021.
Nie and Zare (1997). *Annu. Rev. Biophys. Biomol. Struct.* 26: 567-596.
Nilsson et al. (1997). *Nature Genetics* 16: 252-255.
Nilsson et al. (1994). *Science* 265: 2085-2088.
Nyren, Pal (1994). *J. Biolumin. Chemilumin* 9: 29-34.
Nyren et al. (1997). *Anal. Biochem.* 244: 367-373.
Nyren et al. (1993). *Anal. Biochem.* 208: 171-175.
Nyren, Pal (1987). *Anal. Biochem.* 167: 235-238.
Oda et al. (1998). *Anal Chem.* 70: 4361-4368.
Oker-Blom et al. (1993). *BioTechniques* 14: 800-809.
Pantano and Walt (1996). *Chem. Mater.* 8: 2832-2835.
Parthasarathy and Martin (1994). *Nature* 369: 298-301.
Pierce et al. (1997). *Nature* 388: 338.
Pirrung and Huang (1996). *Bioconjugate Chem.* 7: 317-321.
Rawlinson et al. (1996). *J. Virology* 70: 8833-8849.
Ribeiro et al. (1998). *J. Biolumin Chemilumin* 13: 371-378.
Ronaghi et al. (1996). *Anal. Biochem.* 242: 84-89.
Ronaghi et al. (1998). *Science* 281: 363-365.
Ronaghi et al. (1999). *Anal. Biochem.* 267:65-71.
Sasaki et al. (1997). *DNA Res.* 4: 387-391.
Schneegaβ et al. (2001). *Royal Soc. Chem.-Lab on a Chip* 1: 42-49.
Sepp et al. (2002). *FEBS Letters* 532: 455-458.
Service, Robert (1998). *Science* 282: 396-401.
Tawfik & Griffiths (1998). *Nat Biotechnol* 16: 652-656.
Venter et al. (1998). *Science* 280: 1540-1542.
Walker et al. (1992). *Nuc. Acids Res.* 20: 1691-1696.
Walker et al. (1992). *Proc. Natl. Acad. Sci. USA* 89: 392-396.
Wang et al. (1997). *Anal. Biochem.* 246: 133-139.
Wang et al. (1998). *Science* 280: 1077-1082.
Wang et al. (1998). *Science* 282: 902-907.
Weisiger, Richard, "Impact of Extracellular Diffusion on Hepatic Uptake Kinetics", 1998, pp. 389-423.
Wooster et al. (1994). *Science* 265: 2088-2090.
Xie and Lu (1999). *J. Biol. Chem.* 274: 15967-15970.
Yin et al. (1995). *Science* 270: 1653-1657.
Alderborn (2000). *Genome Research*, 10:1249-1258.
Nakano, et al. (2003). *Journal of Biotechnology*, 102: 117-124.
Margulies et al. (2005). *Nature* 437:376-380.
PubMed Record 16056220 (2007). PubMed record proving that the article Margulies, Marcel et al., was published on Jul. 31, 2005.
Margulies et al (2005). *Nature*, Supplementary 03959-s1 (12 pages); Supplementary Table 1 03959-S2 (6 pages); Materials and Methods, Library Preparation (Supplementary Figure 1) 03959s3 (34 pages).
454 Life Sciences Publishes Breakthrough Genome Sequencing Technique (2005) (2 pages).
International Search Report for PCT/US2006/030235 dated Sep. 26, 2007.

* cited by examiner

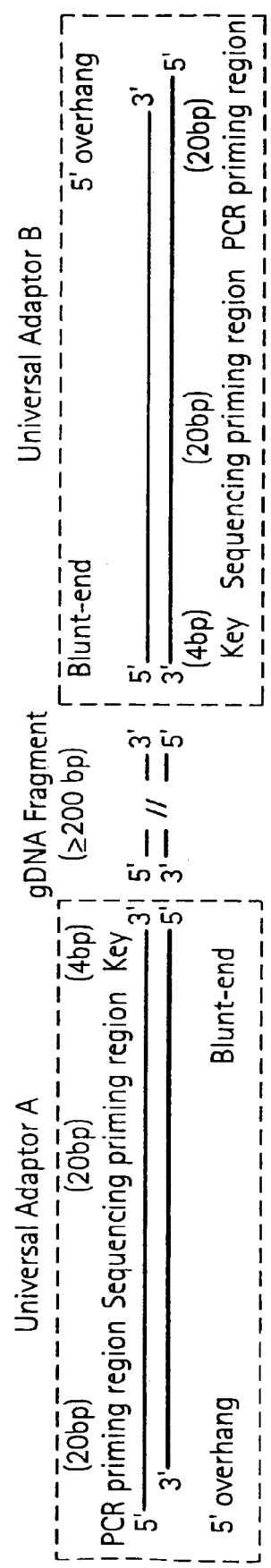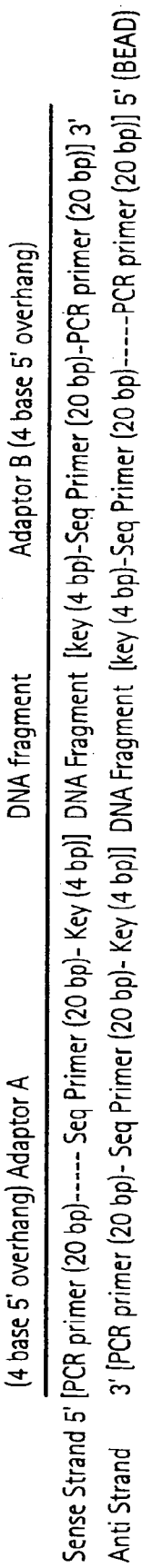

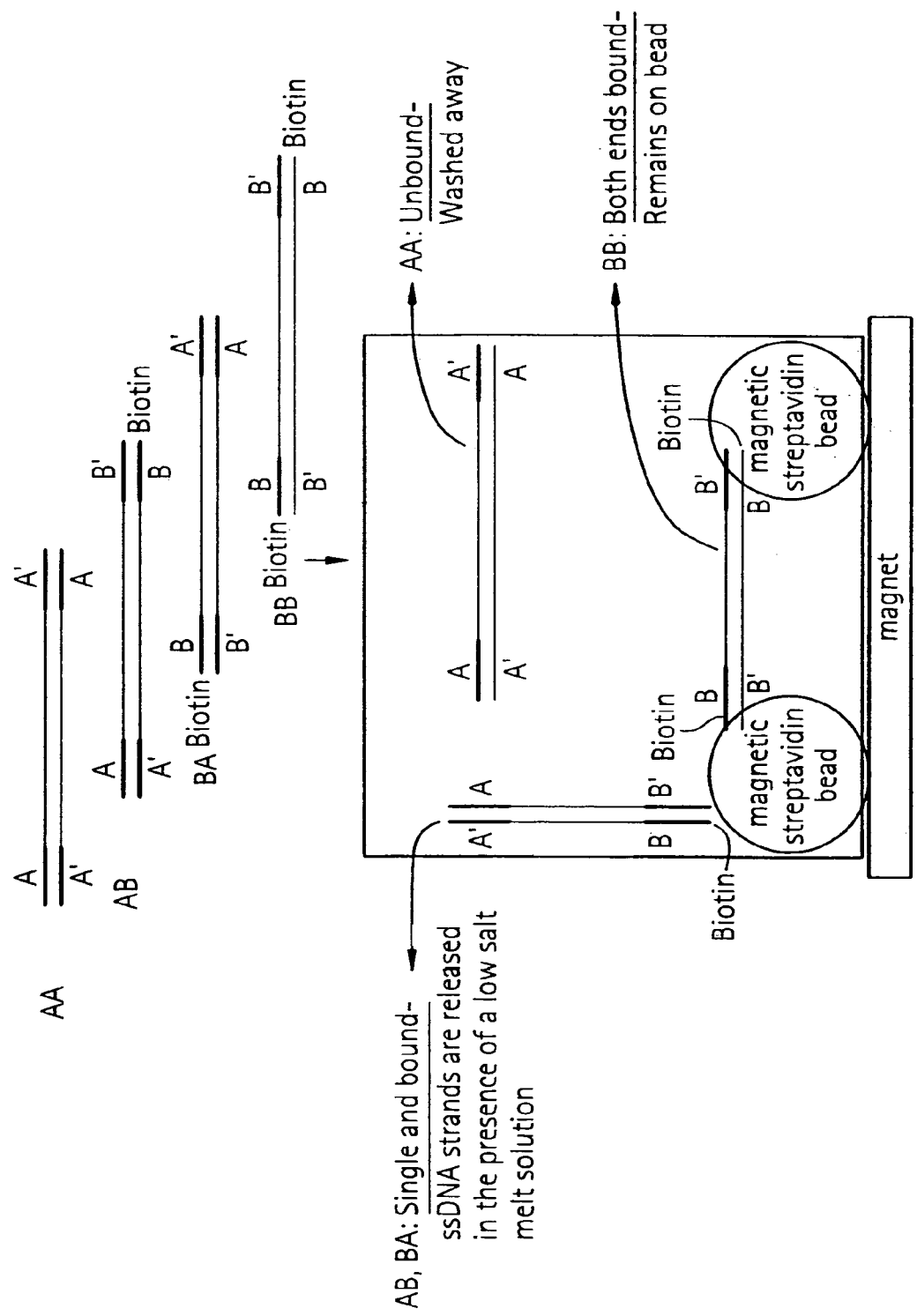

Schematic Process Flow for Bead Separation

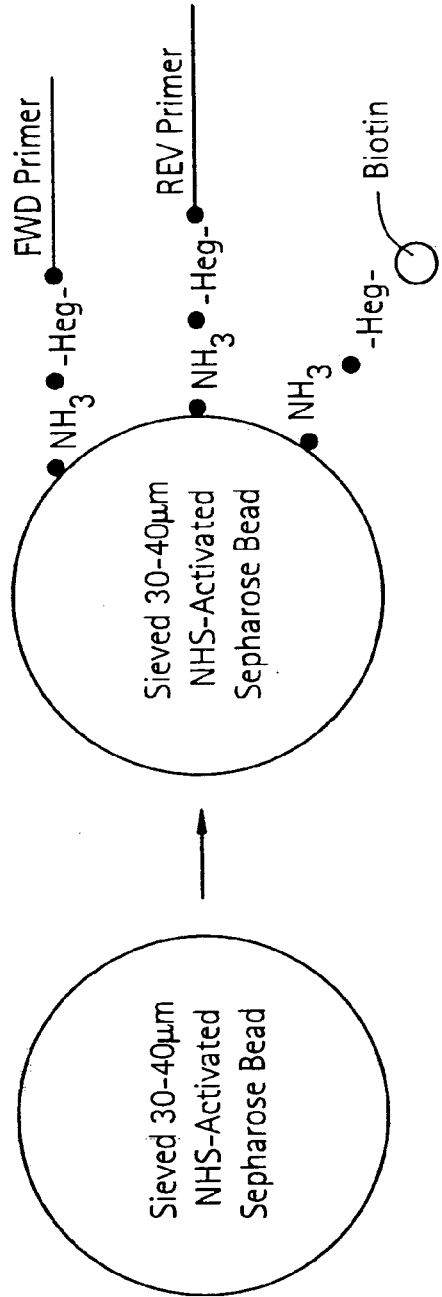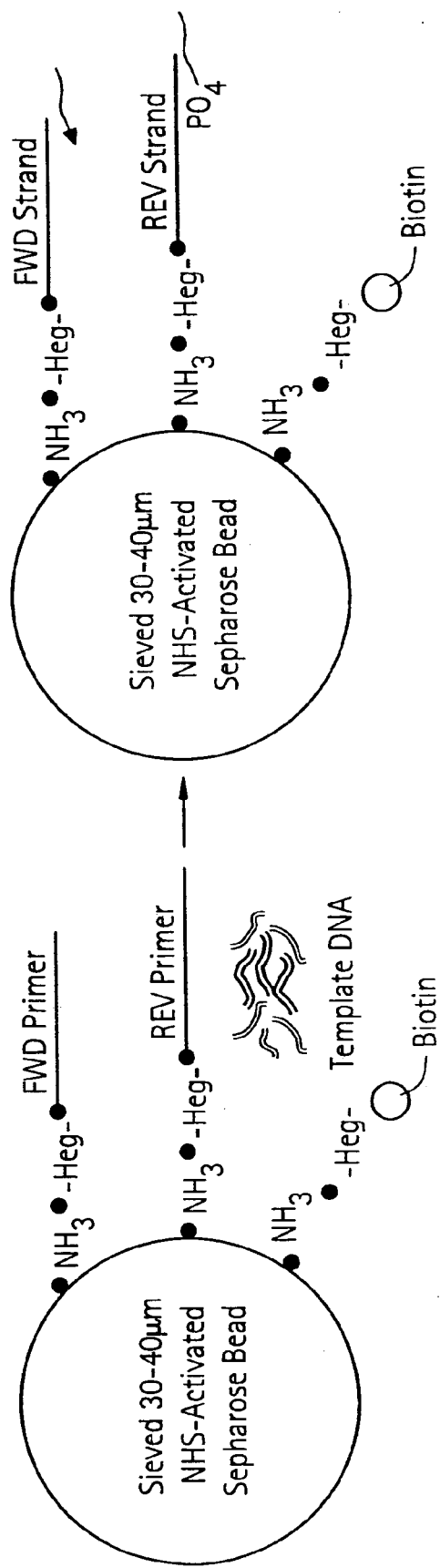

FIG. 10F
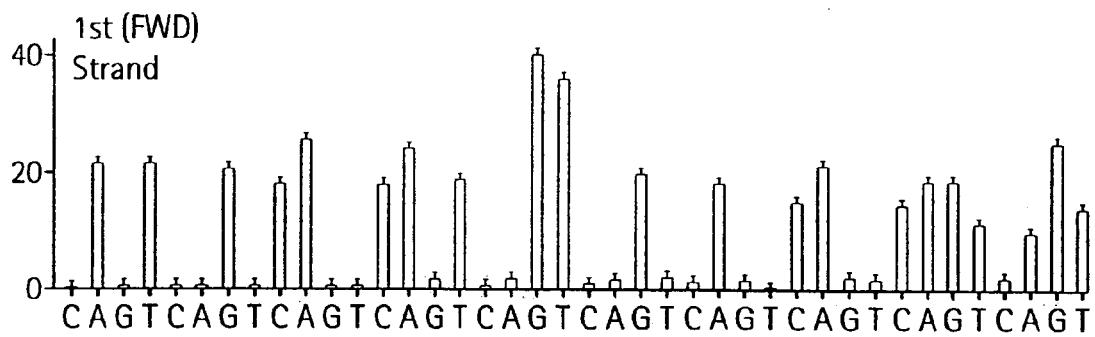
1st Strand (FWD)
| Sample | Well Location | Sequence | Perfect Match Length |
|---|---|---|---|
|  |  |  |  |
| F6_14_1 | 00001_1362_1660.well | ATGCACATGGTTGACACAGTGGT | 22 |
ATGC ACATGGTTGACACAGTGG
ATGC CACCGACCTAGTCTCAAACTT
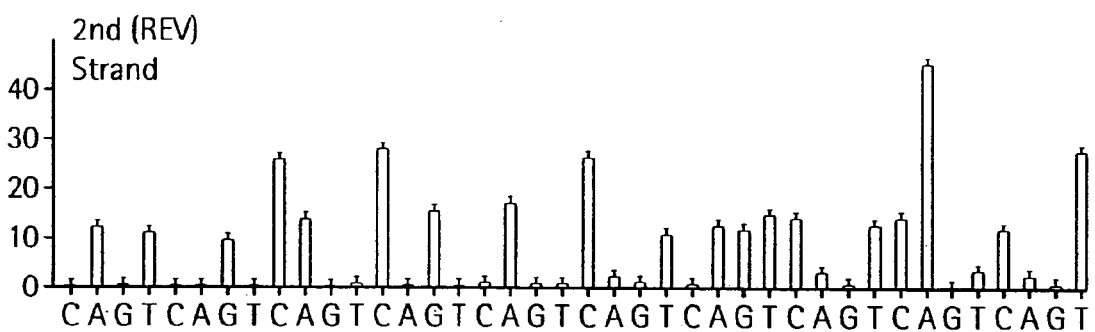
2nd Strand (REV)
| Sample | Well Location | Sequence | Perfect Match Length |
|---|---|---|---|
|  |  |  |  |
| F6_14_1 | 00003_1363_1660.well | ATGCCACCGACCTAGTCTCAAACTT | 25 |

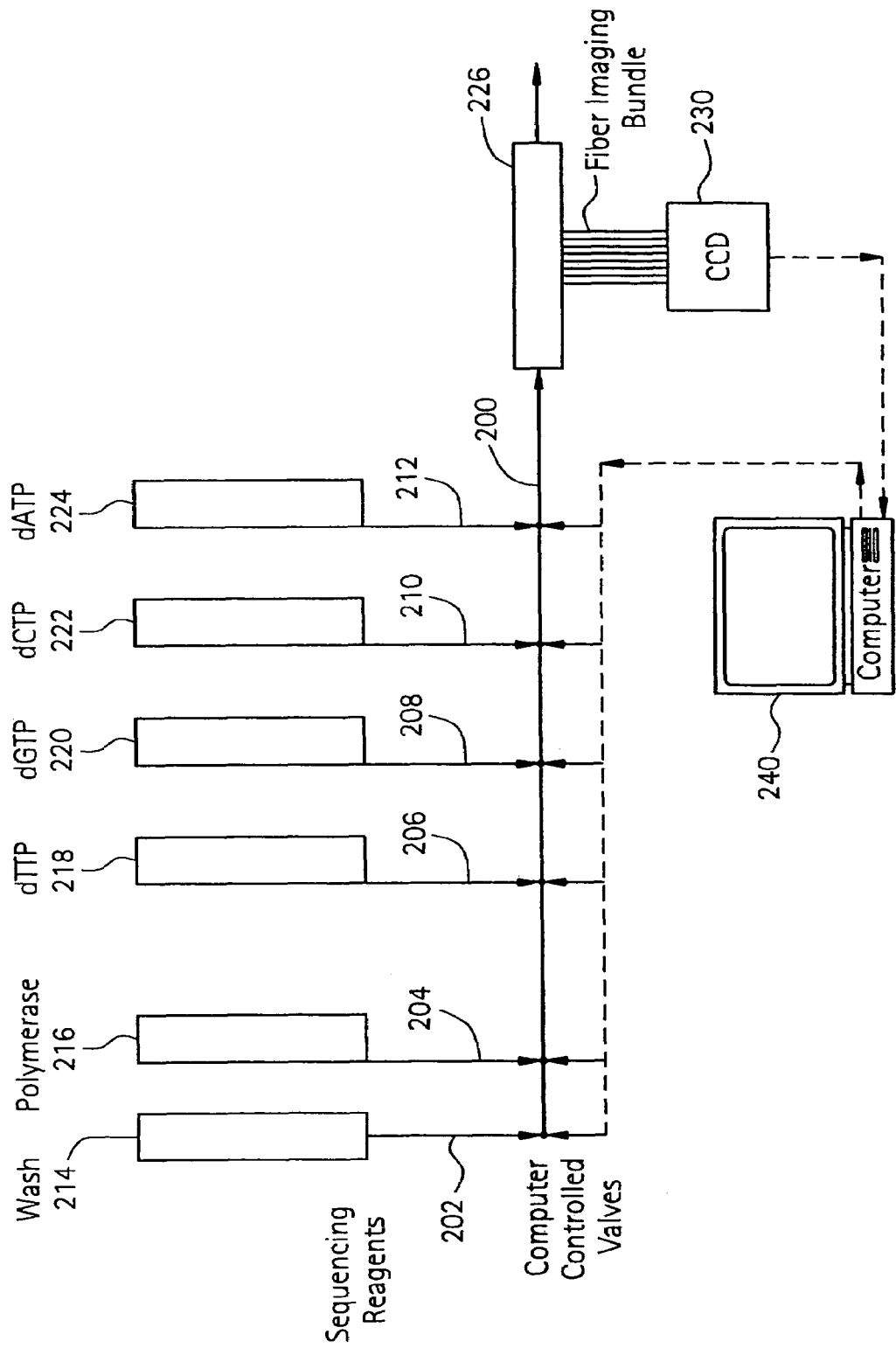

FIG. 13
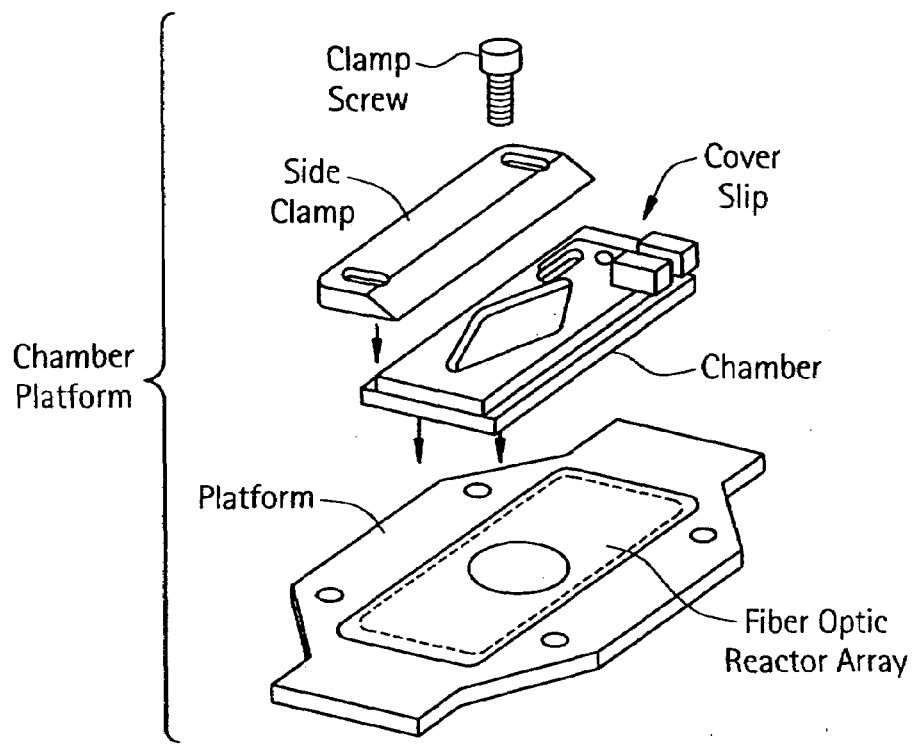
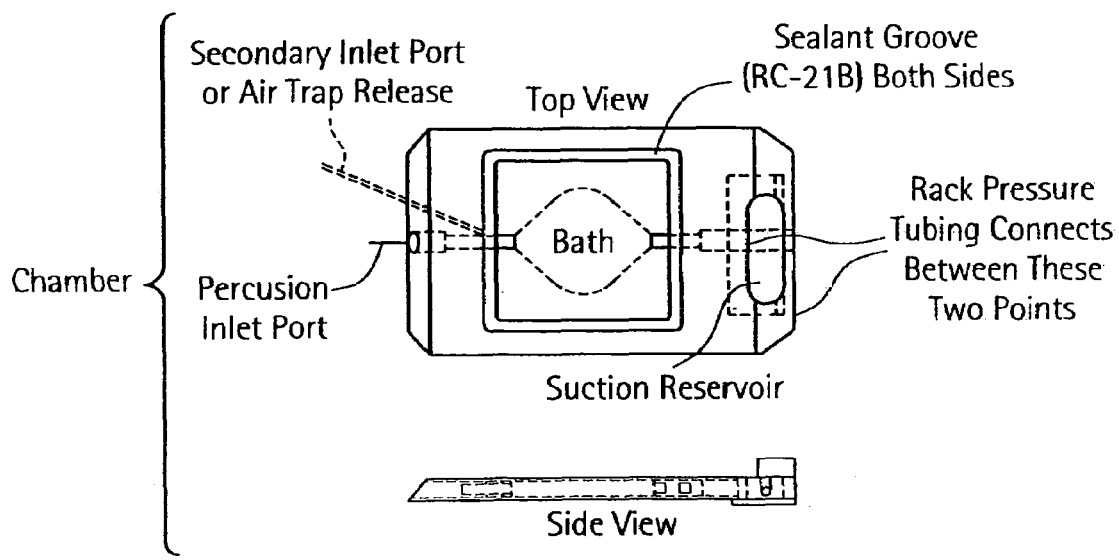
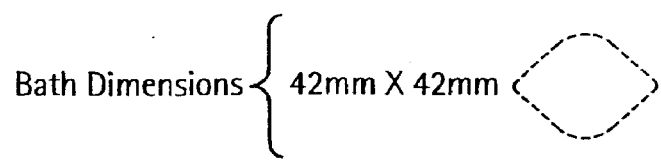

FIG. 14
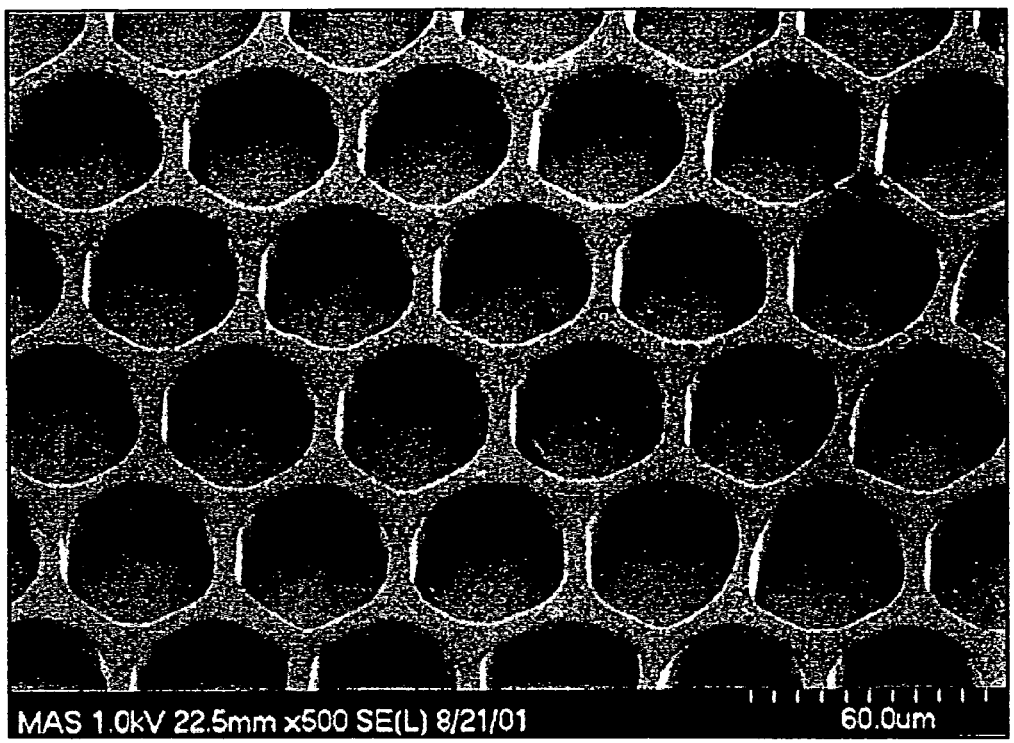
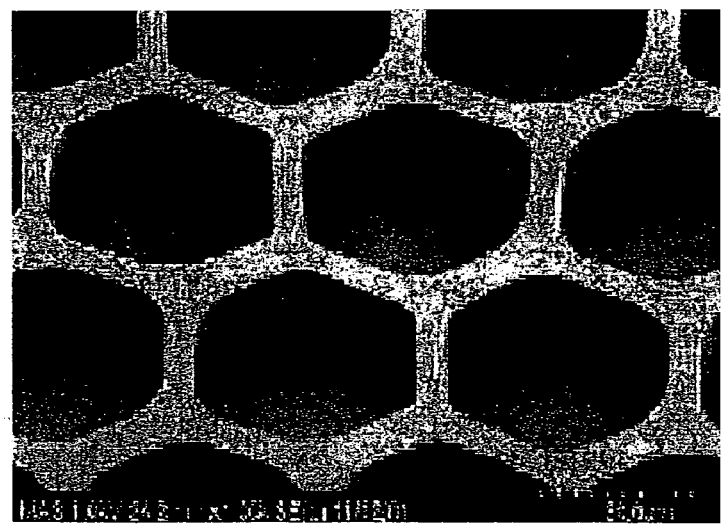

FIG. 25

| PCR Primer A | SEQ Primer A | Genomic Insert | SEQ Primer B | PCR Primer B |

FIG. 26

| PCR Primer A | SEQ Primer A | Genomic Insert | CHR | SEQ Primer B | PCR Primer B |

PCR Primer B →

FIG. 34
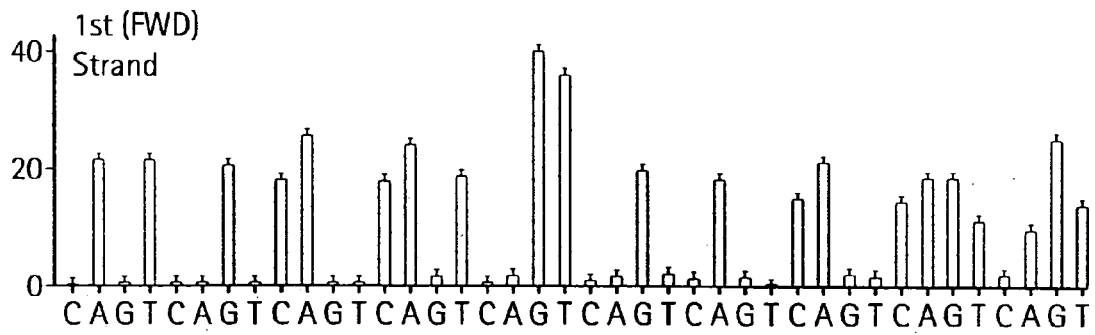
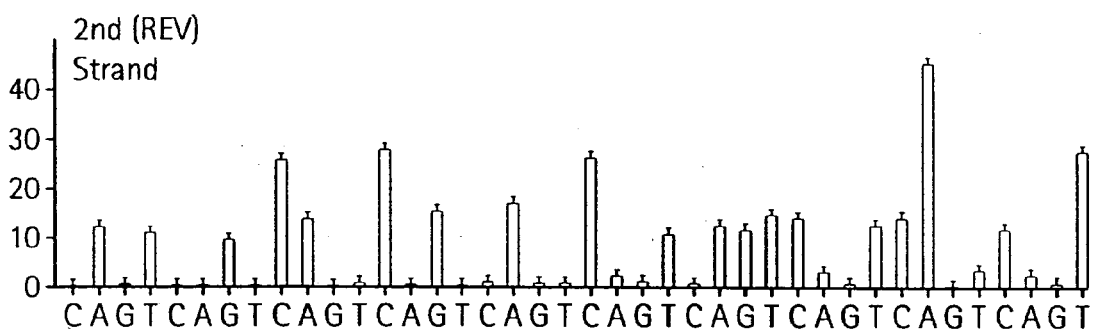
| 1st Strand (FWD) | Sample | Well Location | Sequence | Perfect Match Length |
|---|---|---|---|---|
| | | | | |
| | F6_14_1 | 00001_1362_1660.well | ATGCACATGGTTGACACAGTGGT | 22 |
ATGC ACATGGTTGACACAGTGG
ATGC CACCGACCTAGTCTCAAACTT
| 2nd Strand (REV) | Sample | Well Location | Sequence | Perfect Match Length |
|---|---|---|---|---|
| | | | | |
| | F6_14_1 | 00003_1363_1660.well | ATGCCACCGACCTAGTCTCAAACTT | 25 |

Emulsion breaking

2nd strand removal and enrichment

Annealing sequencing primers

1st segment sequencing

FIG. 39A
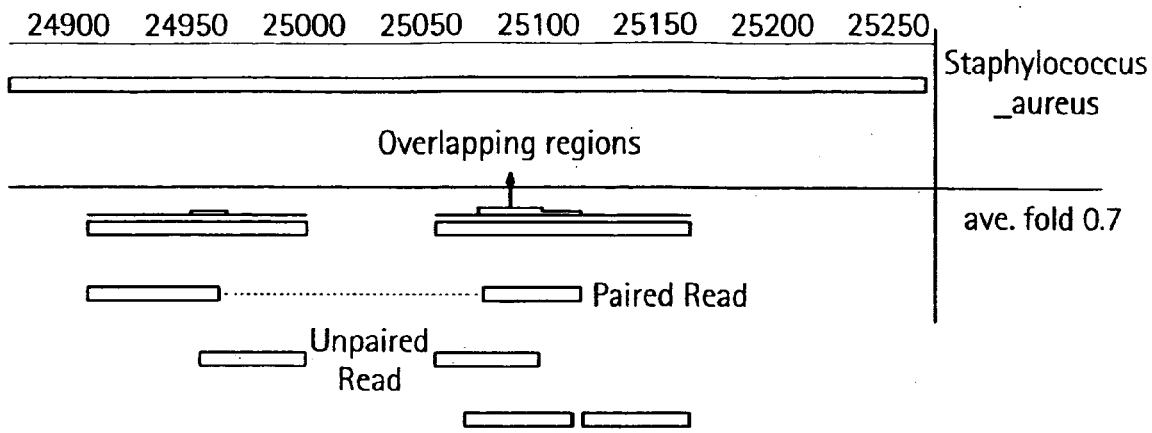
FIG. 39B
| Total Reads | 31,785 |
|---|---|
| Total 1st Strand | 15,770 |
| Total 2nd Strand | 16,015 |
| | |
| Paired | 11,799 |
| Non Paired Reads | 8,187 |
| Total Coverage | 38% |
FIG. 40
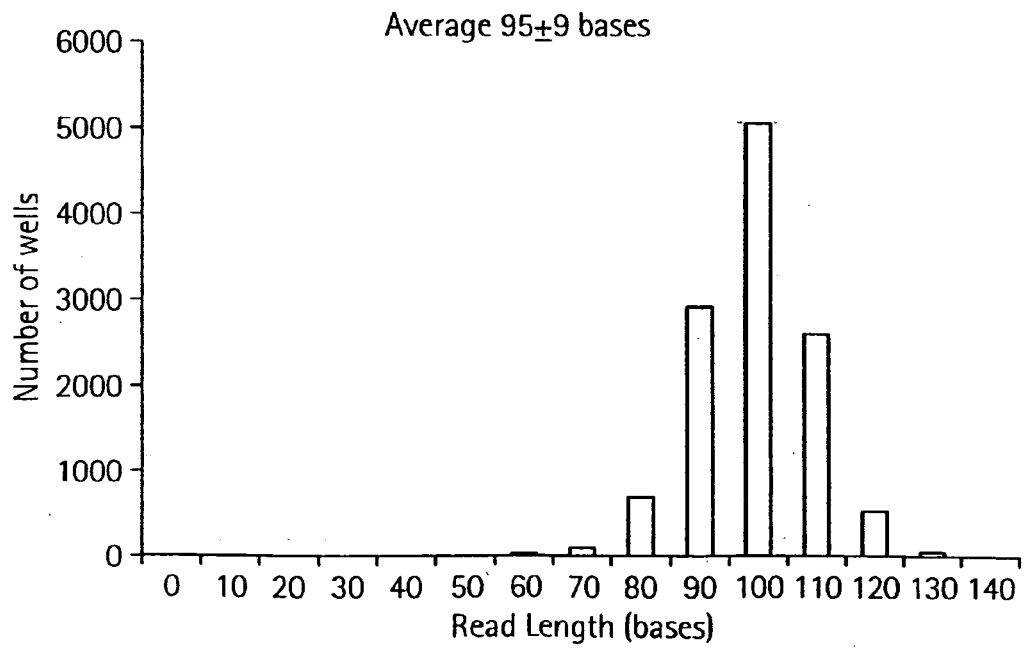

FIG. 41

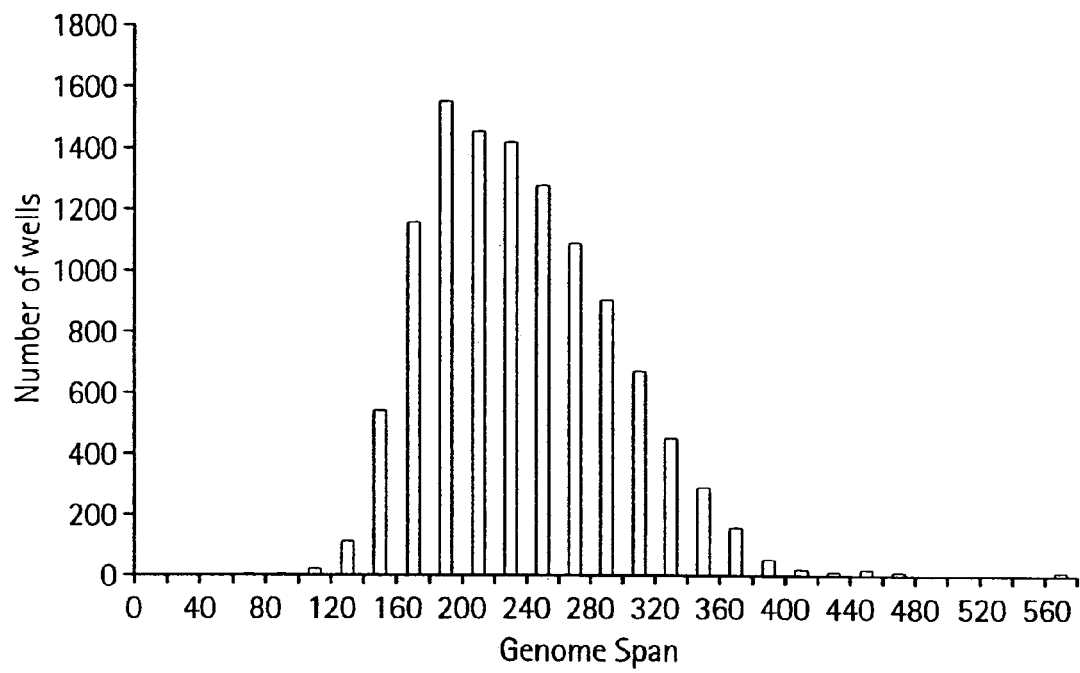

FIG. 42

| Well | Genome Position | Orientation | Alignment String |
|---|---|---|---|
| 00364_0548_2509 | 571366 | F | TATTGTTGATGCTGTAAAAaGAAGCTACTGGTGTAGtATTTTTATGAAGTT |
| 00364_0548_2509_D2 | 571512 | R | TGCTCAAAGAATTCATTTAAAATATGACCATATTTCATTGTATCTTT |
| 00383_0985_2232 | 1487890 | R | AAGCGAACAGTCAAGTACCACAGTCAGTTGACtTTTACACAAGCGGAT |
| 00383_0985_2232_D2 | 1487769 | F | TACAGGTGTTGGTATGCCATTTGCGATTTGTTGCGCTTGGTTAGCCG |
| 00397_0940_2923 | 2611033 | F | AACATATAAACATCCCCTATCTCAATTTCCGCTTCCATGTAaCAAAAAAAGC |
| 00397_0940_2923_D2 | 2611164 | R | TAGATATCACTTGCGTGTTACTGGTAATGCAGGCATGAG |
| 00417_0611_1933 | 122001 | R | ATTCAACTCTGGAAATGCtTTCTTGATACGCCTCGATGATG |
| 00417_0611_1933_D2 | 121930 | F | GATGAGGAGCTGCAATGGCAATGGGTTAAAGGCATCATCG |
| 00434_0595_0993 | 2022591 | R | TGTATCTCGATTTGGATTAGTTGCtTTTTGCATCTTCATTAGACC |
| 00434_0595_0993_D2 | 2022473 | F | CATTAACATCTGCACCAGAAATAGCTTCTAATACGATTGC |
| 00443_1003_0754 | 107373 | F | GCGACGACGTCCAGCTAATAACGCTGCACCTAAGGCTAATGATAAT |
| 00443_1003_0754_D2 | 107502 | R | AAACCATGCAGATGCTAACAAAGCTCAAGCATTACCAGAAACT |
| 00454_1257_3047 | 59038 | R | TGTTGCTGCATCATAATTTAATACTACATCATTTAAtTCTTTGG |
| 00454_1257_3047_D2 | 58880 | F | GCAGATGGTGTGACTAACCAAGTTGGTCAAAATGCCCTAAATACAAAAGAT |

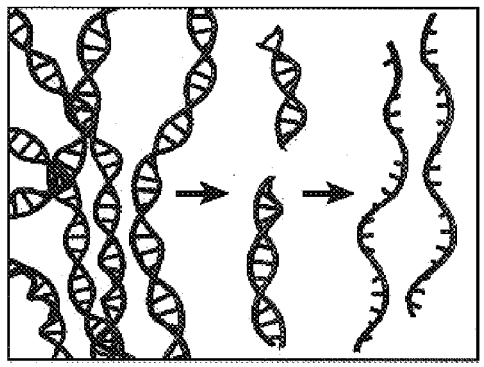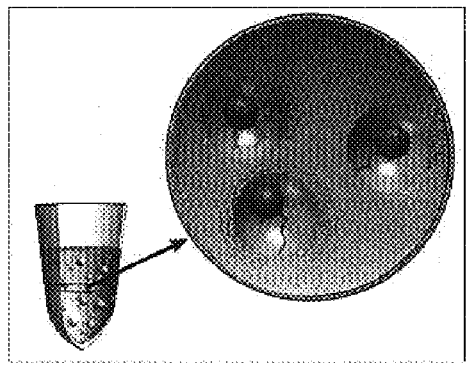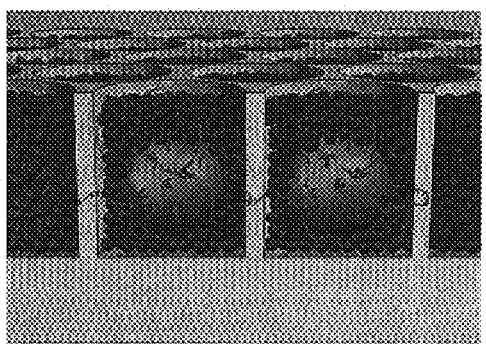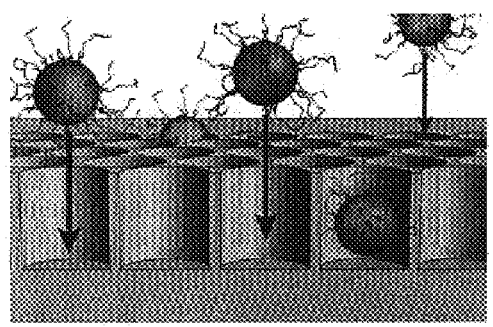
Figure 43A
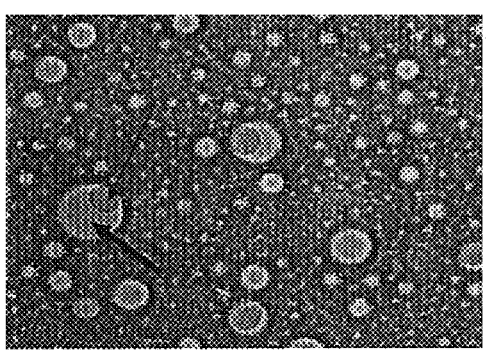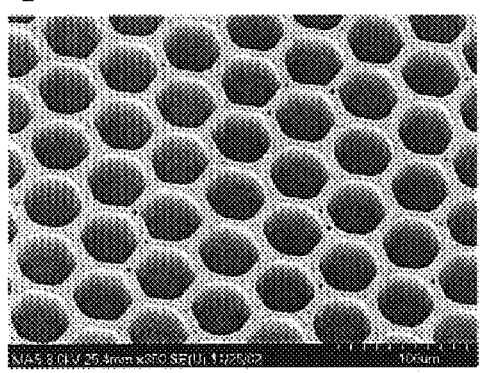
Figure 43B
Figure 43C

SEQUENCE LISTING

<160> NUMBER OF SEQ ID NOS: 77

<210> SEQ ID NO 1
<211> LENGTH: 44
<212> TYPE: DNA
<213> ORGANISM: Artificial
<220> FEATURE:
<223> OTHER INFORMATION: Primer

<400> SEQUENCE: 1
cgtttcccct gtgtgccttg ccatctgttc cctccctgtc atgc        44

<210> SEQ ID NO 2
<211> LENGTH: 40
<212> TYPE: DNA
<213> ORGANISM: Artificial
<220> FEATURE:
<223> OTHER INFORMATION: Primer

<400> SEQUENCE: 2
gcatgacagg gagggaacag atggcaaggc acacagggga        40

<210> SEQ ID NO 3
<211> LENGTH: 40
<212> TYPE: DNA
<213> ORGANISM: Artificial
<220> FEATURE:
<223> OTHER INFORMATION: Primer

<400> SEQUENCE: 3
gcatgacacg caacagggga tagggacacg cacgcaacag        40

<210> SEQ ID NO 4
<211> LENGTH: 44
<212> TYPE: DNA
<213> ORGANISM: Artificial
<220> FEATURE:
<223> OTHER INFORMATION: Primer

<400> SEQUENCE: 4
ccatctgttg cgtgcgtgtc cctatccccT gttgcgtgtc atgc        44

<210> SEQ ID NO 5
<211> LENGTH: 64
<212> TYPE: DNA
<213> ORGANISM: Artificial
<220> FEATURE:
<223> OTHER INFORMATION: Primer

<400> SEQUENCE: 5
tcgtgtgagg tctcagcatc ttatgtatat ttacttctat tctcagttgc ctaagctgca        60
gcca        64

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
gacctcacac gatggctgca gctt        24

```
<210> SEQ ID NO 7
<211> LENGTH: 24
<212> TYPE: DNA
<213> ORGANISM: Artificial
<220> FEATURE:
<223> OTHER INFORMATION: Primer

<400> SEQUENCE: 7
gacctcacac gatggctgca gctt                                          24

<210> SEQ ID NO 8
<211> LENGTH: 64
<212> TYPE: DNA
<213> ORGANISM: Artificial
<220> FEATURE:
<223> OTHER INFORMATION: Primer

<400> SEQUENCE: 8
tttatatgta ttctacgact ctggagtgtg ctaccgacgt cgaatccgtt gactcttatc   60
ttca                                                                64

<210> SEQ ID NO 9
<211> LENGTH: 34
<212> TYPE: DNA
<213> ORGANISM: Artificial
<220> FEATURE:
<223> OTHER INFORMATION: Primer

<400> SEQUENCE: 9
ctagctcgta catataaatg aagataagat cctg                               34

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
gacctcacac gagtagcatg gctgcagctt                                    30

<210> SEQ ID NO 11
<211> LENGTH: 64
<212> TYPE: DNA
<213> ORGANISM: Artificial
<220> FEATURE:
<223> OTHER INFORMATION: Primer

<400> SEQUENCE: 11
tcgtgtgagg tctcagcatc ttatgtatat ttacttctat tctcagttgc ctaagctgca   60
gcca                                                                64

<210> SEQ ID NO 12
<211> LENGTH: 40
<212> TYPE: DNA
<213> ORGANISM: Artificial
<220> FEATURE:
<223> OTHER INFORMATION: Primer

<400> SEQUENCE: 12
gcttacctga ccgacctctg cctatcccct gttgcgtgtc                         40

<210> SEQ ID NO 13
<211> LENGTH: 40
<212> TYPE: DNA
```

```
<213> ORGANISM: Artificial
<220> FEATURE:
<223> OTHER INFORMATION: Primer

<400> SEQUENCE: 13
ccattcccca gctcgtcttg ccatctgttc cctccctgtc                    40

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
gcttacctga ccgacctctg                                          20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
ccattcccca gctcgtcttg                                          20

<210> SEQ ID NO 16
<211> LENGTH: 44
<212> TYPE: DNA
<213> ORGANISM: Artificial
<220> FEATURE:
<223> OTHER INFORMATION: Primer

<400> SEQUENCE: 16
ccattcccca gctcgtcttg ccatctgttc cctccctgtc tcag               44

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ccatctgttc cctccctgtc                                          20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
cctatcccct gttgcgtgtc                                          20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
cgtttcccct gtgtgccttg                                          20
```

```
<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
ccatctgttg cgtgcgtgtc                                                   20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
ccatctgttc cctccctgtc                                                   20

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
cctatcccct gttgcgtgtc                                                   20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
ccatctgttg cgtgcgtgtc                                                   20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
cgtttcccct gtgtgccttg                                                   20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
catcttgtcc actaggctct                                                   20

<210> SEQ ID NO 26
<211> LENGTH: 20
<212> TYPE: DNA
<213> ORGANISM: Artificial
<220> FEATURE:
```

<223> OTHER INFORMATION: Primer

<400> SEQUENCE: 26
ccatctgttg cgtgcgtgtc                                           20

<210> SEQ ID NO 27
<211> LENGTH: 18
<212> TYPE: DNA
<213> ORGANISM: Artificial
<220> FEATURE:
<223> OTHER INFORMATION: Primer

<400> SEQUENCE: 27
accagcactc gcaccacc                                             18

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
cgtttcccct gtgtgccttg                                           20

<210> SEQ ID NO 29
<211> LENGTH: 18
<212> TYPE: DNA
<213> ORGANISM: Artificial
<220> FEATURE:
<223> OTHER INFORMATION: Primer

<400> SEQUENCE: 29
tacctctccg cgtaggcg                                             18

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
ccatctgttg cgtgcgtgtc                                           20

<210> SEQ ID NO 31
<211> LENGTH: 17
<212> TYPE: DNA
<213> ORGANISM: Artificial
<220> FEATURE:
<223> OTHER INFORMATION: Primer

<400> SEQUENCE: 31
ccccggacga gacgcag                                              17

<210> SEQ ID NO 32
<211> LENGTH: 23
<212> TYPE: DNA
<213> ORGANISM: Artificial
<220> FEATURE:
<223> OTHER INFORMATION: Primer

<400> SEQUENCE: 32
atctctgcct actaaccatg aag                                       23

```
<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
catcttgtcc actaggctct                                              20

<210> SEQ ID NO 34
<211> LENGTH: 23
<212> TYPE: DNA
<213> ORGANISM: Artificial
<220> FEATURE:
<223> OTHER INFORMATION: Primer

<400> SEQUENCE: 34
gtttctctcc agcctctcac cga                                          23

<210> SEQ ID NO 35
<211> LENGTH: 18
<212> TYPE: DNA
<213> ORGANISM: Artificial
<220> FEATURE:
<223> OTHER INFORMATION: Primer

<400> SEQUENCE: 35
accagcactc gcaccacc                                                18

<210> SEQ ID NO 36
<211> LENGTH: 23
<212> TYPE: DNA
<213> ORGANISM: Artificial
<220> FEATURE:
<223> OTHER INFORMATION: Primer

<400> SEQUENCE: 36
atctctgcct actaaccatg aag                                          23

<210> SEQ ID NO 37
<211> LENGTH: 18
<212> TYPE: DNA
<213> ORGANISM: Artificial
<220> FEATURE:
<223> OTHER INFORMATION: Primer

<400> SEQUENCE: 37
tacctctccg cgtaggcg                                                18

<210> SEQ ID NO 38
<211> LENGTH: 23
<212> TYPE: DNA
<213> ORGANISM: Artificial
<220> FEATURE:
<223> OTHER INFORMATION: Primer

<400> SEQUENCE: 38
gtttctctcc agcctctcac cga                                          23

<210> SEQ ID NO 39
<211> LENGTH: 17
<212> TYPE: DNA
<213> ORGANISM: Artificial
<220> FEATURE:
<223> OTHER INFORMATION: Primer
```

```
<400> SEQUENCE: 39
ccccggacga gacgcag                                                    17

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
cgtttcccct gtgtgccttg                                                 20

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
ccatctgttg cgtgcgtgtc                                                 20

<210> SEQ ID NO 42
<211> LENGTH: 27
<212> TYPE: DNA
<213> ORGANISM: Artificial
<220> FEATURE:
<223> OTHER INFORMATION: Primer

<400> SEQUENCE: 42
ctagctagca tggaagcgcc agcagca                                         27

<210> SEQ ID NO 43
<211> LENGTH: 28
<212> TYPE: DNA
<213> ORGANISM: Artificial
<220> FEATURE:
<223> OTHER INFORMATION: Primer

<400> SEQUENCE: 43
ccgggatccc tcgatgacga ccagcggc                                        28

<210> SEQ ID NO 44
<211> LENGTH: 23
<212> TYPE: DNA
<213> ORGANISM: Artificial
<220> FEATURE:
<223> OTHER INFORMATION: Primer

<400> SEQUENCE: 44
atgcacatgg ttgacacagt ggt                                             23

<210> SEQ ID NO 45
<211> LENGTH: 22
<212> TYPE: DNA
<213> ORGANISM: Artificial
<220> FEATURE:
<223> OTHER INFORMATION: Primer

<400> SEQUENCE: 45
atgcacatgg ttgacacagt gg                                              22

<210> SEQ ID NO 46
<211> LENGTH: 25
```

```
<212> TYPE: DNA
<213> ORGANISM: Artificial
<220> FEATURE:
<223> OTHER INFORMATION: Primer

<400> SEQUENCE: 46
atgccaccga cctagtctca aactt                                          25

<210> SEQ ID NO 47
<211> LENGTH: 51
<212> TYPE: DNA
<213> ORGANISM: Artificial
<220> FEATURE:
<223> OTHER INFORMATION: Primer

<400> SEQUENCE: 47
tattgttgat gctgtaaaaa gaagctactg gtgtagtatt tttatgaagt t             51

<210> SEQ ID NO 48
<211> LENGTH: 47
<212> TYPE: DNA
<213> ORGANISM: Artificial
<220> FEATURE:
<223> OTHER INFORMATION: Primer

<400> SEQUENCE: 48
tgctcaaaga attcatttaa aatatgacca tatttcattg tatcttt                  47

<210> SEQ ID NO 49
<211> LENGTH: 48
<212> TYPE: DNA
<213> ORGANISM: Artificial
<220> FEATURE:
<223> OTHER INFORMATION: Primer

<400> SEQUENCE: 49
aagcgaacag tcaagtacca cagtcagttg acttttacac aagcggat                 48

<210> SEQ ID NO 50
<211> LENGTH: 47
<212> TYPE: DNA
<213> ORGANISM: Artificial
<220> FEATURE:
<223> OTHER INFORMATION: Primer

<400> SEQUENCE: 50
tacaggtgtt ggtatgccat ttgcgatttg ttgcgcttgg ttagccg                  47

<210> SEQ ID NO 51
<211> LENGTH: 52
<212> TYPE: DNA
<213> ORGANISM: Artificial
<220> FEATURE:
<223> OTHER INFORMATION: Primer

<400> SEQUENCE: 51
aacatataaa catcccctat ctcaatttcc gcttccatgt aacaaaaaaa gc            52

<210> SEQ ID NO 52
<211> LENGTH: 39
<212> TYPE: DNA
<213> ORGANISM: Artificial
<220> FEATURE:
<223> OTHER INFORMATION: Primer

<400> SEQUENCE: 52
```
tagatatcac ttgcgtgtta ctggtaatgc aggcatgag        39

<210> SEQ ID NO 53
<211> LENGTH: 41
<212> TYPE: DNA
<213> ORGANISM: Artificial
<220> FEATURE:
<223> OTHER INFORMATION: Primer

<400> SEQUENCE: 53
attcaactct ggaaatgctt tcttgatacg cctcgatgat g        41

<210> SEQ ID NO 54
<211> LENGTH: 40
<212> TYPE: DNA
<213> ORGANISM: Artificial
<220> FEATURE:
<223> OTHER INFORMATION: Primer

<400> SEQUENCE: 54
gatgaggagc tgcaatggca atgggttaaa ggcatcatcg        40

<210> SEQ ID NO 55
<211> LENGTH: 45
<212> TYPE: DNA
<213> ORGANISM: Artificial
<220> FEATURE:
<223> OTHER INFORMATION: Primer

<400> SEQUENCE: 55
tgtatctcga tttggattag ttgcttttg catcttcatt agacc        45

<210> SEQ ID NO 56
<211> LENGTH: 40
<212> TYPE: DNA
<213> ORGANISM: Artificial
<220> FEATURE:
<223> OTHER INFORMATION: Primer

<400> SEQUENCE: 56
cattaacatc tgcaccagaa atagcttcta atacgattgc        40

<210> SEQ ID NO 57
<211> LENGTH: 46
<212> TYPE: DNA
<213> ORGANISM: Artificial
<220> FEATURE:
<223> OTHER INFORMATION: Primer

<400> SEQUENCE: 57
gcgacgacgt ccagctaata acgctgcacc taaggctaat gataat        46

<210> SEQ ID NO 58
<211> LENGTH: 43
<212> TYPE: DNA
<213> ORGANISM: Artificial
<220> FEATURE:
<223> OTHER INFORMATION: Primer

<400> SEQUENCE: 58
aaaccatgca gatgctaaca aagctcaagc attaccagaa act        43

<210> SEQ ID NO 59
<211> LENGTH: 44
<212> TYPE: DNA
<213> ORGANISM: Artificial

```
<220> FEATURE:
<223> OTHER INFORMATION: Primer

<400> SEQUENCE: 59
tgttgctgca tcataattta atactacatc atttaattct ttgg            44

<210> SEQ ID NO 60
<211> LENGTH: 51
<212> TYPE: DNA
<213> ORGANISM: Artificial
<220> FEATURE:
<223> OTHER INFORMATION: Primer

<400> SEQUENCE: 60
gcagatggtg tgactaacca agttggtcaa aatgccctaa atacaaaaga t    51

<210> SEQ ID NO 61
<211> LENGTH: 44
<212> TYPE: DNA
<213> ORGANISM: Artificial
<220> FEATURE:
<223> OTHER INFORMATION: Primer

<400> SEQUENCE: 61
ccatctcatc cctgcgtgtc ccatctgttc cctccctgtc tcag            44

<210> SEQ ID NO 62
<211> LENGTH: 44
<212> TYPE: DNA
<213> ORGANISM: Artificial
<220> FEATURE:
<223> OTHER INFORMATION: Primer

<400> SEQUENCE: 62
cctatcccct gtgtgccttg cctatcccct gttgcgtgtc tcag            44

<210> SEQ ID NO 63
<211> LENGTH: 20
<212> TYPE: DNA
<213> ORGANISM: Artificial
<220> FEATURE:
<223> OTHER INFORMATION: Primer

<400> SEQUENCE: 63
ccatctgttg cgtgcgtgtc                                       20

<210> SEQ ID NO 64
<211> LENGTH: 20
<212> TYPE: DNA
<213> ORGANISM: Artificial
<220> FEATURE:
<223> OTHER INFORMATION: Primer

<400> SEQUENCE: 64
cgtttcccct gtgtgccttg                                       20

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
ccatctgttg cgtgcgtgtc                                       20
```

```
<210> SEQ ID NO 66
<211> LENGTH: 40
<212> TYPE: DNA
<213> ORGANISM: Artificial
<220> FEATURE:
<223> OTHER INFORMATION: Primer

<400> SEQUENCE: 66
cgtttcccct gtgtgccttg ccatctgttc cctccctgtc                              40

<210> SEQ ID NO 67
<211> LENGTH: 20
<212> TYPE: DNA
<213> ORGANISM: Artificial
<220> FEATURE:
<223> OTHER INFORMATION: Primer

<400> SEQUENCE: 67
ccatctgttc cctccctgtc                                                    20

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
cgtttcccct gtgtgccttg                                                    20

<210> SEQ ID NO 69
<211> LENGTH: 20
<212> TYPE: DNA
<213> ORGANISM: Artificial
<220> FEATURE:
<223> OTHER INFORMATION: Primer

<400> SEQUENCE: 69
ccatctgttg cgtgcgtgtc                                                    20

<210> SEQ ID NO 70
<211> LENGTH: 20
<212> TYPE: DNA
<213> ORGANISM: Artificial
<220> FEATURE:
<223> OTHER INFORMATION: Primer

<400> SEQUENCE: 70
ccatctgttc cctccctgtc                                                    20

<210> SEQ ID NO 71
<211> LENGTH: 24
<212> TYPE: DNA
<213> ORGANISM: Artificial
<220> FEATURE:
<223> OTHER INFORMATION: Primer

<400> SEQUENCE: 71
gacctcacac gatggctgca gctt                                               24

<210> SEQ ID NO 72
<211> LENGTH: 64
<212> TYPE: DNA
<213> ORGANISM: Artificial
<220> FEATURE:
<223> OTHER INFORMATION: Primer
```

<400> SEQUENCE: 72
tcgtgtgagg tctcagcatc ttatgtatat ttacttctat tctcaggtgc ccaagctgca    60
gcca    64

<210> SEQ ID NO 73
<211> LENGTH: 64
<212> TYPE: DNA
<213> ORGANISM: Artificial
<220> FEATURE:
<223> OTHER INFORMATION: Primer

<400> SEQUENCE: 73
acttctattc tcagttgcct aagctgcagc cattgtgtga ggtctcagca tcttatgtat    60
attt    64

<210> SEQ ID NO 74
<211> LENGTH: 32
<212> TYPE: DNA
<213> ORGANISM: Artificial
<220> FEATURE:
<223> OTHER INFORMATION: Primer

<400> SEQUENCE: 74
gtcctagaat agaagtaaat atacatgctc ga    32

<210> SEQ ID NO 75
<211> LENGTH: 30
<212> TYPE: DNA
<213> ORGANISM: Artificial
<220> FEATURE:
<223> OTHER INFORMATION: Primer

<400> SEQUENCE: 75
gacctcacac gagtagcatg gctgcagctt    30

<210> SEQ ID NO 76
<211> LENGTH: 64
<212> TYPE: DNA
<213> ORGANISM: Artificial
<220> FEATURE:
<223> OTHER INFORMATION: Primer

<400> SEQUENCE: 76
tcgtgtgagg tctcagcatc ttatgtatat ttacttctat tctcagttgc ctaagctgca    60
gcca    64

<210> SEQ ID NO 77
<211> LENGTH: 6
<212> TYPE: DNA
<213> ORGANISM: Artificial
<220> FEATURE:
<223> OTHER INFORMATION: Primer

<400> SEQUENCE: 77 tgctac    6

METHODS OF AMPLIFYING AND SEQUENCING NUCLEIC ACIDS

RELATED APPLICATIONS

This application is a continuation-in-part of U.S. application Ser. No. 10/767,779 filed Sep. 22, 2004, which claims the benefit of priority to the following applications: U.S. Ser. No. 60/476,602, filed Jun. 6, 2003; U.S. Ser. No. 60/476,504, filed Jun. 6, 2003; U.S. Ser. No. 60/443,471, filed Jan. 29, 2003; U.S. Ser. No. 60/476,313, filed Jun. 6, 2003; U.S. Ser. No. 60/476,592, filed Jun. 6, 2003; U.S. Ser. No. 60/465,071, filed Apr. 23, 2003; and U.S. Ser. No. 60/497,985; filed Aug. 25, 2003.

All patent and patent applications referred to in this disclosure are hereby fully incorporated by reference.

FIELD OF THE INVENTION

This invention relates to a method and apparatus for determining the base sequences of DNA. More particularly, this invention relates to methods and an apparatus with which the base sequences of a genome can be amplified and determined automatically or semiautomatically.

BACKGROUND OF THE INVENTION

Development of rapid and sensitive nucleic acid sequencing methods utilizing automated DNA sequencers has revolutionized modern molecular biology. Analysis of entire genomes of plants, fungi, animals, bacteria, and viruses is now possible with a concerted effort by a series of machines and a team of technicians. However, the goal of rapid and automated or semiautomatic sequencing of a genome in a short time has not been possible. There continues to be technical problems for accurate sample preparation, amplification and sequencing.

One technical problem which hinders sequence analysis of genomes has been the inability of the investigator to rapidly prepare numerous nucleic acid sample encompassing a complete genome in a short period of time.

Another technical problem is the inability to representatively amplified a genome to a level that is compatible with the sensitivity of current sequencing methods. Modern economically feasible sequencing machines, while sensitive, still require in excess of one million copies of a DNA fragment for sequencing. Current methods for providing high copies of DNA sequencing involves variations of cloning or in vitro amplification which cannot amplify the number of individual clones (600,000 or more, and tens of millions for a human genome) necessary for sequencing a whole genome economically.

Yet another technical problem in the limitation of current sequencing methods which can perform, at most, one sequencing reaction per hybridization of oligonucleotide primer. The hybridization of sequencing primers is often the rate limiting step constricting the throughput of DNA sequencers.

In most cases, Polymerase Chain Reaction (PCR; Saiki, R. K., et al., *Science* 1985, 230, 1350-1354; Mullis, K., et al., *Cold Spring Harb. Symp. Quant. Biol.* 1986, 51 Pt 1, 263-273) plays an integral part in obtaining DNA sequence information, amplifying minute amounts of specific DNA to obtain concentrations sufficient for sequencing. Yet, scaling current PCR technology to meet the increasing demands of modern genetics is neither cost effective nor efficient, especially when the requirements for full genome sequencing are considered.

Efforts to maximize time and cost efficiencies have typically focused on two areas: decreasing the reaction volume required for amplifications and increasing the number of simultaneous amplifications performed. Miniaturization confers the advantage of lowered sample and reagent utilization, decreased amplification times and increased throughput scalability.

While conventional thermocyclers require relatively long cycling times due to thermal mass restrictions (Woolley, A. T., et al., *Anal. Chem.* 1996, 68, 4081-4086), smaller reaction volumes can be cycled more rapidly. Continuous flow PCR devices have utilized etched microchannels in conjunction with fixed temperature zones to reduce reaction volumes to sub-microliter sample levels (Lagally, E. T., et al., Analytical Chemistry 2001, 73, 565-570; Schneegas, I., et al., *Lab on a Chip—The Royal Society of Chemistry* 2001, 1, 42-49).

Glass microcapillaries, heated by air (Kalinina, O., et al., *Nucleic Acids Res.* 1997, 25, 1999-2004) or infrared light (Oda, R. P., et al., *Anal. Chem.* 1998, 70, 4361-4368; Huhmer, A. F. and Landers, J. P., *Anal. Chem.* 2000, 72, 5507-5512), have also served as efficient vessels for nanoliter scale reactions. Similar reaction volumes have been attained with microfabricated silicon thermocyclers (Burns, M. A., et al., *Proc. Natl. Acad. Sci. USA* 1996, 93, 5556-5561).

In many cases, these miniaturizations have reduced total PCR reaction times to less than 30 minutes for modified electric heating elements (Kopp, M. U., et al., *Science* 1998, 280, 1046-1048; Chiou, J., Matsudaira, P., Sonin, A. and Ehrlich, D., *Anal. Chem.* 2001, 73, 2018-2021) and hot air cyclers (Kalinina, O., et al., *Nucleic Acids Res.* 1997, 25, 1999-2004), and to 240 seconds for some infrared controlled reactions (Giordano, B. C., et al., *Anal. Biochem.* 2001, 291, 124-132).

Certain technologies employ increased throughput and miniaturization simultaneously; as in the 1536-well system design by Sasaki et al. (Sasaki, N., et al., *DNA Res.* 1997, 4, 387-391), which maintained reaction volumes under 1 µl. As another example, Nagai et al. (Nagai, H., et al., *Biosens. Bioelectron.* 2001, 16, 1015-1019; Nagai, H., et al., *Anal. Chem.* 2001, 73, 1043-1047) reported amplification of a single test fragment in ten thousand 86 pl reaction pits etched in a single silicon wafer. Unfortunately, recovery and utilization of the amplicon from these methods have proven problematic, requiring evaporation through selectively permeable membranes.

Despite these remarkable improvements in reactions volumes and cycle times, none of the previous strategies have provided the massively parallel amplification required to dramatically increase throughput to levels required for analysis of the entire human genome. DNA sequencers continue to be slower and more expensive than would be desired. In the pure research setting it is perhaps acceptable if a sequencer is slow and expensive. But when it is desired to use DNA sequencers in a clinical diagnostic setting such inefficient sequencing methods are prohibitive even for a well financed institution. The large-scale parallel sequencing of thousands of clonally amplified targets would greatly facilitate large-scale, whole genome library analysis without the time consuming sample preparation process and expensive, error-prone cloning processes. Successful high capacity, solid-phase, clonal DNA amplification can be used for numerous applications. Accordingly, it is clear that there exists a need for preparation of a genome or large template nucleic acids for sequencing, for amplification of the nucleic acid template, and for the sequencing of the amplified template nucleic acids without the constraint of one sequencing reaction per hybridization.

Furthermore, there is a need for a system to connect these various technologies into a viable automatic or semiautomatic sequencing machine.

BRIEF SUMMARY OF THE INVENTION

This invention describes an integrated system, comprising novel methods and novel apparatus for (1) nucleic acid sample preparation, (2) nucleic acid amplification, and (3) DNA sequencing.

The invention provides a novel method for preparing a library of multiple DNA sequences, particularly derived from large template DNA or whole (or partial) genome DNA. Sequences of single stranded DNA are prepared from a sample of large template DNA or whole or partial DNA genomes through fragmentation, polishing, adaptor ligation, nick repair, and isolation of single stranded DNA. The method provides for generating a ssDNA library linked to solid supports comprising: (a) generating a library of ssDNA templates; (b) attaching the ssDNA templates to solid supports; and (c) isolating the solid supports on which one ssDNA template is attached.

The invention also provides for a method of amplifying each individual member of a DNA library in a single reaction tube, by, e.g., encapsulating a plurality of DNA samples individually in a microcapsule of an emulsion, performing amplification of the plurality of encapsulated nucleic acid samples simultaneously, and releasing said amplified plurality of DNA from the microcapsules for subsequent reactions. In one embodiment, single copies of the nucleic acid template species are hybridized to DNA capture beads, suspended in complete amplification solution and emulsified into microreactors (typically 100 to 200 microns in diameter), after which amplification (e.g., PCR) is used to clonally increase copy number of the initial template species to more than 1,000,000 copies of a single nucleic acid sequence, preferably between 2 and 20 million copies of a single nucleic acid. The amplification reaction, for example, may be performed simultaneously with at least 3,000 microreactors per microliter of reaction mix, and may be performed with over 300,000 microreactors in a single 100 µl volume test tube (e.g., a PCR reaction tube). The present invention also provides for a method of enriching for those beads that contains a successful DNA amplification event (i.e., by removing beads that have no DNA attached thereto).

The invention also provides for a method of sequencing a nucleic acid from multiple primers with a single primer hybridization step. Two or more sequencing primers are hybridized to the template DNA to be sequenced. All the sequencing primers are then protected except for one. Sequencing (e.g., pyrophosphate sequencing) is performed again by elongating the unprotected primer. The elongation is either allowed to go to completion (with additional polymerase and dNTPs if necessary) or is terminated (by polymerase and ddNTPs). Chain completion and/or termination reagents are removed. Then one of the protected primers is unprotected and sequencing is performed by elongating the newly unprotected primer. This process is continued until all the sequencing primers are deprotected and sequenced. In a preferred embodiment, two primers (one protected and one unprotected) are used to sequence both ends of a double stranded nucleic acid.

The invention also provides an apparatus and methods for sequencing nucleic acids using a pyrophosphate based sequencing approach. The apparatus has a charge coupled device (CCD) camera, microfluidics chamber, sample cartridge holder, pump and flow valves. The apparatus uses chemiluminescence as the detection method, which for pyrophosphate sequencing has an inherently low background. In a preferred embodiment, the sample cartridge for sequencing is termed the 'PicoTiter plate,' and is formed from a commercial fiber optics faceplate, acid-etched to yield hundreds of thousands of very small wells, each well volume of 75 pL. The apparatus includes a novel reagent delivery cuvette adapted for use with the arrays described herein, to provide fluid reagents to the picotiter plate, and a reagent delivery means in communication with the reagent delivery cuvette. Photons from each well on the picotiter plate are channeled into specific pixels on the CCD camera to detect sequencing reactions.

An embodiment of the invention is directed to a method for sequencing a nucleic acid, the method comprising: (a) providing a plurality of single-stranded nucleic acid templates disposed within a plurality of cavities on a planar surface, each cavity forming an analyte reaction chamber, wherein the reaction chambers have a center to center spacing of between 20 to 100 µm and the planar surface has at least 10,000 reaction chambers; (b) performing a pyrophosphate based sequencing reaction simultaneously on all reaction chambers by annealing an effective amount of a sequencing primer to the nucleic acid templates and extending the sequencing primer with a polymerase and a predetermined nucleotide triphosphate to yield a sequencing product and, if the predetermined nucleotide triphosphate is incorporated onto the 3' end of said sequencing primer, a sequencing reaction byproduct; and (c) identifying the sequencing reaction byproduct, thereby determining the sequence of the nucleic acid in each reaction chamber.

In any of the methods of the invention, the sequencing reaction may be performed in the presence of apyrase. The apyrase may be in solution or the apyrase may be immobilized on a surface (for example, in the analyte reaction chamber). Alternatively, the apyrase may be immobilized on a mobile solid support disposed at a analyte reaction chamber of a sequencing reaction/method of the invention.

In any of the embodiments of the invention which involves sequencing, the sequencing may be performed by a pyrophosphate based sequencing reaction. Furthermore, the sequencing reaction may be performed at at 34° C. to 36° C. In a more preferred embodiment, the sequencing reaction is performed at 35° C. This temperature is selected to optimize the function of the sequencing reagents, such as, for example, apyrase. In a most preferred embodiment, the sequencing reaction is performed in the presence of apyrase.

Another embodiment of the invention is directed to a method for sequencing nucleic acids comprising: (a) fragmenting large template nucleic acid molecules to generate a plurality of fragmented nucleic acids; (b) delivering the fragmented nucleic acids into aqueous microreactors in a water-in-oil emulsion such that a plurality of aqueous microreactors comprise a single copy of a fragmented nucleic acid, a single bead capable of binding to the fragmented nucleic acid, and amplification reaction solution containing reagents necessary to perform nucleic acid amplification; (c) amplifying the fragmented nucleic acids in the microreactors to form amplified copies of the nucleic acids and binding the amplified copies to beads in the microreactors; (d) delivering the beads to an array of at least 10,000 reaction chambers on a planar surface, wherein a plurality of the reaction chambers comprise no more than a single bead; and (e) performing a sequencing reaction simultaneously on a plurality of the reaction chambers.

Furthermore, the method just described may have the following additional characteristics: The reaction chambers may have a center to center spacing of 20 to 100 μm. The fragmented nucleic acids may be 30-500 bases in length. A plurality of the beads bind at least 10,000 amplified copies. Step (c) may be performed using polymerase chain reaction. The sequencing reaction may be a pyrophosphate-based sequencing reaction. For example, the sequencing reaction may comprise the steps of: (a) annealing an effective amount of a sequencing primer to the amplified copies of the nucleic acid and extending the sequencing primer with a polymerase and a predetermined nucleotide triphosphate to yield a sequencing product and, if the predetermined nucleotide triphosphate is incorporated onto a 3' end of the sequencing primer, a sequencing reaction byproduct; and (b) identifying the sequencing reaction byproduct, thereby determining the sequence of the nucleic acid in a plurality of the reaction chambers. As another example, sequencing may comprise the steps of: (a) hybridizing two or more sequencing primers to one or a plurality of single strands of the nucleic acid molecule wherein all the primers except for one are reversibly blocked primers; (b) incorporating at least one base onto the nucleic acid molecule by polymerase elongation from an unblocked primer; (c) preventing further elongation of the unblocked primer; (d) deblocking one of the reversibly blocked primers into an unblocked primer; and (e) repeating steps (b) to (d) until at least one of the reversibly blocked primers are deblocked and used for determining a sequence. The reaction chambers in these methods may be formed by etching one end of a fiber optic bundle.

Another embodiment of the invention is directed to an array comprising a planar surface with a plurality of cavities thereon, each cavity forming an analyte reaction chamber, wherein the reaction chambers have a center to center spacing of between 20 to 100 μm and each cavity has a width in at least one dimension of between 20 μm and 70 μm, and wherein there are at least 10,000 reaction chambers. The plurality of reaction chambers may contain at least 100,000 copies of a single species of single stranded nucleic acid template. The single stranded nucleic acid templates may be immobilized on mobile solid supports disposed in the reaction chambers. The cavities may have a center to center spacing of between 40 to 60 μm and each cavity may have a depth of between 20 μm and 60 μm.

Another embodiment of the invention is directed to an array comprising a planar top surface and a planar bottom surface wherein the planar top surface has at least 10,000 cavities thereon, each cavity forming an analyte reaction chamber, the planar bottom surface is optically conductive such that optical signals from the reaction chambers can be detected through the bottom planar surface, wherein the distance between the top surface and the bottom surface is no greater than 5 mm, wherein the reaction chambers have a center to center spacing of between 20 to 100 μm and each chamber having a width in at least one dimension of between 20 μm and 70 μm. In this array, the distance between the top surface and the bottom surface is no greater than 2 mm. The number of cavities on the array may be greater than 50,000, greater than 100,000. The shape of each reaction chamber may be substantially hexagonal. Furthermore, each cavity may have at least one irregular wall surface. In addition, the cavities may have a smooth wall surface.

The array may be formed in a fused fiber optic bundle. This may be performed, for example, by etching one end of the fiber optic bundle. Each cavity may contain reagents for analyzing a nucleic acid or protein. The array may further comprise a second surface spaced apart from the planar array and in opposing contact therewith such that a flow chamber is formed over the array.

Another embodiment of the invention is directed to an array means for carrying out separate parallel common reactions in an aqueous environment, wherein the array means comprises a substrate comprising at least 10,000 discrete reaction chambers containing a starting material that is capable of reacting with a reagent, each of the reaction chambers being dimensioned such that when one or more fluids containing at least one reagent is delivered into each reaction chamber, the diffusion time for the reagent to diffuse out of the well exceeds the time required for the starting material to react with the reagent to form a product. Each cavity of the array may contain reagents for analyzing a nucleic acid or protein. The array may further comprise a population of mobile solid supports disposed in the reaction chambers, each mobile solid support having one or more bioactive agents attached thereto. The cavities in the array may be formed in the substrate via etching, molding or micromaching. The substrate may be a fiber optic bundle.

In any arrays of the invention, at least 5% to 20%, at least 20% to 60%, or at least 50% to 100% of the reaction chambers may contain at least one mobile solid support having at least one reagent immobilized thereon. The reagent immobilized on the mobile solid support may be a polypeptide with sulfurylase activity, a polypeptide with luciferase activity or a polypeptide with both sulfurylase and luciferase immobilized. The plurality of reaction chambers may contain at least 100,000 copies of a single species of single stranded nucleic acid template. The array may contain single stranded nucleic acid templates immobilized on mobile solid supports disposed in the reaction chambers. The arrays of the invention may be suitable for use in a pyrosequencing reaction.

Another embodiment of the invention is directed to a method for delivering a bioactive agent to an array, comprising dispersing over the array a plurality of mobile solid supports, each mobile solid support having at least one reagent immobilized thereon, wherein the reagent is suitable for use in a nucleic acid sequencing reaction, where the array comprises a planar surface with a plurality of reaction chambers disposed thereon, wherein the reaction chambers have a center to center spacing of between 20 to 100 μm and each reaction chamber has a width in at least one dimension of between 20 μm and 70 μm.

Another embodiment of the invention is directed to an apparatus for simultaneously monitoring an array of reaction chambers for light indicating that a reaction is taking place at a particular site, the apparatus comprising the following components: (a) an array of reaction chambers formed from a planar substrate comprising a plurality of cavitated surfaces, each cavitated surface forming a reaction chamber adapted to contain analytes, and wherein the reaction chambers have a center to center spacing of between 20 to 100 μm, each reaction chamber having a volume of between 10 to 150 pL, the array comprising more than 10,000 discrete reaction chambers; (b) an optically sensitive device arranged so that in use the light from a particular reaction chamber will impinge upon a particular predetermined region of the optically sensitive device; (c) means for determining the light level impinging upon each of the predetermined regions and (d) means to record the variation of the light level with time for each of the reaction chamber.

Another embodiment of the invention is directed to an analytic sensor, comprising the following components: (a) an array formed from a first bundle of optical fibers with a plurality of cavitated surfaces at one end thereof, each cavitated surface forming a reaction chamber adapted to contain analytes, and wherein the reaction chambers have a center to center spacing of between 20 to 100 μm, a width of 20 to 70

μm, the array comprising more than 10,000 discrete reaction chambers; (b) an enzymatic or fluorescent means for generating light in the reaction chambers; (c) light detection means comprising a light capture means and a second fiber optic bundle for transmitting light to the light detecting means, the second fiber optic bundle being in optical contact with the array, such that light generated in an individual reaction chamber is captured by a separate fiber or groups of separate fibers of the second fiber optic bundle for transmission to the light capture means. This sensor may be suitable for use in a biochemical assay or a cell-based assay. The light capture means may be a CCD camera. The reaction chambers may contain one or more mobile solid supports with a bioactive agent immobilized thereon.

Another embodiment of the invention is directed to a method for carrying out separate parallel common reactions in an aqueous environment, comprising the steps of: (a) delivering a fluid containing at least one reagent to an array, wherein the array comprises a substrate comprising at least 10,000 discrete reaction chambers, each reaction chamber adapted to contain analytes, and wherein the reaction chambers have a volume of between 10 to 150 pL and containing a starting material that is capable of reacting with the reagent, each of the reaction chambers being dimensioned such that when the fluid is delivered into each reaction chamber, the diffusion time for the reagent to diffuse out of the well exceeds the time required for the starting material to react with the reagent to form a product; and (b) washing the fluid from the array in the time period (i) after the starting material has reacted with the reagent to form a product in each reaction chamber but (ii) before the reagent delivered to any one reaction chamber has diffused out of that reaction chamber into any other reaction chamber. In one aspect, the product formed in any one reaction chamber is independent of the product formed in any other reaction chamber, but is generated using one or more common reagents. In another aspect, the starting material is a nucleic acid sequence and at least one reagent in the fluid is a nucleotide or nucleotide analog. In another aspect, the fluid additionally comprises a polymerase capable of reacting the nucleic acid sequence and the nucleotide or nucleotide analog. In another aspect, steps (a) and (b) may be repeated sequentially.

Another embodiment of the invention is directed to a method for delivering nucleic acid sequencing enzymes to an array, the array having a planar surface with a plurality of cavities thereon, each cavity forming an analyte reaction chamber, wherein the reaction chambers have a center to center spacing of between 20 to 100 μm; the method comprising dispersing over the array a plurality of mobile solid supports having one or more nucleic acid sequencing enzymes immobilized thereon, such that a plurality of the reaction chambers contain at least one mobile solid support. One of the nucleic acid sequencing enzymes is a polypeptide having sulfurylase activity, luciferase activity or both.

Another embodiment of the invention is directed to a method for delivering a plurality of nucleic acid templates to an array, the array having a planar surface with a plurality of cavities thereon, each cavity forming an analyte reaction chamber, wherein the reaction chambers have a center to center spacing of between 20 to 100 μm and the array having at least 10,000 reaction chambers; the method comprising dispersing over the array a plurality of mobile solid supports, each mobile solid support having no more than a single species of nucleic acid template immobilized thereon, the dispersion causing no more than one mobile solid support to be disposed within any one reaction chamber. In one aspect, the nucleic acid sequence may be a single stranded nucleic acid.

In another aspect, at least 100,000 copies of a single species of nucleic acid template may be immobilized on a plurality of the mobile solid supports. Each single species of nucleic acid template may be amplified on a picotiter plate to produce at least 2,000,000 copies per well of the nucleic acid template after being disposed in the reaction chamber. As an example, the amplification may be performed by polymerase chain reaction, ligase chain reaction or isothermal DNA amplification.

Another embodiment of the invention is directed to a method for sequencing a nucleic acid, the method comprising the steps of: (a) providing a plurality of single-stranded nucleic acid templates disposed within a plurality of cavities on a planar surface, each cavity forming an analyte reaction chamber, wherein the reaction chambers have a center to center spacing of between 20 to 100 μm and the planar surface has at least 10,000 reaction chambers; (b) performing a pyrophosphate based sequencing reaction simultaneously on all reaction chambers by annealing an effective amount of a sequencing primer to the nucleic acid templates and extending the sequencing primer with a polymerase and a predetermined nucleotide triphosphate to yield a sequencing product and, if the predetermined nucleotide triphosphate is incorporated onto the 3' end of the sequencing primer, a sequencing reaction byproduct; and (c) identifying the sequencing reaction byproduct, thereby determining the sequence of the nucleic acid in each reaction chamber. In the method, the sequencing reaction byproduct may be PPi and a coupled sulfurylase/luciferase reaction may be used used to generate light for detection. Further, either or both of the sulfurylase and luciferase are immobilized on one or more mobile solid supports disposed at each reaction site.

Another embodiment of the invention is directed to a method of determining the base sequence of a plurality of nucleotides on an array, the method comprising the steps of: (a) providing at least 10,000 DNA templates, each separately disposed within a plurality of cavities on a planar surface, each cavity forming an analyte reaction chamber, wherein the reaction chambers have a center to center spacing of between 20 to 100 μm, and a volume of between 10 to 150 pL; (b) adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) detecting whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor; (d) sequentially repeating steps (b) and (c), wherein each sequential repetition adds and, detects the incorporation of one type of activated nucleoside 5'-triphosphate precursor of known nitrogenous base composition; and (e) determining the base sequence of the unpaired nucleotide residues of the template in each reaction chamber from the sequence of incorporation of the nucleoside precursors.

Another embodiment of the invention is directed to a method of identifying the base in a target position in a DNA sequence of template DNA, wherein: (a) at least 10,000 separate DNA templates are separately disposed within a plurality of cavities on a planar surface, each cavity forming an analyte reaction chamber, wherein the reaction chambers have a center to center spacing of between 20 to 100 µm, the DNA being rendered single stranded either before or after being disposed in the reaction chambers; (b) an extension primer is provided which hybridizes to the immobilized single-stranded DNA at a position immediately adjacent to the target position; (c) the immobilized single-stranded DNA is subjected to a polymerase reaction in the presence of a predetermined deoxynucleotide or dideoxynucleotide, wherein if the predetermined deoxynucleotide or dideoxynucleotide is incorporated onto the 3' end of the sequencing primer then a sequencing reaction byproduct is formed; and (d) identifying the sequencing reaction byproduct, thereby determining the nucleotide complementary to the base at the target position in each of the 10,000 DNA templates. In the method, in place of deoxy- or dideoxy adenosine triphosphate (ATP), a dATP or ddATP analogue which is capable of acting as a substrate for a polymerase but incapable of acting as a substrate for the PPi—detection enzyme may be used.

Another embodiment of the invention is directed to an apparatus for analyzing a nucleic acid sequence, the apparatus comprising the following components: (a) a reagent delivery cuvette, wherein the cuvette includes an array comprising a planar surface with a plurality of cavities thereon, each cavity forming an analyte reaction chamber, wherein the reaction chambers have a center to center spacing of between 20 to 100 µm, and there are in excess of 10,000 reaction chambers, and wherein the reagent delivery cuvette contains reagents for use in a sequencing reaction; (b) a reagent delivery means in communication with the reagent delivery cuvette; (c) an imaging system in communication with the reagent delivery chamber; and (d) a data collection system in communication with the imaging system.

Another embodiment of the invention is directed to an apparatus for determining the base sequence of a plurality of nucleotides on an array, the apparatus comprising: (a) a reagent cuvette containing a plurality of cavities on a planar surface, each cavity forming an analyte reaction chamber, wherein there are in excess of 10,000 reaction chambers, each having a center to center spacing of between 20 to 100 µm and a volume of between 10 to 150 pL; (b) reagent delivery means for simultaneously adding to each reaction chamber an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; and (c) detection means for detecting in each reaction chamber whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor; (d) means for sequentially repeating steps (b) and (c), wherein each sequential repetition adds and, detects the incorporation of one type of activated nucleoside 5'-triphosphate precursor of known nitrogenous base composition; and (e) data processing means for determining the base sequence of the unpaired nucleotide residues of the template simultaneously in each reaction chamber from the sequence of incorporation of the nucleoside precursors.

Another embodiment of the invention is directed to an apparatus for processing a plurality of analytes, the apparatus comprising the following components: (a) a flow chamber having disposed therein a substrate comprising at least 50,000 cavitated surfaces on a fiber optic bundle, each cavitated surface forming a reaction chamber adapted to contain analytes, and wherein the reaction chambers have a center to center spacing of between 20 to 100 µm and a diameter of 20 to 70 µm; (b) fluid means for delivering processing reagents from one or more reservoirs to the flow chamber so that the analytes disposed in the reaction chambers are exposed to the reagents; and (c) detection means for simultaneously detecting a sequence of optical signals from each of the reaction chambers, each optical signal of the sequence being indicative of an interaction between a processing reagent and the analyte disposed in the reaction chamber, wherein the detection means is in communication with the cavitated surfaces. The detection means may be a CCD camera. The analyte may be a nucleic acid. Further, the analyte may be immobilized on one or more mobile solid supports that are disposed in the reaction chamber. The processing reagents may be immobilized on one or more mobile solid supports.

Another embodiment of the invention is directed to a method for sequencing a nucleic acid comprising the steps of: (a) providing a plurality of single-stranded nucleic acid templates in an array having at least 50,000 discrete reaction sites; (b) contacting the nucleic acid templates with reagents necessary to perform a pyrophosphate-based sequencing reaction coupled to light emission; (c) detecting the light emitted from a plurality of reaction sites on respective portions of an optically sensitive device; (d) converting the light impinging upon each of the portions of the optically sensitive device into an electrical signal which is distinguishable from the signals from all of the other reaction sites; and (e) determining the sequence of the nucleic acid templates based on light emission for each of the discrete reaction sites from the corresponding electrical signal. The method may further comprise the steps of (a) uniquely tagging fragmented nucleic acids from different biological sources libraries to create libraries of fragmented nucleic acids with different detectable sequence tags; and (b) sequencing the fragmented nucleic acids and detecting the detectable sequence tag from each the tagged nucleic acid fragment. The libraries may be delivered individually or the libraries may be mixed and delivered simultaneously. The detectable sequence tag may comprise an oligonucleotide of between 2 and 50 bases.

Another embodiment of the invention is directed to a method for sequencing nucleic acids comprising the steps of: (a) fragmenting large template nucleic acid molecules to generate a plurality of fragmented nucleic acids; (b) attaching one strand of a plurality of the fragmented nucleic acids individually to beads to generate single stranded nucleic acids attached individually to beads; (c) delivering a population of the single stranded fragmented nucleic acids attached individually to beads to an array of at least 10,000 reaction chambers on a planar surface, wherein a plurality of the wells comprise no more than a one bead with on single stranded fragmented nucleic acid; and (d) performing a sequencing reaction simultaneously on a plurality of the reaction chambers. In this method, the reaction chambers may have a center to center spacing of between 20 to 100 μm. The fragmented nucleic acids may be between 30-500 bases in length. Further, the fragmented nucleic acids may be amplified in the reaction chambers prior to step (d). The amplification may be accomplished using polymerase chain reaction. The sequencing reaction, may be, for example, a pyrophosphate-based sequencing reaction. As another example, the sequencing reaction may comprise the steps of: (f) annealing an effective amount of a sequencing primer to the single stranded fragmented nucleic acid templates and extending the sequencing primer with a polymerase and a predetermined nucleotide triphosphate to yield a sequencing product and, if the predetermined nucleotide triphosphate is incorporated onto the 3' end of the sequencing primer, a sequencing reaction byproduct; and (g) identifying the sequencing reaction byproduct, thereby determining the sequence of the nucleic acid in a plurality of the reaction chambers. As another example, the sequencing reaction may comprise the steps of: (a) hybridizing two or more sequencing primers to one or a plurality of single strands of the nucleic acid molecule wherein all the primers except for one are reversibly blocked primers; (b) incorporating at least one base onto the nucleic acid molecule by polymerase elongation from an unblocked primer; (c) preventing further elongation of the unblocked primer; (d) deblocking one of the reversibly blocked primers into an unblocked primer; and (e) repeating steps (b) to (d) until at least one of the reversibly blocked primers are deblocked and used for determining a sequence. The reaction chambers may be cavities formed by etching one end of a fiber optic bundle.

BRIEF DESCRIPTION OF THE FIGURES

FIG. 2A depicts a schematic representation of the universal adaptor design according to the present invention. Each universal adaptor is generated from two complementary ssDNA oligonucleotides that are designed to contain a 20 bp nucleotide sequence for PCR priming, a 20 bp nucleotide sequence for sequence priming and a unique 4 bp discriminating sequence comprised of a non-repeating nucleotide sequence (i.e., ACGT, CAGT, etc.). FIG. 2B depicts a representative universal adaptor sequence pair for use with the invention. Adaptor A sense strand: SEQ ID NO:1; Adaptor A antisense strand: SEQ ID NO:2; Adaptor B sense strand: SEQ ID NO:3; Adaptor B antisense strand: SEQ ID NO:4. FIG. 2C depicts a schematic representation of universal adaptor design for use with the invention.

FIG. 4 depicts the isolation of directionally-ligated single-stranded DNA according to the present invention using streptavidin-coated beads. Following ligation with universal adaptors A and B (the two different adaptors are sometimes referred to as a "first" and "second" universal adaptor), double-stranded DNA will contain adaptors in four possible combinations: AA, BB, AB and BA. When universal adaptor B contains a 5'-biotin, magnetic streptavidin-coated solid supports are used to capture and isolate the AB, BA and BB populations (population AA is washed away). The BB population is retained on the beads as each end of the double-stranded DNA is attached to a bead and is not released. However, upon washing in the presence of a low salt buffer, only populations AB and BA will release a single-stranded DNA fragment that is complementary to the bound strand. Single-stranded DNA fragments are isolated from the supernatant and used as template for subsequent amplification and sequencing. This method is described below in more detail.

FIGS. 10A-F depict an exemplary double ended sequencing process. SEQ ID NO:44: atgcacatggttgacacagtggt; SEQ ID NO:45: atgcacatggttgacacagtgg; SEQ ID NO:46: atgccaccgacctagtctcaaactt.

FIG. 12 depicts a drawing of a sequencing apparatus according to the present invention.

FIG. 13 depicts a drawing of a reagent delivery/perfusion chamber according to the present invention.

FIG. 14 depicts a micrograph of a cavitated fiber optic bundle, termed a PicoTiter Plate™, of the invention.

FIGS. 23A (upper left) and 23B (upper right) illustrate the specificity of a mixed population of probes hybridized to fragment A and fragment B immobilized on control beads, respectively. Fragment B beads exhibited the Alexa Fluor 647 signal (red), and the fragment A beads exhibited the Alexa Fluor 488 signal (green). FIG. 23C (bottom panel) depicts probe fluorescence from DNA capture beads after PTPCR. Beads displayed homogenous fragment A and fragment B signals, as well as mixes of templates, shown as varying degrees of yellow.

FIG. 25 depicts an insert flanked by PCR primers and sequencing primers.

FIG. 26 depicts truncated product produced by PCR primer mismatch at cross-hybridization region (CHR).

FIG. 34 depiction of double ended sequencing results showing that the sequence of both ends of a DNA template are determined. SEQ ID NO:44: atgcacatggttgacacagtggt; SEQ ID NO:45: atgcacatggttgacacagtgg; SEQ ID NO:46: atgccaccgacctagtctcaaactt.

FIG. 39 illustrates the results of sequencing a *Staphylococcus aureus* genome.

FIG. 40 illustrates the average read lengths in one experiment involving double ended sequencing.

FIG. 41 illustrates the number of wells for each genome span in a double ended sequencing experiment.

FIG. 42 illustrates a typical output and alignment string from a double ended sequencing procedure. Sequences shown in order, from top to bottom: SEQ ID NO:47-SEQ ID NO:60.

FIG. 43 Sample Preparation. (A) Clockwise from top left: (i) genomic DNA is isolated, fragmented, ligated to adapters and separated into single strands; (ii) fragments are bound to beads under conditions which favor one fragment per bead, the beads are captured in the droplets of a PCR-reaction-mixture-in-oil emulsion and PCR amplification occurs within each droplet, resulting in beads each carrying ten million copies of a unique DNA template; (iii) the emulsion is broken, the DNA strands are denatured, and beads carrying single-stranded DNA clones are deposited into wells of a fibre optic slide; (iv) smaller beads carrying immobilized enzymes required for pyrophosphate sequencing are deposited into each well. (B) Microscope photograph of emulsion showing both droplets containing a bead and empty droplets. The thin arrow points to a 28 μm bead, the thick arrow points to an approximately 100 μm droplet. (C) SEM photograph of portion of a fibre optic slide, showing fibre optic cladding and wells prior to bead deposition.

DETAILED DESCRIPTION OF THE INVENTION

Figure 1A:
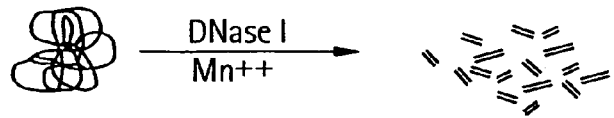
FIG. 1 depicts a schematic representation of the entire process of library preparation including the steps of template DNA fragmentation (FIG. 1A), end polishing (FIG. 1B), adaptor ligation (FIG. 1C), nick repair, strand extension and gel isolation (FIG. 1D).
FIG. 1E depicts a schematic representation of the stages for amplification and sequencing of template DNA (FIG. 1E).
FIG. 1F depicts a representative agarose gel containing a sample preparation of a 180-350 base pair adenovirus DNA library according to the methods of this invention.
FIG. 1G depicts a detailed schematic representation of library preparation, amplification, and sequencing.
Figure 1B:
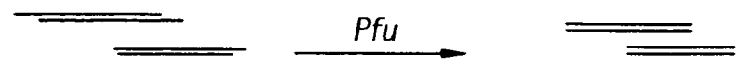
Figure 1C:
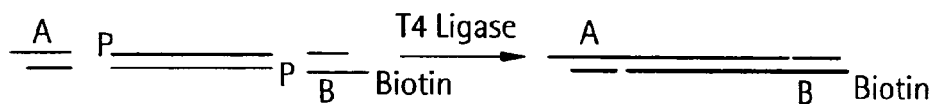
Figure 1D:
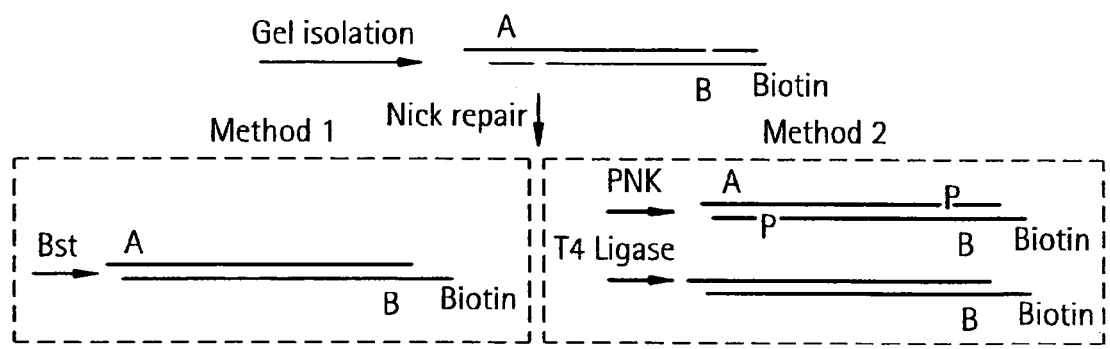
Figure 1E:
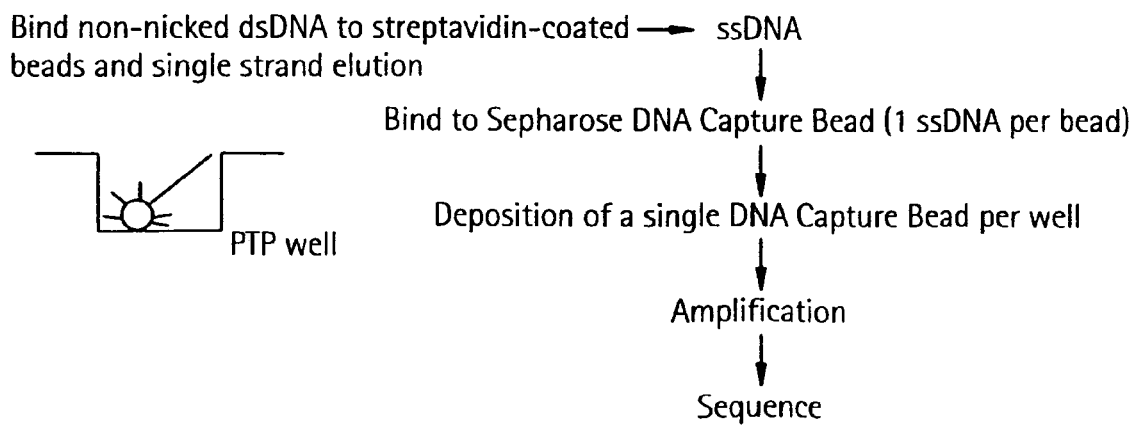
Figure 1F:
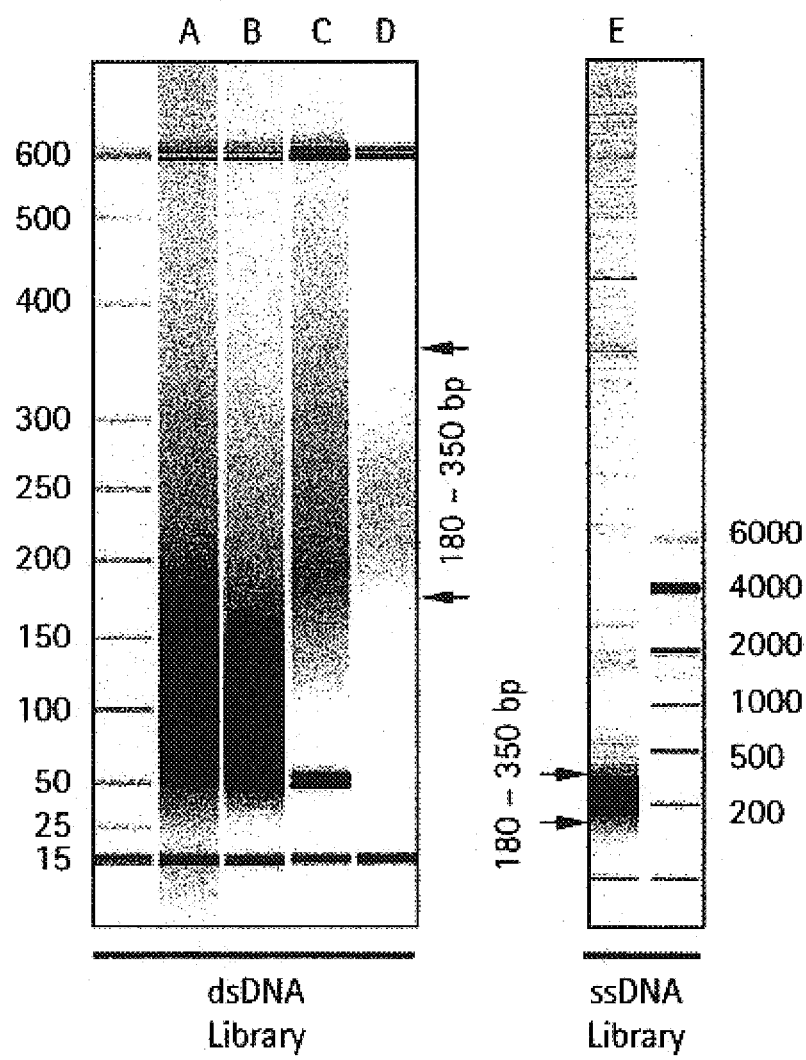
Figure 1G:
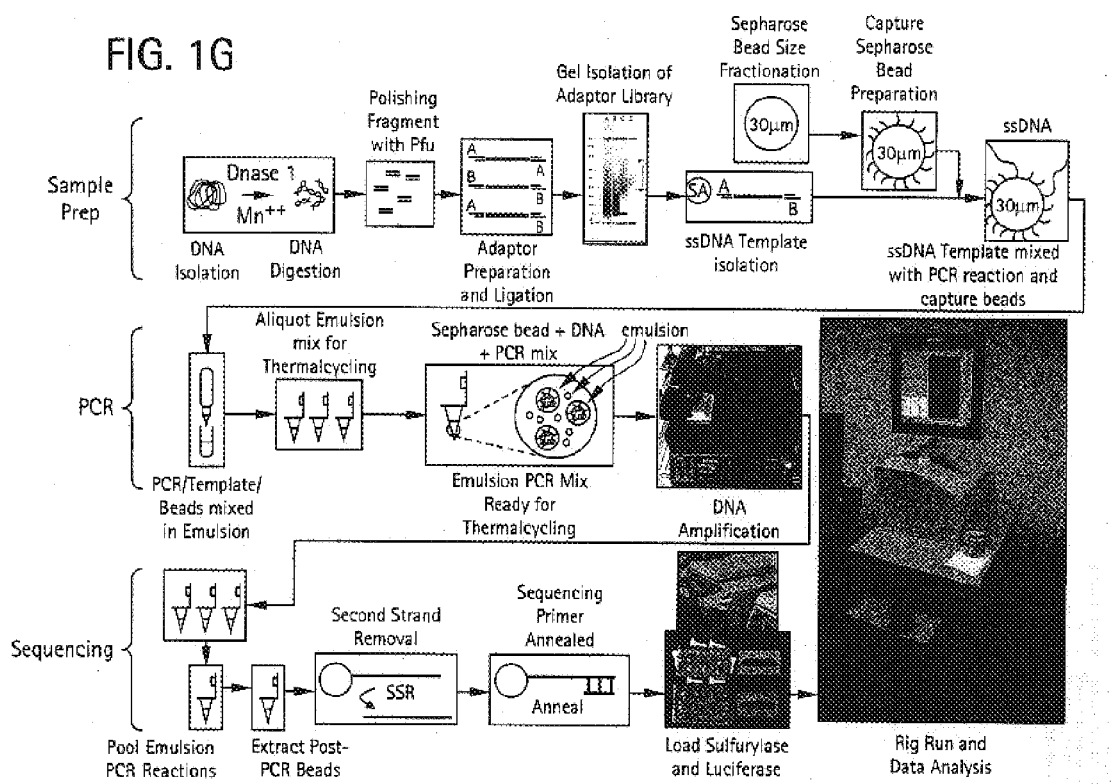

A novel platform is described herein which permits simultaneous amplification of three hundred thousand discrete PCR reactions (PTPCR) in volumes as low as 39.5 picoliters. The pooled PTPCR products from the entire reaction can be recovered through a wash step and assayed via real-time PCR for the presence and abundance of specific templates. Of greater interest, it is shown herein that these PTPCR products can be driven to solid supports and detected by hybridization with two color fluorescent probes, allowing high capacity, solid-phase, clonal DNA amplification and large-scale parallel sequencing.

The present invention is directed to a method and apparatus for performing genomic sequencing which satisfies the objectives of (1) preparing a nucleic acid (e.g., a genome) in a rapid and efficient manner for sequencing, (2) amplifying the nucleic acid in a representative manner, and (3) performing multiple sequencing reactions with only one primer hybridization. The present invention is particularly suited for genotyping, detection and diagnosis from a small sample of nucleic acid in a cost efficient manner. Each of these objectives are listed below.

Definitions:

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents and other references are incorporated in toto herein by reference. In addition, the materials, methods, and examples are illustrative only and not intended to be limiting.

As used herein, the term "universal adaptor" refers to two complementary and annealed oligonucleotides that are designed to contain a nucleotide sequence for PCR priming and a nucleotide sequence for sequence priming. Optionally, the universal adaptor may further include a unique discriminating key sequence comprised of a non-repeating nucleotide sequence (i.e., ACGT, CAGT, etc.). A set of universal adaptors comprises two unique and distinct double-stranded sequences that can be ligated to the ends of double-stranded DNA. Therefore, the same universal adaptor or different universal adaptors can be ligated to either end of the DNA molecule. When comprised in a larger DNA molecule that is single stranded or when present as an oligonucleotide, the universal adaptor may be referred to as a single stranded universal adaptor.

"Target DNA" shall mean a DNA whose sequence is to be determined by the methods and apparatus of the invention.

Binding pair shall mean a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, substrate analog-enzyme, inhibitor-enzyme, carbohydrate-lectin, biotin-avidin, and virus-cellular receptor.

As used herein, the term "discriminating key sequence" refers to a sequence consisting of at least one of each of the four deoxyribonucleotides (i.e., A, C, G, T). The same discriminating sequence can be used for an entire library of DNA fragments. Alternatively, different discriminating key sequences can be used to track libraries of DNA fragments derived from different organisms.

As used herein, the term "plurality of molecules" refers to DNA isolated from the same source, whereby different organisms may be prepared separately by the same method. In one embodiment, the plurality of DNA samples is derived from large segments of DNA, whole genome DNA, cDNA, viral DNA or from reverse transcripts of viral RNA. This DNA may be derived from any source, including mammal (i.e., human, nonhuman primate, rodent or canine), plant, bird, reptile, fish, fungus, bacteria or virus.

As used herein, the term "library" refers to a subset of smaller sized DNA species generated from a single DNA template, either segmented or whole genome.

As used herein, the term "unique", as in "unique PCR priming regions" refers to a sequence that does not exist or exists at an extremely low copy level within the DNA molecules to be amplified or sequenced.

As used herein, the term "compatible" refers to an end of double stranded DNA to which an adaptor molecule may be attached (i.e., blunt end or cohesive end).

As used herein, the term "fragmenting" refers to a process by which a larger molecule of DNA is converted into smaller pieces of DNA.

As used herein, "large template DNA" would be DNA of more than 25 kb, preferably more than 500 kb, more preferably more than 1 MB, and most preferably 5 MB or larger.

As used herein, the term "stringent hybridization conditions" refers to those conditions under which only complimentary sequences will hybridize to each other.

The invention described here is generally a system and methods for processing nucleic acids. The system and methods can be used to process nucleic acids in a multitude of ways that utilize sequencing of nucleic acids. Such sequencing can be performed to determine the identity of a sequence of nucleic acids, or for single nucleotide polymorphism detection in nucleic acid fragments, for nucleic acid expression profiling (comparing the nucleic acid expression profile between two or more states—e.g., comparing between diseased and normal tissue or comparing between untreated tissue and tissue treated with drug, enzymes, radiation or chemical treatment), for haplotyping (comparing genes or variations in genes on each of the two alleles present in a human subject), for karyotyping (diagnostically comparing one or more genes in a test tissue—typically from an embryo/fetus prior to conception to detect birth defects—with the same genes from "normal" karyotyped subjects), and for genotyping (comparing one or more genes in a first individual of a species with the same genes in other individuals of the same species).

The system has a number of components. These include (1) the nucleic acid template that is to be processed, (2) a picotiter plate for containing the nucleic acid template, (3) a flow chamber and fluid delivery means that permits flow of nucleic acid processing reagents over the nucleic acid template where the processing reagents generate light as the nucleic acid is processed, (4) a light capture means that detects light emitted as the nucleic acid is processed and that converts the captured light into data, and (5) data processing means that processes the data to yield meaningful information about the nucleic acid that has been processed. Each of these components of the system will be discussed in detail below.

1. Nucleic Acid Template and Preparation Thereof

Nucleic Acid Templates

The nucleic acid templates that can be sequenced according to the invention, e.g., a nucleic acid library, in general can include open circular or closed circular nucleic acid molecules. A "closed circle" is a covalently closed circular nucleic acid molecule, e.g., a circular DNA or RNA molecule.

An "open circle" is a linear single-stranded nucleic acid molecule having a 5' phosphate group and a 3' hydroxyl group.

In one embodiment, the single stranded nucleic acid contains at least 100 copies of a specific nucleic acid sequence, each copy covalently linked end to end. In some embodiments, the open circle is formed in situ from a linear double-stranded nucleic acid molecule. The ends of a given open circle nucleic acid molecule can be ligated by DNA ligase. Sequences at the 5' and 3' ends of the open circle molecule are complementary to two regions of adjacent nucleotides in a second nucleic acid molecule, e.g., an adapter region of an anchor primer (sometimes referred to as an adapter), or to two regions that are nearly adjoining in a second DNA molecule. Thus, the ends of the open-circle molecule can be ligated using DNA ligase, or extended by DNA polymerase in a gap-filling reaction. Open circles are described in detail in Lizardi, U.S. Pat. No. 5,854,033, fully incorporated herein by reference. An open circle can be converted to a closed circle in the presence of a DNA ligase (for DNA) or RNA ligase following, e.g., annealing of the open circle to an anchor primer.

If desired, nucleic acid templates can be provided as padlock probes. Padlock probes are linear oligonucleotides that include target-complementary sequences located at each end, and which are separated by a linker sequence. The linkers can be ligated to ends of members of a library of nucleic acid sequences that have been, e.g., physically sheared or digested with restriction endonucleases. Upon hybridization to a target-sequence, the 5'- and 3'-terminal regions of these linear oligonucleotides are brought in juxtaposition. This juxtaposition allows the two probe segments (if properly hybridized) to be covalently-bound by enzymatic ligation (e.g., with T4 DNA ligase), thus converting the probes to circularly-closed molecules which are catenated to the specific target sequences (see e.g., Nilsson, et al., 1994. Science 265: 2085-2088). The resulting probes are suitable for the simultaneous analysis of many gene sequences both due to their specificity and selectivity for gene sequence variants (see e.g., Lizardi, et al., 1998. Nat. Genet. 19: 225-232; Nilsson, et al., 1997. Nat. Genet. 16: 252-255) and due to the fact that the resulting reaction products remain localized to the specific target sequences. Moreover, intramolecular ligation of many different probes is expected to be less susceptible to non-specific cross-reactivity than multiplex PCR-based methodologies where non-cognate pairs of primers can give rise to irrelevant amplification products (see e.g., Landegren and Nilsson, 1997. Ann. Med. 29: 585-590).

A starting nucleic acid template library can be constructed comprising either single-stranded or double-stranded nucleic acid molecules, provided that the nucleic acid sequence includes a region that, if present in the library, is available for annealing, or can be made available for annealing, to an anchor primer sequence. For example, when used as a template for rolling circle amplification, a region of a double-stranded template needs to be at least transiently single-stranded in order to act as a template for extension of the anchor primer.

Library templates can include multiple elements, including, but not limited to, one or more regions that are complementary to the anchor primer. For example, the template libraries may include a region complementary to a sequencing primer, a control nucleotide region, and an insert sequence comprised of the sequencing template to be subsequently characterized. As is explained in more detail below, the control nucleotide region is used to calibrate the relationship between the amount of byproduct and the number of nucleotides incorporated. As utilized herein the term "complement" refers to nucleotide sequences that are able to hybridize to a specific nucleotide sequence to form a matched duplex.

In one embodiment, a library template includes: (i) two distinct regions that are complementary to the anchor primer, (ii) one region homologous to the sequencing primer, (iii) one optional control nucleotide region, (iv) an insert sequence of, e.g., 30-500, 50-200, or 60-100 nucleotides, that is to be sequenced. The template can, of course, include two, three, or all four of these features.

The template nucleic acid can be constructed from any source of nucleic acid, e.g., any cell, tissue, or organism, and can be generated by any art-recognized method. Suitable methods include, e.g., sonication of genomic DNA and digestion with one or more restriction endonucleases (RE) to generate fragments of a desired range of lengths from an initial population of nucleic acid molecules. Preferably, one or more of the restriction enzymes have distinct four-base recognition sequences. Examples of such enzymes include, e.g., Sau3A1, MspI, and TaqI. Preferably, the enzymes are used in conjunction with anchor primers having regions containing recognition sequences for the corresponding restriction enzymes. In some embodiments, one or both of the adapter regions of the anchor primers contain additional sequences adjoining known restriction enzyme recognition sequences, thereby allowing for capture or annealing to the anchor primer of specific restriction fragments of interest to the anchor primer. In other embodiments, the restriction enzyme is used with a type IIS restriction enzyme.

Alternatively, template libraries can be made by generating a complementary DNA (cDNA) library from RNA, e.g., messenger RNA (mRNA). The cDNA library can, if desired, be further processed with restriction endonucleases to obtain a 3' end characteristic of a specific RNA, internal fragments, or fragments including the 3' end of the isolated RNA. Adapter regions in the anchor primer may be complementary to a sequence of interest that is thought to occur in the template library, e.g., a known or suspected sequence polymorphism within a fragment generated by endonuclease digestion.

In one embodiment, an indexing oligonucleotide can be attached to members of a template library to allow for subsequent correlation of a template nucleic acid with a population of nucleic acids from which the template nucleic acid is derived. For example, one or more samples of a starting DNA population can be fragmented separately using any of the previously disclosed methods (e.g., restriction digestion, sonication). An indexing oligonucleotide sequence specific for each sample is attached to, e.g., ligated to, the termini of members of the fragmented population. The indexing oligonucleotide can act as a region for circularization, amplification and, optionally, sequencing, which permits it to be used to index, or code, a nucleic acid so as to identify the starting sample from which it is derived.

Distinct template libraries made with a plurality of distinguishable indexing primers can be mixed together for subsequent reactions. Determining the sequence of the member of the library allows for the identification of a sequence corresponding to the indexing oligonucleotide. Based on this information, the origin of any given fragment can be inferred.

The invention includes a sample preparation process that results in a solid or a mobile solid substrate array containing a plurality of anchor primers or adapters covalently linked to template nucleic acids.

When the template nucleic acid is circular, formation of the covalently linked anchor primer and one or more copies of the target nucleic acid preferably occurs by annealing the anchor primer to a complementary region of a circular nucleic acid, and then extending the annealed anchor primer with a polymerase to result in formation of a nucleic acid containing one or more copies of a sequence complementary to the circular nucleic acid.

Attachment of the anchor primer to a solid or mobile solid substrate can occur before, during, or subsequent to extension of the annealed anchor primer. Thus, in one embodiment, one or more anchor primers are linked to the solid or a mobile solid substrate, after which the anchor primer is annealed to a target nucleic acid and extended in the presence of a polymerase. Alternatively, in a second embodiment, an anchor primer is first annealed to a target nucleic acid, and a 3'OH terminus of the annealed anchor primer is extended with a polymerase. The extended anchor primer is then linked to the solid or mobile solid substrate. By varying the sequence of anchor primers, it is possible to specifically amplify distinct target nucleic acids present in a population of nucleic acids.

Outlined below is a preferred embodiment for the preparation of template nucleic acids for amplification and sequencing reactions. The invention includes a method for preparing the sample DNA comprised of seven general steps: (a) fragmenting large template DNA or whole genomic DNA samples to generate a plurality of digested DNA fragments; (b) creating compatible ends on the plurality of digested DNA samples; (c) ligating a set of universal adaptor sequences onto the ends of fragmented DNA molecules to make a plurality of adaptor-ligated DNA molecules, wherein each universal adaptor sequence has a known and unique base sequence comprising a common PCR primer sequence, a common sequencing primer sequence and a discriminating four base key sequence and wherein one adaptor is attached to biotin; (d) separating and isolating the plurality of ligated DNA fragments; (e) removing any portion of the plurality of ligated DNA fragments; (f) nick repair and strand extension of the plurality of ligated DNA fragments; (g) attaching each of the ligated DNA fragments to a solid support; and (h) isolating populations comprising single-stranded adaptor-ligated DNA fragments for which there is a unique adaptor at each end (i.e., providing directionality).

The following discussion summarizes the basic steps involved in the methods of the invention. The steps are recited in a specific order, however, as would be known by one of skill in the art, the order of the steps may be manipulated to achieve the same result. Such manipulations are contemplated by the inventors. Further, some steps may be minimized as would also be known by one of skill in the art.

Fragmentation

In the practice of the methods of the present invention, the fragmentation of the DNA sample can be done by any means known to those of ordinary skill in the art. Preferably, the fragmenting is performed by enzymatic or mechanical means. The mechanical means may be sonication or physical shearing. The enzymatic means may be performed by digestion with nucleases (e.g., Deoxyribonuclease I (DNase I)) or one or more restriction endonucleases. In a preferred embodiment, the fragmentation results in ends for which the sequence is not known.

In a preferred embodiment, the enzymatic means is DNase I. DNase I is a versatile enzyme that nonspecifically cleaves double-stranded DNA (dsDNA) to release 5'-phosphorylated di-, tri-, and oligonucleotide products. DNase I has optimal activity in buffers containing $Mn^{2+}$, $Mg^{2+}$ and $Ca^{2+}$, but no other salts. The purpose of the DNase I digestion step is to fragment a large DNA genome into smaller species comprising a library. The cleavage characteristics of DNase I will result in random digestion of template DNA (i.e., no sequence bias) and in the predominance of blunt-ended dsDNA fragments when used in the presence of manganese-based buffers (Melgar, E. and D. A. Goldthwait. 1968. Deoxyribonucleic acid nucleases. II. The effects of metal on the mechanism of action of deoxyribonuclease I. *J. Biol. Chem.* 243: 4409). The range of digestion products generated following DNase I treatment of genomic templates is dependent on three factors: i) amount of enzyme used (units); ii) temperature of digestion (° C.); and iii) incubation time (minutes). The DNase I digestion conditions outlined below have been optimized to yield genomic libraries with a size range from 50-700 base pairs (bp).

In a preferred embodiment, the DNase I digests large template DNA or whole genome DNA for 1-2 minutes to generate a population of polynucleotides. In another preferred embodiment, the DNase I digestion is performed at a temperature between 10° C.-37° C. In yet another preferred embodiment, the digested DNA fragments are between 50 bp to 700 bp in length.

Polishing

Digestion of genomic DNA (gDNA) templates with DNase I in the presence of $Mn^{2+}$ will yield fragments of DNA that are either blunt-ended or have protruding termini with one or two nucleotides in length. In a preferred embodiment, an increased number of blunt ends are created with Pfu DNA polymerase. In other embodiments, blunt ends can be created with less efficient DNA polymerases such as T4 DNA polymerase or Klenow DNA polymerase. Pfu "polishing" or blunt ending is used to increase the amount of blunt-ended species generated following genomic template digestion with DNase I. Use of Pfu DNA polymerase for fragment polishing will result in the fill-in of 5' overhangs. Additionally, Pfu DNA polymerase does not exhibit DNA extendase activity but does have 3'→5' exonuclease activity that will result in the removal of single and double nucleotide extensions to further increase the amount of blunt-ended DNA fragments available for adaptor ligation (Costa, G. L. and M. P. Weiner. 1994a. Protocols for cloning and analysis of blunt-ended PCR-generated DNA fragments. *PCR Methods Appl* 3(5):S95; Costa, G. L., A. Grafsky and M. P. Weiner. 1994b. Cloning and analysis of PCR-generated DNA fragments. *PCR Methods Appl* 3(6): 338; Costa, G. L. and M. P. Weiner. 1994c. Polishing with T4 or Pfu polymerase increases the efficiency of cloning of PCR products. *Nucleic Acids Res.* 22(12):2423).

Adaptor Ligation

If the libraries of nucleic acids are to be attached to the solid substrate, then preferably the nucleic acid templates are annealed to anchor primer sequences using recognized techniques (see, e.g., Hatch, et al., 1999. *Genet. Anal. Biomol. Engineer.* 15: 35-40; Kool, U.S. Pat. No. 5,714,320 and Lizardi, U.S. Pat. No. 5,854,033). In general, any procedure for annealing the anchor primers to the template nucleic acid sequences is suitable as long as it results in formation of specific, i.e., perfect or nearly perfect, complementarity between the adapter region or regions in the anchor primer sequence and a sequence present in the template library.

In a preferred embodiment, following fragmentation and blunt ending of the DNA library, universal adaptor sequences are added to each DNA fragment. The universal adaptors are designed to include a set of unique PCR priming regions that are typically 20 bp in length located adjacent to a set of unique sequencing priming regions that are typically 20 bp in length optionally followed by a unique discriminating key sequence consisting of at least one of each of the four deoxyribonucleotides (i.e., A, C, G, T). In a preferred embodiment, the discriminating key sequence is 4 bases in length. In another embodiment, the discriminating key sequence may be combinations of 1-4 bases. In yet another embodiment, each unique universal adaptor is forty-four bp (44 bp) in length. In a preferred embodiment the universal adaptors are ligated, using T4 DNA ligase, onto each end of the DNA fragment to generate a total nucleotide addition of 88 bp to each DNA fragment. Different universal adaptors are designed specifically for each DNA library preparation and will therefore provide a unique identifier for each organism. The size and sequence of the universal adaptors may be modified as would be apparent to one of skill in the art.

For example, to prepare two distinct universal adaptors (i.e., "first" and "second"), single-stranded oligonucleotides may be ordered from a commercial vendor (i.e., Integrated DNA Technologies, IA or Operon Technologies, CA). In one embodiment, the universal adaptor oligonucleotide sequences are modified during synthesis with two or three phosphorothioate linkages in place of phosphodiester linkages at both the 5' and 3' ends. Unmodified oligonucleotides are subject to rapid degradation by nucleases and are therefore of limited utility. Nucleases are enzymes that catalyze the hydrolytic cleavage of a polynucleotide chain by cleaving the phosphodiester linkage between nucleotide bases. Thus, one simple and widely used nuclease-resistant chemistry available for use in oligonucleotide applications is the phosphorothioate modification. In phosphorothioates, a sulfur atom replaces a non-bridging oxygen in the oligonucleotide backbone making it resistant to all forms of nuclease digestion (i.e. resistant to both endonuclease and exonuclease digestion). Each oligonucleotide is HPLC-purified to ensure there are no contaminating or spurious oligonucleotide sequences in the synthetic oligonucleotide preparation. The universal adaptors are designed to allow directional ligation to the blunt-ended, fragmented DNA. Each set of double-stranded universal adaptors are designed with a PCR priming region that contains noncomplementary 5' four-base overhangs that cannot ligate to the blunt-ended DNA fragment as well as prevent ligation with each other at these ends. Accordingly, binding can only occur between the 3' end of the adaptor and the 5' end of the DNA fragment or between the 3' end of the DNA fragment and the 5' end of the adaptor. Double-stranded universal adaptor sequences are generated by using single-stranded oligonucleotides that are designed with sequences that allow primarily complimentary oligonucleotides to anneal, and to prevent cross-hybridization between two non-complimentary oligonucleotides. In one embodiment, 95% of the universal adaptors are formed from the annealing of complimentary oligonucleotides. In a preferred embodiment, 97% of the universal adaptors are formed from the annealing of complimentary oligonucleotides. In a more preferred embodiment, 99% of the universal adaptors are formed from the annealing of complimentary oligonucleotides. In a most preferred embodiment, 100% of the universal adaptors are formed from the annealing of complimentary oligonucleotides.

One of the two adaptors can be linked to a support binding moiety. In a preferred embodiment, a 5' biotin is added to the first universal adaptor to allow subsequent isolation of ssDNA template and noncovalent coupling of the universal adaptor to the surface of a solid support that is saturated with a biotin-binding protein (i.e. streptavidin, neutravidin or avidin). Other linkages are well known in the art and may be used in place of biotin-streptavidin (for example antibody/antigen-epitope, receptor/ligand and oligonucleotide pairing or complimentarity) one embodiment, the solid support is a bead, preferably a polystyrene bead. In one preferred embodiment, the bead has a diameter of about 2.8 μm. As used herein, this bead is referred to as a "sample prep bead".

Each universal adaptor may be prepared by combining and annealing two ssDNA oligonucleotides, one containing the sense sequence and the second containing the antisense (complementary) sequence. Schematic representation of the universal adaptor design is outlined in FIG. 2.

Isolation of Ligation Products

The universal adaptor ligation results in the formation of fragmented DNAs with adaptors on each end, unbound single adaptors, and adaptor dimers. In a preferred embodiment, agarose gel electrophoresis is used as a method to separate and isolate the adapted DNA library population from the unligated single adaptors and adaptor dimer populations. In other embodiments, the fragments may be separated by size exclusion chromatography or sucrose sedimentation. The procedure of DNase I digestion of DNA typically yields a library population that ranges from 50-700 bp. In a preferred embodiment, upon conducting agarose gel electrophoresis in the presence of a DNA marker, the addition of the 88 bp universal adaptor set will shift the DNA library population to a larger size and will result in a migration profile in the size range of approximately 130-800 bp; adaptor dimers will migrate at 88 bp; and adaptors not ligated will migrate at 44 bp. Therefore, numerous double-stranded DNA libraries in sizes ranging from 200-800 bp can be physically isolated from the agarose gel and purified using standard gel extraction techniques. In one embodiment, gel isolation of the adapted ligated DNA library will result in the recovery of a library population ranging in size from 200-400 bp. Other methods of distinguishing adaptor-ligated fragments are known to one of skill in the art.

Nick Repair

Figure 3A:
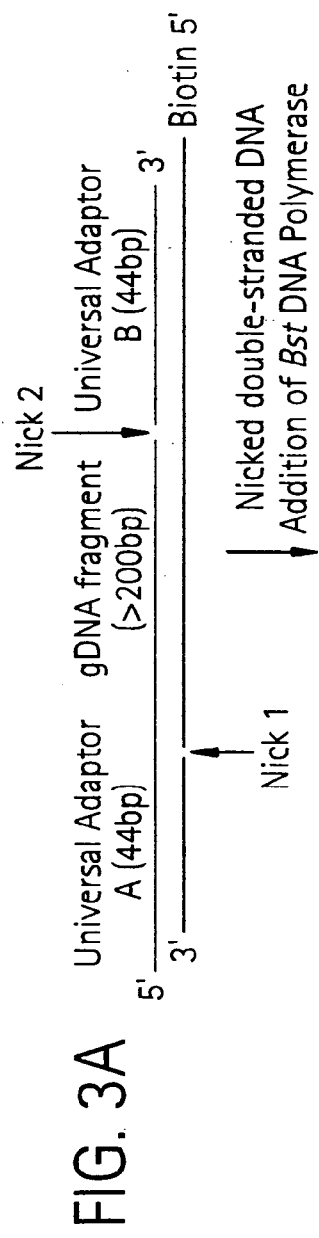
FIG. 3 depicts the strand displacement and extension of nicked double-stranded DNA fragments according to the present invention. Following the ligation of universal adaptors generated from synthetic oligonucleotides, double-stranded DNA fragments will be generated that contain two nicked regions following T4 DNA ligase treatment (FIG. 3A). The addition of a strand displacing enzyme (i.e., Bst DNA polymerase I) will bind nicks (FIG. 3B), strand displace the nicked strand and complete nucleotide extension of the strand (FIG. 3C) to produce non-nicked double-stranded DNA fragments (FIG. 3D).
Figure 3B:
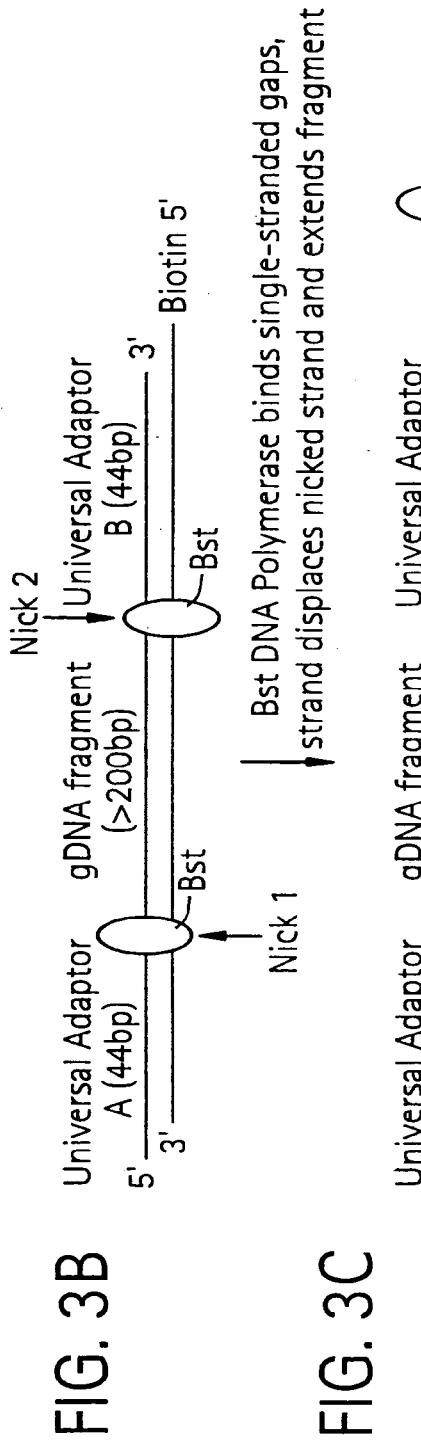
Figure 3C:
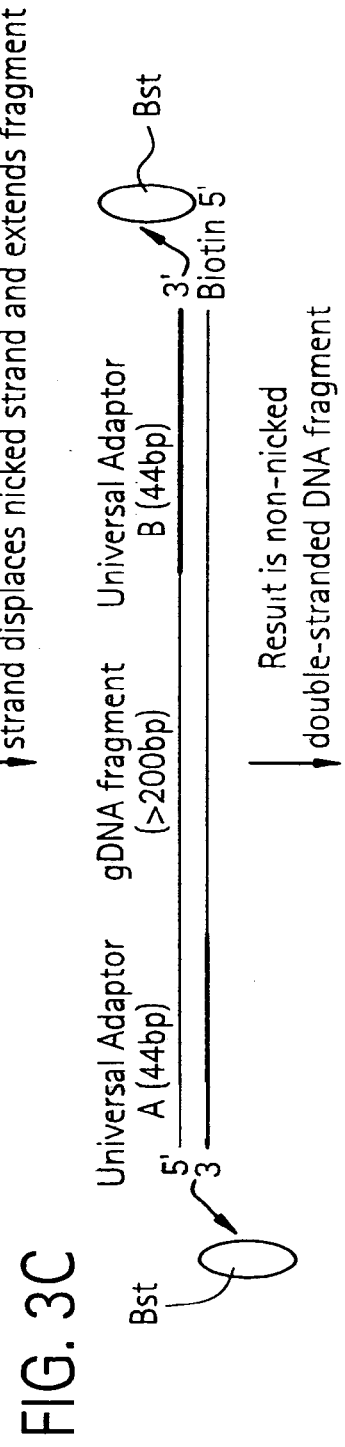

Because the DNA oligonucleotides used for the universal adaptors are not 5' phosphorylated, gaps will be present at the 3' junctions of the fragmented DNAs following ligase treatment (see FIG. 3A). These two "gaps" or "nicks" can be filled in by using a DNA polymerase enzyme that can bind to, strand displace and extend the nicked DNA fragments. DNA polymerases that lack 3'→5' exonuclease activity but exhibit 5'→3' exonuclease activity have the ability to recognize nicks, displace the nicked strands, and extend the strand in a manner that results in the repair of the nicks and in the formation of non-nicked double-stranded DNA (see FIG. 3B and 3C) (Hamilton, S. C., J. W. Farchaus and M. C. Davis. 2001. DNA polymerases as engines for biotechnology. *BioTechniques* 31:370).

Figure 3D:
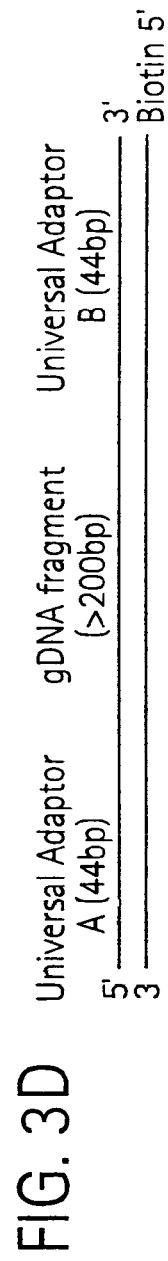
Figure 5:
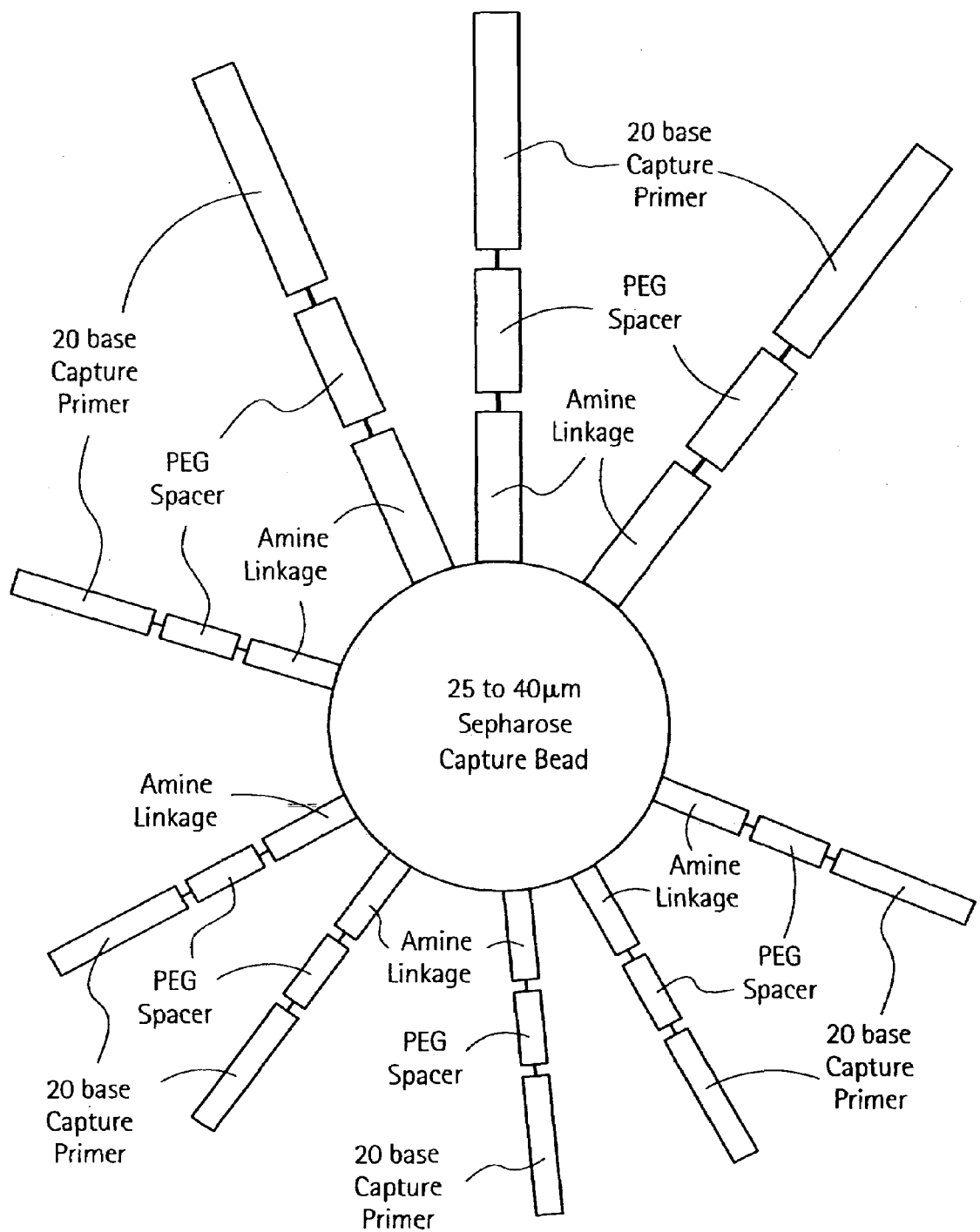
FIG. 5 depicts a schematic of the structure of a DNA capture bead.

Several modifying enzymes are utilized for the nick repair step, including but not limited to polymerase, ligase and kinase. DNA polymerases that can be used for this application include, for example, *E. coli* DNA pol I, *Thermoanaerobacter thermohydrosulfuricus* pol I, and bacteriophage phi 29. In a preferred embodiment, the strand displacing enzyme *Bacillus stearothermophilus* pol I (Bst DNA polymerase I) is used to repair the nicked dsDNA and results in non-nicked dsDNA (see FIG. 3D). In another preferred embodiment, the ligase is T4 and the kinase is polynucleotide kinase.

Isolation of Single-Stranded DNA

Following the generation of non-nicked dsDNA, ssDNAs comprising both the first and second adaptor molecules are to be isolated (desired populations are designated below with asterisks; "A" and "B" correspond to the first and second adaptors). Double-stranded DNA libraries will have adaptors bound in the following configurations:

Universal Adaptor A-DNA fragment-Universal Adaptor A
Universal Adaptor B-DNA fragment-Universal Adaptor A*
Universal Adaptor A-DNA fragment-Universal Adaptor B*
Universal Adaptor B-DNA fragment-Universal Adaptor B Universal adaptors are designed such that only one universal adaptor has a 5' biotin moiety. For example, if universal adaptor B has a 5' biotin moiety, streptavidin-coated sample prep beads can be used to bind all double-stranded DNA library species with universal adaptor B. Genomic library populations that contain two universal adaptor A species will not contain a 5' biotin moiety and will not bind to streptavidin-containing sample prep beads and thus can be washed away. The only species that will remain attached to beads are those with universal adaptors A and B and those with two universal adaptor B sequences. DNA species with two universal adaptor B sequences (i.e., biotin moieties at each 5' end) will be bound to streptavidin-coated sample prep beads at each end, as each strand comprised in the double strand will be bound. Double-stranded DNA species with a universal adaptor A and a universal adaptor B will contain a single 5' biotin moiety and thus will be bound to streptavidin-coated beads at only one end. The sample prep beads are magnetic, therefore, the sample prep beads will remain coupled to a solid support when magnetized. Accordingly, in the presence of a low-salt ("melt" or denaturing) solution, only those DNA fragments that contain a single universal adaptor A and a single universal adaptor B sequence will release the complementary unbound strand. This single-stranded DNA population may be collected and quantitated by, for example, pyrophosphate sequencing, real-time quantitative PCR, agarose gel electrophoresis or capillary gel electrophoresis.

Attachment of Template to Beads

In one embodiment, ssDNA libraries that are created according to the methods of the invention are quantitated to calculate the number of molecules per unit volume. These molecules are annealed to a solid support (bead) that contain oligonucleotide capture primers that are complementary to the PCR priming regions of the universal adaptor ends of the ssDNA species. Beads are then transferred to an amplification protocol. Clonal populations of single species captured on DNA beads may then sequenced. In one embodiment, the solid support is a bead, preferably a sepharose bead. As used herein, this bead is referred to as a "DNA capture bead".

The beads used herein may be of any convenient size and fabricated from any number of known materials. Example of such materials include: inorganics, natural polymers, and synthetic polymers. Specific examples of these materials include: cellulose, cellulose derivatives, acrylic resins, glass; silica gels, polystyrene, gelatin, polyvinyl pyrrolidone, co-polymers of vinyl and acrylamide, polystyrene cross-linked with divinylbenzene or the like (see, Merrifield Biochemistry 1964, 3, 1385-1390), polyacrylamides, latex gels, polystyrene, dextran, rubber, silicon, plastics, nitrocellulose, celluloses, natural sponges, silica gels, glass, metals plastic, cellulose, cross-linked dextrans (e.g., Sephadex™) and agarose gel (Sepharose™) and solid phase supports known to those of skill in the art.

In one embodiment, the diameter of the DNA capture bead is in the range of 20-70 µm. In a preferred embodiment, the diameter of the DNA capture bead is in a range of 20-50 µm. In a more preferred embodiment, the diameter of the DNA capture bead is about 30 µm.

In one aspect, the invention includes a method for generating a library of solid supports comprising: (a) preparing a population of ssDNA templates according to the methods disclosed herein; (b) attaching each DNA template to a solid support such that there is one molecule of DNA per solid support; (c) amplifying the population of single-stranded templates such that the amplification, generates a clonal population of each DNA fragment on each solid support; (d) sequencing clonal populations of beads.

In one embodiment, the solid support is a DNA capture bead. In another embodiment, the DNA is genomic DNA, cDNA or reverse transcripts of viral RNA. The DNA may be attached to the solid support, for example, via a biotin-streptavidin linkage, a covalent linkage or by complementary oligonucleotide hybridization. In one embodiment, each DNA template is ligated to a set of universal adaptors. In another embodiment, the universal adaptor pair comprises a common PCR primer sequence, a common sequencing primer sequence and a discriminating key sequence. Single-stranded DNAs are isolated that afford unique ends; single stranded molecules are then attached to a solid support and exposed to amplification techniques for clonal expansion of populations. The DNA may be amplified by PCR.

In another aspect, the invention provides a library of solid supports made by the methods described herein.

The nucleic acid template (e.g., DNA template) prepared by this method may be used for many molecular biological procedures, such as linear extension, rolling circle amplification, PCR and sequencing. This method can be accomplished in a linkage reaction, for example, by using a high molar ratio of bead to DNA. Capture of single-stranded DNA molecules will follow a poisson distribution and will result in a subset of beads with no DNA attached and a subset of beads with two molecules of DNA attached. In a preferred embodiment, there would be one bead to one molecule of DNA. In addition, it is possible to include additional components in the adaptors that may be useful for additional manipulations of the isolated library.

2. Nucleic Acid Template Amplification

In order for the nucleic acid template to be sequenced according to the methods of this invention the copy number must be amplified to generate a sufficient number of copies of the template to produce a detectable signal by the light detection means. Any suitable nucleic acid amplification means may be used.

A number of in vitro nucleic acid amplification techniques have been described. These amplification methodologies may be differentiated into those methods: (i) which require temperature cycling—polymerase chain reaction (PCR) (see e.g., Saiki, et al., 1995. *Science* 230: 1350-1354), ligase chain reaction (see e.g., Barany, 1991. *Proc. Natl. Acad. Sci. USA* 88: 189-193; Barringer, et al., 1990. *Gene* 89: 117-122) and transcription-based amplification (see e.g., Kwoh, et al., 1989. *Proc. Natl. Acad. Sci. USA* 86: 1173-1177) and (ii) isothermal amplification systems—self-sustaining, sequence replication (see e.g., Guatelli, et al., 1990. *Proc. Natl. Acad. Sci. USA* 87: 1874-1878); the Qβ replicase system (see e.g., Lizardi, et al., 1988. *BioTechnology* 6: 1197-1202); strand displacement amplification Nucleic Acids Res. 1992 Apr. 11;20(7):1691-6.; and the methods described in PNAS 1992 Jan. 1;89(1):392-6; and NASBA J Virol Methods. 1991 December;35(3):273-86.

In one embodiment, isothermal amplification is used. Isothermal amplification also includes rolling circle-based amplification (RCA). RCA is discussed in, e.g., Kool, U.S. Pat. No. 5,714,320 and Lizardi, U.S. Pat. No. 5,854,033; Hatch, et al., 1999. *Genet. Anal. Biomol. Engineer.* 15: 35-40. The result of the RCA is a single DNA strand extended from the 3' terminus of the anchor primer (and thus is linked to the solid support matrix) and including a concatamer containing multiple copies of the circular template annealed to a primer sequence. Typically, 1,000 to 10,000 or more copies of circular templates, each having a size of, e.g., approximately 30-500, 50-200, or 60-100 nucleotides size range, can be obtained with RCA.

Figures 11A, 11B:
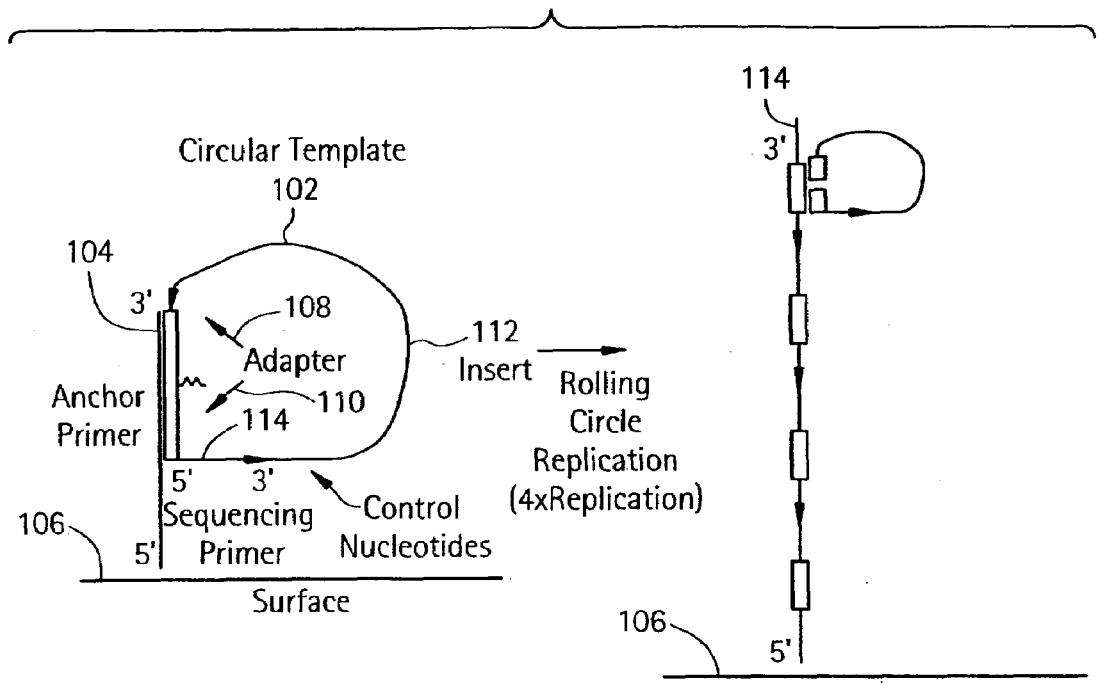
FIGS. 11A-D depict schematic illustrations of rolling circle-based amplification using an anchor primer. In panel B, the sequences are as follows: gacctcacac gatggctgca gctt (SEQ ID NO:71) and tcgtgtgagg tctcagcatc ttatgtatat ttacttctat tctcaggtgc ccaagctgca gcca (SEQ ID NO:72). In panel C, the sequences are as follows: gacctcacac gatggctgca gctt (SEQ ID NO:71), acttctattc tcagttgcct aagctgcagc cattgtga ggtctcagca tcttatgtat attt (SEQ ID NO:73), and gtcctagaat agaagtaaat atacatgctc ga (SEQ ID NO:74). In panel D, the sequences are as follows: gacctcacac gagtagcatg gctgcagctt (SEQ ID NO: 75), tcgtgtgagg tctcagcatc ttatgtatat ttacttctat tctcagttgc ctaagctgca gcca (SEQ ID NO:76), and tgctac (SEQ ID NO:77).

The product of RCA amplification following annealing of a circular nucleic acid molecule to an anchor primer is shown schematically in FIG. 11A. A circular template nucleic acid 102 is annealed to an anchor primer 104, which has been linked to a surface 106 at its 5' end and has a free 3' OH available for extension. The circular template nucleic acid 102 includes two adapter regions 108 and 110 which are complementary to regions of sequence in the anchor primer 104. Also included in the circular template nucleic acid 102 is an insert 112 and a region 114 homologous to a sequencing primer, which is used in the sequencing reactions described below.

Upon annealing, the free 3'-OH on the anchor primer 104 can be extended using sequences within the template nucleic acid 102. The anchor primer 102 can be extended along the template multiple times, with each iteration adding to the sequence extended from the anchor primer a sequence complementary to the circular template nucleic acid. Four iterations, or four rounds of rolling circle replication, are shown in FIG. 11A as the extended anchor primer amplification product 114. Extension of the anchor primer results in an amplification product covalently or otherwise physically attached to the substrate 106. A number of in vitro nucleic acid amplification techniques may be utilized to extend the anchor primer sequence. The amplification is typically performed in the presence of a polymerase, e.g., a DNA or RNA-directed DNA polymerase, and one, two, three, or four types of nucleotide triphosphates, and, optionally, auxiliary binding proteins. In general, any polymerase capable of extending a primed 3'-OH group can be used a long as it lacks a 3' to 5' exonuclease activity. Suitable polymerases include, e.g., the DNA polymerases from *Bacillus stearothermophilus, Thermus acquaticus, Pyrococcus furiosis, Thermococcus litoralis*, and *Thermus thermophilus*, bacteriophage T4 and T7, and the *E. coli* DNA polymerase I Klenow fragment. Suitable RNA-directed DNA polymerases include, e.g., the reverse transcriptase from the Avian Myeloblastosis Virus, the reverse transcriptase from the Moloney Murine Leukemia Virus, and the reverse transcriptase from the Human Immunodeficiency Virus-I.

Figure 11C:
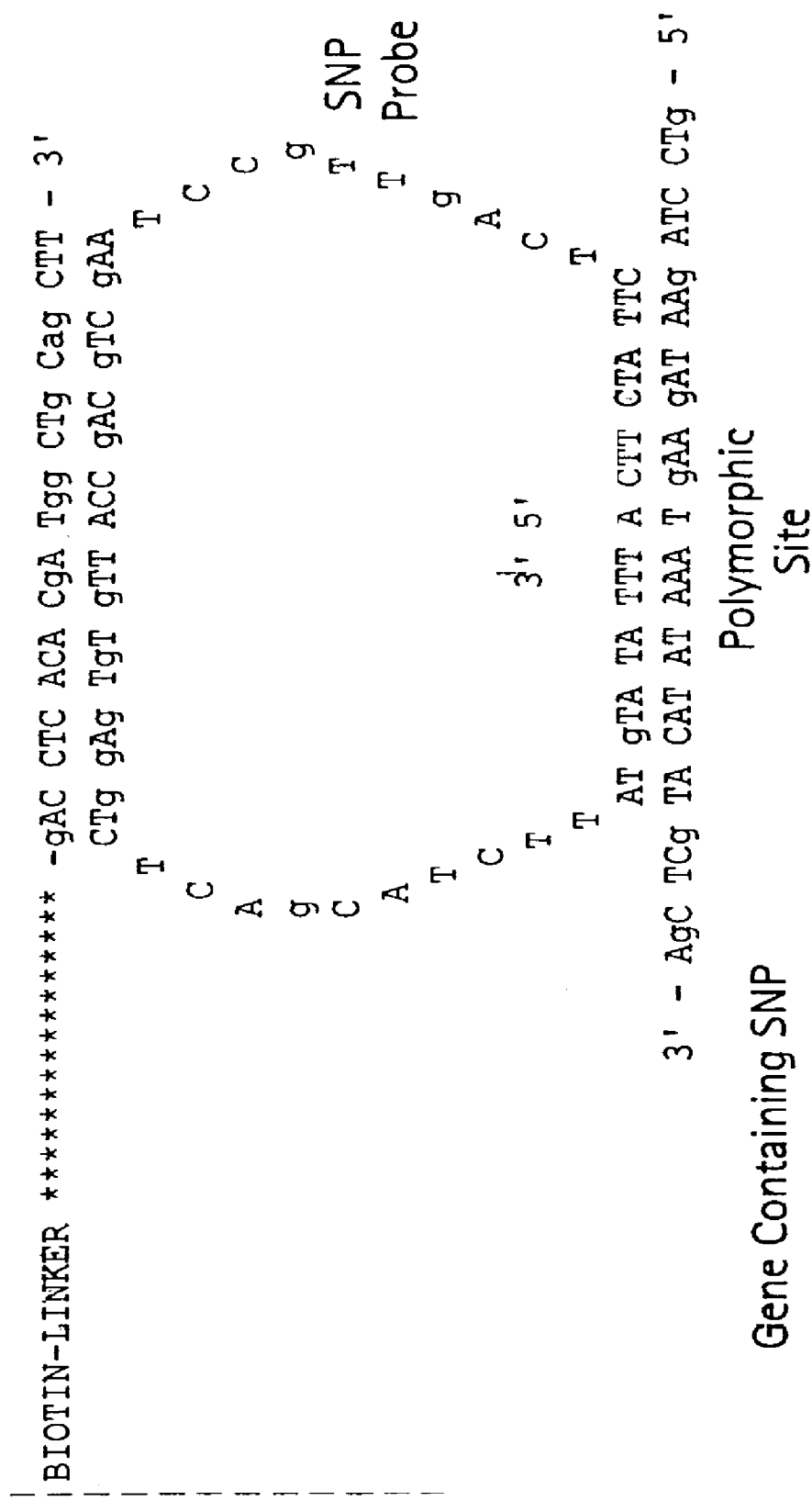
Figure 11D:
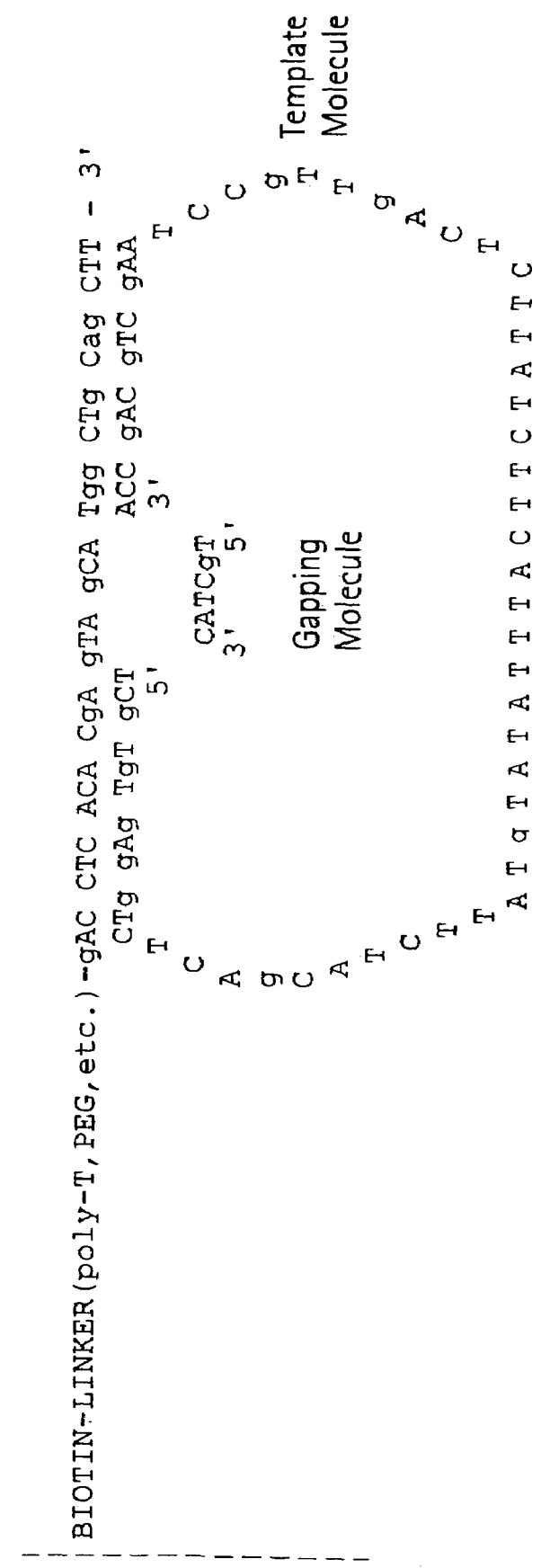

Additional embodiments of circular templates and anchor primers are shown in more detail in FIG. 11B-11D. FIG. 11B illustrates an annealed open circle linear substrate that can serve, upon ligation, as a template for extension of an anchor primer. A template molecule having the sequence 5'-tcg tgt gag gtc tca gca tct tat gta tat tta ctt cta ttc tca gtt gcc taa gct gca gcc a-3' (SEQ ID NO:5) is annealed to an anchor primer having a biotin linker at its 5' terminus and the sequence 5'-gac ctc aca cga tgg ctg cag ctt-3' (SEQ ID NO:6). Annealing of the template results in juxtaposition of the 5' and 3' ends of the template molecule. The 3'OH of the anchor primer can be extended using the circular template.

The use of a circular template and an anchor primer for identification of single nucleotide polymorphisms is shown in FIG. 11C. Shown is a generic anchor primer having the sequence 5'-gac ctc aca cga tgg ctg cag ctt-3'(SEQ ID NO:7). The anchor primer anneals to an SNP probe having the sequence 5'-ttt ata tgt att cta cga ctc tgg agt gtg cta ccg acg tcg aat ccg ttg act ctt atc ttc a-3' (SEQ ID NO:8). The SNP probe in turn hybridizes to a region of a SNP-containing region of a gene having the sequence 5'-cta gct cgt aca tat aaa tga aga taa gat cct g-3' (SEQ ID NO:9). Hybridization of a nucleic acid sequence containing the polymorphism to the SNP probe complex allows for subsequent ligation and circularization of the SNP probe. The SNP probe is designed so that its 5' and 3' termini anneal to the genomic region so as to abut in the region of the polymorphic site, as is indicated in FIG. 11C. The circularized SNP probe can be subsequently extended and sequenced using the methods described herein. A nucleic acid lacking the polymorphism does not hybridize so as to result in juxtaposition of the 5' and 3' termini of the SNP probe. In this case, the SNP probe cannot be ligated to form a circular substrate needed for subsequent extension.

FIG. 11D illustrates the use of a gap oligonucleotide to along with a circular template molecule. An anchor primer having the sequence 5'-gac ctc aca cga gta gca tgg ctg cag ctt-3' (SEQ ID NO:10) is attached to a surface through a biotin linker. A template molecule having the sequence 5'-tcg tgt gag gtc tca gca tct tat gta tat tta ctt cta ttc tca gtt gcc taa gct gca gcc a-3' (SEQ ID NO:11) is annealed to the anchor primer to result in partially single stranded, or gapped region, in the anchor primer flanked by a double-stranded region. A gapping molecule having the sequence 5'-tgc tac-3' then anneals to the anchor primer. Ligation of both ends of the gap oligonucleotide to the template molecule results in formation of a circular nucleic acid molecule that can act as a template for rolling circle amplification.

RCA can occur when the replication of the duplex molecule begins at the origin. Subsequently, a nick opens one of the strands, and the free 3'-terminal hydroxyl moiety generated by the nick is extended by the action of DNA polymerase. The newly synthesized strand eventually displaces the original parental DNA strand. This aforementioned type of replication is known as rolling-circle replication (RCR) because the point of replication may be envisaged as "rolling around" the circular template strand and, theoretically, it could continue to do so indefinitely. Additionally, because the newly synthesized DNA strand is covalently-bound to the original template, the displaced strand possesses the original genomic sequence (e.g., gene or other sequence of interest) at its 5'-terminus. In RCR, the original genomic sequence is followed by any number of "replication units" complementary to the original template sequence, wherein each replication unit is synthesized by continuing revolutions of said original template sequence. Hence, each subsequent revolution displaces the DNA which is synthesized in the previous replication cycle.

Through the use of the RCA reaction, a strand may be generated which represents many tandem copies of the complement to the circularized molecule. For example, RCA has recently been utilized to obtain an isothermal cascade amplification reaction of circularized padlock probes in vitro in order to detect single-copy genes in human genomic DNA samples (see Lizardi, et al., 1998. Nat. Genet. 19: 225-232). In addition, RCA has also been utilized to detect single DNA molecules in a solid phase-based assay, although difficulties arose when this technique was applied to in situ hybridization (see Lizardi, et al., 1998. Nat. Genet. 19: 225-232).

If desired, RCA can be performed at elevated temperatures, e.g., at temperatures greater than 37° C., 42° C., 45° C., 50° C., 60° C., or 70° C. In addition, RCA can be performed initially at a lower temperature, e.g., room temperature, and then shifted to an elevated temperature. Elevated temperature RCA is preferably performed with thermostable nucleic acid polymerases and with primers that can anneal stably and with specificity at elevated temperatures.

RCA can also be performed with non-naturally occurring oligonucleotides, e.g., peptide nucleic acids. Further, RCA can be performed in the presence of auxiliary proteins such as single-stranded binding proteins.

The development of a method of amplifying short DNA molecules which have been immobilized to a solid support, termed RCA has been recently described in the literature (see e.g., Hatch, et al., 1999. Genet. Anal. Biomol. Engineer. 15: 35-40; Zhang, et al., 1998. Gene 211: 277-85; Baner, et al., 1998. Nucl. Acids Res. 26: 5073-5078; Liu, et al., 1995. J. Am. Chem. Soc. 118: 1587-1594; Fire and Xu, 1995. Proc. Natl. Acad. Sci. USA 92: 4641-4645; Nilsson, et al., 1994. Science 265: 2085-2088). RCA targets specific DNA sequences through hybridization and a DNA ligase reaction. The circular product is then subsequently used as a template in a rolling circle replication reaction.

Other examples of isothermal amplification systems include, e.g., (i) self-sustaining, sequence replication (see e.g., Guatelli, et al., 1990. Proc. Natl. Acad. Sci. USA 87: 1874-1878), (ii) the Qβ replicase system (see e.g., Lizardi, et al., 1988. BioTechnology 6: 1197-1202), and (iii) nucleic acid sequence-based amplification (NASBA™; see Kievits, et al., 1991. J. Virol. Methods 35: 273-286).

PCR Amplification of Nucleic Acid Templates

In a preferred embodiment, polymerase chain reaction ("PCR") is used to generate additional copies of the template nucleic acids. The PCR amplification step may be performed prior to distribution of the nucleic acid templates onto the picotiter plate or may be performed after the nucleic acid templates have been distributed onto the picotiter plate.

Bead Emulsion PCR Amplification

In a preferred embodiment, a PCR amplification step is performed prior to distribution of the nucleic acid templates onto the picotiter plate.

In a particularly preferred embodiment, a novel amplification system, herein termed "bead emulsion amplification" is performed by attaching a template nucleic acid (e.g., DNA) to be amplified to a solid support, preferably in the form of a generally spherical bead. A library of single stranded template DNA prepared according to the sample preparation methods of this invention is an example of one suitable source of the starting nucleic acid template library to be attached to a bead for use in this amplification method.

Figure 6A:
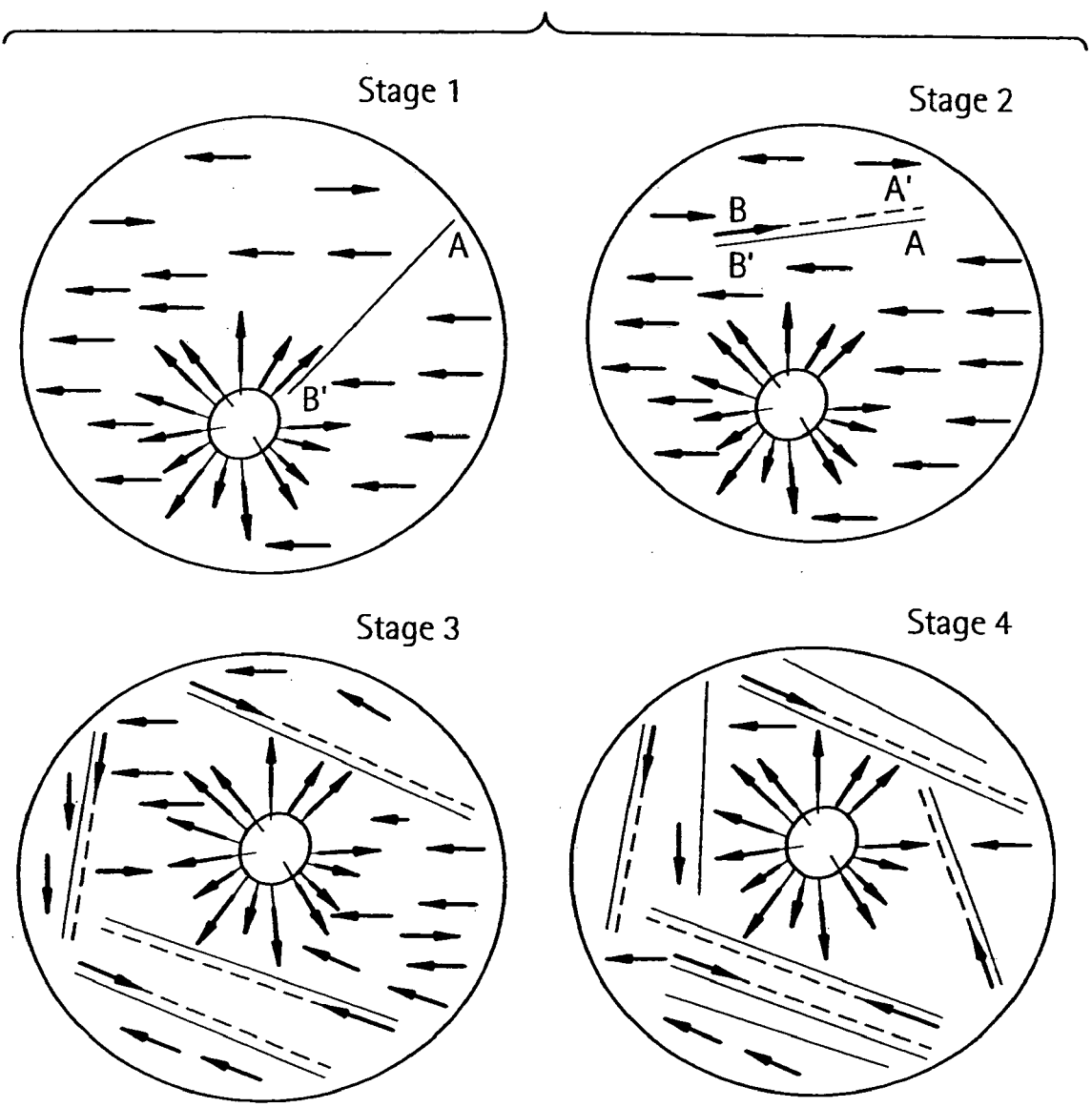
FIG. 6 depicts a schematic of one embodiment of a bead emulsion amplification process.
Figure 6B:
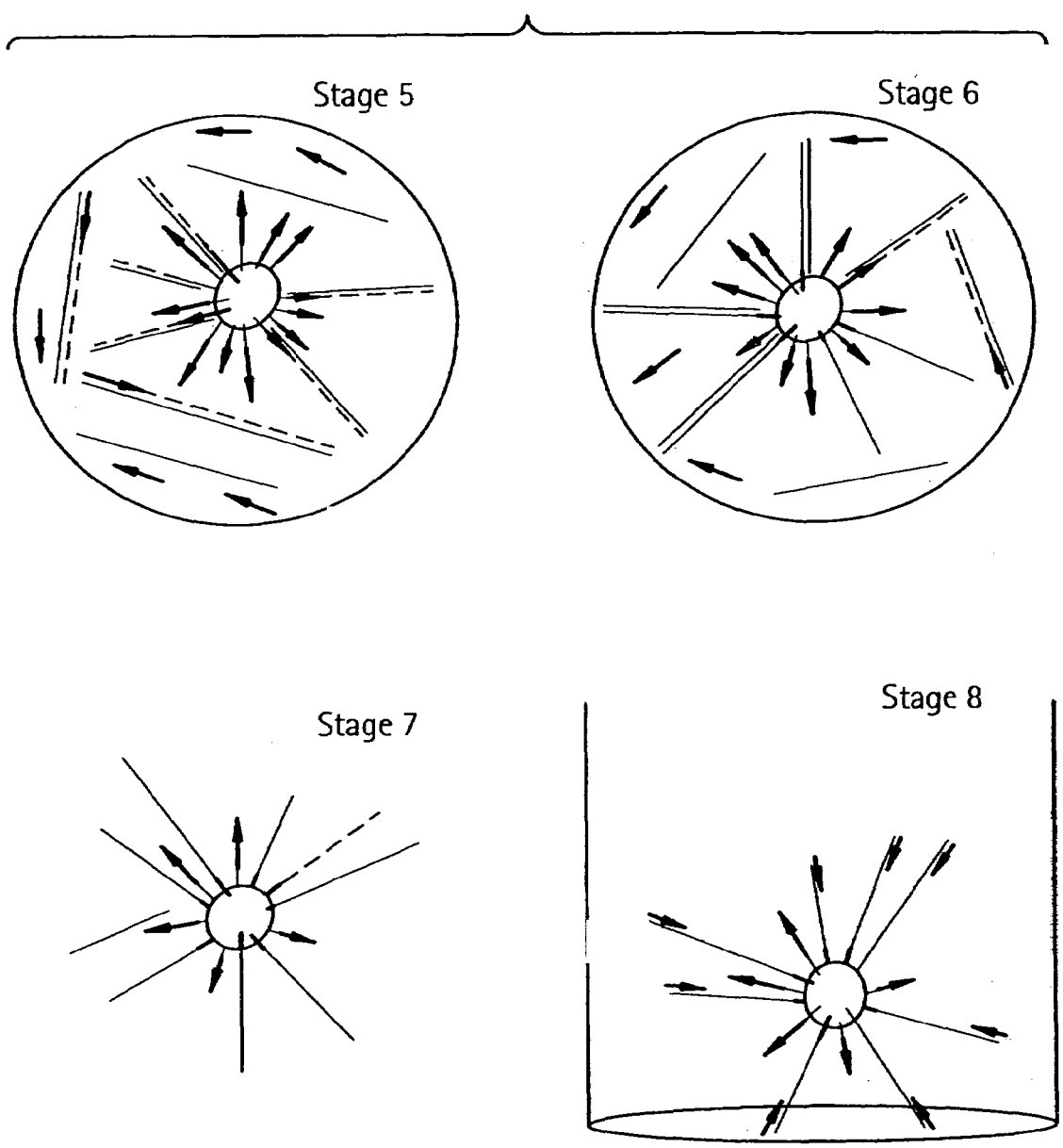

The bead is linked to a large number of a single primer species (i.e., primer B in FIG. 6) that is complementary to a region of the template DNA. Template DNA annealed to the bead bound primer. The beads are suspended in aqueous reaction mixture and then encapsulated in a water-in-oil emulsion. The emulsion is composed of discrete aqueous phase microdroplets, approximately 60 to 200 um in diameter, enclosed by a thermostable oil phase. Each microdroplet contains, preferably, amplification reaction solution (i.e., the reagents necessary for nucleic acid amplification). An example of an amplification would be a PCR reaction mix (polymerase, salts, dNTPs) and a pair of PCR primers (primer A and primer B). See, FIG. 6A. A subset of the microdroplet population also contains the DNA bead comprising the DNA template. This subset of microdroplet is the basis for the amplification. The microcapsules that are not within this subset have no template DNA and will not participate in amplification. In one embodiment, the amplification technique is PCR and the PCR primers are present in a 8:1 or 16:1 ratio (i.e., 8 or 16 of one primer to 1 of the second primer) to perform asymmetric PCR.

In this overview, the DNA is annealed to an oligonucleotide (primer B) which is immobilized to a bead. During thermocycling (FIG. 6B), the bond between the single stranded DNA template and the immobilized B primer on the bead is broken, releasing the template into the surrounding microencapsulated solution. The amplification solution, in this case, the PCR solution, contains addition solution phase primer A and primer B. Solution phase B primers readily bind to the complementary b' region of the template as binding kinetics are more rapid for solution phase primers than for immobilized primers. In early phase PCR, both A and B strands amplify equally well (FIG. 6C).

By midphase PCR (i.e., between cycles 10 and 30) the B primers are depleted, halting exponential amplification. The reaction then enters asymmetric amplification and the amplicon population becomes dominated by A strands (FIG. 6D). In late phase PCR (FIG. 6E), after 30 to 40 cycles, asymmetric amplification increases the concentration of A strands in solution. Excess A strands begin to anneal to bead immobilized B primers. Thermostable polymerases then utilize the A strand as a template to synthesize an immobilized, bead bound B strand of the amplicon.

In final phase PCR (FIG. 6F), continued thermal cycling forces additional annealing to bead bound primers. Solution phase amplification may be minimal at this stage but concentration of immobilized B strands increase. Then, the emulsion is broken and the immobilized product is rendered single stranded by denaturing (by heat, pH etc.) which removes the complimentary A strand. The A primers are annealed to the A' region of immobilized strand, and immobilized strand is loaded with sequencing enzymes, and any necessary accessory proteins. The beads are then sequenced using recognized pyrophosphate techniques (described, e.g., in U.S. Pat. Nos. 6,274,320, 6,258,568 and 6,210,891, incorporated in toto herein by reference).

Template Design

In a preferred embodiment, the DNA template to be amplified by bead emulsion amplification can be a population of DNA such as, for example, a genomic DNA library or a cDNA library. It is preferred that each member of the population have a common nucleic acid sequence at the first end and a common nucleic acid sequence at a second end. This can be accomplished, for example, by ligating a first adaptor DNA sequence to one end and a second adaptor DNA sequence to a second end of the DNA population. Many DNA and cDNA libraries, by nature of the cloning vector (e.g., Bluescript, Stratagene, La Jolla, Calif.) fit this description of having a common sequence at a first end and a second common sequence at a second end of each member DNA. The DNA template may be of any size amenable to in vitro amplification (including the preferred amplification techniques of PCR and asymmetric PCR). In a preferred embodiment, the DNA template is between about 150 to 750 bp in size, such as, for example about 250 bp in size.

Binding Nucleic Acid Template to Capture Beads

In a first step, a single stranded nucleic acid template to be amplified is attached to a capture bead. The nucleic acid template may be attached to the solid support capture bead in any manner known in the art. Numerous methods exist in the art for attaching DNA to a solid support such as the preferred microscopic bead. According to the present invention, covalent chemical attachment of the DNA to the bead can be accomplished by using standard coupling agents, such as water-soluble carbodiimide, to link the 5'-phosphate on the DNA to amine-coated capture beads through a phosphoamidate bond. Another alternative is to first couple specific oligonucleotide linkers to the bead using similar chemistry, and to then use DNA ligase to link the DNA to the linker on the bead. Other linkage chemistries to join the oligonucleotide to the beads include the use of N-hydroxysuccinamide (NHS) and its derivatives. In such a method, one end of the oligonucleotide may contain a reactive group (such as an amide group) which forms a covalent bond with the solid support, while the other end of the linker contains a second reactive group that can bond with the oligonucleotide to be immobilized. In a preferred embodiment, the oligonucleotide is bound to the DNA capture bead by covalent linkage. However, non-covalent linkages, such as chelation or antigen-antibody complexes, may also be used to join the oligonucleotide to the bead.

Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially. These methods are described in detail in U.S. Pat. No. 5,674,743. It is preferred that any method used to immobilize the beads will continue to bind the immobilized oligonucleotide throughout the steps in the methods of the invention.

In one embodiment, each capture bead is designed to have a plurality of nucleic acid primers that recognize (i.e., are complementary to) a portion of the nucleic template, and the nucleic acid template is thus hybridized to the capture bead. In the methods described herein, clonal amplification of the template species is desired, so it is preferred that only one unique nucleic acid template is attached to any one capture bead.

The beads used herein may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and solid phase supports known to those of skill in the art. In a preferred embodiment, the capture beads are Sepharose beads approximately 25 to 40 μm in diameter.

Emulsification

Capture beads with attached single strand template nucleic acid are emulsified as a heat stable water-in-oil emulsion. The emulsion may be formed according to any suitable method known in the art. One method of creating emulsion is described below but any method for making an emulsion may be used. These methods are known in the art and include adjuvant methods, counterflow methods, crosscurrent methods, rotating drum methods, and membrane methods. Furthermore, the size of the microcapsules may be adjusted by varying the flow rate and speed of the components. For example, in dropwise addition, the size of the drops and the total time of delivery may be varied. Preferably, the emulsion contains a density of bead "microreactors" at a density of about 3,000 beads per microliter.

The emulsion is preferably generated by suspending the template-attached beads in amplification solution. As used herein, the term "amplification solution" means the sufficient mixture of reagents that is necessary to perform amplification of template DNA. One example of an amplification solution, a PCR amplification solution, is provided in the Examples below—it will be appreciated that various modifications may be made to the PCR solution.

In one embodiment, the bead/amplification solution mixture is added dropwise into a spinning mixture of biocompatible oil (e.g., light mineral oil, Sigma) and allowed to emulsify. The oil used may be supplemented with one or more biocompatible emulsion stabilizers. These emulsion stabilizers may include Atlox 4912, Span 80, and other recognized and commercially available suitable stabilizers. Preferably, the droplets formed range in size from 5 micron to 500 microns, more preferably, from between about 50 to 300 microns, and most preferably, from 100 to 150 microns.

There is no limitation in the size of the microreactors. The microreactors should be sufficiently large to encompass sufficient amplification reagents for the degree of amplification required. However, the microreactors should be sufficiently small so that a population of microreactors, each containing a member of a DNA library, can be amplified by conventional laboratory equipment (e.g., PCR thermocycling equipment, test tubes, incubators and the like).

With the limitations described above, the optimal size of a microreactor may be between 100 to 200 microns in diameter. Microreactors of this size would allow amplification of a DNA library comprising about 600,000 members in a suspension of microreactors of less than 10 ml in volume. For example, if PCR was the chosen amplification method, 10 mls would fit in 96 tubes of a regular thermocycler with 96 tube capacity. In a preferred embodiment, the suspension of 600,000 microreactors would have a volume of less than 1 ml. A suspension of less than 1 ml may be amplified in about 10 tubes of a conventional PCR thermocycler. In a most preferred embodiment, the suspension of 600,000 microreactors would have a volume of less than 0.5 ml.

Amplification

After encapsulation, the template nucleic acid may be amplified by any suitable method of DNA amplification including transcription-based amplification systems (Kwoh D. et al., Proc. Natl. Acad. Sci. (U.S.A.) 86:1173 (1989); Gingeras T. R. et al., PCT appl. WO 88/10315; Davey, C. et al., European Patent Application Publication No. 329,822; Miller, H. I. et al., PCT appl. WO 89/06700, and "race" (Frohman, M. A., In: PCR Protocols: A Guide to Methods and Applications, Academic Press, NY (1990)) and "one-sided PCR" (Ohara, O. et al., Proc. Natl. Acad. Sci. (U.S.A.) 86.5673-5677 (1989)). Still other less common methods such as "di-oligonucleotide" amplification, isothermal amplification (Walker, G. T. et al., Proc. Natl. Acad. Sci. (U.S.A.) 89:392-396 (1992)), and rolling circle amplification (reviewed in U.S. Pat. No. 5,714,320), may be used in the present invention.

In a preferred embodiment, DNA amplification is performed by PCR. PCR according to the present invention may be performed by encapsulating the target nucleic acid, bound to a bead, with a PCR solution comprising all the necessary reagents for PCR. Then, PCR may be accomplished by exposing the emulsion to any suitable thermocycling regimen known in the art. In a preferred embodiment, between 30 and 50 cycles, preferably about 40 cycles, of amplification are performed. It is desirable, but not necessary, that following the amplification procedure there be one or more hybridization and extension cycles following the cycles of amplification. In a preferred embodiment, between 10 and 30 cycles, preferably about 25 cycles, of hybridization and extension are performed (e.g., as described in the examples). Routinely, the template DNA is amplified until typically at least two million to fifty million copies, preferably about ten million to thirty million copies of the template DNA are immobilized per bead.

Breaking the Emulsion and Bead Recovery

Following amplification of the template, the emulsion is "broken" (also referred to as "demulsification" in the art). There are many methods of breaking an emulsion (see, e.g., U.S. Pat. No. 5,989,892 and references cited therein) and one of skill in the art would be able to select the proper method. In the present invention, one preferred method of breaking the emulsion is to add additional oil to cause the emulsion to separate into two phases. The oil phase is then removed, and a suitable organic solvent (e.g., hexanes) is added. After mixing, the oil/organic solvent phase is removed. This step may be repeated several times. Finally, the aqueous layers above the beads are removed. The beads are then washed with an organic solvent/annealing buffer mixture (e.g., one suitable annealing buffer is described in the examples), and then washed again in annealing buffer. Suitable organic solvents include alcohols such as methanol, ethanol and the like.

The amplified template-containing beads may then be resuspended in aqueous solution for use, for example, in a sequencing reaction according to known technologies. (See, Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363, 365 (1998); Lysov, I. et al., Dokl Akad Nauk SSSR 303, 1508-1511 (1988); Bains W. & Smith G. C. J. Theor Biol 135, 303-307(1988); Drnanac, R. et al., Genomics 4, 114-128 (1989); Khrapko, K. R. et al., FEBS Lett 256. 118-122 (1989); Pevzner P. A. J Biomol Struct Dyn 7, 63-73 (1989); Southern, E. M. et al., Genomics 13, 1008-1017 (1992).) If the beads are to be used in a pyrophosphate-based sequencing reaction (described, e.g., in U.S. Pat. No. 6,274,320, 6,258,568 and 6,210,891, and incorporated in toto herein by reference), then it is necessary to remove the second strand of the PCR product and anneal a sequencing primer to the single stranded template that is bound to the bead.

Briefly, the second strand is melted away using any number of commonly known methods such as NaOH, low ionic (e.g., salt) strength, or heat processing. Following this melting step, the beads are pelleted and the supernatant is discarded. The beads are resuspended in an annealing buffer, the sequencing primer added, and annealed to the bead-attached single stranded template using a standard annealing cycle.

Purifying the Beads

At this point, the amplified DNA on the bead may be sequenced either directly on the bead or in a different reaction vessel. In an embodiment of the present invention, the DNA is sequenced directly on the bead by transferring the bead to a reaction vessel and subjecting the DNA to a sequencing reaction (e.g., pyrophosphate or Sanger sequencing). Alternatively, the beads may be isolated and the DNA may be removed from each bead and sequenced. In either case, the sequencing steps may be performed on each individual bead. However, this method, while commercially viable and technically feasible, may not be most effective because many of the beads will be negative beads (a bead that does not have amplified DNA attached). Accordingly, the following optional process may be used for removing beads that contain no nucleic acid template prior to distribution onto the picotiter plate.

A high percentage of the beads may be "negative" (i.e., have no amplified nucleic acid template attached thereto) if the goal of the initial DNA attachment is to minimize beads with two different copies of DNA. For useful pyrophosphate sequencing, each bead should contain multiple copies of a single species of DNA. This requirement is most closely approached by maximizing the total number of beads with a single fragment of DNA bound (before amplification). This goal can be achieved by the observation of a mathematical model.

For the general case of "N" number of DNAs randomly distributed among M number of beads, the relative bead population containing any number of DNAs depends on the ratio of N/M. The fraction of beads containing N DNAs R(N) may be calculated using the Poisson distribution:

$$R(N) = \exp(-(N/M)) \times (N/M)^N / N!$$ (where × is the multiplication symbol)

The table below shows some calculated values for various N/M (the average DNA fragment to bead ratio) and N (the number of fragments actually bound to a bead).

| N/M     | 0.1   | 0.5  | 1    | 2    |
|---------|-------|------|------|------|
| R(0)    | 0.9   | 0.61 | 0.37 | 0.13 |
| R(1)    | 0.09  | 0.3  | 0.37 | 0.27 |
| R(N > 1)| 0.005 | 0.09 | 0.26 | 0.59 |

In the table the top row denotes the various ratios of N/M. R(0) denotes the fraction of beads with no DNA, R(1) denotes the fraction of beads with one DNA attached (before amplification) and R(N>1) denotes the fraction of DNA with more than one DNA attached (before amplification).

The table indicates that the maximum fraction of beads containing a single DNA fragment is 0.37 (37%) and occurs at a fragment to bead ratio of one. In this mixture, about 63% of the beads is useless for sequencing because they have either no DNA or more than a single species of DNA. Additionally, controlling the fragment to bead ratio require complex calculations and variability could produce bead batches with a significantly smaller fraction of useable beads.

This inefficiency could be significantly ameliorated if beads containing amplicon (originating from the binding of at least one fragment) could be separated from those without amplicon (originating from beads with no bound fragments). An amplicon is defined as any nucleic acid molecules produced by an in vitro nucleic amplification technique. Binding would be done at low average fragment-to-bead ratios (N/M<1), minimizing the ratio of beads with more than one DNA bound. A separation step would remove most or all of the beads with no DNA leaving an enriched population of beads with one species of amplified DNA. These beads may be applied to any method of sequencing such as, for example, pyrophosphate sequencing. Because the fraction of beads with one amplicon (N=1) has been enriched, any method of sequencing would be more efficient.

As an example, with an average fragment to bead ratio of 0.1, 90% of the beads will have no amplicon, 9% of the beads would be useful with one amplicon, and 0.5% of the beads will have more than one amplicon. An enrichment process of the invention will remove the 90% of the zero amplicon beads leaving a population of beads where the sequenceable fraction (N=1) is:

1−(0.005/0.09)=94%.

Dilution of the fragment to bead mixture, along with separation of beads containing amplicon can yield an enrichment of 2.5 folds over the optimal unenriched method. 94%/37% (see table above N/M=1)=2.5. An additional benefit of the enrichment procedure of the invention is that the ultimate fraction of sequenceable beads is relatively insensitive to variability in N/M. Thus, complex calculations to derive the optimal N/M ratio are either unnecessary or may be performed to a lower level of precision. This will ultimately make the procedure more suitable to performance by less trained personnel or automation. An additional benefit of the procedure is that the zero amplicon beads may be recycled and reused. While recycling is not necessary, it may reduce cost or the total bulk of reagents making the method of the invention more suitable for some purposes such as, for example, portable sampling, remote robotic sampling and the like. In addition, all the benefits of the procedure (i.e., less trained personnel, automation, recycling of reagents) will reduce the cost of the procedure. The procedure is described in more detail below.

The enrichment procedure may be used to treat beads that have been amplified in the bead emulsion method above. The amplification is designed so that each amplified molecule contains the same DNA sequence at its 3' end. The nucleotide sequence may be a 20 mer but may be any sequence from 15 bases or more such as 25 bases, 30 bases, 35 bases, or 40 bases or longer. Naturally, while longer oligonucleotide ends are functional, they are not necessary. This DNA sequence may be introduced at the end of an amplified DNA by one of skill in the art. For example, if PCR is used for amplification of the DNA, the sequence may be part of one member of the PCR primer pair.

Figure 7:
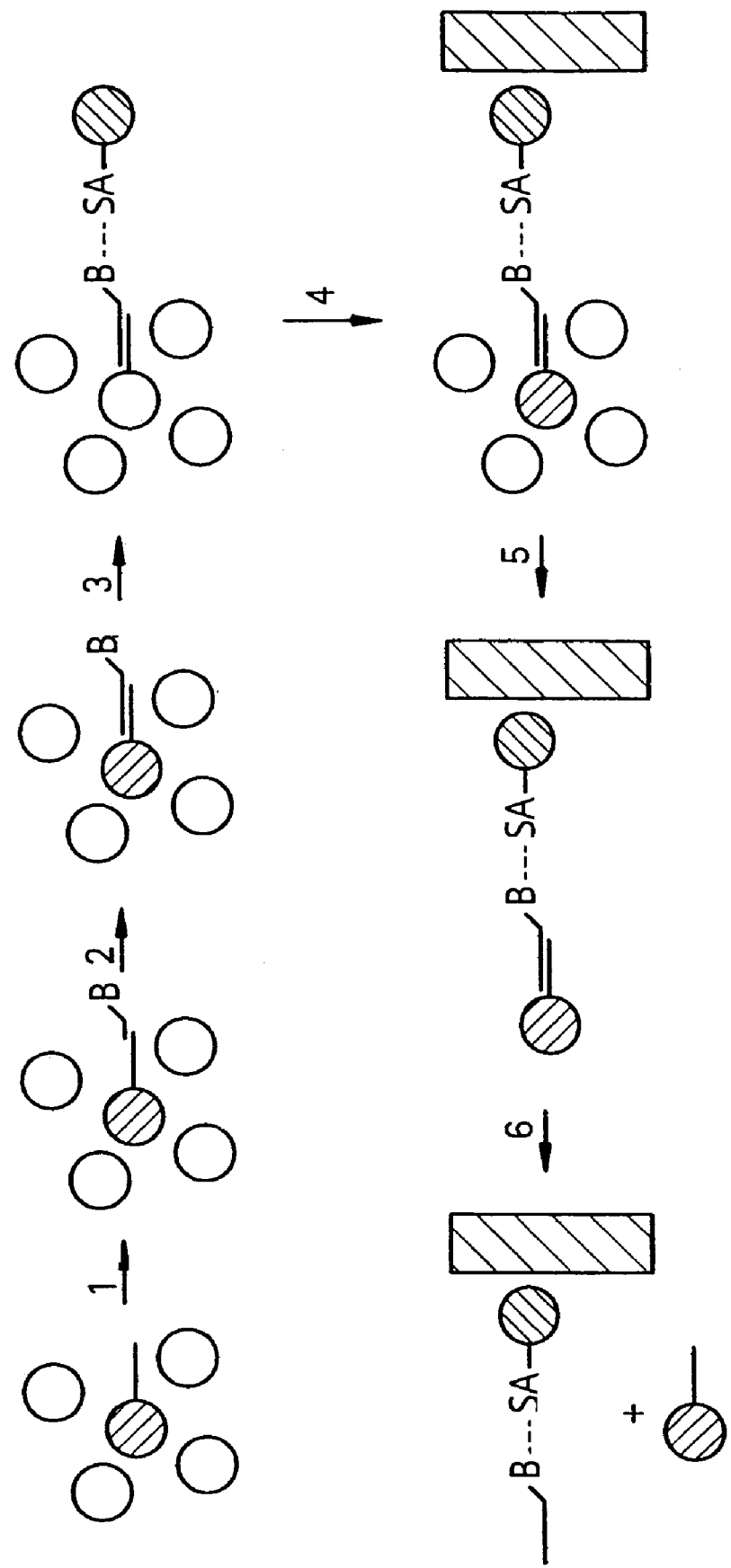
FIG. 7 depicts a schematic of an enrichment process to remove beads that do not have any DNA attached thereto.
Figure 8A:
FIGS. 8A-B depict a schematic representation of the double ended sequencing reaction according to the present invention.
Figure 8B:
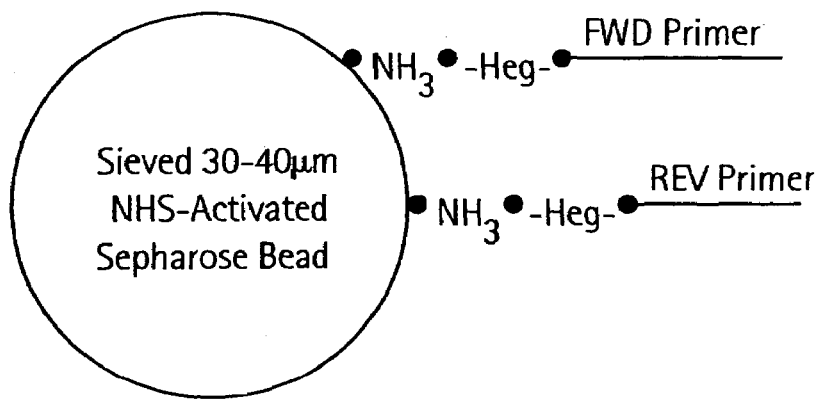
Figure 8C:
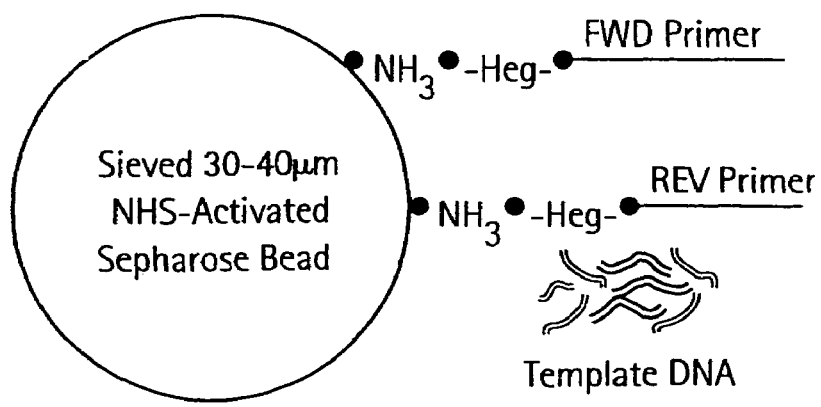
Figure 8D:
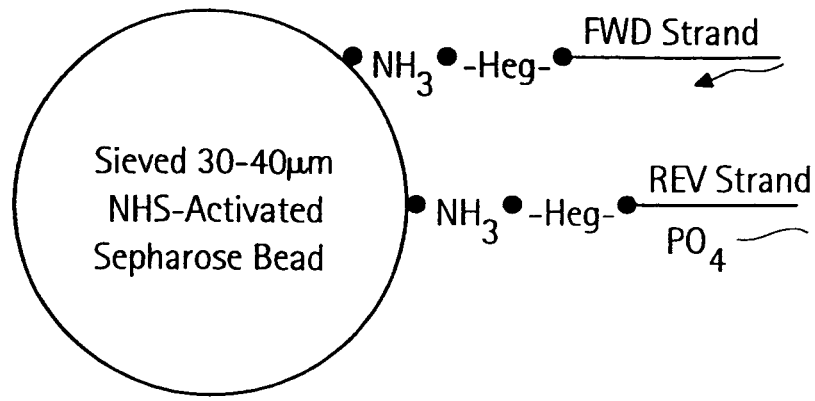
Figure 8E:
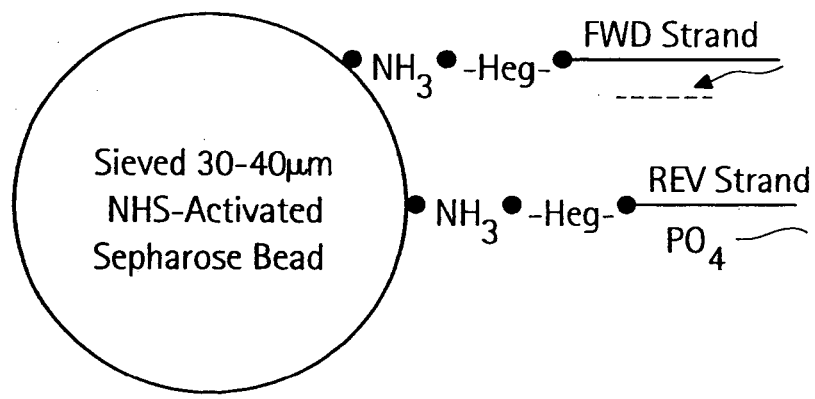
Figure 8F:
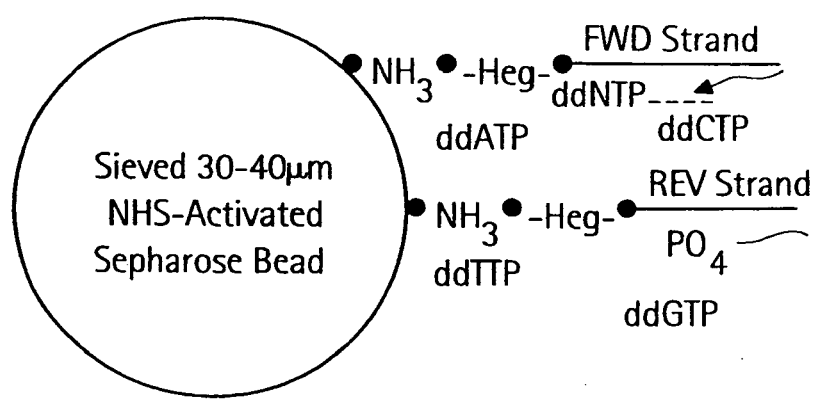
Figure 8G:
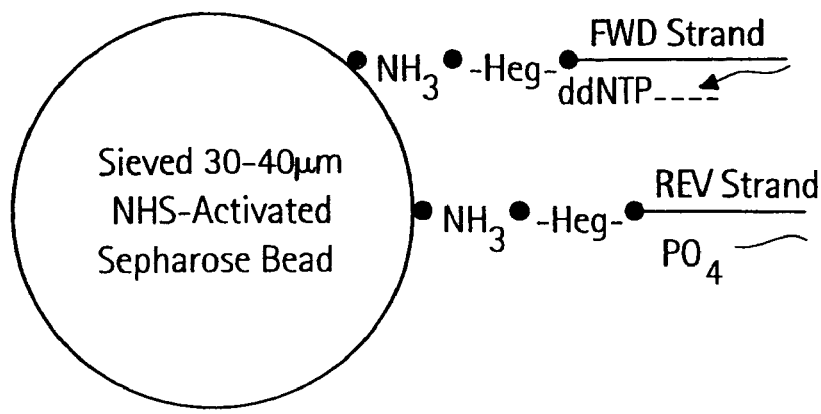
Figure 8H:
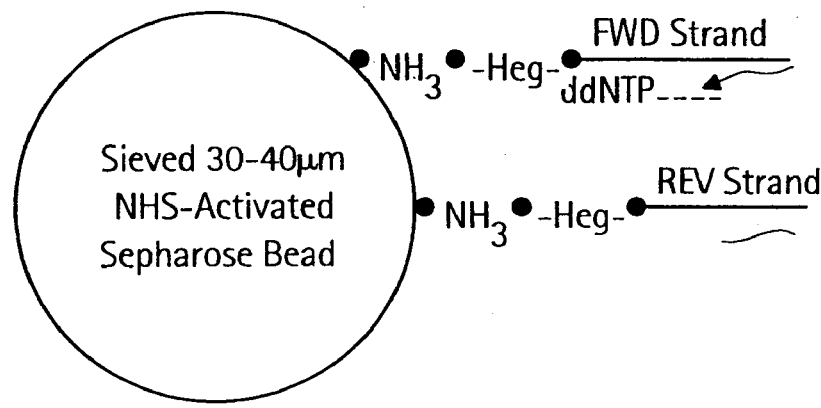
Figure 8I:
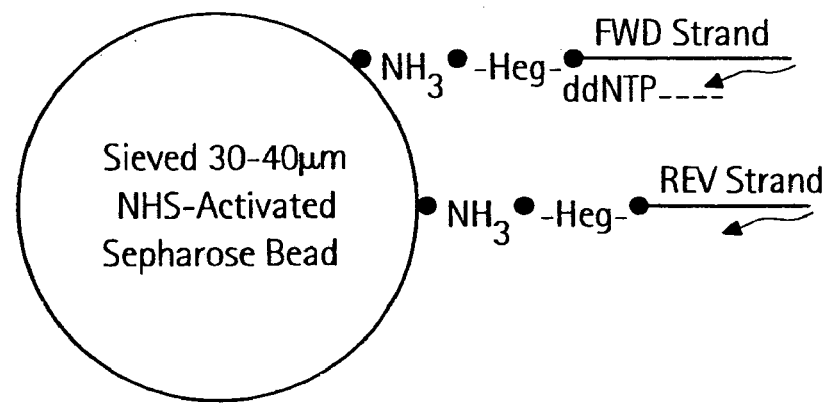
Figure 8J:
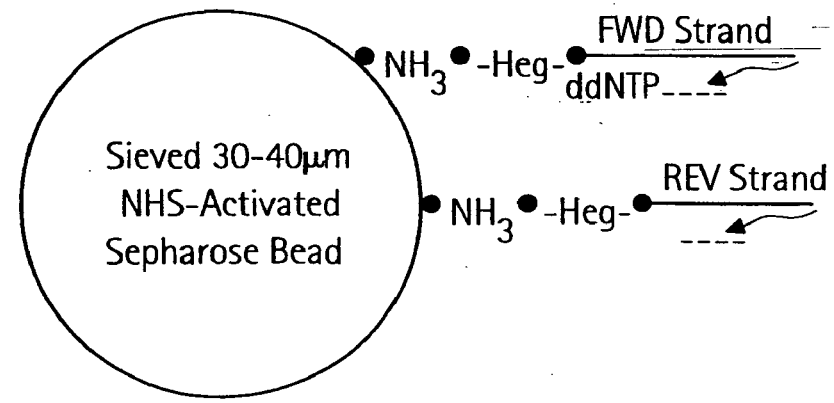
Figure 9:
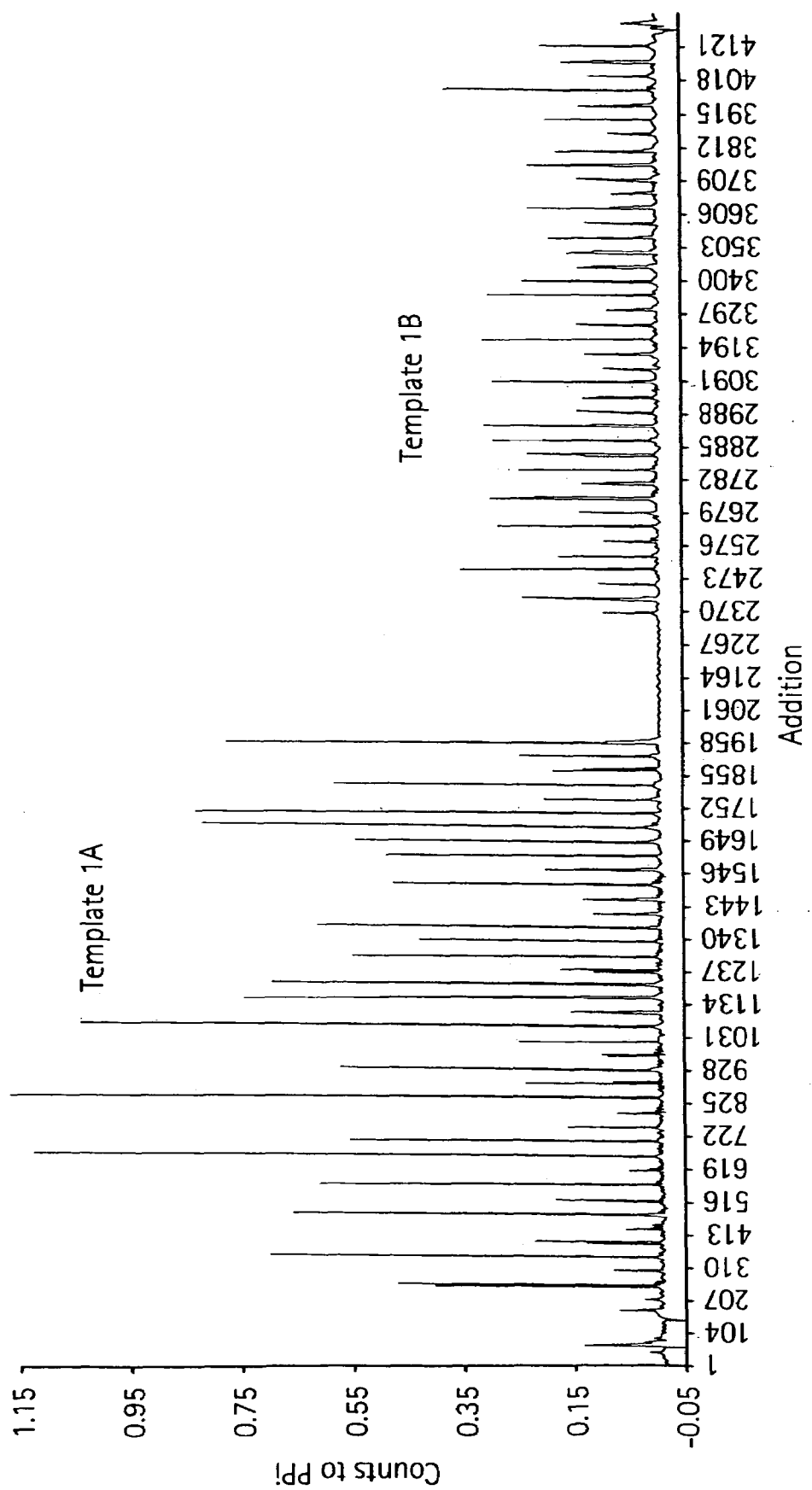
FIG. 9 depicts a double-ended sequencing demonstration on a pyrosequencing apparatus according to the invention.

A schematic of the enrichment process is illustrated in FIG. 7. Here, the amplicon-bound bead mixed with 4 empty beads represents the fragment-diluted amplification bead mixture. In step 1, a biotinylated primer complementary to the 3' end of the amplicon is annealed to the amplicon. In step 2, DNA polymerase and the four natural deoxynucleotides triphosphates (dNTPs) are added to the bead mix and the biotinylated primer is extended. This extension is to enhance the bonding between the biotinylated primer and the bead-bound DNA. This step may be omitted if the biotinylated primer—DNA bond is strong (e.g., in a high ionic environment). In step 3, streptavidin coated beads susceptible to attraction by a magnetic field (referred to herein as "magnetic streptavidin beads") are introduced to the bead mixtures. Magnetic beads are commercially available, for example, from Dynal (M290). The streptavidin capture moieties binds biotins hybridized to the amplicons, which then specifically fix the amplicon-bound beads to the magnetic streptavidin beads.

In step 5, a magnetic field (represented by a magnet) is applied near the reaction mixture, which causes all the "magnetic streptavidin beads/amplicon bound bead complexes" to be positioned along one side of the tube most proximal to the magnetic field. Magnetic beads without amplicon bound beads attached are also expected to be positioned along the same side. Beads without amplicons remain in solution. The bead mixture is washed and the beads not immobilized by the magnet (i.e., the empty beads) are removed and discarded. In step 6, the extended biotinylated primer strand is separated from the amplicon strand by "melting"—a step that can be accomplished, for example, by heat or a change in pH. The heat may be 60° C. in low salt conditions (e.g., in a low ionic environment such as 0.1×SSC). The change in pH may be accomplished by the addition of NaOH. The mixture is then washed and the supernatant, containing the amplicon bound beads, is recovered while the now unbound magnetic beads are retained by a magnetic field. The resultant enriched beads may be used for DNA sequencing. It is noted that the primer on the DNA capture bead may be the same as the primer of step 2 above. In this case, annealing of the amplicon-primer complementary strands (with or without extension) is the source of target-capture affinity.

The biotin streptavidin pair could be replaced by a variety of capture-target pairs. Two categories are pairs whose binding can be subsequently cleaved and those which bind irreversibly, under conditions that are practically achievable. Cleavable pairs include thiol-thiol, Digoxigenin/anti-Digoxigenin, -Captavidin™ if cleavage of the target-capture complex is desired.

As described above, step 2 is optional. If step 2 is omitted, it may not be necessary to separate the magnetic beads from the amplicon bound beads. The amplicon bound beads, with the magnetic beads attached, may be used directly for sequencing. If the sequencing were to be performed in a microwell, separation would not be necessary if the amplicon bound bead-magnetic bead complex can fit inside the microwell.

While the use of magnetic capture beads is convenient, capture moieties can be bound to other surfaces. For example, streptavidin could be chemically bound to a surface, such as, the inner surface of a tube. In this case, the amplified bead mixture may be flowed through. The amplicon bound beads will tend to be retained until "melting" while the empty beads will flow through. This arrangement may be particularly advantageous for automating the bead preparation process.

While the embodiments described above is particularly useful, other methods can be envisioned to separate beads. For example, the capture beads may be labeled with a fluorescent moiety which would make the target-capture bead complex fluorescent. The target capture bead complex may be separated by flow cytometry or fluorescence cell sorter. Using large capture beads would allow separation by filtering or other particle size separation techniques. Since both capture and target beads are capable of forming complexes with a number of other beads, it is possible to agglutinate a mass of cross-linked capture-target beads. The large size of the agglutinated mass would make separation possible by simply washing away the unagglutinated empty beads. The methods described are described in more detail, for example, in Bauer, J.; J. Chromatography B, 722 (1999) 55-69 and in Brody et al., Applied Physics Lett. 74 (1999) 144-146.

The DNA capture beads each containing multiple copies of a single species of nucleic acid template prepared according to the above method are then suitable for distribution onto the picotiter plate.

Nucleic Acid Amplification on the Picotiter Plate

In an alternative embodiment, the nucleic acid template is distributed onto the picotiter plate prior to amplification and then amplified in situ on the picotiter plate. This method is described in detail in the Examples.

3. Sequencing the Nucleic Acid Template

Pyrophosphate sequencing is used according to the methods of this invention to sequence the nucleic acid template. This technique is based on the detection of released pyrophosphate (Ppi) during DNA synthesis. See, e.g., Hyman, 1988. A new method of sequencing DNA. *Anal Biochem.* 174:423-36; Ronaghi, 2001. Pyrosequencing sheds light on DNA sequencing. *Genome Res.* 11:3-11.

In a cascade of enzymatic reactions, visible light is generated proportional to the number of incorporated nucleotides. The cascade starts with a nucleic acid polymerization reaction in which inorganic Ppi is released with nucleotide incorporation by polymerase. The released Ppi is converted to ATP by ATP sulfurylase, which provides the energy to luciferase to oxidize luciferin and generates light. Because the added nucleotide is known, the sequence of the template can be determined. Solid-phase pyrophosphate sequencing utilizes immobilized DNA in a three-enzyme system (see Figures). To increase the signal-to-noise ratio, the natural dATP has been replaced by dATPαS. Typically dATPαS is a mixture of two isomers (Sp and Rp); the use of pure 2'-deoxyadenosine-5'-O-(1-thiotriphosphate) Sp-isomer in pyrophosphate sequencing allows substantially longer reads, up to doubling of the read length.

4. Apparatus for Sequencing Nucleic Acids

This invention provides an apparatus for sequencing nucleic acids, which generally comprises one or more reaction chambers for conducting a sequencing reaction, means for delivering reactants to and from the reaction chamber(s), and means for detecting a sequencing reaction event. In another embodiment, the apparatus includes a reagent delivery cuvette containing a plurality of cavities on a planar surface. In a preferred embodiment, the apparatus is connected to at least one computer for controlling the individual components of the apparatus and for storing and/or analyzing the information obtained from detection of the sequence reaction event.

The invention also provides one or more reaction chambers are arranged on an inert substrate material, also referred to herein as a "solid support", that allows for discrete localization of the nucleic acid template and of the reactants in a sequencing reaction in a defined space, as well as for detection of the sequencing reaction event. Thus, as used herein, the terms "reaction chamber" or "analyte reaction chamber" refer to a localized area on the substrate material that facilitates interaction of reactants, e.g., in a nucleic acid sequencing reaction. As discussed more fully below, the sequencing reactions contemplated by the invention preferably occur on numerous individual nucleic acid samples in tandem, in particular simultaneously sequencing numerous nucleic acid samples derived from genomic and chromosomal nucleic acid templates (e.g., DNA).

The apparatus of the invention therefore preferably comprises a sufficient number of reaction chambers to carry out such numerous individual sequencing reactions. In one embodiment, there are at least 10,000 reaction chambers, preferably at least 50,000 reaction chambers, more preferably greater than 100,000 reaction chambers, even more preferably greater than 200,000 reaction chambers.

Since the number of simultaneous sequencing reactions is limited by the number of reaction chambers, the throughput may be increased by fabricating plates containing increasing densities of wells. The table below shows this progression for a 14×43 mm and 30×60 mm active areas, derived from 25×75 mm and 40×75 mm arrays, respectively.

TABLE

| Development of higher well count arrays. | | | |
|---|---|---|---|
| Pitch (um) | Well Diameter (um) | # of Wells (14 × 43 mm) | # of Wells (30 × 60 mm) |
| 50 | 44 | 275K | 800K |
| 43 | 38 | 375K | 1.2M |
| 35 | 31 | 575K | 1.6M |
| 25 | 22 | 1.1M | 3.2M |

The reaction chambers on the array typically take the form of a cavity or well in the substrate material, having a width and depth, into which reactants can be deposited. Typically the nucleic acid template is distributed into the reaction chamber on one or more solid supports or beads; the reactants are in a medium which facilitates the reaction and which flows through the reaction chamber. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In one preferred embodiment, the shape of the well or cavity is substantially hexagonal. The cavity can have a smooth wall surface. In an additional embodiment, the cavity can have at least one irregular wall surface. The cavities can have a planar bottom or a concave bottom.

The reaction chambers can be spaced between 5 µm and 200 µm apart. Spacing is determined by measuring the center-to-center distance between two adjacent reaction chambers. Typically, the reaction chambers can be spaced between 10 µm and 150 µm apart, preferably between 20 µm and 100 µm apart, most preferably between 40 and 60 µm apart. In one embodiment, the reaction chambers have a width (diameter) in one dimension of between 0.3 µm and 100 µm, more preferably between 20 µm and 70 µm and most preferably about 30 and 50 µm. The depth of the reaction chambers are preferably between 10 µm and 100 µm, preferably between 20 µm and 60 µm. Alternatively, the reaction chambers may have a depth that is between 0.25 and 5 times the width in one dimension of the reaction chamber or, in another embodiment, between 0.3 and 1 times the width in one dimension of the reaction chamber.

In a preferred embodiment, the array is fashioned from a sliced fiber optic bundle (i.e., a bundle of fused fiber optic cables) and the reaction chambers are formed by etching one surface of the fiber optic reactor array. The cavities can also be formed in the substrate via etching, molding or micromachining.

Each cavity or reaction chamber typically has a depth of between 10 µm and 100 µm; alternatively, the depth is between 0.25 and 5 times the size of the width of the cavity, preferably between 0.3 and 1 times the size of the width of the cavity.

In one embodiment, the arrays described herein typically include a planar top surface and a planar bottom surface, which is optically conductive such that optical signals from the reaction chambers can be detected through the bottom planar surface. In these arrays, typically the distance between the top surface and the bottom surface is no greater than 10 cm, preferably no greater than 2 cm, and usually between 0.5 mm to 5 mm, most preferably about 2 mm.

In a particularly preferred embodiment, the solid support is termed a picotiterplate, with reaction chambers having a center to center spacing of about 43 µm to 50 µm, a well diameter of between 38 µm to 44 µm, and a well volume of between 10 to 150 pL, preferably between 20 to 90 pL, more preferably between 40 to 85 pL, and most preferably about 75 pL.

In one embodiment, each cavity or reaction chamber of the array contains reagents for analyzing a nucleic acid or protein. Typically those reaction chambers that contain a nucleic acid (not all reaction chambers in the array are required to) contain only a single species of nucleic acid (i.e., a single sequence that is of interest). There may be a single copy of this species of nucleic acid in any particular reaction chamber, or there may be multiple copies. It is generally preferred that a reaction chamber contain at least 100,000 copies of the nucleic acid template sequence, preferably at least 1,000,000 copies, and more preferably between 2,000,000 to 20,000,000 copies, and most preferably between 5,000,000 to 15,000,000 copies of the nucleic acid. The ordinarily skilled artisan will appreciate that changes in the number of copies of a nucleic acid species in any one reaction chamber will affect the number of photons generated in a pyrosequencing reaction, and can be routinely adjusted to provide more or less photon signal as is required. In one embodiment the nucleic acid species is amplified to provide the desired number of copies using PCR, RCA, ligase chain reaction, other isothermal amplification, or other conventional means of nucleic acid amplification. In one embodiment, the nucleic acid is single stranded.

Solid Support Material

Any material can be used as the solid support material, as long as the surface allows for stable attachment of the primers and detection of nucleic acid sequences. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME I: MICROLITHOGRAPHY, Volume PM39, SPIE Press (1997); Madou, CRC Press (1997), Aoki, *Biotech. Histochem.* 67: 98-9 (1992); Kane et al., Biomaterials. 20: 2363-76 (1999); Deng et al., *Anal. Chem.* 72:3176-80 (2000); Zhu et al., *Nat. Genet.* 26:283-9 (2000). In some embodiments, the solid support is optically transparent, e.g., glass.

An array of attachment sites on an optically transparent solid support can be constructed using lithographic techniques commonly used in the construction of electronic integrated circuits as described in, e.g., techniques for attachment described in U.S. Pat. Nos. 5,143,854, 5,445,934, 5,744,305, and 5,800,992; Chee et al., *Science* 274: 610-614 (1996); Fodor et al., *Nature* 364: 555-556 (1993); Fodor et al., *Science* 251: 767-773 (1991); Gushin, et al., *Anal. Biochem.* 250:203-211 (1997); Kinosita et al., *Cell* 93: 21-24 (1998); Kato-Yamada et al., *J. Biol. Chem.* 273: 19375-19377 (1998); and Yasuda et al., *Cell* 93: 1117-1124 (1998). Photolithography and electron beam lithography sensitize the solid support or substrate with a linking group that allows attachment of a modified biomolecule (e.g., proteins or nucleic acids). See e.g., Service, *Science* 283: 27-28 (1999); Rai-Choudhury, HANDBOOK OF MICROLITHOGRAPHY, MICROMACHINING, AND MICROFABRICATION, VOLUME I: MICROLITHOGRAPHY, Volume PM39, SPIE Press (1997). Alternatively, an array of sensitized sites can be generated using thin-film technology as described in Zasadzinski et al., *Science* 263: 1726-1733 (1994).

The substrate material is preferably made of a material that facilitates detection of the reaction event. For example, in a typical sequencing reaction, binding of a dNTP to a sample nucleic acid to be sequenced can be monitored by detection of photons generated by enzyme action on phosphate liberated in the sequencing reaction. Thus, having the substrate material made of a transparent or light conductive material facilitates detection of the photons.

In some embodiments, the solid support can be coupled to a bundle of optical fibers that are used to detect and transmit the light product. The total number of optical fibers within the bundle may be varied so as to match the number of individual reaction chambers in the array utilized in the sequencing reaction. The number of optical fibers incorporated into the bundle is designed to match the resolution of a detection device so as to allow 1:1 imaging. The overall sizes of the bundles are chosen so as to optimize the usable area of the detection device while maintaining desirable reagent (flow) characteristics in the reaction chamber. Thus, for a 4096× 4096 pixel CCD (charge-coupled device) array with 15 µm pixels, the fiber bundle is chosen to be approximately 60 mm×60 mm or to have a diameter of approximately 90 mm. The desired number of optical fibers are initially fused into a bundle or optical fiber array, the terminus of which can then be cut and polished so as to form a "wafer" of the required thickness (e.g., 1.5 mm). The resulting optical fiber wafers possess similar handling properties to that of a plane of glass. The individual fibers can be any size diameter (e.g., 3 µm to 100 µm).

In some embodiments two fiber optic bundles are used: a first bundle is attached directly to the detection device (also referred to herein as the fiber bundle or connector) and a second bundle is used as the reaction chamber substrate (the wafer or substrate). In this case the two are placed in direct contact, optionally with the use of optical coupling fluid, in order to image the reaction centers onto the detection device. If a CCD is used as the detection device, the wafer could be slightly larger in order to maximize the use of the CCD area, or slightly smaller in order to match the format of a typical microscope slide—25 mm×75 mm. The diameters of the individual fibers within the bundles are chosen so as to maximize the probability that a single reaction will be imaged onto a single pixel in the detection device, within the constraints of the state of the art. Exemplary diameters are 6-8 µm for the fiber bundle and 6-50 µm for the wafer, though any diameter in the range 3-100 µm can be used. Fiber bundles can be obtained commercially from CCD camera manufacturers. For example, the wafer can be obtained from Incom, Inc. (Charlton, Mass.) and cut and polished from a large fusion of fiber optics, typically being 2 mm thick, though possibly being 0.5 to 5 mm thick. The wafer has handling properties similar to a pane of glass or a glass microscope slide.

Reaction chambers can be formed in the substrate made from fiber optic material. The surface of the optical fiber is cavitated by treating the termini of a bundle of fibers, e.g., with acid, to form an indentation in the fiber optic material. Thus, in one embodiment cavities are formed from a fiber optic bundle, preferably cavities can be formed by etching one end of the fiber optic bundle. Each cavitated surface can form a reaction chamber. Such arrays are referred to herein as fiber optic reactor arrays or FORA. The indentation ranges in depth from approximately one-half the diameter of an individual optical fiber up to two to three times the diameter of the fiber. Cavities can be introduced into the termini of the fibers by placing one side of the optical fiber wafer into an acid bath for a variable amount of time. The amount of time can vary depending upon the overall depth of the reaction cavity desired (see e.g., Walt, et al., 1996. *Anal. Chem.* 70: 1888). A wide channel cavity can have uniform flow velocity dimensions of approximately 14 mm×43 mm. Thus, with this approximate dimension and at approximately $4.82 \times 10^{-4}$ cavities/mm$^2$ density, the apparatus can have approximately 290,000 fluidically accessible cavities. Several methods are known in the art for attaching molecules (and detecting the attached molecules) in the cavities etched in the ends of fiber optic bundles. See, e.g., Michael, et al., *Anal. Chem.* 70: 1242-1248 (1998); Ferguson, et al., *Nature Biotechnology* 14: 1681-1684 (1996); Healey and Walt, *Anal. Chem.* 69: 2213-2216 (1997). A pattern of reactive sites can also be created in the microwell, using photolithographic techniques similar to those used in the generation of a pattern of reaction pads on a planar support. See, Healey, et al., *Science* 269: 1078-1080 (1995); Munkholm and Walt, *Anal. Chem.* 58: 1427-1430 (1986), and Bronk, et al., *Anal. Chem.* 67: 2750-2757 (1995).

The opposing side of the optical fiber wafer (i.e., the non-etched side) is typically highly polished so as to allow optical-coupling (e.g., by immersion oil or other optical coupling fluids) to a second, optical fiber bundle. This second optical fiber bundle exactly matches the diameter of the optical wafer containing the reaction chambers, and serve to act as a conduit for the transmission of light product to the attached detection device, such as a CCD imaging system or camera.

In one preferred embodiment, the fiber optic wafer is thoroughly cleaned, e.g. by serial washes in 15% $H_2O_2$/15% $NH_4OH$ volume:volume in aqueous solution, then six deionized water rinses, then 0.5M EDTA, then six deionized water, then 15% $H_2O_2$/15%$NH_4OH$, then six deionized water (one-half hour incubations in each wash).

The surface of the fiber optic wafer is preferably coated to facilitate its use in the sequencing reactions. A coated surface is preferably optically transparent, allows for easy attachment of proteins and nucleic acids, and does not negatively affect the activity of immobilized proteins. In addition, the surface preferably minimizes non-specific absorption of macromolecules and increases the stability of linked macromolecules (e.g., attached nucleic acids and proteins).

Suitable materials for coating the array include, e.g., plastic (e.g. polystyrene). The plastic can be preferably spin-coated or sputtered (0.1 µm thickness). Other materials for coating the array include gold layers, e.g. 24 karat gold, 0.1 µm thickness, with adsorbed self-assembling monolayers of long chain thiol alkanes. Biotin is then coupled covalently to the surface and saturated with a biotin-binding protein (e.g. streptavidin or avidin).

Coating materials can additionally include those systems used to attach an anchor primer to a substrate. Organosilane reagents, which allow for direct covalent coupling of proteins via amino, sulfhydryl or carboxyl groups, can also be used to coat the array. Additional coating substances include photoreactive linkers, e.g. photobiotin, (Amos et al., "Biomaterial Surface Modification Using Photochemical Coupling Technology," in *Encyclopedic Handbook of Biomaterials and Bioengineering, Part A: Materials*, Wise et al. (eds.), New York, Marcel Dekker, pp. 895926, 1995).

Additional coating materials include hydrophilic polymer gels (polyacrylamide, polysaccharides), which preferably polymerize directly on the surface or polymer chains covalently attached post polymerization (Hjerten, *J. Chromatogr.* 347,191 (1985); Novotny, *Anal. Chem.* 62,2478 (1990), as well as pluronic polymers (triblock copolymers, e.g. PPO-PEO-PPO, also known as F-108), specifically adsorbed to either polystyrene or silanized glass surfaces (Ho et al., *Langmuir* 14:3889-94, 1998), as well as passively adsorbed layers of biotin-binding proteins. The surface can also be coated with an epoxide which allows the coupling of reagents via an amine linkage.

In addition, any of the above materials can be derivatized with one or more functional groups, commonly known in the art for the immobilization of enzymes and nucleotides, e.g. metal chelating groups (e.g. nitrilo triacetic acid, iminodiacetic acid, pentadentate chelator), which will bind 6×His-tagged proteins and nucleic acids.

Surface coatings can be used that increase the number of available binding sites for subsequent treatments, e.g. attachment of enzymes (discussed later), beyond the theoretical binding capacity of a 2D surface.

In a preferred embodiment, the individual optical fibers utilized to generate the fused optical fiber bundle/wafer are larger in diameter (i.e., 6 µm to 12 µm) than those utilized in the optical imaging system (i.e., 3 µm). Thus, several of the optical imaging fibers can be utilized to image a single reaction site.

In a particularly preferred embodiment, the sample cartridge for nucleic acid template sequencing, termed the 'Pico-Titer plate' is formed from a commercial fiber optics face-plate, acid-etched to yield well structures. Each optic fiber core is about 44 microns in diameter, with a 2-3 micron cladding, each well formed by acid etching to form a reaction well volume of about 65 pL to 85 pL, most preferably about 75 pL. The use of etched wells on a fiber optics faceplate surface serves a threefold purpose; i) delayed diffusion of the luminescence from emitting light in a different region of the array, ii) isolation of reaction chambers ("test-tubes") that contain the amplified template molecules, and iii) very efficient, high numerical aperture optical coupling to the CCD. Finally, the larger the amount of sequencing template immobilized within a well, the more optical signal one is able to achieve.

Delivery Means

An example of the means for delivering reactants to the reaction chamber is the perfusion chamber of the present invention is illustrated in FIG. 13. The perfusion chamber includes a sealed compartment with transparent upper and lower side. It is designed to allow flow of solution over the surface of the substrate surface and to allow for fast exchange of reagents. Thus, it is suitable for carrying out, for example, the pyrophosphate sequencing reactions. The shape and dimensions of the chamber can be adjusted to optimize reagent exchange to include bulk flow exchange, diffusive exchange, or both in either a laminar flow or a turbulent flow regime.

The perfusion chamber is preferably detached from the imaging system while it is being prepared and only placed on the imaging system when sequencing analysis is performed. In one embodiment, the solid support (i.e., a DNA chip or glass slide) is held in place by a metal or plastic housing, which may be assembled and disassembled to allow replacement of said solid support. The lower side of the solid support of the perfusion chamber carries the reaction chamber array and, with a traditional optical-based focal system, a high numerical aperture objective lens is used to focus the image of the reaction center array onto the CCD imaging system.

Many samples can thereby be analyzed in parallel. Using the method of the invention, many nucleic acid templates may be analyzed in this was by allowing the solution containing the enzymes and one nucleotide to flow over the surface and then detecting the signal produced for each sample. This procedure can then be repeated. Alternatively, several different oligonucleotides complementary to the template may be distributed over the surface followed by hybridization of the template. Incorporation of deoxynucleotides or dideoxynucleotides may be monitored for each oligonucleotide by the signal produced using the various oligonucleotides as primer. By combining the signals from different areas of the surface, sequence-based analyses may be performed by four cycles of polymerase reactions using the various dideoxynucleotides.

When the support is in the form of a cavitated array, e.g., in the termini of a picotiter plate or other array of microwells, suitable delivery means for reagents include flowing and washing and also, e.g., flowing, spraying, electrospraying, ink jet delivery, stamping, ultrasonic atomization (Sonotek Corp., Milton, N.Y.) and rolling. When spraying is used, reagents may be delivered to the picotiter plate in a homogeneous thin layer produced by industrial type spraying nozzles (Spraying Systems, Co., Wheaton, Ill.) or atomizers used in thin layer chromatography (TLC), such as CAMAG TLC Sprayer (Camag Scientific Inc., Wilmington, N.C.). These sprayers atomize reagents into aerosol spray particles in the size range of 0.3 to 10 µm.

Successive reagent delivery steps are preferably separated by wash steps using techniques commonly known in the art. These washes can be performed, e.g., using the above described methods, including high-flow sprayers or by a liquid flow over the picotiter plate or microwell array surface. The washes can occur in any time period after the starting material has reacted with the reagent to form a product in each reaction chamber but before the reagent delivered to any one reaction chamber has diffused out of that reaction chamber into any other reaction chamber. In one embodiment, any one reaction chamber is independent of the product formed in any other reaction chamber, but is generated using one or more common reagents.

An embodiment of a complete apparatus is illustrated in FIG. 12. The apparatus includes an inlet conduit 200 in communication with a detachable perfusion chamber 226. The inlet conduit 200 allows for entry of sequencing reagents via a plurality of tubes 202-212, which are each in communication with a plurality of sequencing dispensing reagent vessels 214-224.

Reagents are introduced through the conduit 200 into the perfusion chamber 226 using either a pressurized system or pumps to drive positive flow. Typically, the reagent flow rates are from 0.05 to 50 ml/minute (e.g., 1 to 50 ml/minute) with volumes from 0.100 ml to continuous flow (for washing). Valves are under computer control to allow cycling of nucleotides and wash reagents. Sequencing reagents, e.g., polymerase can be either pre-mixed with nucleotides or added in stream. A manifold brings all six tubes 202-212 together into one for feeding the perfusion chamber. Thus several reagent delivery ports allow access to the perfusion chamber. For example, one of the ports may be utilized to allow the input of the aqueous sequencing reagents, while another port allows these reagents (and any reaction products) to be withdrawn from the perfusion chamber.

In a preferred embodiment, one or more reagents are delivered to an array immobilized or attached to a population of mobile solid supports, e.g., a bead or microsphere. The bead or microsphere need not be spherical, irregular shaped beads may be used. They are typically constructed from numerous substances, e.g., plastic, glass or ceramic and bead sizes ranging from nanometers to millimeters depending on the width of the reaction chamber. Various bead chemistries can be used e.g., methylstyrene, polystyrene, acrylic polymer, latex, paramagnetic, thoria sol, carbon graphite and titanium dioxide. The construction or chemistry of the bead can be chosen to facilitate the attachment of the desired reagent.

In another embodiment, the bioactive agents are synthesized first, and then covalently attached to the beads. As is appreciated by someone skilled in the art, this will be done depending on the composition of the bioactive agents and the beads. The functionalization of solid support surfaces such as certain polymers with chemically reactive groups such as thiols, amines, carboxyls, etc. is generally known in the art.

In a preferred embodiment, the nucleic acid template is delivered to the picotiter plate on beads. The luciferase and sulfurylase enzymes are likewise delivered to each well on beads (see Figure), as is the DNA polymerase. It is noted that the one or more of the nucleic acid template, luciferase and sulfurylase may be delivered each on separate beads, or together on the same bead. To allow sequencing DNA at raised temperatures, we have cloned and modified the thermostable sulfurylase from *Bacillus steareothermophilus*. We have also cloned and modified several luciferase enzymes for solid-phase enzyme activity, including *P. pennsylvanica* and *P. pyralis*. The *P. pyralis* luciferase is used in a preferred embodiment.

"Blank" beads may be used that have surface chemistries that facilitate the attachment of the desired functionality by the user. Additional examples of these surface chemistries for blank beads include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated here by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the candidate agent) may be derivatized using well known linkers (see Pierce catalog). For example, carbodiimides activate carboxyl groups for attack by good nucleophiles such as amines (see Torchilin et al., *Critical Rev. Therapeutic Drug Carrier Systems,* 7(4):275-308 (1991)). Proteinaceous candidate agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj. Chem.* 3:323-327 (1992); King et al., *Cancer Res.* 54:6176-6185 (1994); and Wilbur et al., *Bioconjugate Chem.* 5:220-235 (1994). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target.

Specific techniques for immobilizing enzymes on beads are known in the prior art. In one case, $NH_2$ surface chemistry beads are used. Surface activation is achieved with a 2.5% glutaraldehyde in phosphate buffered saline (10 mM) providing a pH of 6.9 (138 mM NaCl, 2.7 mM KCl). This mixture is stirred on a stir bed for approximately 2 hours at room temperature. The beads are then rinsed with ultrapure water plus 0.01% Tween 20 (surfactant)—0.02%, and rinsed again with a pH 7.7 PBS plus 0.01% tween 20. Finally, the enzyme is added to the solution, preferably after being prefiltered using a 0.45 µm amicon micropure filter.

The population of mobile solid supports are disposed in the reaction chambers. In some embodiments, 5% to 20% of the reaction chambers can have a mobile solid support with at least one reagent immobilized thereon, 20% to 60% of the reaction chambers can have a mobile solid support with at least one reagent immobilized thereon or 50% to 100% of the reaction chambers can have a mobile solid support with at least one reagent immobilized thereon. Preferably, at least one reaction chamber has a mobile solid support having at least one reagent immobilized thereon and the reagent is suitable for use in a nucleic acid sequencing reaction.

In some embodiments, the reagent immobilized to the mobile solid support can be a polypeptide with sulfurylase activity, a polypeptide with luciferase activity or a chimeric polypeptide having both sulfurylase and luciferase activity. In one embodiment, it can be a ATP sulfurylase and luciferase fusion protein. Since the product of the sulfurylase reaction is consumed by luciferase, proximity between these two enzymes may be achieved by covalently linking the two enzymes in the form of a fusion protein. This invention would be useful not only in substrate channeling but also in reducing production costs and potentially doubling the number of binding sites on streptavidin-coated beads.

In another embodiment, the sulfurylase is a thermostable ATP sulfurylase. In a preferred embodiment, the thermostable sulfurylase is active at temperatures above ambient (to at least 50° C.). In one embodiment, the ATP sulfurylase is from a thermophile. In an additional embodiment, the mobile solid support can have a first reagent and a second reagent immobilized thereon, the first reagent is a polypeptide with sulfurylase activity and the second reagent is a polypeptide with luciferase activity.

In another embodiment, the reagent immobilized to the mobile solid support can be a nucleic acid; preferably the nucleic acid is a single stranded concatamer. In a preferred embodiment, the nucleic acid can be used for sequencing a nucleic acid, e.g., a pyrosequencing reaction.

The invention also provides a method for detecting or quantifying ATP activity using a mobile solid support; preferably the ATP can be detected or quantified as part of a nucleic acid sequencing reaction.

Figure 15:
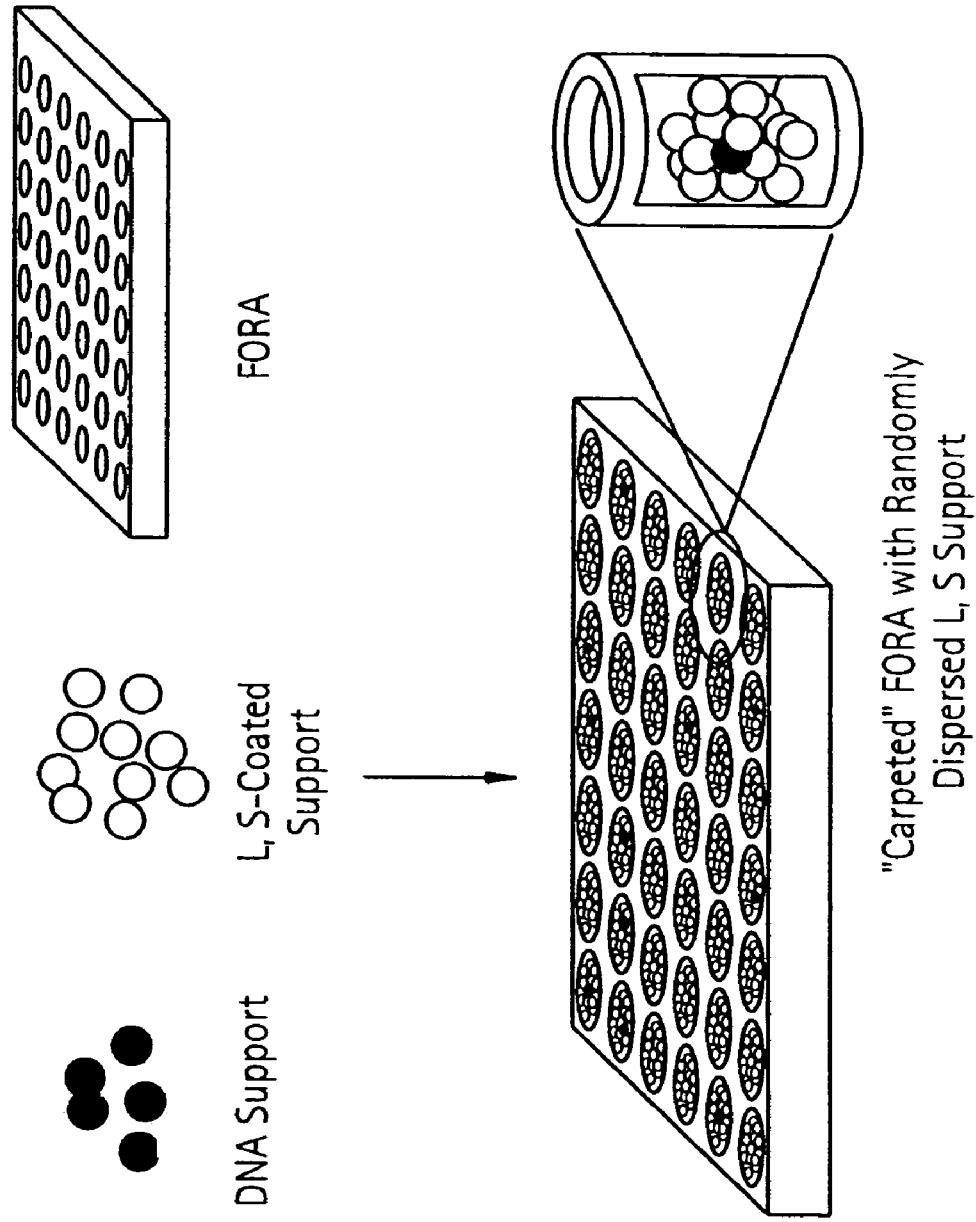
FIG. 15 depicts a micrograph of a picotiter plate carpeted with beads having DNA template immobilized thereon and sulfurylase and luciferase immobilized thereon.
Figure 16:
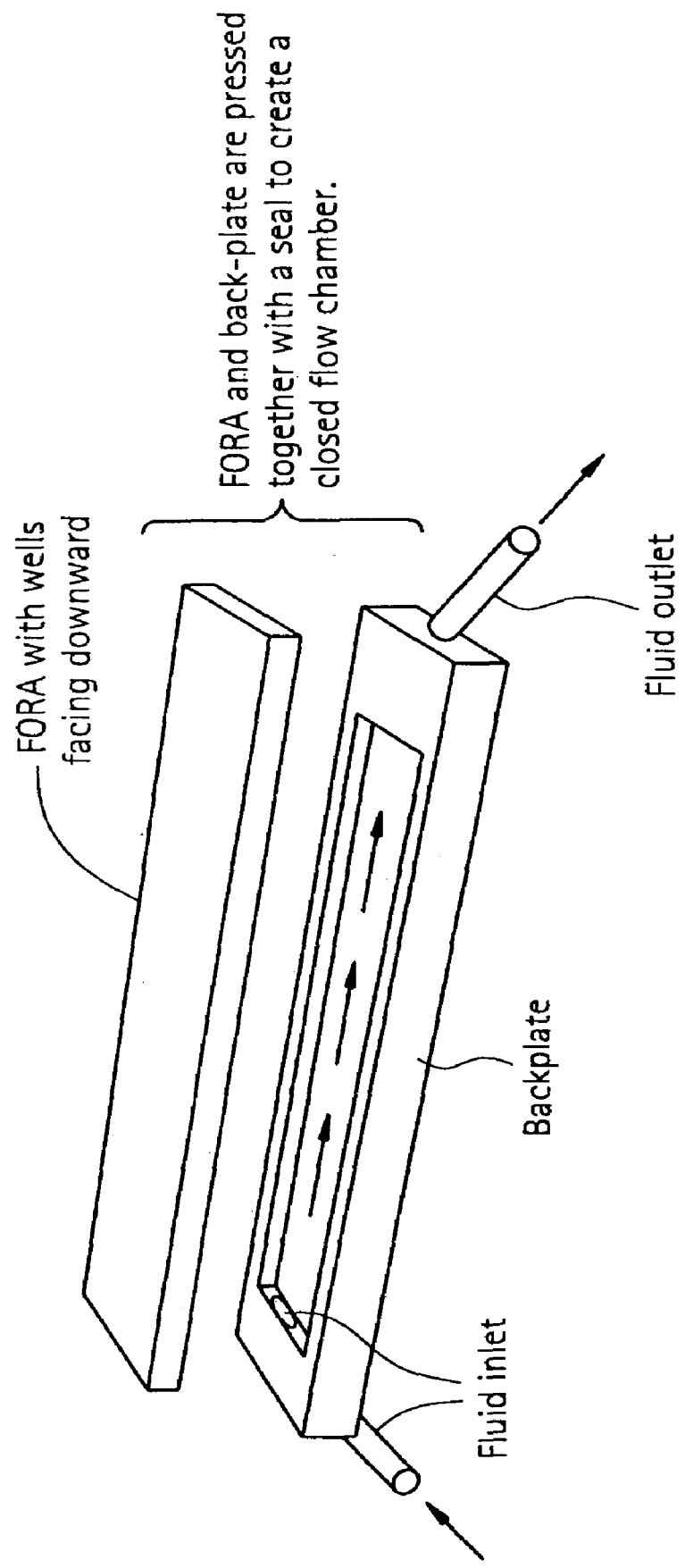
FIG. 16 depicts a schematic illustration of the reagent flow chamber and FORA (PicoTiter Plate™).
Figure 17:
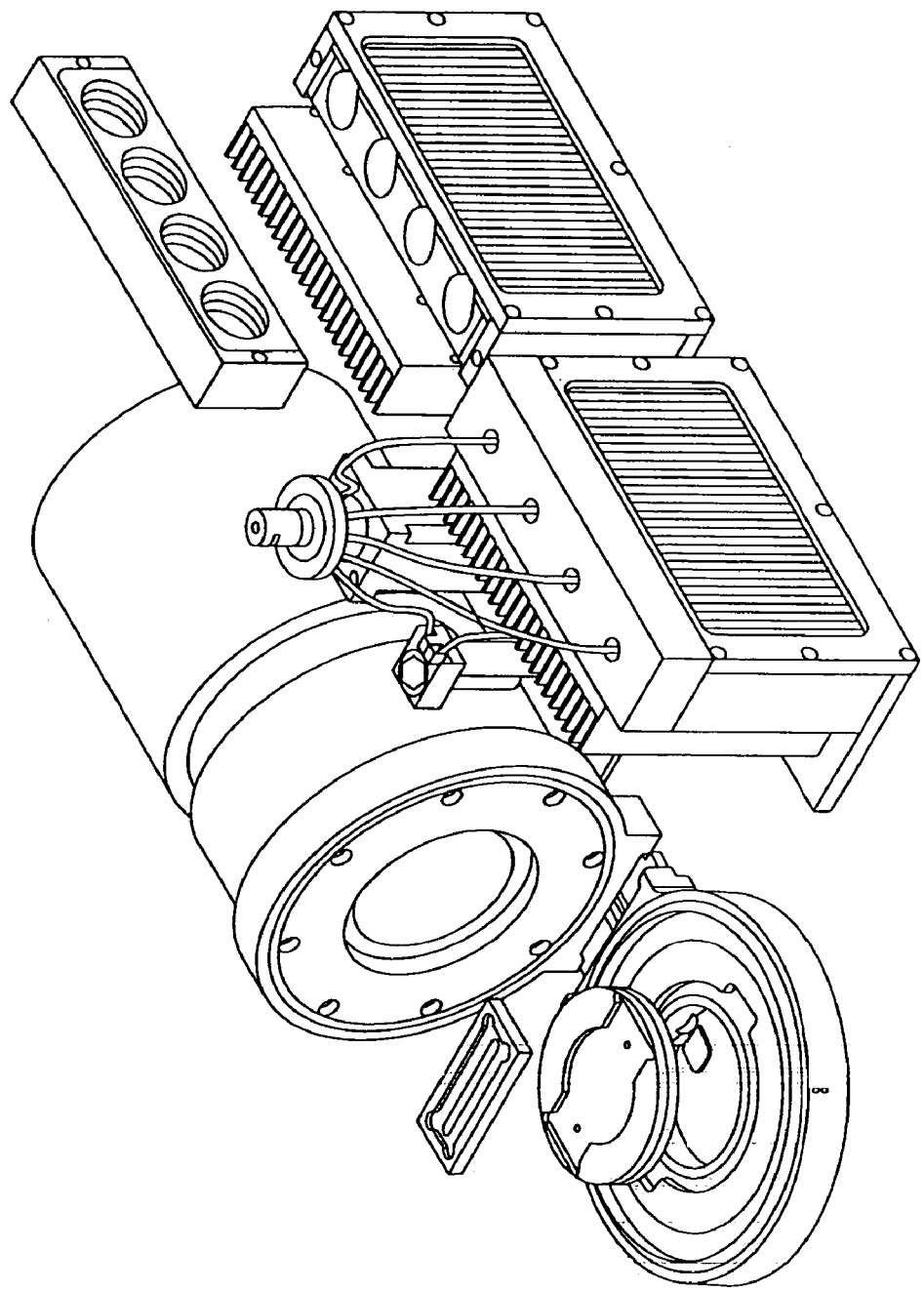
FIG. 17 depicts a diagram of the analytical instrument of the present invention.
Figure 18:
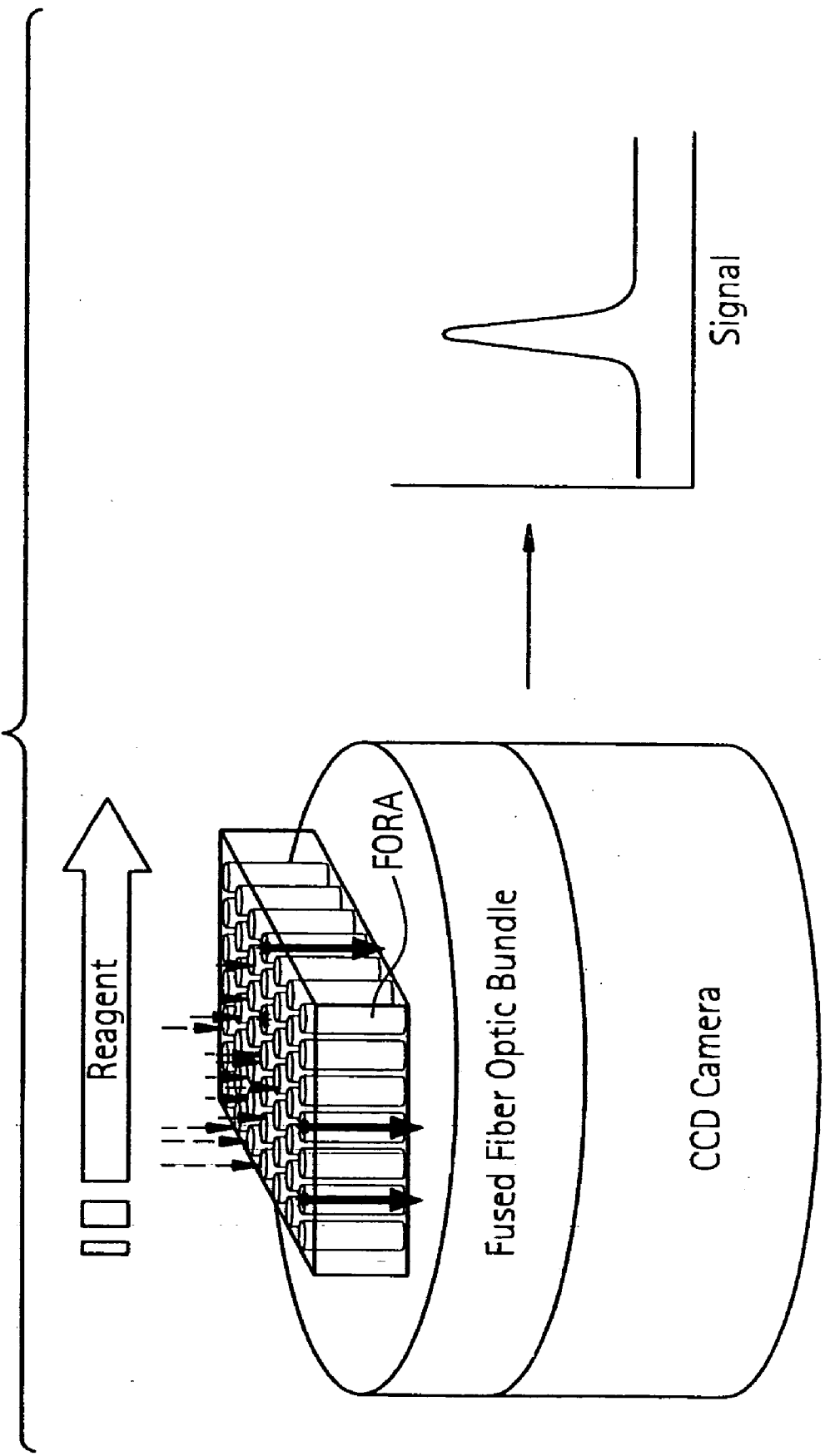
FIG. 18 depicts a schematic illustration of microscopic parallel sequencing reactions within a PicoTiter Plate™.
Figure 19:
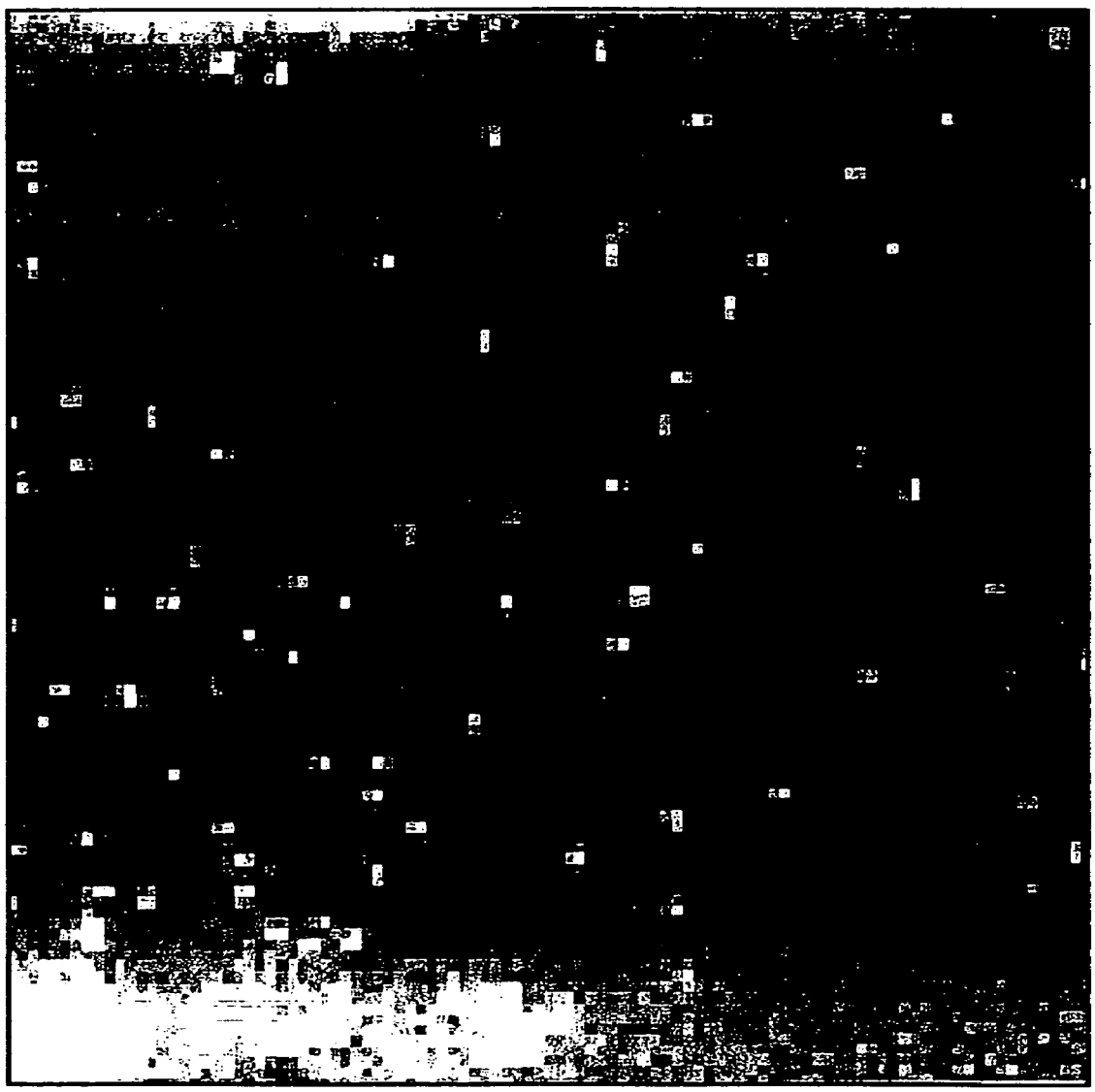
FIG. 19 depicts a micrograph of single well reactions.

A picotiter plate that has been "carpeted" with mobile solid supports with either nucleic acid or reagent enzymes attached thereto is shown as FIG. 15.

5. Methods of Sequencing Nucleic Acids

Pyrophosphate-based sequencing is then performed. The sample DNA sequence and the extension primer are then subjected to a polymerase reaction in the presence of a nucleotide triphosphate whereby the nucleotide triphosphate will only become incorporated and release pyrophosphate (PPi) if it is complementary to the base in the target position, the nucleotide triphosphate being added either to separate aliquots of sample-primer mixture or successively to the same sample-primer mixture. The release of PPi is then detected to indicate which nucleotide is incorporated.

In one embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides. The sequence can be determined by detecting a sequence reaction byproduct, as is described below.

The sequence primer can be any length or base composition, as long as it is capable of specifically annealing to a region of the amplified nucleic acid template. No particular structure for the sequencing primer is required so long as it is able to specifically prime a region on the amplified template nucleic acid. Preferably, the sequencing primer is complementary to a region of the template that is between the sequence to be characterized and the sequence hybridizable to the anchor primer. The sequencing primer is extended with the DNA polymerase to form a sequence product. The extension is performed in the presence of one or more types of nucleotide triphosphates, and if desired, auxiliary binding proteins.

Incorporation of the dNTP is preferably determined by assaying for the presence of a sequencing byproduct. In a preferred embodiment, the nucleotide sequence of the sequencing product is determined by measuring inorganic pyrophosphate (PPi) liberated from a nucleotide triphosphate (dNTP) as the dNMP is incorporated into an extended sequence primer. This method of sequencing, termed Pyrosequencing™ technology (PyroSequencing AB, Stockholm, Sweden) can be performed in solution (liquid phase) or as a solid phase technique. PPi-based sequencing methods are described generally in, e.g., WO9813523A1, Ronaghi, et al., 1996. *Anal. Biochem.* 242: 84-89, Ronaghi, et al., 1998. *Science* 281: 363-365 (1998) and U.S. Ser. No. 2001/0024790. These disclosures of PPi sequencing are incorporated herein in their entirety, by reference. See also , e.g., U.S. Pat. Nos. 6,210,891 and 6,258,568, each fully incorporated herein by reference.

Pyrophosphate released under these conditions can be detected enzymatically (e.g., by the generation of light in the luciferase-luciferin reaction). Such methods enable a nucleotide to be identified in a given target position, and the DNA to be sequenced simply and rapidly while avoiding the need for electrophoresis and the use of potentially dangerous radiolabels.

PPi can be detected by a number of different methodologies, and various enzymatic methods have been previously described (see e.g., Reeves, et al., 1969. *Anal. Biochem.* 28: 282-287; Guillory, et al., 1971. *Anal. Biochem.* 39: 170-180; Johnson, et al., 1968. *Anal. Biochem.* 15: 273; Cook, et al., 1978. *Anal. Biochem.* 91: 557-565; and Drake, et al., 1979. *Anal. Biochem.* 94: 117-120).

PPi liberated as a result of incorporation of a dNTP by a polymerase can be converted to ATP using, e.g., an ATP sulfurylase. This enzyme has been identified as being involved in sulfur metabolism. Sulfur, in both reduced and oxidized forms, is an essential mineral nutrient for plant and animal growth (see e.g., Schmidt and Jager, 1992. *Ann. Rev. Plant Physiol. Plant Mol. Biol.* 43: 325-349). In both plants and microorganisms, active uptake of sulfate is followed by reduction to sulfide. As sulfate has a very low oxidation/reduction potential relative to available cellular reductants, the primary step in assimilation requires its activation via an ATP-dependent reaction (see e.g., Leyh, 1993. *Crit. Rev. Biochem. Mol. Biol.* 28: 515-542). ATP sulfurylase (ATP: sulfate adenylyltransferase; EC 2.7.7.4) catalyzes the initial reaction in the metabolism of inorganic sulfate ($SO_4^{-2}$); see e.g., Robbins and Lipmann, 1958. *J. Biol. Chem.* 233: 686-690; Hawes and Nicholas, 1973. *Biochem. J.* 133: 541-550). In this reaction $SO_4^{-2}$ is activated to adenosine 5'-phosphosulfate (APS).

ATP sulfurylase has been highly purified from several sources, such as *Saccharomyces cerevisiae* (see e.g., Hawes and Nicholas, 1973. *Biochem. J.* 133: 541-550); *Penicillium chrysogenum* (see e.g., Renosto, et al., 1990. *J. Biol. Chem.* 265: 10300-10308); rat liver (see e.g., Yu, et al., 1989. *Arch. Biochem. Biophys.* 269: 165-174); and plants (see e.g., Shaw and Anderson, 1972. *Biochem. J.* 127: 237-247; Osslund, et al., 1982. *Plant Physiol.* 70: 39-45). Furthermore, ATP sulfurylase genes have been cloned from prokaryotes (see e.g., Leyh, et al., 1992. *J. Biol. Chem.* 267: 10405-10410; Schwedock and Long, 1989. *Mol. Plant Microbe Interaction* 2: 181-194; Laue and Nelson, 1994. *J. Bacteriol.* 176: 3723-3729); eukaryotes (see e.g., Cherest, et al., 1987. *Mol. Gen. Genet.* 210: 307-313; Mountain and Korch, 1991. *Yeast* 7: 873-880; Foster, et al., 1994. *J. Biol. Chem.* 269: 19777-19786); plants (see e.g., Leustek, et al., 1994. *Plant Physiol.* 105: 897-90216); and animals (see e.g., Li, et al., 1995. *J. Biol. Chem.* 270: 29453-29459). The enzyme is a homooligomer or heterodimer, depending upon the specific source (see e.g., Leyh and Suo, 1992. *J. Biol. Chem.* 267: 542-545).

In some embodiments, a thermostable sulfurylase is used. Thermostable sulfurylases can be obtained from, e.g., *Archaeoglobus* or *Pyrococcus* spp. Sequences of thermostable sulfurylases are available at database Acc. No. 028606, Acc. No. Q9YCR4, and Acc. No. P56863.

ATP sulfurylase has been used for many different applications, for example, bioluminometric detection of ADP at high concentrations of ATP (see e.g., Schultz, et al., 1993. *Anal. Biochem.* 215: 302-304); continuous monitoring of DNA polymerase activity (see e.g., Nyrbn, 1987. *Anal. Biochem.* 167: 235-238); and DNA sequencing (see e.g., Ronaghi, et al., 1996. *Anal. Biochem.* 242: 84-89; Ronaghi, et al., 1998. *Science* 281: 363-365; Ronaghi, et al., 1998. *Anal. Biochem.* 267: 65-71).

Several assays have been developed for detection of the forward ATP sulfurylase reaction. The colorimetric molybdolysis assay is based on phosphate detection (see e.g., Wilson and Bandurski, 1958. *J. Biol. Chem.* 233: 975-981), whereas the continuous spectrophotometric molybdolysis assay is based upon the detection of NADH oxidation (see e.g., Seubert, et al., 1983. *Arch. Biochem. Biophys.* 225: 679-691; Seubert, et al., 1985. *Arch. Biochem. Biophys.* 240: 509-523). The later assay requires the presence of several detection enzymes. In addition, several radioactive assays have also been described in the literature (see e.g., Daley, et al., 1986. *Anal. Biochem.* 157: 385-395). For example, one assay is based upon the detection of $^{32}$PPi released from $^{32}$P-labeled ATP (see e.g., Seubert, et al., 1985. *Arch. Biochem. Biophys.* 240: 509-523) and another on the incorporation of $^{35}$S into [$^{35}$S]-labeled APS (this assay also requires purified APS kinase as a coupling enzyme; see e.g., Seubert, et al., 1983. *Arch. Biochem. Biophys.* 225: 679-691); and a third reaction depends upon the release of $^{35}SO_4^{-2}$ from [$^{35}$S]-labeled APS (see e.g., Daley, et al, 1986. *Anal. Biochem.* 157: 385-395).

For detection of the reversed ATP sulfurylase reaction a continuous spectrophotometric assay (see e.g., Segel, et al., 1987. *Methods Enzymol.* 143: 334-349); a bioluminometric assay (see e.g., Balharry and Nicholas, 1971. *Anal. Biochem.* 40: 1-17); an $^{35}SO_4^{-2}$ release assay (see e.g., Seubert, et al., 1985. *Arch. Biochem. Biophys.* 240: 509-523); and a $^{32}$PPi incorporation assay (see e.g., Osslund, et al., 1982. *Plant Physiol.* 70: 39-45) have been previously described.

ATP produced by an ATP sulfurylase can be hydrolyzed using enzymatic reactions to generate light. Light-emitting chemical reactions (i.e., chemiluminescence) and biological reactions (i.e., bioluminescence) are widely used in analytical biochemistry for sensitive measurements of various metabolites. In bioluminescent reactions, the chemical reaction that leads to the emission of light is enzyme-catalyzed. For example, the luciferin-luciferase system allows for specific assay of ATP and the bacterial luciferase-oxidoreductase system can be used for monitoring of NAD(P)H. Both systems have been extended to the analysis of numerous substances by means of coupled reactions involving the production or utilization of ATP or NAD(P)H (see e.g., Kricka, 1991. Chemiluminescent and bioluminescent techniques. *Clin. Chem.* 37: 1472-1281).

The development of new reagents have made it possible to obtain stable light emission proportional to the concentrations of ATP (see e.g., Lundin, 1982. Applications of firefly luciferase In; *Luminescent Assays* (Raven Press, New York) or NAD(P)H (see e.g., Lovgren, et al., Continuous monitoring of NADH-converting reactions by bacterial luminescence. *J. Appl. Biochem.* 4: 103-111). With such stable light emission reagents, it is possible to make endpoint assays and to calibrate each individual assay by addition of a known amount of ATP or NAD(P)H. In addition, a stable lightemitting system also allows continuous monitoring of ATP- or NAD(P)H-converting systems.

Suitable enzymes for converting ATP into light include luciferases, e.g., insect luciferases. Luciferases produce light as an end-product of catalysis. The best known light-emitting enzyme is that of the firefly, *Photinus pyralis* (*Coleoptera*). The corresponding gene has been cloned and expressed in bacteria (see e.g., de Wet, et al., 1985. *Proc. Natl. Acad. Sci. USA* 80: 7870-7873) and plants (see e.g., Ow, et al., 1986. *Science* 234: 856-859), as well as in insect (see e.g., Jha, et al., 1990. *FEBS Lett.* 274: 24-26) and mammalian cells (see e.g., de Wet, et al., 1987. *Mol. Cell. Biol.* 7: 725-7373; Keller, et al., 1987. *Proc. Natl. Acad. Sci. USA* 82: 3264-3268). In addition, a number of luciferase genes from the Jamaican click beetle, *Pyroplorus plagiophihalamus* (*Coleoptera*), have recently been cloned and partially characterized (see e.g., Wood, et al., 1989. *J. Biolumin. Chemilumin.* 4: 289-301; Wood, et al., 1989. *Science* 244: 700-702). Distinct luciferases can sometimes produce light of different wavelengths, which may enable simultaneous monitoring of light emissions at different wavelengths. Accordingly, these aforementioned characteristics are unique, and add new dimensions with respect to the utilization of current reporter systems.

Firefly luciferase catalyzes bioluminescence in the presence of luciferin, adenosine 5'-triphosphate (ATP), magnesium ions, and oxygen, resulting in a quantum yield of 0.88 (see e.g., McElroy and Selinger, 1960. *Arch. Biochem. Biophys.* 88: 136-145). The firefly luciferase bioluminescent reaction can be utilized as an assay for the detection of ATP with a detection limit of approximately $1 \times 10^{-13}$ M (see e.g., Leach, 1981. *J. Appl. Biochem.* 3: 473-517). In addition, the overall degree of sensitivity and convenience of the luciferase-mediated detection systems have created considerable interest in the development of firefly luciferase-based biosensors (see e.g., Green and Kricka, 1984. *Talanta* 31: 173-176; Blum, et al., 1989. *J. Biolumin. Chemilumin.* 4: 543-550).

Using the above-described enzymes, the sequence primer is exposed to a polymerase and a known dNTP. If the dNTP is incorporated onto the 3' end of the primer sequence, the dNTP is cleaved and a PPi molecule is liberated. The PPi is then converted to ATP with ATP sulfurylase. Preferably, the ATP sulfurylase is present at a sufficiently high concentration that the conversion of PPi proceeds with first-order kinetics with respect to PPi. In the presence of luciferase, the ATP is hydrolyzed to generate a photon. The reaction preferably has a sufficient concentration of luciferase present within the reaction mixture such that the reaction, ATP→ADP+$PO_4^{3-}$+photon (light), proceeds with first-order kinetics with respect to ATP. The photon can be measured using methods and apparatuses described below. In one embodiment, the PPi and a coupled sulfurylase/luciferase reaction is used to generate light for detection. In some embodiments, either or both the sulfurylase and luciferase are immobilized on one or more mobile solid supports disposed at each reaction site.

The present invention thus permits PPi release to be detected during the polymerase reaction giving a real-time signal. The sequencing reactions may be continuously monitored in real-time. A procedure for rapid detection of PPi release is thus enabled by the present invention. The reactions have been estimated to take place in less than 2 seconds (Nyren and Lundin, supra). The rate limiting step is the conversion of PPi to ATP by ATP sulfurylase, while the luciferase reaction is fast and has been estimated to take less than 0.2 seconds. Incorporation rates for polymerases have also been estimated by various methods and it has been found, for example, that in the case of Klenow polymerase, complete incorporation of one base may take less than 0.5 seconds. Thus, the estimated total time for incorporation of one base and detection by this enzymatic assay is approximately 3 seconds. It will be seen therefore that very fast reaction times are possible, enabling real-time detection. The reaction times could further be decreased by using a more thermostable luciferase.

For most applications it is desirable to use reagents free of contaminants like ATP and PPi. These contaminants may be removed by flowing the reagents through a pre-column containing apyrase and/-or pyrophosphatase bound to resin. Alternatively, the apyrase or pyrophosphatase can be bound to magnetic beads and used to remove contaminating ATP and PPi present in the reagents. In addition it is desirable to wash away diffusible sequencing reagents, e.g., unincorporated dNTPs, with a wash buffer. Any wash buffer used in pyrophosphate sequencing can be used.

In some embodiments, the concentration of reactants in the sequencing reaction include 1 pmol DNA, 3 pmol polymerase, 40 pmol dNTP in 0.2 ml buffer. See Ronaghi, et al., *Anal. Biochem.* 242: 84-89 (1996).

The sequencing reaction can be performed with each of four predetermined nucleotides, if desired. A "complete" cycle generally includes sequentially administering sequencing reagents for each of the nucleotides dATP, dGTP, dCTP and dTTP (or dUTP), in a predetermined order. Unincorporated dNTPs are washed away between each of the nucleotide additions. Alternatively, unincorporated dNTPs are degraded by apyrase (see below). The cycle is repeated as desired until the desired amount of sequence of the sequence product is obtained. In some embodiments, about 10-1000, 10-100, 10-75, 20-50, or about 30 nucleotides of sequence information is obtained from extension of one annealed sequencing primer.

In some embodiments, the nucleotide is modified to contain a disulfide-derivative of a hapten such as biotin. The addition of the modified nucleotide to the nascent primer annealed to the anchored substrate is analyzed by a post-polymerization step that includes i) sequentially binding of, in the example where the modification is a biotin, an avidin- or streptavidin-conjugated moiety linked to an enzyme molecule, ii) the washing away of excess avidin- or streptavidin-linked enzyme, iii) the flow of a suitable enzyme substrate under conditions amenable to enzyme activity, and iv) the detection of enzyme substrate reaction product or products. The hapten is removed in this embodiment through the addition of a reducing agent. Such methods enable a nucleotide to be identified in a given target position, and the DNA to be sequenced simply and rapidly while avoiding the need for electrophoresis and the use of potentially dangerous radiolabels.

A preferred enzyme for detecting the hapten is horse-radish peroxidase. If desired, a wash buffer, can be used between the addition of various reactants herein. Apyrase can be used to remove unreacted dNTP used to extend the sequencing primer. The wash buffer can optionally include apyrase.

Example haptens, e.g., biotin, digoxygenin, the fluorescent dye molecules cy3 and cy5, and fluorescein, are incorporated at various efficiencies into extended DNA molecules. The attachment of the hapten can occur through linkages via the sugar, the base, and via the phosphate moiety on the nucleotide. Example means for signal amplification include fluorescent, electrochemical and enzymatic. In a preferred embodiment using enzymatic amplification, the enzyme, e.g. alkaline phosphatase (AP), horse-radish peroxidase (HRP), beta-galactosidase, luciferase, can include those for which light-generating substrates are known, and the means for detection of these light-generating (chemiluminescent) substrates can include a CCD camera.

In a preferred mode, the modified base is added, detection occurs, and the hapten-conjugated moiety is removed or inactivated by use of either a cleaving or inactivating agent. For example, if the cleavable-linker is a disulfide, then the cleaving agent can be a reducing agent, for example dithiothreitol (DTT), beta-mercaptoethanol, etc. Other embodiments of inactivation include heat, cold, chemical denaturants, surfactants, hydrophobic reagents, and suicide inhibitors.

Luciferase can hydrolyze dATP directly with concomitant release of a photon. This results in a false positive signal because the hydrolysis occurs independent of incorporation of the dATP into the extended sequencing primer. To avoid this problem, a dATP analog can be used which is incorporated into DNA, i.e., it is a substrate for a DNA polymerase, but is not a substrate for luciferase. One such analog is α-thio-dATP. Thus, use of α-thio-dATP avoids the spurious photon generation that can occur when dATP is hydrolyzed without being incorporated into a growing nucleic acid chain.

Typically, the PPi-based detection is calibrated by the measurement of the light released following the addition of control nucleotides to the sequencing reaction mixture immediately after the addition of the sequencing primer. This allows for normalization of the reaction conditions. Incorporation of two or more identical nucleotides in succession is revealed by a corresponding increase in the amount of light released. Thus, a two-fold increase in released light relative to control nucleotides reveals the incorporation of two successive dNTPs into the extended primer.

If desired, apyrase may be "washed" or "flowed" over the surface of the solid support so as to facilitate the degradation of any remaining, non-incorporated dNTPs within the sequencing reaction mixture. Apyrase also degrades the generated ATP and hence "turns off" the light generated from the reaction. Upon treatment with apyrase, any remaining reactants are washed away in preparation for the following dNTP incubation and photon detection steps. Alternatively, the apyrase may be bound to the solid or mobile solid support.

Double Ended Sequencing

In a preferred embodiment we provide a method for sequencing from both ends of a nucleic acid template. Traditionally, the sequencing of two ends of a double stranded DNA molecule would require at the very least the hybridization of primer, sequencing of one end, hybridization of a second primer, and sequencing of the other end. The alternative method is to separate the individual strands of the double stranded nucleic acid and individually sequence each strand. The present invention provides a third alternative that is more rapid and less labor intensive than the first two methods.

The present invention provides for a method of sequential sequencing of nucleic acids from multiple primers. References to DNA sequencing in this application are directed to sequencing using a polymerase wherein the sequence is determined as the nucleotide triphosphate (NTP) is incorporated into the growing chain of a sequencing primer. One example of this type of sequencing is the pyro-sequencing detection pyrophosphate method (see, e.g., U.S. Pat. Nos. 6,274,320, 6,258,568 and 6,210,891, each of which is incorporated in total herein by reference.).

In one embodiment, the present invention provides for a method for sequencing two ends of a template double stranded nucleic acid. The double stranded DNA is comprised of two single stranded DNA; referred to herein as a first single stranded DNA and a second single stranded DNA. A first primer is hybridized to the first single stranded DNA and a second primer is hybridized to the second single stranded DNA. The first primer is unprotected while the second primer is protected. "Protection" and "protected" are defined in this disclosure as being the addition of a chemical group to reactive sites on the primer that prevents a primer from polymerization by DNA polymerase. Further, the addition of such chemical protecting groups should be reversible so that after reversion, the now deprotected primer is once again able to serve as a sequencing primer. The nucleic acid sequence is determined in one direction (e.g., from one end of the template) by elongating the first primer with DNA polymerase using conventional methods such as pyrophosphate sequencing. The second primer is then deprotected, and the sequence is determined by elongating the second primer in the other direction (e.g., from the other end of the template) using DNA polymerase and conventional methods such as pyrophosphate sequencing. The sequences of the first and second primers are specifically designed to hybridize to the two ends of the double stranded DNA or at any location along the template in this method.

In another embodiment, the present invention provides for a method of sequencing a nucleic acid from multiple primers. In this method a number of sequencing primers are hybridized to the template nucleic acid to be sequenced. All the sequencing primers are reversibly protected except for one. A protected primer is an oligonucleotide primer that cannot be extended with polymerase and dNTPs which are commonly used in DNA sequencing reactions. A reversibly protected primer is a protected primer which can be deprotected. All protected primers referred to in this invention are reversibly protected. After deprotection, a reversibly protected primer functions as a normal sequencing primer and is capable of participating in a normal sequencing reaction.

The present invention provides for a method of sequential sequencing a nucleic acid from multiple primers. The method comprises the following steps: First, one or more template nucleic acids to be sequenced are provided. Second, a plurality of sequencing primers are hybridized to the template nucleic acid or acids. The number of sequencing primers may be represented by the number n where n can be any positive number greater than 1. That number may be, for example, 2, 3, 4, 5, 6, 7, 8, 9, 10 or greater. Of the primers, n−1 number may be protected by a protection group. So, for example, if n is 2, 3, 4, 5, 6, 7, 8, 9 or 10, n−1 would be 1, 2, 3, 4, 5, 6, 7, 8, 9 respectively. The remaining primer (e.g., n number primers−(n−1) number of protected primers=one remaining primer) is unprotected. Third, the unprotected primer is extended and the template DNA sequence is determined by conventional methods such as, for example, pyrophosphate sequencing. Fourth, after the sequencing of the first primer, one of the remaining protected primers is unprotected. Fifth, unprotected primer is extended and the template DNA sequence is determined by conventional methods such as, for example, pyrophosphate sequencing. Optionally, the method may be repeated until sequencing is performed on all the protected primers.

In another aspect, the present invention includes a method of sequential sequencing of a nucleic acid comprising the steps of: (a) hybridizing 2 or more sequencing primers to the nucleic acid wherein all the primers except for one are reversibly protected; (b) determining a sequence of one strand of the nucleic acid by polymerase elongation from the unprotected primer; (c) deprotecting one of the reversibly protected primers into an unprotected primer; (d) repeating steps (b) and (c) until all the reversibly protected primers are deprotected and used for determining a sequence. In one embodiment, this method comprises one additional step between steps (b) and (c), i.e., the step of terminating the elongation of the unprotected primer by contacting the unprotected primer with DNA polymerase and one or more of a nucleotide triphosphate or a dideoxy nucleotide triphosphate. In yet another embodiment, this method further comprises an additional step between said step (b) and (c), i.e., terminating the elongation of the unprotected primer by contacting the unprotected primer with DNA polymerase and a dideoxy nucleotide triphosphate from ddATP, ddTTP, ddCTP, ddGTP or a combination thereof.

In another aspect, this invention includes a method of sequencing a nucleic acid comprising: (a) hybridizing a first unprotected primer to a first strand of the nucleic acid; (b) hybridizing a second protected primer to a second strand; (c) exposing the first and second strands to polymerase, such that the first unprotected primer is extended along the first strand; (d) completing the extension of the first sequencing primer; (e) deprotecting the second sequencing primer; and (f) exposing the first and second strands to polymerase so that the second sequencing primer is extended along the second strand. In a preferred embodiment, completing comprises capping or terminating the elongation.

In another embodiment, the present invention provides for a method for sequencing two ends of a template double stranded nucleic acid that comprises a first and a second single stranded DNA. In this embodiment, a first primer is hybridized to the first single stranded DNA and a second primer is hybridized to the second single stranded DNA in the same step. The first primer is unprotected while the second primer is protected.

Following hybridization, the nucleic acid sequence is determined in one direction (e.g., from one end of the template) by elongating the first primer with DNA polymerase using conventional methods such as pyrophosphate sequencing. In a preferred embodiment, the polymerase is devoid of 3' to 5' exonuclease activity. The second primer is then deprotected, and its sequence is determined by elongating the second primer in the other direction (e.g., from the other end of the template) with DNA polymerase using conventional methods such as pyrophosphate sequencing. As described earlier, the sequences of the first primer and the second primer are designed to hybridize to the two ends of the double stranded DNA or at any location along the template. This technique is especially useful for the sequencing of many template DNAs that contain unique sequencing primer hybridization sites on its two ends. For example, many cloning vectors provide unique sequencing primer hybridization sites flanking the insert site to facilitate subsequent sequencing of any cloned sequence (e.g., Bluescript, Stratagene, La Jolla, Calif.).

One benefit of this method of the present invention is that both primers may be hybridized in a single step. The benefits of this and other methods are especially useful in parallel sequencing systems where hybridizations are more involved than normal. Examples of parallel sequencing systems are disclosed in copending U.S. patent application Ser. No. 10/104,280, the disclosure of which is incorporated in total herein.

The oligonucleotide primers of the present invention may be synthesized by conventional technology, e.g., with a commercial oligonucleotide synthesizer and/or by ligating together subfragments that have been so synthesized.

In another embodiment of the invention, the length of the double stranded target nucleic acid may be determined. Methods of determining the length of a double stranded nucleic acid are known in the art. The length determination may be performed before or after the nucleic acid is sequenced. Known methods of nucleic acid molecule length determination include gel electrophoresis, pulsed field gel electrophoresis, mass spectroscopy and the like. Since a blunt ended double stranded nucleic acid is comprised of two single strands of identical lengths, the determination of the length of one strand of a nucleic acid is sufficient to determine the length of the corresponding double strand.

The sequence reaction according to the present invention also allows a determination of the template nucleic acid length. First, a complete sequence from one end of the nucleic acid to another end will allow the length to be determined. Second, the sequence determination of the two ends may overlap in the middle allowing the two sequences to be linked. The complete sequence may be determined and the length may be revealed. For example, if the template is 100 bps long, sequencing from one end may determine bases 1 to 75; sequencing from the other end may determine bases 25 to 100; there is thus a 51 base overlap in the middle from base 25 to base 75; and from this information, the complete sequence from 1 to 100 may be determined and the length, of 100 bases, may be revealed by the complete sequence.

Another method of the present invention is directed to a method comprising the following steps. First a plurality of sequencing primers, each with a different sequence, is hybridized to a DNA to be sequenced. The number of sequencing primers may be any value greater than one such as, for example, 2, 3, 4, 5, 6, 7, 8, 9, 10 or more. All of these primers are reversibly protected except for one. The one unprotected primer is elongated in a sequencing reaction and a sequence is determined. Usually, when a primer is completely elongated, it cannot extend and will not affect subsequent sequencing from another primer. If desired, the sequenced primer may be terminated using excess polymerase and dNTP or using ddNTPs. If a termination step is taken, the termination reagents (dNTPs and ddNTPs) should be removed after the step. Then, one of the reversibly protected primers is unprotected and sequencing from the second primer proceeds. The steps of deprotecting a primer, sequencing from the deprotected primer, and optionally, terminating sequencing from the primer is repeated until all the protected primers are unprotected and used in sequencing.

The reversibly protected primers should be protected with different chemical groups. By choosing the appropriate method of deprotection, one primer may be deprotected without affecting the protection groups of the other primers. In a preferred embodiment, the protection group is $PO_4$. That is, the second primer is protected by $PO_4$ and deprotection is accomplished by T4 polynucleotide kinase (utilizing its 3'-phosphatase activity). In another preferred embodiment, the protection is a thio group or a phosphorothiol group.

The template nucleic acid may be a DNA, RNA, or peptide nucleic acid (PNA). While DNA is the preferred template, RNA and PNA may be converted to DNA by known techniques such as random primed PCR, reverse transcription, RT-PCR or a combination of these techniques. Further, the methods of the invention are useful for sequencing nucleic acids of unknown and known sequence. The sequencing of nucleic acid of known sequence would be useful, for example, for confirming the sequence of synthesized DNA or for confirming the identity of suspected pathogen with a known nucleic acid sequence. The nucleic acids may be a mixture of more than one population of nucleic acids. It is known that a sequencing primer with sufficient specificity (e.g., 20 bases, 25 bases, 30 bases, 35 bases, 40 bases, 45 bases, or 50 bases) may be used to sequence a subset of sequences in a long nucleic acid or in a population of unrelated nucleic acids. Thus, for example, the template may be one sequence of 10 Kb or ten sequences of 1 Kb each. In a preferred embodiment, the template DNA is between 50 bp to 700 bp in length. The DNA can be single stranded or double stranded.

In the case where the template nucleic acid is single stranded, a number of primers may be hybridized to the template nucleic acid as shown below:

```
5'--primer 4 --3'   5'-primer 3 --3'   5'-primer 2 -3'   5'-primer 1-3'

3'--------------------------template nucleic acid ----------------------------------5'
```

In this case, it is preferred that the initial unprotected primer would be the primer that hybridizes at the most 5' end of the template. See primer 1 in the above illustration. In this orientation, the elongation of primer 1 would not displace (by strand displacement) primer 2, 3, or 4. When sequencing from primer 1 is finished, primer 2 can be unprotected and nucleic acid sequencing can commence. The sequencing from primer 2 may displace primer 1 or the elongated version of primer one but would have no effect on the remaining protected primers (primers 3 and 4). Using this order, each primer may be used sequentially and a sequencing reaction from one primer would not affect the sequencing from a subsequent primer.

One feature of the invention is the ability to use multiple sequencing primers on one or more nucleic acids and the ability to sequence from multiple primers using only one hybridization step. In the hybridization step, all the sequencing primers (e.g., the n number of sequencing primers) may be hybridized to the template nucleic acid(s) at the same time. In conventional sequencing, usually one hybridization step is required for sequencing from one primer. One feature of the invention is that the sequencing from n primers (as defined above) may be performed by a single hybridization step. This effectively eliminates n–1 hybridization step.

In a preferred embodiment, the sequences of the n number of primers are sufficiently different that the primers do not cross hybridize or self-hybridize. Cross hybridization refers to the hybridization of one primer to another primer because of sequence complementarity. One form of cross hybridization is commonly referred to as a "primer dimer." In the case of a primer dimer, the 3' ends of two primers are complementary and form a structure that when elongated, is approximately the sum of the length of the two primers. Self-hybridization refers to the situation where the 5' end of a primer is complementary to the 3' end of the primer. In that case, the primer has a tendency to self hybridize to form a hairpin-like structure.

A primer can interact or become associated specifically with the template molecule. By the terms "interact" or "associate", it is meant herein that two substances or compounds (e.g., primer and template; chemical moiety and nucleotide) are bound (e.g., attached, bound, hybridized, joined, annealed, covalently linked, or otherwise associated) to one another sufficiently that the intended assay can be conducted. By the terms "specific" or "specifically", it is meant herein that two components bind selectively to each other. The parameters required to achieve specific interactions can be determined routinely, e.g., using conventional methods in the art.

To gain more sensitivity or to help in the analysis of complex mixtures, the protected primers can be modified (e.g., derivatized) with chemical moieties designed to give clear unique signals. For example, each protected primer can be derivatized with a different natural or synthetic amino acid attached through an amide bond to the oligonucleotide strand at one or more positions along the hybridizing portion of the strand. The chemical modification can be detected, of course, either after having been cleaved from the target nucleic acid, or while in association with the target nucleic acid. By allowing each protected target nucleic acid to be identified in a distinguishable manner, it is possible to assay (e.g., to screen) for a large number of different target nucleic acids in a single assay. Many such assays can be performed rapidly and easily. Such an assay or set of assays can be conducted, therefore, with high throughput efficiency as defined herein.

In the methods of the invention, after a first primer is elongated and the sequence of the template DNA is determined, a second primer is deprotected and sequenced. There is no interference between the sequencing reaction of the first primer with the sequencing reaction of the second, now unprotected, primer because the first primer is completely elongated or terminated. Because the first primer is completely elongated, the sequencing from the second primer, using conventional methods such a pyrophosphate sequencing, will not be affected by the presence of the elongated first primer. The invention also provides a method of reducing any possible signal contamination from the first primer. Signal contamination refers to the incidences where the first primer is not completely elongated. In that case, the first primer will continue to elongate when a subsequent primer is deprotected and elongated. The elongation of both the first and second primers may interfere with the determination of DNA sequence.

In a preferred embodiment, the sequencing reaction (e.g., the chain elongation reaction) from one primer is first terminated or completed before a sequencing reaction is started on a second primer. A chain elongation reaction of DNA can be terminated by contacting the template DNA with DNA polymerase and dideoxy nucleotide triphosphates (ddNTPs) such as ddATP, ddTTP, ddGTP and ddCTP. Following termination, the dideoxy nucleotide triphosphates may be removed by washing the reaction with a solution without ddNTPs. A second method of preventing further elongation of a primer is to add nucleotide triphosphates (dNTPs such as dATP, dTTP, dGTP and dCTP) and DNA polymerase to a reaction to completely extend any primer that is not completely extended. Following complete extension, the dNTPs and the polymerases are removed before the next primer is deprotected. By completing or terminating one primer before deprotecting another primer, the signal to noise ratio of the sequencing reaction (e.g., pyrophosphate sequencing) can be improved.

The steps of (a) optionally terminating or completing the sequencing, (b) deprotecting a new primer, and (c) sequencing from the deprotected primer may be repeated until a sequence is determined from the elongation of each primer. In this method, the hybridization step comprises "n" number of primers and one unprotected primer. The unprotected primer is sequenced first and the steps of (a), (b) and (c) above may be repeated.

In a preferred embodiment, pyrophosphate sequencing is used for all sequencing conducted in accordance with the method of the present invention.

Figure 10C:
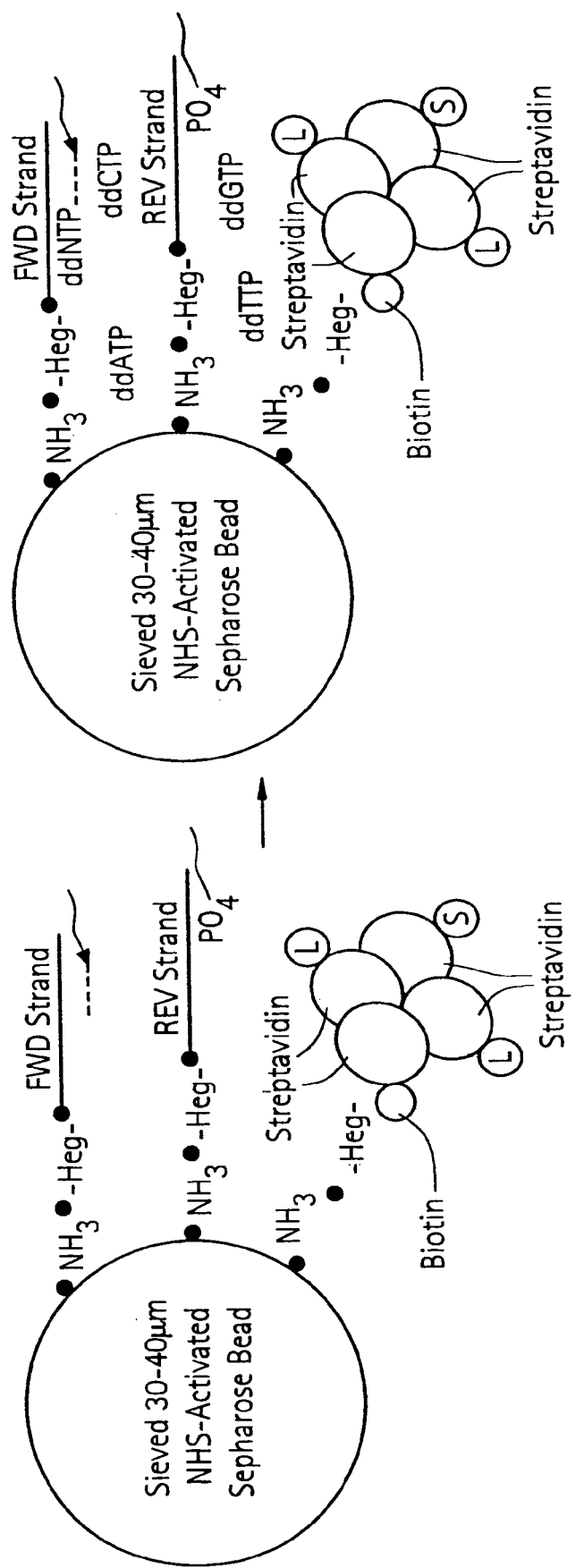
Figure 10D:
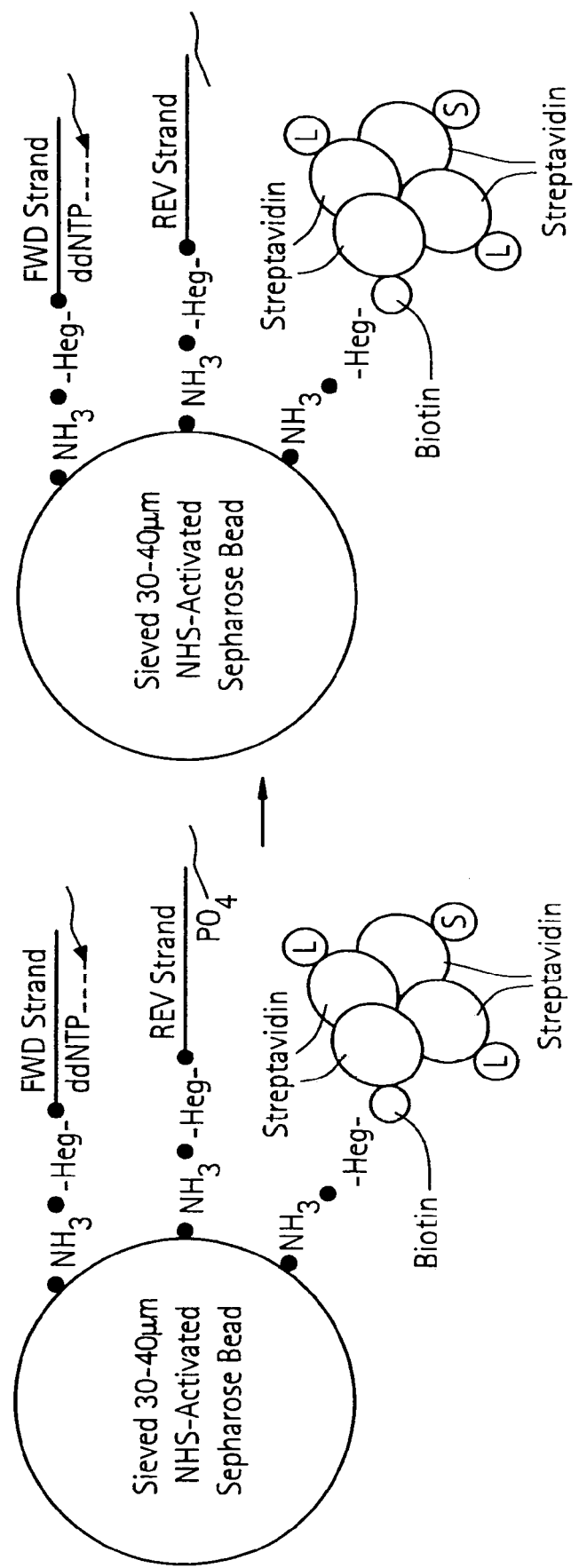
Figure 10E:
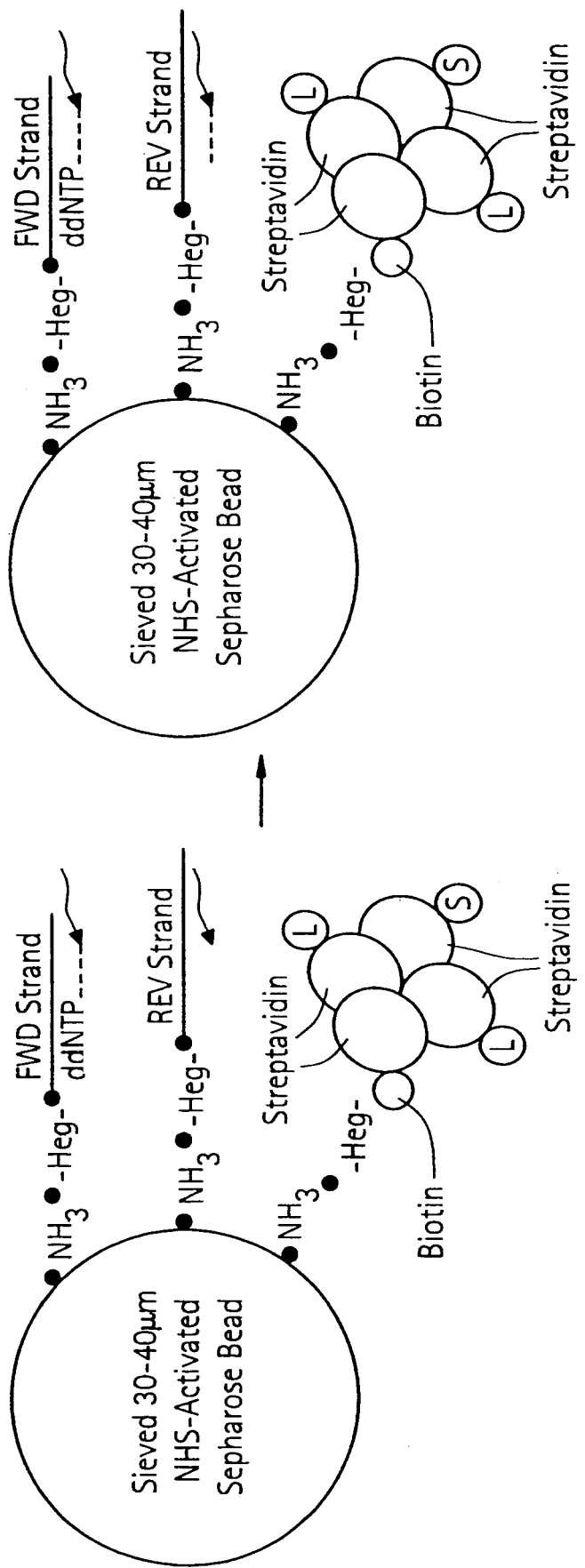

In another preferred embodiment, the double ended sequencing is performed according to the process outlined in FIG. 10. This process may be divided into six steps: (1) creation of a capture bead (FIG. 10A); (2) drive to bead (DTB) PCR amplification (FIG. 10B); (3) SL reporter system preparation (FIG. 10C); (4) sequencing of the first strand (FIG. 10D); (5) preparation of the second strand (FIGS. 10E and 10F); and (6) analysis of each strand (FIG. 10G). This exemplary process is outlined below.

In step 1, an N-hydroxysuccinimide (NHS)-activated capture bead (e.g., Amersham Biosciences, Piscataway, N.J.) is coupled to both a forward primer and a reverse primer. NHS coupling forms a chemically stable amide bond with ligands containing primary amino groups. The capture bead is also coupled to biotin (FIG. 10A). The beads (i.e., solid nucleic acid capturing supports) used herein may be of any convenient size and fabricated from any number of known materials. Example of such materials include: inorganics, natural polymers, and synthetic polymers. Specific examples of these materials include: cellulose, cellulose derivatives, acrylic resins, glass; silica gels, polystyrene, gelatin, polyvinyl pyrrolidone, co-polymers of vinyl and acrylamide, polystyrene cross-linked with divinylbenzene or the like (see, Merrifield Biochemistry 1964, 3, 1385-1390), polyacrylamides, latex gels, polystyrene, dextran, rubber, silicon, plastics, nitrocellulose, celluloses, natural sponges, silica gels, glass, metals plastic, cellulose, cross-linked dextrans (e.g., Sephadex™) and agarose gel (Sepharose™) and solid phase supports known to those of skill in the art. In a preferred embodiment, the capture beads are Sepharose beads approximately 25 to 40 µM in diameter.

In step 2, template DNA which has hybridized to the forward and reverse primers is added, and the DNA is amplified through a PCR amplification strategy (FIG. 10B). In one embodiment, the DNA is amplified by Emulsion Polymerase Chain Reaction, Drive to Bead Polymerase Chain Reaction, Rolling Circle Amplification or Loop-mediated Isothermal Amplification. In step 3, streptavidin is added followed by the addition of sulfurylase and luciferase which are coupled to the streptavidin (FIG. 10C). The addition of auxiliary enzymes during a sequencing method has been disclosed in U.S. Ser. No. 10/104,280 and U.S. Ser. No. 10/127,906, which are incorporated herein in their entireties by reference. In one embodiment, the template DNA has a DNA adaptor ligated to both the 5' and 3' end. In a preferred embodiment, the DNA is coupled to the DNA capture bead by hybridization of one of the DNA adaptors to a complimentary sequence on the DNA capture bead.

In the first step, single stranded nucleic acid template to be amplified is attached to a capture bead. The nucleic acid template may be attached to the capture bead in any manner known in the art. Numerous methods exist in the art for attaching the DNA to a microscopic bead. Covalent chemical attachment of the DNA to the bead can be accomplished by using standard coupling agents, such as water-soluble carbodiimide, to link the 5'-phosphate on the DNA to amine-coated microspheres through a phosphoamidate bond. Another alternative is to first couple specific oligonucleotide linkers to the bead using similar chemistry, and to then use DNA ligase to link the DNA to the linker on the bead. Other linkage chemistries include the use of N-hydroxysuccinamide (NHS) and its derivatives, to join the oligonucleotide to the beads. In such a method, one end of the oligonucleotide may contain a reactive group (such as an amide group) which forms a covalent bond with the solid support, while the other end of the linker contains another reactive group which can bond with the oligonucleotide to be immobilized. In a preferred embodiment, the oligonucleotide is bound to the DNA capture bead by covalent linkage. However, non-covalent linkages, such as chelation or antigen-antibody complexes, may be used to join the oligonucleotide to the bead.

Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially. These methods are described in detail in U.S. Pat. No. 5,674,743, the disclosure of which is incorporated in toto herein. It is preferred that any method used to immobilize the beads will continue to bind the immobilized oligonucleotide throughout the steps in the methods of the invention. In a preferred embodiment, the oligonucleotide is bound to the DNA capture bead by covalent linkage. However, non-covalent linkages, such as chelation or antigen-antibody complexes, may be used to join the oligonucleotide to the bead.

In step 4, the first strand of DNA is sequenced by depositing the capture beads onto a PicoTiter plate (PTP), and sequencing by a method known to one of ordinary skill in the art (e.g., pyrophosphate sequencing) (FIG. 10D). Following sequencing, a mixture of dNTPs and ddNTPs are added in order to "cap" or terminate the sequencing process (FIG. 10E). In step 5, the second strand of nucleic acid is prepared by adding apyrase to remove the ddNTPs and polynucleotide kinase (PNK) to remove the 3' phosphate group from the blocked primer strand (FIG. 10F). Polymerase is then added to prime the second strand followed by sequencing of the second strand according to a standard method known to one of ordinary skill in the art (FIG. 10G). In step 7, the sequence of the both the first and second strand is analyzed such that a contiguous DNA sequence is determined.

Detection Means

The solid support is optically linked to an imaging system 230, which includes a CCD system in association with conventional optics or a fiber optic bundle. In one embodiment the perfusion chamber substrate includes a fiber optic array wafer such that light generated near the aqueous interface is transmitted directly through the optical fibers to the exterior of the substrate or chamber. When the CCD system includes a fiber optic connector, imaging can be accomplished by placing the perfusion chamber substrate in direct contact with the connector. Alternatively, conventional optics can be used to image the light, e.g., by using a 1-1 magnification high numerical aperture lens system, from the exterior of the fiber optic substrate directly onto the CCD sensor. When the substrate does not provide for fiber optic coupling, a lens system can also be used as described above, in which case either the substrate or the perfusion chamber cover is optically transparent. An exemplary CCD imaging system is described above.

The imaging system 230 is used to collect light from the reactors on the substrate surface. Light can be imaged, for example, onto a CCD using a high sensitivity low noise apparatus known in the art. For fiber-optic based imaging, it is preferable to incorporate the optical fibers directly into the cover slip or for a FORA to have the optical fibers that form the microwells also be the optical fibers that convey light to the detector.

The imaging system is linked to a computer control and data collection system 240. In general, any commonly available hardware and software package can be used. The computer control and data collection system is also linked to the conduit 200 to control reagent delivery.

The photons generated by the pyrophosphate sequencing reaction are captured by the CCD only if they pass through a focusing device (e.g., an optical lens or optical fiber) and are focused upon a CCD element. However, the emitted photons will escape equally in all directions. In order to maximize their subsequent "capture" and quantitation when utilizing a planar array (e.g., a DNA chip), it is preferable to collect the photons as close as possible to the point at which they are generated, e.g. immediately at the planar solid support. This is accomplished by either: (i) utilizing optical immersion oil between the cover slip and a traditional optical lens or optical fiber bundle or, preferably, (ii) incorporating optical fibers directly into the cover slip itself. Similarly, when a thin, optically transparent planar surface is used, the optical fiber bundle can also be placed against its back surface, eliminating the need to "image" through the depth of the entire reaction/perfusion chamber.

The reaction event, e.g., photons generated by luciferase, may be detected and quantified using a variety of detection apparatuses, e.g., a photomultiplier tube, a CCD, CMOS, absorbance photometer, a luminometer, charge injection device (CID), or other solid state detector, as well as the apparatuses described herein. In a preferred embodiment, the quantitation of the emitted photons is accomplished by the use of a CCD camera fitted with a fused fiber optic bundle. In another preferred embodiment, the quantitation of the emitted photons is accomplished by the use of a CCD camera fitted with a microchannel plate intensifier. A back-thinned CCD can be used to increase sensitivity. CCD detectors are described in, e.g., Bronks, et al., 1995. *Anal. Chem.* 65: 2750-2757.

An exemplary CCD system is a Spectral Instruments, Inc. (Tucson, Ariz.) Series 600 4-port camera with a Lockheed-Martin LM485 CCD chip and a 1-1 fiber optic connector (bundle) with 6-8 µm individual fiber diameters. This system has 4096×4096, or greater than 16 million pixels and has a quantum efficiency ranging from 10% to >40%. Thus, depending on wavelength, as much as 40% of the photons imaged onto the CCD sensor are converted to detectable electrons.

In other embodiments, a fluorescent moiety can be used as a label and the detection of a reaction event can be carried out using a confocal scanning microscope to scan the surface of an array with a laser or other techniques such as scanning near-field optical microscopy (SNOM) are available which are capable of smaller optical resolution, thereby allowing the use of "more dense" arrays. For example, using SNOM, individual polynucleotides may be distinguished when separated by a distance of less than 100 nm, e.g., 10 nm×10 nm. Additionally, scanning tunneling microscopy (Binning et al., *Helvetica Physica Acta,* 55:726-735, 1982) and atomic force microscopy (Hanswa et al., *Annu Rev Biophys Biomol Struct,* 23:115-139, 1994) can be used.

Haplotype Application

Virtually any sequencing application can be accomplished using the methods and apparatus of this invention. In one embodiment we contemplate haplotype mapping. Human gene diversity is an important factor in the variability of patient response to pharmaceuticals. The most precise measurement of this diversity is the haplotype, which is the organization of polymorphic variation as it is found on a chromosome. Recently, major government and academic genome researchers in the US, Canada and Europe have agreed that haplotypes are a powerful tool that can reduce the complexity of genetic information to a practical form. Haplotypes can be used in drug discovery to improve the outcome of target validation and drug screening studies and in drug development to improve the design and reliability of clinical trials. Haplotype markers can be used to predict the efficacy and safety of new and approved drugs and will serve as the foundation for a new paradigm of personalized medicine matching patients to the right drug at the right dose via guidance from a database of clinical marker-associations.

Numerous empirical studies have shown that nearby SNP alleles are often in linkage disequilibrium (LD) with each other, such that the state of one SNP allele is often highly correlated with the allele of another close SNP. These correlations exist because of the shared history of tightly linked SNP's, which are co-transmitted from generation to generation. Patterns of human sequence variation (haplotypes) thus represent ancestral DNA segments. Historical meioses have slowly dissociated alleles from neighboring alleles on ancestral chromosomes, except for tightly linked variants. The extent of linkage disequilibrium in founder populations with recent bottlenecks had been the object of numerous studies—particularly in the cloning of simple Mendelian disorders disorders such as cystic fibrosis (16), Huntington's disease (11), diastrophic dysplasia (DTD) (8). Whereas these cloning studies benefited from the large chromosomal segments showing LD spanning over large distances (often in the megabase range), very little empirical data was available until recently regarding LD across the human genome in the world population.

We focus on three recent examples of large-scale surveys of LD (and haplotypes): (see, e.g., Reich, D. E., Cargill, M., Bolk, S., Ireland, J., Sabeti, P. C., Richter, D. J., Lavery, T., Kouyoumjian, R., Farhadian, S. F., Ward, R. & Lander, E. S. 2001. Linkage disequilibrium in the human genome. Nature 411, 199-204.26). We sampled 19 chromosome regions for their SNP content. High frequency SNP's spanning intervals of 2 to 160 kb were first genotyped in a Caucasian samples. Over all regions, LD was detectable at distances of about 60 kb, with a significant difference between regions, as the range was as short as 6 kb at one locus and as long 155 kb in another. Not surprisingly, LD was significantly correlated with the estimated local recombination rates. Further analysis in a Nigerian sample provided evidence of shorter LD in this population—although the allelic combinations over short distances were similar to the Caucasian sample. Overall—this work provided evidence that large blocks of LD are common across the human genome, and that genome-wide LD mapping of disease genes will be feasible.

Kits

The invention also comprises kits for use in methods of the invention which could include one or more of the following components: (a) a test specific primer which hybridizes to sample DNA so that the target position is directly adjacent to the 3' end of the primer; (b) a polymerase; (c) detection enzyme means for identifying PPi release; (d) deoxynucleotides including, in place of dATP, a dATP analogue which is capable of acting as a substrate for a polymerase but incapable of acting as a substrate for a said PPi-detection enzyme; and (e) optionally dideoxynucleotides, optionally ddATP being replaced by a ddATP analogue which is capable of acting as a substrate for a polymerase but incapable of acting as a substrate for a said PPi-detection enzyme. If the kit is for use with initial PCR amplification then it could also include the following components: (i) a pair of primers for PCR, at least one primer having means permitting immobilization of said primer; (ii) a polymerase which is preferably heat stable, for example Taq1 polymerase; (iii) buffers for the PCR reaction; and (iv) deoxynucleotides. Where an enzyme label is used to evaluate PCR, the kit will advantageously contain a substrate for the enzyme and other components of a detection system.

One embodiment of the invention is directed to a method for sequencing nucleic acids. The method involves fragmenting large template nucleic acid molecules to generate a plurality of fragmented nucleic acids. Then the fragmented nucleic acids are delivered into aqueous microreactors in a water-in-oil emulsion such that a plurality of aqueous microreactors comprise a single copy of a fragmented nucleic acid, a single bead capable of binding to the fragmented nucleic acid, and amplification reaction solution containing reagents necessary to perform nucleic acid amplification. In the next step, the fragmented nucleic acids is amplified in the microreactors to form amplified copies of the nucleic acids and binding the amplified copies to beads in the microreactors. Next, the beads are delivered to an array of at least 10,000 reaction chambers on a planar surface, wherein a plurality of the reaction chambers comprise no more than a single bead. Finally, a sequencing reaction is performed simultaneously on a plurality of the reaction chambers.

Another embodiment of the invention is directed to an array comprising a planar surface with a plurality of cavities thereon, each cavity forming an analyte reaction chamber, wherein the reaction chambers have a center to center spacing of between 20 to 100 µm and each cavity has a width in at least one dimension of between 20 µm and 70 µm. Further, there are at least 10,000 reaction chambers in the array. Each reaction chambers may contain at least 100,000 copies of a single species of single stranded nucleic acid template.

Another embodiment of the invention is directed to an array comprising a planar top surface and a planar bottom surface wherein the planar top surface has at least 10,000 cavities thereon, each cavity forming an analyte reaction chamber, the planar bottom surface is optically conductive such that optical signals from the reaction chambers can be detected through the bottom planar surface, wherein the distance between the top surface and the bottom surface is no greater than 5 mm, wherein the reaction chambers have a center to center spacing of between 20 to 100 µm and each chamber having a width in at least one dimension of between 20 µm and 70 µm. The distance between the top surface and the bottom surface, in one embodiment, is no greater than 2 mm.

Another embodiment of the invention is directed to an array means for carrying out separate parallel common reactions in an aqueous environment. The array means may comprise a substrate comprising at least 10,000 discrete reaction chambers containing a starting material that is capable of reacting with a reagent, each of the reaction chambers being dimensioned such that when one or more fluids containing at least one reagent is delivered into each reaction chamber, the diffusion time for the reagent to diffuse out of the well exceeds the time required for the starting material to react with the reagent to form a product.

Another embodiment of the invention is directed to a method for delivering a bioactive agent to an array. The method comprises dispersing over the array a plurality of mobile solid supports, each mobile solid support having at least one reagent immobilized thereon, wherein the reagent is suitable for use in a nucleic acid sequencing reaction, where the array comprises a planar surface with a plurality of reaction chambers disposed thereon. The the reaction chambers may have a center to center spacing of between 20 to 100 µm and each reaction chamber has a width in at least one dimension of between 20 µm and 70 µm.

Another embodiment of the invention is directed to an apparatus for simultaneously monitoring an array of reaction chambers for light indicating that a reaction is taking place at a particular site. The apparatus comprises (a) an array of reaction chambers formed from a planar substrate comprising a plurality of cavitated surfaces, each cavitated surface forming a reaction chamber adapted to contain analytes, and wherein the reaction chambers have a center to center spacing of between 20 to 100 µm, each reaction chamber having a volume of between 10 to 150 pL, the array comprising more than 10,000 discrete reaction chambers; (b) an optically sensitive device arranged so that in use the light from a particular reaction chamber will impinge upon a particular predetermined region of the optically sensitive device; (c) means for determining the light level impinging upon each of the predetermined regions; and (d) means to record the variation of the light level with time for each of the reaction chamber.

Another embodiment of the invention is directed to an analytic sensor, comprising (a) an array formed from a first bundle of optical fibers with a plurality of cavitated surfaces at one end thereof, each cavitated surface forming a reaction chamber adapted to contain analytes, and wherein the reaction chambers have a center to center spacing of between 20 to 100 µm, a width of 20 to 70 µm, the array comprising more than 10,000 discrete reaction chambers; (b) an enzymatic or fluorescent means for generating light in the reaction chambers; and (c) light detection means comprising a light capture means and a second fiber optic bundle for transmitting light to the light detecting means, the second fiber optic bundle being in optical contact with the array, such that light generated in an individual reaction chamber is captured by a separate fiber or groups of separate fibers of the second fiber optic bundle for transmission to the light capture means.

Another embodiment of the invention is directed to a method for carrying out separate parallel common reactions in an aqueous environment. The first step involves delivering a fluid containing at least one reagent to an array, wherein the array comprises a substrate comprising at least 10,000 discrete reaction chambers, each reaction chamber adapted to contain analytes, and wherein the reaction chambers have a volume of between 10 to 150 pL and containing a starting material that is capable of reacting with the reagent, each of the reaction chambers being dimensioned such that when the fluid is delivered into each reaction chamber, the diffusion time for the reagent to diffuse out of the well exceeds the time required for the starting material to react with the reagent to form a product. The second step involves washing the fluid from the array in the time period (i) after the starting material has reacted with the reagent to form a product in each reaction chamber but (ii) before the reagent delivered to any one reaction chamber has diffused out of that reaction chamber into any other reaction chamber.

Another embodiment of the invention is directed to a method for delivering nucleic acid sequencing enzymes to an array. The array having a planar surface with a plurality of cavities thereon, each cavity forming an analyte reaction chamber, wherein the reaction chambers have a center to center spacing of between 20 to 100 µm. The method involves the step of dispersing over the array a plurality of mobile solid supports having one or more nucleic acid sequencing enzymes immobilized thereon, such that a plurality of the reaction chambers contain at least one mobile solid support.

Another embodiment of the invention is directed to a method for delivering a plurality of nucleic acid templates to an array. The array may have a planar surface with a plurality of cavities thereon, each cavity forming an analyte reaction chamber, wherein the reaction chambers have a center to center spacing of between 20 to 100 µm and the array having at least 10,000 reaction chambers. The method comprise the step of dispersing over the array a plurality of mobile solid supports, each mobile solid support having no more than a single species of nucleic acid template immobilized thereon, the dispersion causing no more than one mobile solid support to be disposed within any one reaction chamber.

Another embodiment of the invention is directed to a method for sequencing a nucleic acid. The method comprises the step of providing a plurality of single-stranded nucleic acid templates disposed within a plurality of cavities on a planar surface, each cavity forming an analyte reaction chamber, wherein the reaction chambers have a center to center spacing of between 20 to 100 μm and the planar surface has at least 10,000 reaction chambers. The next step involves performing a pyrophosphate based sequencing reaction simultaneously on all reaction chambers by annealing an effective amount of a sequencing primer to the nucleic acid templates and extending the sequencing primer with a polymerase and a predetermined nucleotide triphosphate to yield a sequencing product and, if the predetermined nucleotide triphosphate is incorporated onto the 3' end of the sequencing primer, a sequencing reaction byproduct. The third step involves identifying the sequencing reaction byproduct, thereby determining the sequence of the nucleic acid in each reaction chamber.

Another embodiment of the invention is directed to a method of determining the base sequence of a plurality of nucleotides on an array. The first step involves providing at least 10,000 DNA templates, each separately disposed within a plurality of cavities on a planar surface, each cavity forming an analyte reaction chamber, wherein the reaction chambers have a center to center spacing of between 20 to 100 μm, and a volume of between 10 to 150 pL. The second step involves adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates. The third step involves detecting whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor. The fourth step involves sequentially repeating steps (b) and (c), wherein each sequential repetition adds and, detects the incorporation of one type of activated nucleoside 5'-triphosphate precursor of known nitrogenous base composition. The fifth step involves determining the base sequence of the unpaired nucleotide residues of the template in each reaction chamber from the sequence of incorporation of the nucleoside precursors.

Another embodiment of the invention is directed to a method of identifying the base in a target position in a DNA sequence of template DNA. The first step involves providing at least 10,000 separate DNA templates are separately disposed within a plurality of cavities on a planar surface, each cavity forming an analyte reaction chamber, wherein the reaction chambers have a center to center spacing of between 20 to 100 μm, the DNA being rendered single stranded either before or after being disposed in the reaction chambers. The second step involves providing an extension primer is provided which hybridizes to the immobilized single-stranded DNA at a position immediately adjacent to the target position. The immobilized single-stranded DNA is subjected to a polymerase reaction in the presence of a predetermined deoxynucleotide or dideoxynucleotide, wherein if the predetermined deoxynucleotide or dideoxynucleotide is incorporated onto the 3' end of the sequencing primer then a sequencing reaction byproduct is formed. The fourth step involves identifying the sequencing reaction byproduct, thereby determining the nucleotide complementary to the base at the target position in each of the 10,000 DNA templates.

Another embodiment of the invention is directed to an apparatus for analyzing a nucleic acid sequence. The apparatus comprises: (a) a reagent delivery cuvette, wherein the cuvette includes an array comprising a planar surface with a plurality of cavities thereon, each cavity forming an analyte reaction chamber, wherein the reaction chambers have a center to center spacing of between 20 to 100 μm, and there are in excess of 10,000 reaction chambers, and wherein the reagent delivery cuvette contains reagents for use in a sequencing reaction; (b) a reagent delivery means in communication with the reagent delivery cuvette; (c) an imaging system in communication with the reagent delivery chamber; and (d) a data collection system in communication with the imaging system.

Another embodiment of the invention is directed to an apparatus for determining the base sequence of a plurality of nucleotides on an array. The apparatus comprises: (a) a reagent cuvette containing a plurality of cavities on a planar surface, each cavity forming an analyte reaction chamber, wherein there are in excess of 10,000 reaction chambers, each having a center to center spacing of between 20 to 100 μm and a volume of between 10 to 150 pL; (b) reagent delivery means for simultaneously adding to each reaction chamber an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) detection means for detecting in each reaction chamber whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor; and (d) means for sequentially repeating (b) and (c), wherein each sequential repetition adds and, detects the incorporation of one type of activated nucleoside 5'-triphosphate precursor of known nitrogenous base composition; and (e) data processing means for determining the base sequence of the unpaired nucleotide residues of the template simultaneously in each reaction chamber from the sequence of incorporation of the nucleoside precursors.

Another embodiment of the invention is directed to an apparatus for processing a plurality of analytes. The apparatus comprises: (a) a flow chamber having disposed therein a substrate comprising at least 50,000 cavitated surfaces on a fiber optic bundle, each cavitated surface forming a reaction chamber adapted to contain analytes, and wherein the reaction chambers have a center to center spacing of between 20 to 100 μm and a diameter of 20 to 70 μm; (b) fluid means for delivering processing reagents from one or more reservoirs to the flow chamber so that the analytes disposed in the reaction chambers are exposed to the reagents; and (c) detection means for simultaneously detecting a sequence of optical signals from each of the reaction chambers, each optical signal of the sequence being indicative of an interaction between a processing reagent and the analyte disposed in the reaction chamber, wherein the detection means is in communication with the cavitated surfaces.

Another embodiment of the invention is directed to a method for sequencing a nucleic acid. The first step involves providing a plurality of single-stranded nucleic acid templates in an array having at least 50,000 discrete reaction sites. The second step involves contacting the nucleic acid templates with reagents necessary to perform a pyrophosphate-based sequencing reaction coupled to light emission. The third step involves detecting the light emitted from a plurality of reaction sites on respective portions of an optically sensitive device. The forth step involves converting the light impinging upon each of the portions of the optically sensitive device into an electrical signal which is distinguishable from the signals from all of the other reaction sites. The fifth step involves determining the sequence of the nucleic acid templates based on light emission for each of the discrete reaction sites from the corresponding electrical signal.

Another embodiment of the invention is directed to a method for sequencing nucleic acids. The first step involves fragmenting large template nucleic acid molecules to generate a plurality of fragmented nucleic acids. The second step involves attaching one strand of a plurality of the fragmented nucleic acids individually to beads to generate single stranded nucleic acids attached individually to beads. The third step involves delivering a population of the single stranded fragmented nucleic acids attached individually to beads to an array of at least 10,000 reaction chambers on a planar surface, wherein a plurality of the wells comprise no more than a one bead with on single stranded fragmented nucleic acid. The fourth step involves performing a sequencing reaction simultaneously on a plurality of the reaction chambers. The sequencing reaction may have the steps of (a) annealing an effective amount of a sequencing primer to the single stranded fragmented nucleic acid templates and extending the sequencing primer with a polymerase and a predetermined nucleotide triphosphate to yield a sequencing product and, if the predetermined nucleotide triphosphate is incorporated onto the 3' end of the sequencing primer, a sequencing reaction byproduct; and (b) identifying the sequencing reaction byproduct, thereby determining the sequence of the nucleic acid in a plurality of the reaction chambers. Alternatively, the sequencing reaction may comprises the steps of: (a) hybridizing two or more sequencing primers to one or a plurality of single strands of the nucleic acid molecule wherein all the primers except for one are reversibly blocked primers; (b) incorporating at least one base onto the nucleic acid molecule by polymerase elongation from an unblocked primer; (c) preventing further elongation of the unblocked primer; (d) deblocking one of the reversibly blocked primers into an unblocked primer; and (e) repeating steps (b) to (d) until at least one of the reversibly blocked primers are deblocked and used for determining a sequence.

Other materials and methods may be found in the following copending U.S. patent applications: U.S. Ser. No. 60/443,471 filed Jan. 29, 2003, U.S. Ser. No. 60/465,071 filed Apr. 23, 2003, U.S. Ser. No. 10/767,894 filed Jan. 28, 2004, U.S. Ser. No. 10/767,899 filed Jan. 28, 2004 and U.S. Ser. No. 10/768, 729 filed Jan. 28, 2004. All patents, patent applications, and references cited in this disclosure are incorporated herein by reference.

EXAMPLES

Example 1

Sample Preparation

DNA Sample:

The DNA should be of high quality and free from contaminants such as proteins, nucleases, lipids, and other chemicals (such as residual EDTA from preparation) and salts. It is preferred that genomic DNA should have a 260/280 ratio of 1.8 or higher. If it is desired to sequence the genome of only one organism, then the DNA should be quality checked to ensure that there is no contaminating DNA. For example: a preparation of human DNA may be checked by PCR to ensure that it is not contaminated by bacterial DNA molecules. Another method of checking for contamination is by restriction digestion patterns and especially restriction digestion followed by Southern Blot using suitable probes known to be specific for an organism (e.g., human or mouse) and a second probe known to be specific for a possible contaminating organism (e.g., *E. coli*). If it is desired, the DNA should originate from a single clone of the organism (e.g., a colony if from bacteria).

Step 1: DNase I Digestion

The purpose of the DNase I digestion step is to fragment a large stretch of DNA such as a whole genome or a large portion of a genome into smaller species. This population of smaller-sized DNA species generated from a single DNA template is referred to as a "library". Deoxyribonuclease I (DNase I) is an endonuclease which cleaves double-stranded template DNA. The cleavage characteristics of DNase I allow random digestion of template DNA (i.e., minimal sequence bias) and will result in the predominance of blunt-ended, double-stranded DNA fragments when used in the presence of manganese-based buffers (Melgar and Goldthwait 1968). The digestion of genomic templates by DNase I is dependent on three factors: i) quantity of enzyme used (units); ii) temperature of digestion (° C.); and iii) incubation time (minutes). The DNase I digestion conditions outlined below were optimized to yield DNA libraries in a size range from 50-700 base pairs (bp).

1. DNA was obtained and prepared to a concentration of 0.3 mg/ml in Tris-HCl (10 mM, pH 7-8). A total of 134 μl of DNA (15 μg) was needed for this preparation. It is recommended to not use DNA preparations diluted with buffers containing EDTA (i.e., TE, Tris/EDTA). The presence of EDTA is inhibitory to enzyme digestion with DNase I. If the DNA preparation contains EDTA, it is important that the DNA be "salted" out of solution and reconstituted with the appropriate Tris-HCl buffer (10 mM, pH 7-8) or nanopure $H_2O$ (pH 7-8).

2. In a 0.2 ml tube, DNase I Buffer, comprising 50 μl Tris pH 7.5 (1M), 10 μl $MnCl_2$ (1M), 1 μl BSA (100 mg/ml), and 39 μl water was prepared.

3. In a separate 0.2 ml tube, 15 μl of DNase I Buffer and 1.5 μl of DNase I (1 U/ml) was added. The reaction tube was placed in a thermal cycler set to 15° C.

4. The 134 μl of DNA (0.3 mg/ml) was added to the DNase I reaction tube placed in the thermal cycler set at 15° C. The lid was closed and the sample was incubated for exactly 1 minute. Following incubation, 50 µl of 50 mM EDTA was added to stop the enzyme digestion.

5. The digested DNA was purified by using the QiaQuick PCR purification kit. The digestion reaction was then split into four aliquots, and four spin columns were used to purify each aliquot (37.5 µl per spin column). Each column was eluted with 30 µl elution buffer (EB) according to the manufacturer's protocol. The eluates were then combined to generate a final reaction volume of 120 µl.

6. One 3 µl aliquot of the digestion reaction was saved for analysis using a BioAnalzyer DNA 1000 LabChip.

Step 2: Pfu Polishing

Digestion of DNA templates with DNase I yields fragments of DNA that are primarily blunt-ended, however, some fragments will have ends that contain protruding termini that are one or two nucleotides in length. Pfu polishing is used to increase the amount of blunt-ended species by fill-in (i.e., "blunting") of 5' overhangs. Additionally, Pfu DNA polymerase has 3'→5' exonuclease activity that will result in the removal of single and double nucleotide extensions. Pfu polishing increases the amount of blunt-ended DNA fragments available for adaptor ligation (Costa 1994a, 1994b, 1994c). The following Pfu polishing protocol was used.

1. In a 0.2 ml tube, 115 µl purified, DNase I-digested DNA fragments, 15 µl 10× Cloned Pfu buffer, 5 µl dNTPs (10 mM), and 15 µl cloned Pfu DNA polymerase (2.5 U/µl) were added in order.

2. The polishing reaction components were mixed well and incubated at 72° C. for 30 minutes.

3. Following incubation, the reaction tube was removed and placed on ice for 2 minutes.

4. The polishing reaction mixture was then split into four aliquots and purified using QiaQuick PCR purification columns (37.5 µL on each column). Each column was eluted with 30 µl buffer EB according to the manufacturer's protocol. The eluates were then combined to generate a final reaction volume of 120 µL.

5. One 3 µl aliquot of the final polishing reaction was saved for analysis using a BioAnalzyer DNA 1000 LabChip.

Step 3: Ligation of Universal Adaptors to Fragmented DNA Library

Following fragmentation and polishing of the genomic DNA library, primer sequences are added to the ends of each DNA fragment. These primer sequences are termed "Universal Adaptors" and are comprised of double-stranded oligonucleotides that contain specific priming regions that afford both PCR amplification and nucleotide sequencing. The Universal Adaptors are designed to include a set of unique PCR priming regions that are 20 base pairs in length located adjacent to a set of unique sequencing priming regions that are 20 base pairs in length, followed by a unique 4-base "key" consisting of one of each deoxyribonucleotide (i.e., A, C, G, T). Each unique Universal Adaptor (termed "Universal Adaptor A" and "Universal Adaptor B") is forty-four base pairs (44 bp) in length. Universal Adaptors are ligated, using T4 DNA ligase, onto each end of the DNA fragment to generate a total nucleotide addition of 88 bp to each DNA fragment. Different Universal Adaptors are designed specifically for each genomic DNA library preparation and will therefore provide a unique identifier for each organism.

To prepare a pair of Universal Adaptors, single-stranded oligonucleotides are designed in-house and are manufactured through a commercial vendor. Universal Adaptor DNA oligonucleotides are designed with two phosphorothioate linkages at each oligonucleotide end that serve to protect against nuclease activity (Samini, T. D., B. Jolles, and A. Laigle. 2001. Best minimally modified antisense oligonucleotides according to cell nuclease activity. *Antisense Nucleic Acid Drug Dev.* 11(3):129., the disclosure of which is incorporated in toto herein by reference.). Each oligonucleotide is HPLC-purified to ensure there are no contaminating or spurious DNA oligonucleotide sequences in the final prep.

The Universal Adaptors are designed to allow directional ligation to the blunt-ended, fragmented genomic DNA. For each Universal Adaptor pair, the PCR priming region contains a 5' four-base overhang and a blunt-ended 3' Key region. Directionality is achieved as the blunt-end side of the Universal Adaptor ligates to the blunt-ended DNA fragment while the 5' overhang of the adaptor cannot ligate to the blunt-ended DNA fragment. Additionally, a 5' biotin is added to the Universal Adaptor B to allow subsequent isolation of ssDNA template (Step 8). Each Universal Adaptor is prepared by annealing, in a single tube, the two single-stranded complementary DNA oligonucleotides (i.e., one oligo containing the sense sequence and the second oligo containing the antisense sequence). The following ligation protocol was used.

1. In a 0.2 ml tube, 39 µl $nH_2O$ (molecular biology grade water), 25 µl digested, polished DNA Library, 100 µl 2× Quick Ligase Reaction Buffer, 20 µl MMP1(10 pm/µl) adaptor set, 100:1 ratio, and 16 µl Quick Ligase were added in order. The ligation reaction was mixed well and incubated at RT for 20 minutes.

2. The ligation reaction was then removed and a 10-µl aliquot of the ligation reaction was purified for use on the BioAnalyzer. A single spin column from the Qiagen MinElute kit was used. The column was eluted with 10 µl EB according to the procedure per manufacturers' protocol. A 1-µl aliquot of the purified ligation reaction was loaded using a BioAnalyzer DNA 1000 LabChip. This purification step is recommended as the unpurified ligation reaction contains high amounts of salt and PEG that will inhibit the sample from running properly on the BioAnalyzer.

3. The remainder of the ligation reaction (190 µL) was used for gel isolation in Step 4.

Step 3a: Microcon Filtration and Adaptor Construction. Total Preparation Time was Approximately 25 min.

The Universal Adaptor ligation reaction requires a 100-fold excess of adaptors. To aid in the removal of these excess adaptors, the double-stranded gDNA library is filtered through a Microcon YM-100 filter device. Microcon YM-100 membranes can be used to remove double stranded DNA smaller than 125 bp. Therefore, unbound adaptors (44 bp), as well as adaptor dimers (88 bp) can be removed from the ligated gDNA library population. The following filtration protocol was used:

1. The 190 µL of the ligation reaction from Step 4 was applied into an assembled Microcon YM-100 device.

2. The device was placed in a centrifuge and spun at 5000×g for approximately 6 minutes, or until membrane was almost dry.

3. To wash, 200 µl of 1×TE was added.

4. Sample was spun at 5000×g for an additional 9 minutes, or until membrane was almost dry.

5. To recover, the reservoir was inserted into a new vial and spun at 3000×g for 3 minutes. The reservoir was discarded. The recovered volume was approximately 10 µl. Next, 80 µl TE was added.

The Adaptors (A and B) were HPLC-purified and modified with phosphorothioate linkages prior to use. For Adaptor "A" (10 µM), 10 µl of 100 µM Adaptor A (44 bp, sense) was mixed with 10 µl of 100 µM Adaptor A (40 bp, antisense), and 30 µl of 1× Annealing Buffer ($V_f$=50 µl) were mixed. The primers were annealed using the ANNEAL program on the Sample Prep Labthermal cycler (see below). For Adaptor "B" (10 µM), 10 µl of 100 µM Adaptor B (40 bp, sense) was mixed with 10 µl of 100 µM Adaptor B (44 bp, antisense), and 30 µl of 1× Annealing Buffer ($V_f$=50 µl). The primers were annealed using the ANNEAL program on the Sample Prep Lab thermal cycler. Adaptor sets could be stored at −20° C. until use.

ANNEAL-A program for primer annealing:
1. Incubate at 95° C., 1 min;
2. Decrease temperature to 15° C., at 0.1° C./sec; and
3. Hold at 15° C.

There was no orientation required for the genomic DNA insert fragment and the adaptors. Fragments could be ligated at either end. Four single-stranded DNA oligonucleotides were included in the Universal Adaptor set. Each single-stranded oligonucleotide was synthesized at 1 micromole scale and HPLC-purified. Each single-stranded oligonucleotide included four phosphorothioate linkages at each end.

Step 4: Gel Electrophoresis and Extraction of Adapted DNA Library

The Universal Adaptor ligation protocol produces the following: 1) fragmented DNAs with adaptors on either end; 2) unbound single adaptors; or 3) the formation of adaptor dimers. Agarose gel electrophoresis is used as a method to separate and isolate the adapted DNA library population from the unligated, single adaptors and adaptor dimer populations. The procedure of DNase I digestion of genomic DNA yields a library population that ranges from 50-700 bp (Step 1). The addition of the 88-bp Universal Adaptor set will shift the population to a larger size and will result in a migration profile in the size range of approximately 130-800 bp. Adaptor dimers will migrate at 88 bp and adaptors unligated will migrate at 44 bp. Therefore, genomic DNA libraries in size ranges>200 bp can be physically isolated from the agarose gel and purified using standard gel extraction techniques. Gel isolation of the adapted DNA library will result in the recovery of a library population in a size range that is≧200 bp (size range of library can be varied depending on application). The following electrophoresis and extraction protocol was used.

1. A 2% agarose gel was prepared.
2. 10 µl of 10× Ready-Load Dye was added to the remaining 90 µl of the DNA ligation mixture.
3. The dye/ligation reaction mixture was loaded into the gel using four adjacent lanes (25 µl per lane).
4. 10 µl of the 100 bp ladder (0.1 µg/µl) was loaded two lanes away from ligation reaction lanes.
5. The gel was run at 100V for 3 hours.
6. When the gel run was complete, the gel was removed from the gel box and transferred to a flat surface covered with plastic wrap. DNA bands were visualized using a hand-held long-wave UV light. Using a sterile, single-use scalpel, the fragment sizes of 200-400 bp were cut out from the agarose gel. Using this approach, libraries with any size range can be isolated. It is also possible to isolate more than one size range. Where the library size range is 200-900 bp, it is possible to isolate several size ranges from a single well (i.e., 200-400 bp and 500-700 bp).
7. The DNA embedded in the agarose gel was isolated using a Qiagen MinElute Gel Extraction kit following the manufacturer's instructions. Briefly, Buffer QG was added to cover the agarose in the tube. The agarose was allowed to completely dissolve. The color of the Buffer QG was maintained by adjusting the pH according to the Qiagen instructions to minimize sample loss. Two MinElute spin columns (Qiagen) were used for purification. The large volume of dissolved agarose required each column to be loaded several times. The columns were eluded with 10 µl of Buffer EB which was pre-warmed at 55° C. The eluates were pooled to produce 20 µl of gDNA library.
8. One 1 µL aliquot of each isolated DNA library was analyzed using a BioAnalyzer DNA 1000 LabChip to assess the exact distribution of the DNA library population.

Step 5: Strand Displacement and Extension of Nicked Double Stranded DNA Library

Because the DNA oligonucleotides used for the Universal Adaptors are not phosphorylated, gaps are present at the 3' junctions of the fragmented gDNAs. These two "gaps" or "nicks" can be filled in by using a strand displacing DNA polymerase. The polymerase recognizes nicks, displaces the nicked strands, and extends the strand in a manner that results in repair of nicks and in the formation of non-nicked double-stranded DNA. The strand displacing enzyme used is the large fragment of Bst DNA polymerase.

1. In a 0.2 ml tube, 19 µl gel-extracted DNA library, 40 µl nH$_2$O, 8 µl 10× ThermoPol Reaction Buffer, 8 µl BSA (1 mg/ml), 2 µl dNTPs (10 mM), and 3 µl Bst I Polymerase (8 U/µl) were added in order.
2. The samples were mixed well and placed in a thermal cycler and incubated using the Strand Displacement incubation program: "BST". BST program for stand displacement and extension of nicked double-stranded DNA:
   1. Incubate at 65° C., 30 minutes;
   2. Incubate at 80° C., 10 minutes;
   3. Incubate at 58° C., 10 minutes; and
   4. Hold at 14° C.
3. One 1 µL aliquot of the Bst-treated DNA library was run using a BioAnalyzer DNA 1000 LabChip.

Step 6: Preparation of Streptavidin Beads

Following the generation of unnicked double-stranded genomic DNA, it is necessary to isolate single-stranded genomic DNAs containing flanking Universal Adaptor sequences. This step outlines the binding of biotin-tagged double-stranded DNA to streptavidin beads. For preparing streptavidin beads, the following protocol was used.

1. 100 µl Dynal M-270 Streptavidin beads were washed two times with 200 µl of 1× Binding Buffer (1 M NaCl, 0.5 mM EDTA, 5 mM Tris, pH 7.5) by applying the magnetic beads to the MPC.
2. The beads were resuspended in 100 µl 2× Binding buffer, then the remaining 79 µl of the Bst-treated DNA sample (from Step 5) and 20 µl water was added.
3. The bead solution was mixed well and placed on a tube rotator at RT for 20 minutes. The bead mixtures were washed, using the MPC, two times with 100 µl of 1× Binding Buffer, then washed two times with nH$_2$O. Binding & Washing (B&W) Buffer (2× and 1×): 2× B&W buffer was prepared by mixing 10 mM Tris•HCl (pH 7.5), 1 mM EDTA, and 2 M NaCl. The reagents were combined as listed above and mixed thoroughly. The solution can be stored at RT for 6 months; 1× B&W buffer was prepared by mixing 2× B&W buffer with nH$_2$O, 1:1. The final concentrations were half the above, i.e., 5 mM Tris•HCl (pH 7.5), 0.5 mM EDTA, and 1 M NaCl.

Step 7: Isolation of Single-Stranded DNA Library using Streptavidin Beads

Following binding of the double-stranded gDNA library to streptavidin beads, it is preferred to isolate from the ligated pool only the single-stranded gDNAs containing Universal Adaptor A and Universal Adaptor B (desired populations are designated below with asterisks). Double-stranded genomic DNA fragment pools will have adaptors bound in the following possible configurations:

Universal Adaptor A-gDNA Fragment-Universal Adaptor A

Universal Adaptor B-gDNA Fragment-Universal Adaptor A*

Universal Adaptor A-gDNA Fragment-Universal Adaptor B*

Universal Adaptor B-gDNA Fragment-Universal Adaptor B

Because only the Universal Adaptor B has a 5' biotin moiety, magnetic streptavidin-containing beads can be used to bind all gDNA library species that possess the Universal Adaptor B. Genomic. library populations that contain two Universal Adaptor A species (or nonligated species) do not bind to streptavidin-containing beads and are removed during the wash procedure. The species that remain bound to bead after washing include those with Universal Adaptors A and B or those with two Universal Adaptor B ends.

Genomic DNA species with two Universal Adaptor B sequences with two biotin molecules can bind to the streptavidin-containing beads at both ends. Species with A and B adaptors having only a single biotin molecule can bind to the beads only at the "B" end. To isolate the single-stranded population, the bead-bound double-stranded DNA is treated with a sodium hydroxide solution that serves to disrupt the hydrogen bonding between the complementary DNA strands. If the DNA fragment has biotin on each end (Universal Adaptor B ends), both resulting single strands remain bound to the beads. If the fragment has only a single biotin (Universal Adaptors A and B), then the complementary strand separates from the DNA-bead complex.

The resulting single-stranded genomic DNA library is collected from the solution phase and is quantitated, e.g., using pyrophosphate sequencing (PyroSequence) or by using a RNA Pico 6000 LabChip (Agilent, Palo Alto, Calif.). Single-stranded genomic DNA libraries are quantitated by calculating the number of molecules per unit volume. Single-stranded gDNA molecules are then annealed (at a half copy per bead to obtain one effective copy per bead) to 25-30 µm sepharose beads containing DNA capture primers (PCR primer B). The templates are then amplified using emulsion polymerase chain reaction protocols. Subsequent sequencing may be conducted using known techniques. For isolation of the single stranded library, the following protocol was used.

1. 250 µl Melt Solution (0.125 M NaOH, 0.1 M NaCl) was added to washed beads from Step 6 above.

2. The bead solution was mixed well and the bead mixture was incubated at room temperature for 10 minutes on a tube rotator.

3. A Dynal MPC (magnetic particle concentrator) was used, the pellet beads were carefully removed, and the supernatant was set aside. The 250-µl supernatant included the single-stranded DNA library.

4. In a separate tube, 1250 µl PB (from QiaQuick Purification kit) was added and the solution was neutralized by adding 9 µl of 20% acetic acid.

5. Using a Dynal MPC, beads from the 250-µl supernatant including the single-stranded gDNA library were pelleted and the supernatant was carefully removed and transferred to the freshly prepared PB/acetic acid solution.

6. The 1500 µl solution was purified using a single QiaQuick purification spin column (load sample through same column two times at 750 µl per load). The single-stranded DNA library was eluted with 50 µl EB.

Step 8a: Single-Stranded gDNA Quantitation using Pyrophosphate Sequencing. Total Preparation Time was Approximately 1 Hr.

1. In a 0.2 ml tube, the following reagents were added in order:

25 µl single-stranded gDNA

1 µl MMP2B sequencing primer

14 µl Library Annealing Buffer

40 µl total

2. The DNA was allowed to anneal using the ANNEAL-S Program (see Appendix, below).

3. The samples were run on PSQ (pyrophosphate sequencing jig) to determine the number of picomoles of template in each sample (see below). Methods of sequencing can be found in U.S. Pat. No. 6,274,320; U.S. Pat. No. 4,863,849; U.S. Pat. No. 6,210,891; and U.S. Pat. No. 6,258,568, the disclosures of which are incorporated in toto herein by reference. Calculations were performed to determine the number of single-stranded gDNA template molecules per microliter. The remaining 25 µL of prepared single-stranded gDNA library was used for amplification and subsequent sequencing (approximately $1 \times 10^6$ reactions).

Step 8b: Single-Stranded gDNA Quantitation using RNA Pico 6000 LabChip. Total Preparation Time was Approximately 30 Minutes.

1. The mRNA Pico assay option was selected on the Bio-Analyzer (Software version 2.12).

2. An RNA Pico 6000 LabChip was prepared on the Bio-Analyzer according to the manufacturers' guidelines.

3. An RNA LabChip ladder (RNA 6000 ladder) was prepared according to manufacturer's (Ambion) directions. Briefly, the RNA LabChip ladder, in solution, was heated to 70° C. for 2 minutes. The solution was chilled on ice for 5 minutes to snap cool the ladder. The solution was briefly centrifuged to clear any condensate from tube walls. The RNA LabChip Ladder was stored on ice and used within one day.

4. The ssDNA library to be analyzed was run in triplicate, in adjacent lanes, using three 1 µl aliquots.

5. The BioAnalyzer software was used to calculate the concentration of each ssDNA library lane (see the Table below and FIG. 24. The average of all three lanes was used to calculate the DNA concentration of the library using the procedure outlined below.

a. The peak integration lower limit line (large dash in FIG. 24) was moved immediately in front of the library peak (see below).

b. The peak integration upper limit line (large dash in the FIG. 24) was moved immediately after the library peak. In this way, the peak integration line connecting the lower and upper integration lines followed the slope of the background.

c. The mouse arrow was used to determine the average size of the peak in bases (usually near the peaks highest point) or a defined peak was used as chosen by the software.

d. The integrated value was used for the amount of material in the peak. The value obtained for picograms recovered was converted into molecules recovered (see Table, below). The library concentration was then determined (molecules per microliter).

TABLE

| 1 | 2 pg/μL (1) | 3 pg/μL (2) | 4 pg/μL (3) | 5 Average pg/μL | 6 Mean Size (bp) 1 | 7 Mean Size (bp) 2 | 8 Mean Size (bp) 3 | 9 Average Size (bp) |
|---|---|---|---|---|---|---|---|---|
| sample | 1633 | 1639 | 1645 | 1639 | 435 | 435 | 432 | 434 |

| 10 Ave MW (g/mole) Ribonucleotide | 11 Ave MW (g/mole) | 12 Library g/μL | 13 moles/g | 14 moles/μL | 15 molecules/μL |
|---|---|---|---|---|---|
| 328.2 | 1.42E+05 | 1.64E−09 | 7.02E−06 | 1.15E−14 | 6.93E+09 |

As shown in the Table above, the concentration of Library 1 was calculated as 1639 pg/μl (Column 5) and the average fragment size was 434 nucleotides (Column 9). These values were obtained from the Agilent 2100 software as described in Steps (a)-(d), above. The average molecular weight (MW) of a ribonucleotide is 328.2 g/mole (Column 10). The MW of the average library fragment (1.42×10$^5$ g/mole, Column 11) was calculated by multiplying the average fragment length (434) by the average ribonucleotide (328.2). The quantitated library (1639 pg/μl) was converted to grams per microliter (1.64× 10$^{-9}$ g/μl, Column 12). The number of moles per microliter (1.15×10$^{-14}$ moles/μl, Column 14) was calculated by dividing the grams per microliter (1.64×10$^{-9}$ g/μl, Column 12) by the average molecular weight of the library fragments (1.42×10$^5$, Column 11). Finally, the number of molecules per microliter (6.93×10$^9$ molecules/μl, Column 15) was derived by multiplying the number of moles per microliter (1.15×10$^{-14}$ moles/μl, Column 14) by Avogadro's number (6.02×10$^{23}$ molecules/mole).

Figure 24:
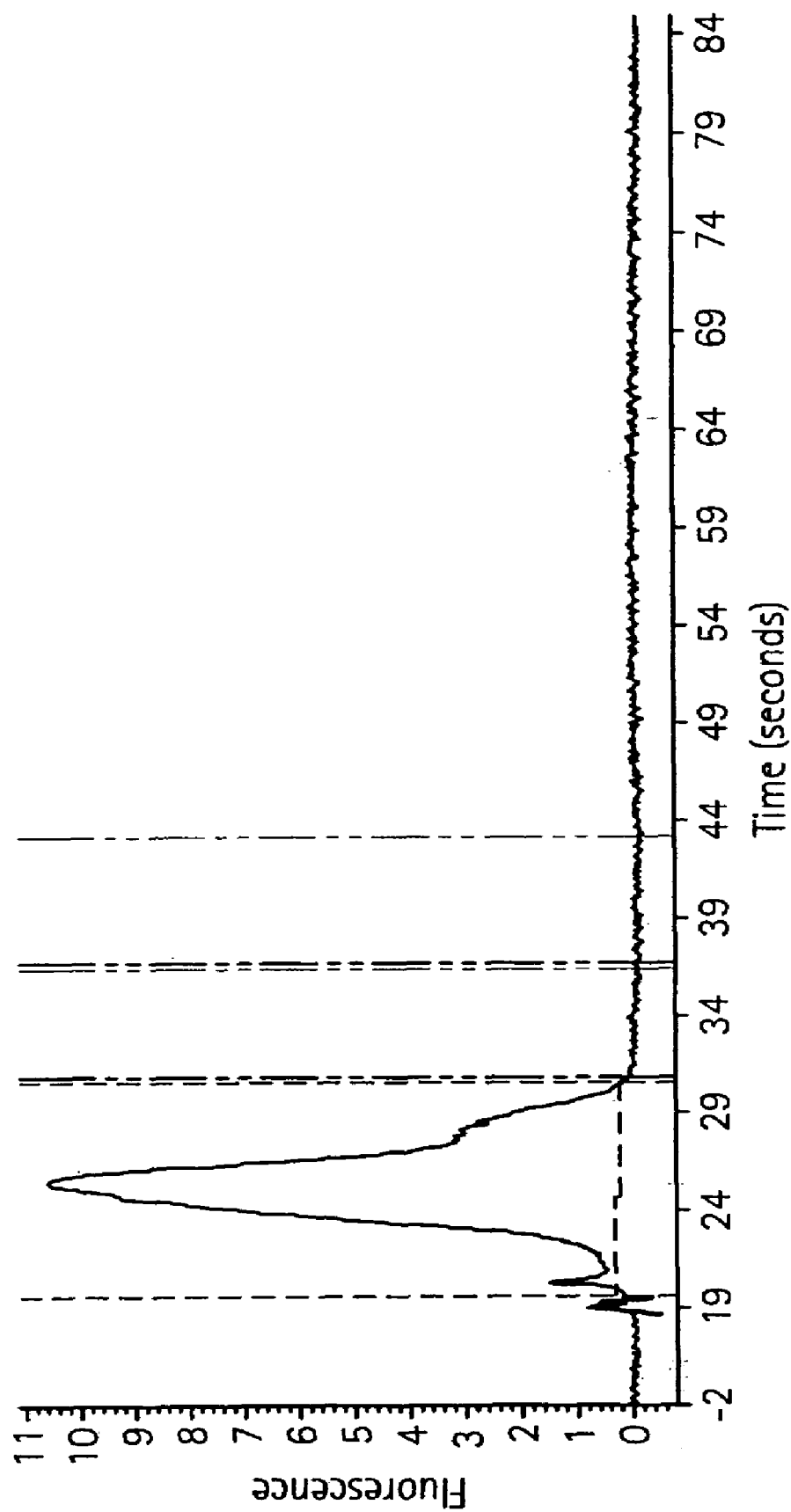
FIG. 24 depicts representative BioAnalyzer output from analysis of a single stranded DNA library.

The final library concentration was expected to be greater than 1×10$^8$ molecules/μl. A more important factor for library quality was adaptor dimer concentration. In FIG. 24, the height of the library peak was determined approximately 10 fold greater than the adaptor dimer peak (the first peak after the marker). A library of good quality is expected to have a peak height at least 2 fold greater than the dimer peak. It should be noted that the RNA Pico 6000 LabChip provided estimates within 500% accuracy of the single-stranded gDNA concentration. Thus, it was important to perform an initial sequencing run using a titration of template to determine the number of copies per bead (cpb) of input gDNA. The recommended input DNA is 2.5 cpb, 1 cpb, 0.5 cpb, and 0.1 cpb. This titration was easily checked using the 4 slot bead loading chamber on a 14×43 PTP.

Step 9: Dilution and Storage of Single-Stranded gDNA Library

The single-stranded gDNA library was eluted and quantitated in Buffer EB. To prevent degradation, the single-stranded gDNA library was stored frozen at −20° C. in the presence of EDTA. After quantitation, an equal volume of 10 mM TE was added to the library stock. All subsequent dilutions was in TE. The yield was as follows:

Remaining final volume of ssDNA library following PSQ analysis=25 μl.

Remaining final volume of ssDNA library following Lab-Chip analysis=47 μl.

For the initial stock dilution, single-stranded gDNA library was diluted to 100 million molecules/μl in 1× Library-Grade Elution Buffer. Aliquots of single-stranded gDNA library were prepared for common use. For this, 200,000 molecules/μl were diluted in 1× Library-Grade Elution Buffer and 20 μl aliquots were measured. Single-use library aliquots were stored at −20° C.

Step 10: Emulsion Polymerase Chain Reaction

Where increased numbers of cpb were preferred, bead emulsion PCR was performed as described in U.S. patent application Ser. No. 06/476,504 filed Jun. 6, 2003, incorporated herein by reference in its entirety.

Reagent Preparation

The Stop Solution (50 mM EDTA) included 100 μl of 0.5 M EDTA mixed with 900 μl of nH$_2$O to obtain 1.0 ml of 50 mM EDTA solution. For 10 mM dNTPs, (10 μl dCTP (100 mM), 10 μl dATP (100 mM), 10 μl dGTP (100 mM), and 10 μl dTTP (100 mM) were mixed with 60 μl molecular biology grade water. All four 100 mM nucleotide stocks were thawed on ice. Then, 10 μl of each nucleotide was combined with 60 μl of nH$_2$O to a final volume of 100 μl, and mixed thoroughly. Next, 1 ml aliquots were dispensed into 1.5 ml microcentrifuge tubes. The stock solutions could be stored at −20° C. for one year.

The 10× Annealing buffer included 200 mM Tris (pH 7.5) and 50 mM magnesium acetate. For this solution, 24.23 g Tris was added to 800 ml nH$_2$O and the mixture was adjusted to pH 7.5. To this solution, 10.72 g of magnesium acetate was added and dissolved completely. The solution was brought up to a final volume of 1000 ml and could be stored at 4° C. for 1 month. The 10×TE included 100 mM Tris•HCl (pH 7.5) and 50 mM EDTA. These reagents were added together and mixed thoroughly. The solution could be stored at room temperature for 6 months.

Example 2

Primer Design

As discussed above, the universal adaptors are designed to include: 1) a set of unique PCR priming regions that are typically 20 bp in length (located adjacent to (2)); 2) a set of unique sequencing priming regions that are typically 20 bp in length; and 3) optionally followed by a unique discriminating key sequence consisting of at least one of each of the four deoxyribonucleotides (i.e., A, C, G, T). The probability of cross-hybridization between primers and unintended regions of the genome of interest is increased as the genome size increases and length of a perfect match with the primer decreases. However, this potential interaction with a cross-hybridizing region (CHR) is not expected to produce problems for the reasons set forth below.

In a preferred embodiment of the present invention, the single-stranded DNA library is utilized for PCR amplification and subsequent sequencing. Sequencing methodology requires random digestion of a given genome into 150 to 500 base pair fragments, after which two unique bipartite primers (composed of both a PCR and sequencing region) are ligated onto the 5' and 3' ends of the fragments (FIG. 25). Unlike typical PCR amplifications where an existing section of the genome is chosen as a priming site based on melting temperature ($T_m$), uniqueness of the priming sequence within the genome and proximity to the particular region or gene of interest, the disclosed process utilizes synthetic priming sites that necessitates careful de novo primer design.

Tetramer Selection:

Strategies for de novo primer design are found in the published literature regarding work conducted on molecular tags for hybridization experiments (see, Hensel, M. and D. W. Holden, Molecular genetic approaches for the study of virulence in both pathogenic bacteria and fungi. Microbiology, 1996. 142(Pt 5): p. 1049-58; Shoemaker, D. D., et al., Quantitative phenotypic analysis of yeast deletion mutants using a highly parallel molecular bar-coding strategy. Nat Genet, 1996. 14(4): p. 450-6) and PCR/LDR (polymerase chain reaction/ligation detection reaction) hybridization primers (see, Gerry, N. P., et al., Universal DNA microarray method for multiplex detection of low abundance point mutations. Journal of Molecular Biology, 1999. 292: p. 251-262; Witowski, N. E., et al., Microarray-based detection of select cardiovascular disease markers. BioTechniques, 2000. 29(5): p. 936-944.).

The PCR/LDR work was particularly relevant and focused on designing oligonucleotide "zipcodes", 24 base primers comprised of six specifically designed tetramers with a similar final $T_m$. (see, Gerry, N. P., et al., Universal DNA microarray method for multiplex detection of low abundance point mutations. Journal of Molecular Biology, 1999. 292: p. 251-262; U.S. Pat. No. 6,506,594). Tetrameric components were chosen based on the following criteria: each tetramer differed from the others by at least two bases, tetramers that induced self-pairing or hairpin formations were excluded, and palindromic (AGCT) or repetitive tetramers (TATA) were omitted as well. Thirty-six of the 256 ($4^4$) possible permutations met the necessary requirements and were then subjected to further restrictions required for acceptable PCR primer design (Table 1).

TABLE 1

|    | TT   | TC   | TG   | TA   | CT   | CC   | CG   | CA   |
|----|------|------|------|------|------|------|------|------|
| TT | TTTT | TTTC | TTTG | TTTA | TTCT | TTCC | TTCG | TTCA |
| TC | TCTT | TCTC | TCTG | TCTA | TCCT | TCCC | TCCG | TCCA |
| TG | TGTT | TGTC | TGTG | TGTA | TGCT | TGCC | TGCG | *TGCA* |
| TA | TATT | TATC | TATG | TATA | TACT | TACC | TACG | TACA |
| CT | CTTT | CTTC | CTTG | CTTA | CTCT | CTCC | CTCG | CTCA |
| CC | CCTT | CCTC | CCTG | CCTA | CCCT | CCCC | CCCG | CCCA |
| CG | CGTT | CGTC | CGTG | CGTA | CGCT | CGCC | CGCG | CGCA |
| CA | CATT | CATC | *CATG* | CATA | CACT | CACC | CACG | CACA |
| GT | GTTT | GTTC | GTTG | GTTA | GTCT | GTCC | GTCG | GTCA |
| GC | GCTT | GCTC | GCTG | GCTA | GCCT | GCCC | GCCG | GCCA |
| GG | GGTT | GGTC | GGTG | GGTA | GGCT | *GGCC* | GGCG | GGCA |
| GA | GATT | *GATC* | GATG | GATA | GACT | GACC | GACG | GACA |
| AT | ATTT | ATTC | ATTG | *ATTA* | ATCT | ATCC | ATCG | ATCA |
| AC | ACTT | ACTC | ACTG | ACTA | ACCT | ACCC | ACCG | ACCA |
| AG | AGTT | AGTC | AGTG | AGTA | *AGCT* | AGCC | AGCG | AGCA |
| AA | *AATT* | AATC | AATG | AATA | AACT | AACC | AACG | AACA |

|    | GT   | GC   | GG   | GA   | AT   | AC   | AG   | AA   |
|----|------|------|------|------|------|------|------|------|
| TT | TTGT | TTGC | TTGG | TTGA | TTAT | TTAC | TTAG | *TTAA* |
| TC | TCGT | TCGC | TCGG | *TCGA* | TCAT | TCAC | TCAG | TCAA |
| TG | TGGT | TGGC | TGGG | TGGA | TGAT | TGAC | TGAG | TGAA |
| TA | TAGT | TAGC | TAGG | TAGA | *TAAT* | TAAC | TAAG | TAAA |
| CT | CTGT | CTGC | CTGG | CTGA | CTAT | CTAC | *CTAG* | CTAA |
| CC | CCGT | CCGC | *CCGG* | CCGA | CCAT | CCAC | CCAG | CCAA |
| CG | CGGT | CGGC | CGGG | CGGA | CGAT | CGAC | CGAG | CGAA |
| CA | CAGT | CAGC | CAGG | CAGA | CAAT | CAAC | CAAG | CAAA |
| GT | GTGT | GTGC | GTGG | GTGA | GTAT | *GTAC* | GTAG | GTAA |
| GC | GCGT | GCGC | GCGG | GCGA | GCAT | GCAC | GCAG | GCAA |
| GG | GGGT | GGGC | GGGG | GGGA | GGAT | GGAC | GGAG | GGAA |
| GA | GAGT | GAGC | GAGG | GAGA | GAAT | GAAC | GAAG | GAAA |
| AT | ATGT | ATGC | ATGG | ATGA | ATAT | ATAC | ATAG | ATAA |
| AC | *ACGT* | ACGC | ACGG | ACGA | ACAT | ACAC | ACAG | ACAA |
| AG | AGGT | AGGC | AGGG | AGGA | AGAT | AGAC | AGAG | AGAA |
| AA | AAGT | AAGC | AAGG | AAGA | AAAT | AAAC | AAAG | AAAA |

The table shows a matrix demonstrating tetrameric primer component selection based on criteria outlined by Gerry et al. 1999. *J. Mol. Bio.* 292: 251-262. Each tetramer was required to differ from all others by at least two bases. The tetramers could not be palindromic or complimentary with any other tetramer. Thirty-six tetramers were selected (bold, underlined); italicized sequences signal palindromic tetramers that were excluded from consideration.

Figure 27:
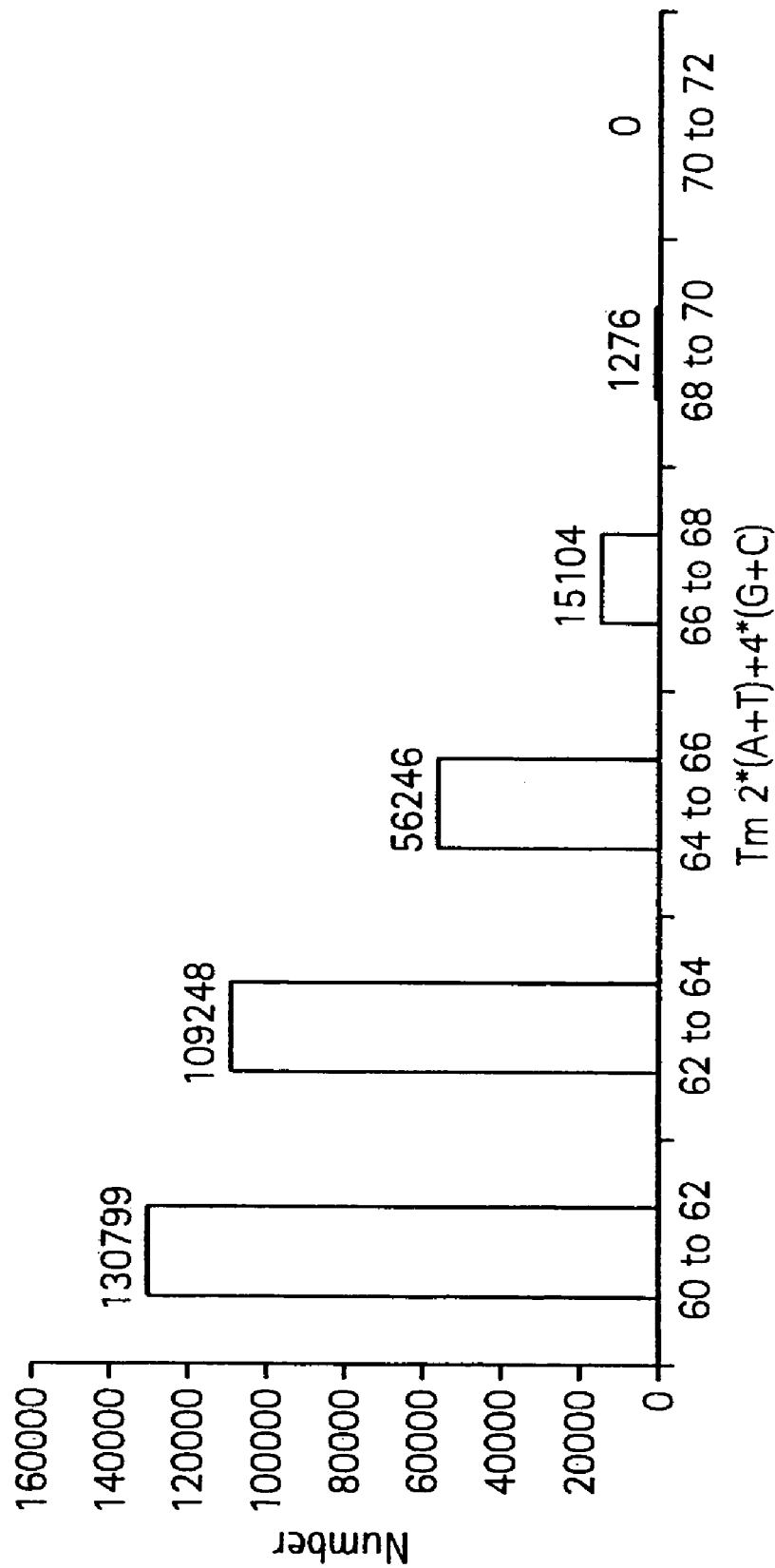
FIG. 27 depicts the calculation for primer candidates based on melting temperature.

Primer Design:

The PCR primers were designed to meet specifications common to general primer design (see, Rubin, E. and A. A. Levy, A mathematical model and a computerized simulation of PCR using complex templates. Nucleic Acids Res, 1996. 24(18): p. 3538-45; Buck, G. A., et al., Design strategies and performance of custom DNA sequencing primers. Biotechniques, 1999. 27(3): p. 528-36), and the actual selection was conducted by a computer program, MMP. Primers were limited to a length of 20 bases (5 tetramers) for efficient synthesis of the total bipartite PCR/sequencing primer. Each primer contained a two base GC clamp on the 5' end, and a single GC clamp on the 3' end (Table 2), and all primers shared similar $T_m$ (+/−2° C.) (FIG. 27). No hairpinning within the primer (internal hairpin stem ΔG>−1.9 kcal/mol) was permitted. Dimerization was also controlled; a 3 base maximum acceptable dimer was allowed, but it could occur in final six 3' bases, and the maximum allowable ΔG for a 3' dimer was −2.0 kcal/mol. Additionally, a penalty was applied to primers in which the 3' ends were too similar to others in the group, thus preventing cross-hybridization between one primer and the reverse complement of another.

TABLE 2

|  | 1-pos | 2-pos | 3-pos | 4-pos | 5-pos |
|---|---|---|---|---|---|
| 1 | CCAT | TGAT | TGAT | TGAT | ATAC |
| 2 | CCTA | CTCA | CTCA | CTCA | AAAG |
| 3 | CGAA | TACA | TACA | TACA | TTAG |
| 4 | CGTT | AGCC | AGCC | AGCC | AATC |
| 5 | GCAA | GACC | GACC | GACC | TGTC |
| 6 | GCTT | TCCC | TCCC | TCCC | AGTG |
| 7 | GGAC | ATCG | ATCG | ATCG | CTTG |
| 8 | GGTA | CACG | CACG | CACG | GATG |
| 9 |  | TGCG | TGCG | TGCG | TCTG |
| 10 |  | ACCT | ACCT | ACCT |  |
| 11 |  | GTCT | GTCT | GTCT |  |
| 12 |  | AGGA | AGGA | AGGA |  |
| 13 |  | TTGA | TTGA | TTGA |  |
| 14 |  | CAGC | CAGC | CAGC |  |
| 15 |  | GTGC | GTGC | GTGC |  |
| 16 |  | ACGG | ACGG | ACGG |  |
| 17 |  | CTGT | CTGT | CTGT |  |
| 18 |  | GAGT | GAGT | GAGT |  |
| 19 |  | TCGT | TCGT | TCGT |  |

Table 2 shows possible permutations of the 36 selected tetrads providing two 5' and a single 3' G/C clamp. The internal positions are composed of remaining tetrads. This results in 8×19×19×19×9 permutations, or 493,848 possible combinations. FIG. 27 shows first pass, $T_m$ based selection of acceptable primers, reducing field of 493,848 primers to 56,246 candidates with $T_m$ of 64 to 66° C.

TABLE 3

The probability of perfect sequence matches for primers increases with decreasing match length requirements and increasing size of the genome of interest.

| Match Length | Perfect match probability (1/(4^length)) | % chance for match in Adeno~35K bases | % chance for match in NCBI bacterial database~488M bases | % chance for match in Human~3B bases |
|---|---|---|---|---|
| 20 | 9.1E−13 | 0.00% | 0.04% | 0.27% |
| 19 | 7.3E−12 | 0.00% | 0.65% | 4.32% |
| 18 | 4.4E−11 | 0.00% | 5.76% | 34.37% |
| 17 | 2.3E−10 | 0.00% | 35.69% | 99.17% |
| 16 | 1.2E−09 | 0.02% | 97.52% | >100% |
| 15 | 5.6E−09 | 0.12% | >100% | >100% |
| 14 | 2.6E−08 | 0.64% | >100% | >100% |
| 13 | 1.2E−07 | 3.29% | >100% | >100% |
| 12 | 5.4E−07 | 15.68% | >100% | >100% |
| 11 | 2.4E−06 | 58.16% | >100% | >100% |
| 10 | 1.0E−05 | 99.35% | >100% | >100% |
| 9 | 4.6E−05 | 99.77% | >100% | >100% |
| 8 | 2.0E−04 | >100% | >100% | >100% |
| 7 | 8.5E−04 | >100% | >100% | >100% |
| 6 | 3.7E−03 | >100% | >100% | >100% |
| 5 | 1.6E−02 | >100% | >100% | >100% |
| 4 | 6.4E−02 | >100% | >100% | >100% |
| 3 | 2.5E−01 | >100% | >100% | >100% |
| 2 | 7.1E−01 | >100% | >100% | >100% |
| 1 | 1.0E+00 | >100% | >100% | >100% |

The possibility of complimentary regions occurring within the genome of interest was not a major concern in the primer design process despite the reported tolerance of PCR to mismatches in complex sample populations (see, e.g., Rubin, E. and A. A. Levy, A mathematical model and a computerized simulation of PCR using complex templates. Nucleic Acids Res, 1996. 24(18): p. 3538-45). Although the probability of finding a perfect match to a 20 base primer is extremely low ($4^{20}$) (Table 3), the probability of finding less non-consecutive matches increases significantly with the size of the genome of interest. As a result, the probability of finding a perfect match of at least 10 of 20 bases is 99.35% for an Adenovirus genome. The probability of finding a 16 base perfect match is 97% for the sequences in the NCBI database (approximately 100 times larger than the Adenovirus genome). The probability of finding a 17 base perfect match to a 20 base primer is 99% for the sequences in the human genome (3 billion bases).

The high probability of primer cross-hybridization to regions of the genome is less problematic than one might expect due to the random DNA digestion used to produce the template fragments. Thus, the effects of a cross-hybridizing region (CHR) are fairly benign. It is unlikely that a CHR would be able to successfully compete with the perfect match between the PCR primers in solution and the template. In addition, any primers that include mismatches at their 3' end would be at a significant competitive disadvantage. Even if a CHR should out compete the intended PCR primer, it would produce a truncated PCR product, without a downstream site for the sequencing primer. If the truncated product could be driven to the capture bead and immobilized, one of two situations would result. If the CHR out-competed the solution-phase primer, then the immobilized product would lack a sequencing primer binding site, and would result in an empty PicoTiter plate (PTP) well. If the CHR out-competed the bead-bound primer, the sequencing primer would still be present, and the only effect would be a shorter insert. Neither result would unduly compromise the sequencing quality. Given the large amount of genomic material used in the sample preparation process (currently 25 μg, containing $5.29 \times 10^{16}$ copies of the 35 Kb Adenovirus genome), oversampling can be used to provide fragments that lack the complete CHR, and allow standard PCR amplification of the region in question.

Example 3

Sample Preparation by Nebulization

Preparation of DNA by Nebulization

The purpose of the Nebulization step is to fragment a large stretch of DNA such as a whole genome or a large portion of a genome into smaller molecular species that are amenable to DNA sequencing. This population of smaller-sized DNA species generated from a single DNA template is referred to as a library. Nebulization shears double-stranded template DNA into fragments ranging from 50 to 900 base pairs. The sheared library contains single-stranded ends that are end-repaired by a combination of T4 DNA polymerase, E. coli DNA polymerase I (Klenow fragment), and T4 polynucleotide kinase. Both T4 and Klenow DNA polymerases are used to "fill-in" 3' recessed ends (5' overhangs) of DNA via their 5'-3' polymerase activity. The single-stranded 3'-5' exonuclease activity of T4 and Klenow polymerases will remove 3' overhang ends and the kinase activity of T4 polynucleotide kinase will add phosphates to 5' hydroxyl termini.

The sample was prepared as follows:

1. 15 µg of gDNA (genomic DNA) was obtained and adjusted to a final volume of 100 µl in 10 mM TE (10 mM Tris, 0.1 mM EDTA, pH 7.6; see reagent list at the end of section). The DNA was analyzed for contamination by measuring the $O.D._{260/280}$ ratio, which was 1.8 or higher. The final gDNA concentration was expected to be approximately 300 µg/ml.

2. 1600 µl of ice-cold Nebulization Buffer (see end of section) was added to the gDNA.

3. The reaction mixture was placed in an ice-cold nebulizer (CIS-US, Bedford, Mass.).

Figure 28A:
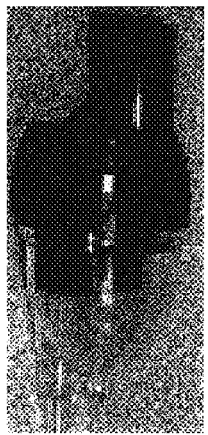
FIGS. 28A-D depict the assembly for the nebulizer used for the methods of the invention. A tube cap was placed over the top of the nebulizer (FIG. 7A) and the cap was secured with a nebulizer clamp assembly (FIG. 7B). The bottom of the nebulizer was attached to the nitrogen supply (FIG. 7C) and the entire device was wrapped in parafilm (FIG. 7D).

4. The cap from a 15 ml snap cap falcon tube was placed over the top of the nebulizer (FIG. 28A).

Figure 28B:

5. The cap was secured with a clean Nebulizer Clamp assembly, consisting of the fitted cover (for the falcon tube lid) and two rubber O-rings (FIG. 28B).

Figure 28C:
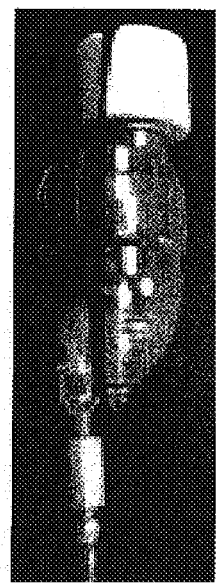
Figure 28D:
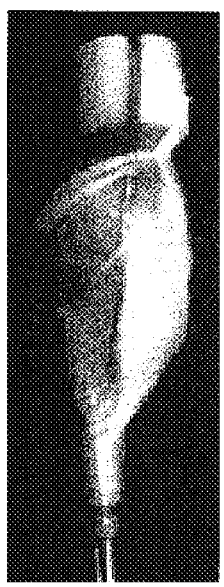

6. The bottom of the nebulizer was attached to a nitrogen supply and the entire device was wrapped in parafilm (FIGS. 28C and 28D).

7. While maintaining nebulizer upright (as shown in FIG. 28D), 50 psi (pounds per square inch) of nitrogen was applied for 5 minutes. The bottom of the nebulizer was tapped on a hard surface every few seconds to force condensed liquid to the bottom.

8. Nitrogen was turned off after 5 minutes. After the pressure had normalized (30 seconds), the nitrogen source was remove from the nebulizer.

9. The parafilm was removed and the nebulizer top was unscrewed. The sample was removed and transferred to a 1.5 ml microcentrifuge tube.

10. The nebulizer top was reinstalled and the nebulizer was centrifuged at 500 rpm for 5 minutes.

11. The remainder of the sample in the nebulizer was collected. Total recovery was about 700 µl.

12. The recovered sample was purified using a QIAquick column (Qiagen Inc., Valencia, Calif.) according to manufacturer's directions. The large volume required the column to be loaded several times. The sample was eluted with 30 µl of Buffer EB (10 mM Tris HCl, pH 8.5; supplied in Qiagen kit) which was pre-warmed at 55° C.

13. The sample was quantitated by UV spectroscopy (2 µl in 198 µl water for 1:100 dilution).

Enzymatic Polishing

Nebulization of DNA templates yields many fragments of DNA with frayed ends. These ends are made blunt and ready for ligation to adaptor fragments by using three enzymes, T4 DNA polymerase, E. coli DNA polymerase (Klenow fragment) and T4 polynucleotide kinase.

The sample was prepared as follows:

1. In a 0.2 ml tube the following reagents were added in order:

| |
|---|
| 28 µl purified, nebulized gDNA fragments |
| 5 µl water |
| 5 µl 10× T4 DNA polymerase buffer |
| 5 µl BSA (1 mg/ml) |
| 2 µl dNTPs (10 mM) |
| 5 µl T4 DNA polymerase (3 units/µl) |
| 50 µl final volume |

2. The solution of step 1 was mixed well and incubated at 25° C. for 10 minutes in a MJ thermocycler (any accurate incubator may be used).

3. 1.25 µl E. coli DNA polymerase (Klenow fragment) (5 units/ml) was added.

4. The reaction was mixed well and incubated in the MJ thermocycler for 10 minutes at 25° C. and for an additional 2 hrs at 16° C.

5. The treated DNA was purified using a QiaQuick column and eluted with 30 µl of Buffer EB (10 mM Tris HCl, pH 8.5) which was pre-warmed at 55° C.

6. The following reagents were combined in a 0.2 ml tube:

| |
|---|
| 30 µl Qiagen purified, polished, nebulized gDNA fragments |
| 5 µl water |
| 5 µl 10 X T4 PNK buffer |
| 5 µl ATP (10 mM) |
| 5 µl T4 PNK (10 units/ml) |
| 50 µl final volume |

7. The solution was mixed and placed in a MJ thermal cycler using the T4 PNK program for incubation at 37° C. for 30 minutes, 65° C. for 20 minutes, followed by storage at 14° C.

8. The sample was purified using a QiaQuick column and eluted in 30 µl of Buffer EB which was pre-warmed at 55° C.

9. A 2 µl aliquot of the final polishing reaction was held for analysis using a BioAnalyzer DNA 1000 LabChip (see below).

Ligation of Adaptors

The procedure for ligating the adaptors was performed as follows:

1. In a 0.2 ml tube the following reagents were added in order:

| |
|---|
| 20.6 µl molecular biology grade water |
| 28 µl digested, polished gDNA Library |
| 60 µl 2× Quick Ligase Reaction Buffer |
| 1.8 µl MMP (200 pmol/µl) Universal Adaptor set |
| 9.6 µl Quick Ligase |
| 120 µl total |

The above reaction was designed for 5 µg and was scaled depending on the amount of gDNA used.

2. The reagents were mixed well and incubated at 25° C. for 20 minutes. The tube was on ice until the gel was prepared for agarose gel electrophoresis.

Gel Electrophoresis and Extraction of Adapted gDNA Library

Nebulization of genomic DNA yields a library population that ranges from 50-900 bp. The addition of the 88-bp Universal Adaptor set will shift the population to a larger size and will result in a migration profile with a larger size range (approximately 130-980 bp). Adaptor dimers will migrate at 88 bp and adaptors not ligated will migrate at 44 bp. Therefore, genomic DNA libraries isolated in size ranges$\geq$250 bp can be physically isolated from the agarose gel and purified using standard gel extraction techniques. Gel isolation of the adapted gDNA library will result in the recovery of a library population in a size range that is$\geq$250 bp (size range of library can be varied depending on application). The library size range after ligation of adapters is 130 to 980 bp. It should be noted that the procedure may be adapted for isolation of any band size range, such as, for example, 130 to 200 bp, 200 to 400 bp, 250 to 500 bp, 300 to 600 bp, 500 to 700 bp and the like by cutting different regions of the gel. The procedure described below was used to isolated fragments of 250 bp to 500 bp.

A 150 ml agarose gel was prepared to include 2% agarose, 1× TBE, and 4.5 µl ethidium bromide (10 mg/ml stock). The ligated DNA was mixed with 10× Ready Load Dye and loaded onto the gel. In addition, 10 µl of a 100-bp ladder (0.1 µg/µl) was loaded on two lanes away from the ligation reaction flanking the sample. The gel was electrophoresed at 100 V for 3 hours. When the gel run was complete, the gel was removed from the gel box, transferred to a GelDoc, and covered with plastic wrap. The DNA bands were visualized using the Prep UV light. A sterile, single-use scalpel, was used to cut out a library population from the agarose gel with fragment sizes of 250-500 bp. This process was done as quickly as possible to prevent nicking of DNA. The gel slices were placed in a 15 ml falcon tube. The agarose-embedded gDNA library was isolated using a Qiagen MinElute Gel Extraction kit. Aliquots of each isolated gDNA library were analyzed using a BioAnalyzer DNA 1000 LabChip to assess the exact distribution of the gDNA library population.

Strand Displacement and Extension of the gDNA Library and Isolation of the Single Stranded gDNA Library using Streptavidin Beads Strand displacement and extension of nicked double-stranded gDNA library was performed as described in Example 1, with the exception that the Bst-treated samples were incubated in the thermal cycler at 65° C. for 30 minutes and placed on ice until needed. Streptavidin beads were prepared as described in Example 1, except that the final wash was performed using two washes with 200 µl 1× Binding buffer and two washes with 200 µl nH$_2$O. Single-stranded gDNA library was isolated using streptavidin beads as follows. Water from the washed beads was removed and 250 µl of Melt Solution (see below) was added. The bead suspension was mixed well and incubated at room temperature for 10 minutes on a tube rotator. In a separate tube, 1250 µl of PB (from the QiaQuick Purification kit) and 9 µl of 20% acetic acid were mixed. The beads in 250 µl Melt Solution were pelleted using a Dynal MPC and the supernatant was carefully removed and transferred to the freshly prepared PB/acetic acid solution. DNA from the 1500 µl solution was purified using a single MinElute purification spin column. This was performed by loading the sample through the same column twice at 750 µl per load. The single stranded gDNA library was eluted with 15 µl of Buffer EB which was pre-warmed at 55° C.

Single Strand gDNA Quantitation and Storage

Single-stranded gDNA was quantitated using RNA Pico 6000 LabChip as described in Example 1. In some cases, the single stranded library was quantitated by a second assay to ensure the initial Agilent 2100 quantitation was performed accurately. For this purpose, RiboGreen quantitation was performed as described (ssDNA Quantitation by Fluorometry) to confirm the Agilent 2100 quantitation. If the two estimates differed by more than 3 fold, each analysis was repeated. If the quantitation showed greater than a 3 fold difference between the two procedures, a broader range of template to bead was used.

Dilution and storage of the single stranded gDNA library was performed as described in Example 1. The yield was as follows:

Remaining final volume of ssDNA library following LabChip analysis=12 µl.

Remaining final volume of ssDNA library following RiboGreen analysis=9 µl.

Final volume of ssDNA library after the addition of TE=18 µl.

An equal volume of TE was added to single-stranded gDNA library stock. Single-stranded gDNA library to 1×10$^8$ molecules/µl in Buffer TE. Stock was diluted (1/500) to 200,000 molecules/µl in TE and 20 µl aliquots were prepared.

Library Fragment Size Distribution After Nebulization

Figure 29A:
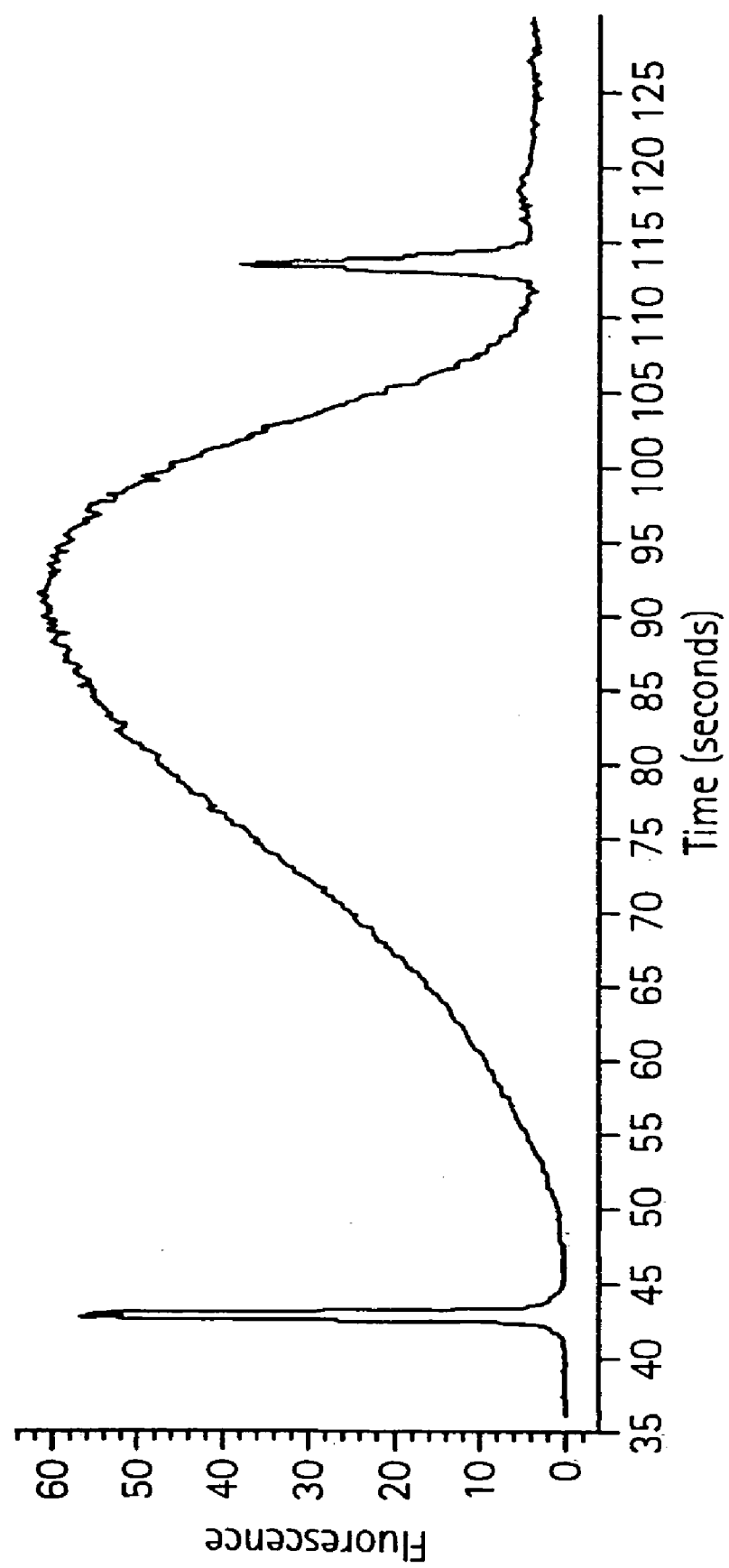
FIG. 29A depicts representative results for LabChip analysis of a single stranded DNA library following nebulization and polishing.
Figure 29B:
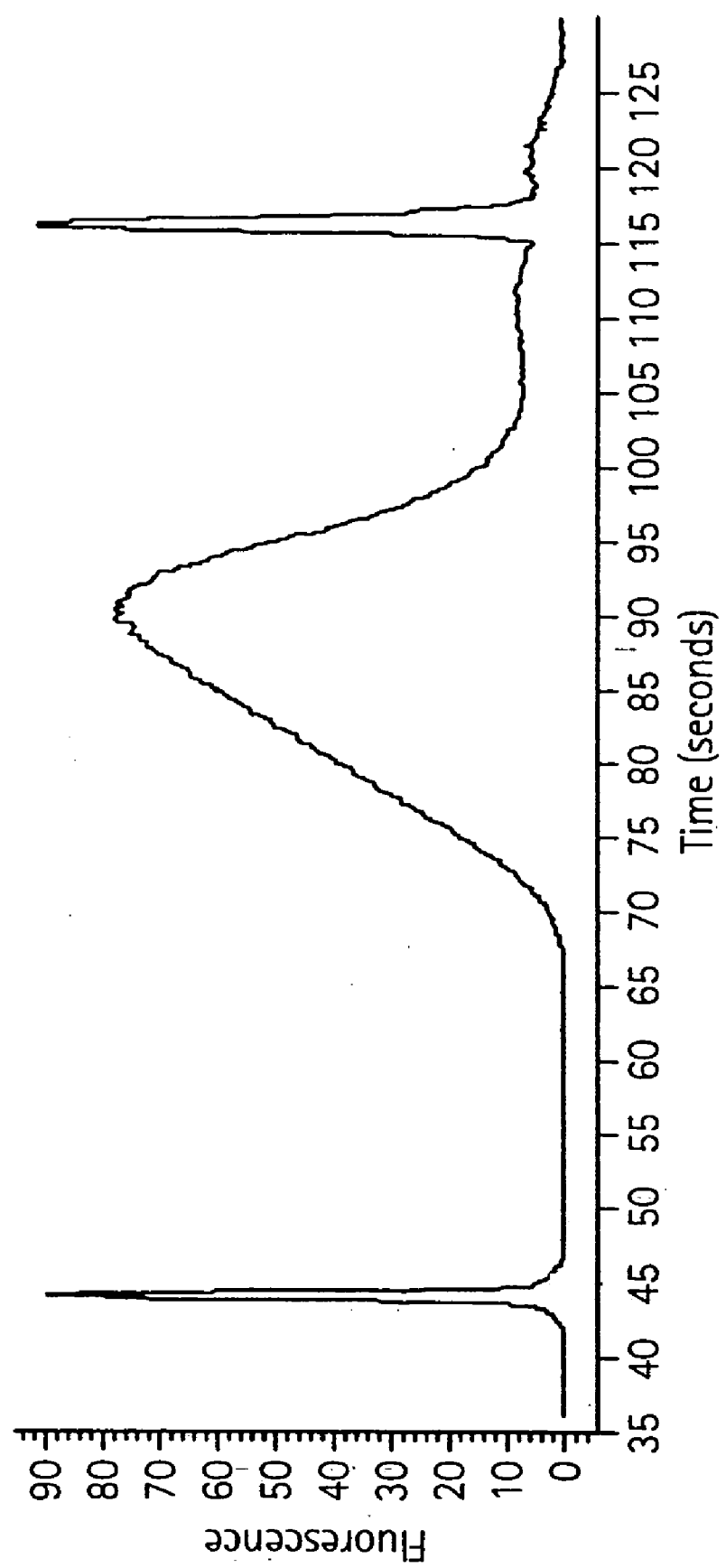
FIG. 29B depicts representative size distribution results for an adaptor-ligated single stranded DNA library following nebulization, polishing, and gel purification.

Typical results from Agilent 2100 DNA 1000 LabChip analysis of 1 µl of the material following Nebulization and polishing are shown in FIG. 29A. The size range distribution of the majority of the product was expected to fall around 50 to 900 base pairs. The mean size (top of peak) was expected to be approximately 450 bp. Typical results from gel purification of adaptor ligated library fragments are shown in FIG. 29B.

Reagents

Unless otherwise specified, the reagents listed in the Examples represent standard reagents that are commercially available. For example, Klenow, T4 DNA polymerase, T4 DNA polymerase buffer, T4 PNK, T4 PNK buffer, Quick T4 DNA Ligase, Quick Ligation Buffer, Bst DNA polymerase (Large Fragment) and ThermoPol reaction buffer are available from New England Biolabs (Beverly, Mass.). dNTP mix is available from Pierce (Rockford, Ill.). Agarose, UltraPure TBE, BlueJuice gel loading buffer and Ready-Load 100 bp DNA ladder may be purchased from Invitrogen (Carlsbad, Calif.). Ethidium Bromide and 2-Propanol may be purchased from Fisher (Hampton, N.H.). RNA Ladder may be purchased from Ambion (Austin, Tex.). Other reagents are either commonly known and/or are listed below:

Melt Solution:

| Ingredient | Quantity Required | Vendor | Stock Number |
|---|---|---|---|
| NaCl (5M) | 200 µl | Invitrogen | 24740-011 |
| NaOH (10N) | 125 µl | Fisher | SS255-1 |
| molecular biology grade water | 9.675 ml | Eppendorf | 0032-006-205 |

The Melt Solution included 100 mM NaCl, and 125 mM NaOH. The listed reagents were combined and mixed thoroughly. The solution could be stored at RT for six months.

Binding & Washing (B&W) Buffer (2× and 1×):

| Ingredient | Quantity Required | Vendor | Stock Number |
|---|---|---|---|
| UltraPure Tris-HCl (pH 7.5, 1M) | 250 µl | Invitrogen | 15567-027 |
| EDTA (0.5M) | 50 µl | Invitrogen | 15575-020 |
| NaCl (5M) | 10 ml | Invitrogen | 24740-011 |
| molecular biology grade water | 14.7 ml | Eppendorf | 0032-006-205 |

The 2× B&W buffer included final concentrations of 10 mM Tris-HCl (pH 7.5), 1 mM EDTA, and 2 M NaCl. The listed reagents were combined by combined and mixed thoroughly. The solution could be stored at RT for 6 months. The 1× B&W buffer was prepared by mixing 2× B&W buffer with picopure $H_2O$, 1:1. The final concentrations was half of that listed the above, i.e., 5 mM Tris-HCl (pH 7.5), 0.5 mM EDTA, and 1 M NaCl.

Other buffers included the following. 1× T4 DNA Polymerase Buffer: 50 mM NaCl, 10 mM Tris-HCl, 10 mM MgCl2, 1 mM dithiothreitol (pH 7.9 @ 25° C.). TE: 10 mM Tris, 1 mM EDTA.

Special Reagent Preparation:

TE (10 mM):

| Ingredient | Quantity Required | Vendor | Stock Number |
|---|---|---|---|
| TE (1M) | 1 ml | Fisher | BP1338-1 |
| molecular biology grade water | 99 ml | Eppendorf | 0032-006-205 |

Reagents were mixed and the solution could be stored RT for six months.

Nebulization Buffer:

| Ingredient | Quantity Required | Vendor | Stock Number |
|---|---|---|---|
| Glycerol | 53.1 ml | Sigma | G5516 |
| molecular biology grade water | 42.1 ml | Eppendorf | 0032-006-205 |
| UltraPure Tris-HCl (pH 7.5, 1M) | 3.7 ml | Invitrogen | 15567-027 |
| EDTA (0.5M) | 1.1 ml | Sigma | M-10228 |

All reagents were added (glycerol was added last) to a Stericup and mixed well. The solution was labeled and could be stored at RT for six months.

ATP (10 mM):

| Ingredient | Quantity Required | Vendor | Stock Number |
|---|---|---|---|
| ATP (100 mM) | 10 µl | Roche | 1140965 |
| molecular biology grade water | 90 µl | Eppendorf | 0032-006-205 |

The reagents were mixed and the solution could be stored at −20° C. for six months.

BSA (1 mg/ml):

| Ingredient | Quantity Required | Vendor | Stock Number |
|---|---|---|---|
| BSA (10 mg/ml) | 10 µl | NEB | M0203 kit |
| Molecular Biology Grade water | 90 µl | Eppendorf | 0032-006-205 |

The reagents were mixed and the solution could be stored at 4° C. for six months.

Library Annealing Buffer, 10×:

| Ingredient | Quantity Req. | Vendor | Stock No. |
|---|---|---|---|
| UltraPure Tris-HCl (pH 7.5, 1M) | 200 ml | Invitrogen | 15567-027 |
| Magnesium acetate, enzyme grade (1M) | 10.72 g | Fisher | BP-215-500 |
| Molecular Biology Grade water | ~1 L | Eppendorf | 0032-006-205 |

The 10× Annealing Buffer included 200 mM Tris (pH 7.5) and 50 mM magnesium acetate. For this buffer, 200 ml of Tris was added to 500 ml picopure $H_2O$. Next, 10.72 g of magnesium acetate was added to the solution and dissolved completely. The solution was adjusted to a final volume of 1000 ml. The solution could be stored at 4° C. for six months. To avoid the potential for contamination of libraries, the buffer was aliquotted for single or short-term usage.

Adaptors:

Adaptor "A" (400 µM):

| Ingredient | Quantity Req. | Vendor | Stock No. |
|---|---|---|---|
| Adaptor A (sense; HPLC-purified, phosphorothioate linkages, 44 bp, 1000 pmol/µl) | 10.0 µl | IDT | custom |
| Adaptor A (antisense; HPLC-purified, Phosphorothioate linkages, 40 bp, 1000 pmol/µl) | 10.0 µl | IDT | custom |
| Annealing buffer (10X) | 2.5 µl | 454 Corp. | previous table |
| molecular biology grade water | 2.5 µl | Eppendorf | 0032-006-205 |

For this solution, 10 µl of 1000 pmol/µl Adaptor A (44 bp, sense) was mixed with 10 µl of 1000 pmol/µl Adaptor A (40 bp, antisense), 2.5 µl of 10× Library Annealing Buffer, and 2.5 µl of water ($V_f$=25 µl). The adaptors were annealed using the ANNEAL-A program (see Appendix, below) on the Sample Prep Lab thermal cycler. More details on adaptor design are provided in the Appendix.

Adaptor "B" (400 µM):

| Ingredient | Quantity Req. | Vendor | Stock No. |
|---|---|---|---|
| Adaptor B (sense; HPLC-purified, phosphorothioate linkages, 40 bp, 1000 pmol/µl)) | 10 µl | IDT | Custom |

-continued

| Ingredient | Quantity Req. | Vendor | Stock No. |
|---|---|---|---|
| Adaptor B (anti; HPLC-purified, phosphorothioate linkages, 5'Biotinylated, 44 bp, 1000 pmol/μl) | 10 μl | IDT | Custom |
| Annealing buffer (10X) | 2.5 μl | 454 Corp. | previous table |
| molecular biology grade water | 2.5 μl | Eppendorf | 0032-006-205 |

For this solution, 10 μl of 1000 pmol/μl Adaptor B (40 bp, sense) was mixed with 10 μl of 1000 pmol/μl Adaptor B (44 bp, anti), 2.5 μl of 10× Library Annealing Buffer, and 2.5 μl of water ($V_f$=25 μl). The adaptors were annealed using the ANNEAL-A program (see Appendix) on the Sample Prep Lab thermal cycler. After annealing, adaptor "A" and adaptor "B" ($V_f$=50 μl) were combined. Adaptor sets could be stored at −20° C. until use.

20% Acetic Acid:

| Ingredient | Quantity Required | Vendor | Stock Number |
|---|---|---|---|
| acetic acid, glacial | 2 ml | Fisher | A35-500 |
| molecular biology grade water | 8 ml | Eppendorf | 0032-006-205 |

For this solution, glacial acetic acid was added to the water. The solution could be stored at RT for six months.

Adaptor Annealing Program:

ANNEAL-A program for primer annealing:
 1. Incubate at 95° C., 1 min;
 2. Reduce temperature to 15° C. at 0.1° C./sec; and
 3. Hold at 14° C.

T4 Polymerase/Klenow POLISH program for end repair:
 1. Incubate at 25° C., 10 minutes;
 2. Incubate at 16° C., 2 hours; and
 3. Hold at 4° C.

T4 PNK Program for end repair:
 1. Incubate at 37° C., 30 minutes;
 2. Incubate at 65° C., 20 minutes; and
 3. Hold at 14° C.

BST program for stand displacement and extension of nicked double-stranded gDNA:
 1. Incubate at 65° C., 30 minutes; and
 2. Hold at 14° C.

Step 9: Dilution and Storage of Single-Stranded DNA Library
 Single-stranded DNA library in EB buffer: remaining final volume=25 μl.
 Initial Stock dilution was made as follows. Using Pyrosequencing (Pyrosequencing AB, Uppsala, Sweden) results, single-stranded DNA library was diluted to 100M molecules/μL in 1× Annealing Buffer (usually this was a 1:50 dilution).
 Aliquots of single-stranded DNA Library were made for common use by diluting 200,000 molecules/μL in 1× Annealing Buffer and preparing 30 μL aliquots. Store at −20° C. Samples were utilized in emulsion PCR.

Reagent Preparation:
 Stop Solution (50 mM EDTA): 100 μl of 0.5 M EDTA was mixed with 900 μl of nH$_2$O to make 1.0 ml of 50 mM EDTA solution.

Solution of 10 mM dNTPs included 10 μl dCTP (100 mM), 10 μl dATP (100 mM), 10 μl dGTP (100 mM), and 10 μl dTTP (100 mM), 60 μl Molecular Biology Grade water, (nH$_2$O). All four 100 mM nucleotide stocks were thawed on ice. 10 μl of each nucleotide was combined with 60 μl of nH$_2$O to a final volume of 100μl, and mixed thoroughly. 1 ml aliquots were dispensed into 1.5 ml microcentrifuge tubes, and stored at −20° C., no longer than one year.

Annealing buffer, 10×: 10× Annealing buffer included 200 mM Tris (pH 7.5) and 50 mM magnesium acetate. For this solution, 24.23 g Tris was added to 800 ml nH$_2$O and adjusted to pH 7.5. To this, 10.72 g magnesium acetate was added and dissolved completely. The solution was brought up to a final volume of 1000 ml. The solution was able be stored at 4° C. for 1 month.

10× TE: 10× TE included 100 mM Tris•HCl (pH 7.5), and 50 mM EDTA. These reagents were added together and mixed thoroughly. The solution could be stored at room temperature for 6 months.

Example 4

Bead Emulsion PCR

The following procedures, including capture of the template DNA, DNA amplification, and recovery of the beads bound to amplified template, can be performed in a single tube. The emulsion format ensures the physical separation of the beads into 100-200 μm "microreactors" within this single tube, thus allowing for clonal amplification of the various templates. Immobilization of the amplification product is achieved through extension of the template along the oligonucleotides bound to the DNA capture beads. Typical, the copy number of the immobilized template ranges from 10 to 30 million copies per bead. The DNA capture beads affixed with multiple copies of a single species of nucleic acid template are ready for distribution onto PTPs.

The 300,000 75-picoliter wells etched in the PTP surface provide a unique array for the sequencing of short DNA templates in a massively parallel, efficient and cost-effective manner. However, this requires fairly large quantities (millions of copies) of clonal templates in each reaction well. The methods of the invention allow the user to clonally amplify single-stranded genomic template species thorough PCR reactions conducted in standard tubes or microtiter plates. Single copies of the template species may be mixed with capture beads, resuspended into complete PCR amplification solution, and emulsified into microreactors (100 to 200 μm in diameter), after which PCR amplification generates $10^7$-fold amplification of the initial template species. This procedure is much simpler and more cost-effective than previous methods.

Binding Nucleic Acid Template to Capture Beads

This example describes preparation of a population of beads that preferably have only one unique nucleic acid template attached thereto. Successful clonal amplification depends on the delivery of a controlled number of template species (0.5 to 1) to each bead. Delivery of excess species can result in PCR amplification of a mixed template population, preventing generation of meaningful sequence data while a deficiency of species will result in fewer wells containing template for sequencing. This can reduce the extent of genome coverage provided by the sequencing phase. As a result, it is preferred that the template concentration be accurately determined through replicated quantitation, and that the binding protocol be followed as outlined below.

Template Quality Control

The success of the Emulsion PCR reaction is related to the quality of the template species. Regardless of the care and detail paid to the amplification phase, poor quality templates will impede successful amplification and the generation of meaningful sequence data. To prevent unnecessary loss of time and money, it is important to check the quality of the template material before initiating the Emulsion PCR phase of the process. Preferably, the library should pass two quality control steps before it is used in Emulsion PCR. Its concentration and the distribution of products it contains should be determined. Ideally, the library should appear as a heterogeneous population of fragments with little or no visible adapter dimers (e.g., ~90 bases). Also, amplification with PCR primers should result in a product smear ranging, for example, from 300 to 500 bp. Absence of amplification product may reflect failure to properly ligate the adaptors to the template, while the presence of a single band of any size may reflect contamination of the template.

Preparation of the PCR Solution

The main consideration for this phase is to prevent contamination of the PCR reaction mixture with stray amplicons. Contamination of the PCR reactions with a residual amplicon is one of the critical issues that can cause failure of a sequencing run. To reduce the possibility of contamination, proper lab technique should be followed, and reaction mixture preparation should be conducted in a clean room in a UV-treated laminar flow hood.

PCR Reaction Mix:

For 200 µl PCR reaction mixture (enough for amplifying 600,000 beads), the following reagents were combined in a 0.2 ml PCR tube:

TABLE 4

|  | Stock | Final | Microliters |
| --- | --- | --- | --- |
| HIFI Buffer | 10 X | 1 X | 20 |
| treated nucleotides | 10 mM | 1 mM | 20 |
| Mg | 50 mM | 2 mM | 8 |
| BSA | 10% | 0.1% | 2 |
| Tween 80 | 1% | 0.01% | 2 |
| Ppase | 2 U | 0.003 U | 0.333333 |
| Primer MMP1a | 100 µM | 0.625 µM | 1.25 |
| Primer MMP1b | 10 µM | 0.078 µM | 1.56 |
| Taq polymerase | 5 U | 0.2 U | 8 |
| Water |  |  | 136.6 |
| Total |  |  | 200 |

The tube was vortexed thoroughly and stored on ice until the beads are annealed with template.

DNA Capture Beads:

1. 600,000 DNA capture beads were transferred from the stock tube to a 1.5 ml microfuge tube. The exact amount used will depend on bead concentration of formalized reagent.

2. The beads were pelleted in a benchtop mini centrifuge and supernatant was removed.

3. Steps 4-11 were performed in a PCR Clean Room.

4. The beads were washed with 1 mL of 1× Annealing Buffer.

5. The capture beads were pelleted in the microcentrifuge. The tube was turned 180° and spun again.

6. All but approximately 10 µl of the supernatant was removed from the tube containing the beads. The beads were not disturbed.

7. 1 mL of 1× Annealing Buffer was added and this mixture was incubated for 1 minute. The beads were then pelleted as in step 5.

8. All but approximately 100 µL of the material from the tube was removed.

9. The remaining beads and solution were transferred to a PCR tube.

10. The 1.5 mL tube was washed with 150 pL of 1× Annealing Buffer by pipetting up and down several times. This was added to the PCR tube containing the beads.

11. The beads were pelleted as in step 5 and all but 10 µL of supernatant was removed, taking care to not disturb the bead pellet.

12. An aliquot of quantitated single-stranded template DNA (sstDNA) was removed. The final concentration was 200,000-sst DNA molecules/µl.

13. 3 µl of the diluted sstDNA was added to PCR tube containing the beads. This was equivalent to 600,000 copies of sstDNA.

14. The tube was vortexed gently to mix contents.

15. The sstDNA was annealed to the capture beads in a PCR thermocycler with the program 80Anneal stored in the EPCR folder on the MJ Thermocycler, using the following protocol:

5 minutes at 65° C.;
Decrease by 0.1° C./sec to 60° C.;
Hold at 60° C. for 1 minute;
Decrease by 0.1° C./sec to 50° C.;
Hold at 50° C. for 1 minute;
Decrease by 0.1° C./sec to 40° C.;
Hold at 40° C. for 1 minute;
Decrease by 0.1° C./sec to 20° C.; and
Hold at 10° C. until ready for next step.

In most cases, beads were used for amplification immediately after template binding. If beads were not used immediately, they should were stored in the template solution at 4° C. until needed. After storage, the beads were treated as follows.

16. As in step 6, the beads were removed from the thermocycler, centrifuged, and annealing buffer was removed without disturbing the beads.

17. The beads were stored in an ice bucket until emulsification (Example 2).

18. The capture beads included, on average, 0.5 to 1 copies of sstDNA bound to each bead, and were ready for emulsification.

Example 5

Emulsification

A PCR solution suitable for use in this step is described below. For 200 µl PCR reaction mix (enough for amplifying 600 K beads), the following were added to a 0.2 ml PCR tube:

|  | Stock | Final | Microliters |
| --- | --- | --- | --- |
| HIFI Buffer | 10 X | 1 X | 20 |
| treated Nukes | 10 mM | 1 mM | 20 |
| Mg | 50 mM | 2 mM | 8 |
| BSA | 10% | 0.1% | 2 |
| Tween 80 | 1% | 0.01% | 2 |
| Ppase | 2 U | 0.003 U | 0.333333 |
| Primer MMP1a | 100 µM | 0.625 µM | 1.25 |
| Primer MMP1b | 10 µM | 0.078 µM | 1.56 |

| | Stock | Final | Microliters |
|---|---|---|---|
| Taq | 5 U | 0.2 U | 8 |
| Water | | | 136.6 |
| Total | | | 200 |

This example describes how to create a heat-stable water-in-oil emulsion containing about 3,000 PCR microreactors per microliter. Outlined below is a protocol for preparing the emulsion.

1. 200 µl of PCR solution was added to the 600,000 beads (both components from Example 1).

2. The solution was pipetted up and down several times to resuspend the beads.

3. The PCR-bead mixture was allowed to incubate at room temperature for 2 minutes to equilibrate the beads with PCR solution.

4. 400 µl of Emulsion Oil was added to a UV-irradiated 2 ml microfuge tube.

5. An "amplicon-free" ¼" stir magnetic stir bar was added to the tube of Emulsion Oil.

An amplicon-free stir bar was prepared as follows. A large stir bar was used to hold a ¼" stir bar. The stir bar was then:

Washed with DNA-Off (drip or spray);

Rinsed with picopure water;

Dried with a Kimwipe edge; and

UV irradiated for 5 minutes.

6. The magnetic insert of a Dynal MPC-S tube holder was removed. The tube of Emulsion Oil was placed in the tube holder. The tube was set in the center of a stir plate set at 600 rpm.

7. The tube was vortexed extensively to resuspend the beads. This ensured that there was minimal clumping of beads.

8. Using a P-200 pipette, the PCR-bead mixture was added drop-wise to the spinning oil at a rate of about one drop every 2 seconds, allowing each drop to sink to the level of the magnetic stir bar and become emulsified before adding the next drop. The solution turned into a homogeneous milky white liquid with a viscosity similar to mayonnaise.

9. Once the entire PCR-bead mixture was been added, the microfuge tube was flicked a few times to mix any oil at the surface with the milky emulsion.

10. Stirring was continued for another 5 minutes.

11. Steps 9 and 10 were repeated.

12. The stir bar was removed from the emulsified material by dragging it out of the tube with a larger stir bar.

13. 10 µL of the emulsion was removed and placed on a microscope slide. The emulsion was covered with a cover slip and the emulsion was inspected at 50× magnification (10× ocular and 5× objective lens). A "good" emulsion was expected to include primarily single beads in isolated droplets (microreactors) of PCR solution in oil.

14. A suitable emulsion oil mixture with emulsion stabilizers was made as follows. The components for the emulsion mixture are shown in Table 5.

TABLE 5

| Ingredient | Quantity Required | Source | Ref. Number |
|---|---|---|---|
| Sigma Light Mineral Oil | 94.5 g | Sigma | M-5904 |
| Atlox 4912 | 1 g | Uniqema | NA |
| Span 80 | 4.5 g | Uniqema | NA |

The emulsion oil mixture was made by prewarming the Atlox 4912 to 60° C. in a water bath. Then, 4.5 grams of Span 80 was added to 94.5 grams of mineral oil to form a mixture. Then, one gram of the prewarmed Atlox 4912 was added to the mixture. The solutions were placed in a closed container and mixed by shaking and inversion. Any sign that the Atlox was settling or solidifying was remedied by warming the mixture to 60° C., followed by additional shaking.

Example 6

Amplification

This example describes amplification of the template DNA in the bead—emulsion mixture.

According to this protocol of the invention, the DNA amplification phase of the process takes 3 to 4 hours. After the amplification is complete, the emulsion may be left on the thermocycler for up to 12 hours before beginning the process of isolating the beads. PCR thermocycling was performed by placing 50 to 100 µl of the emulsified reaction mixture into individual PCR reaction chambers (i.e., PCR tubes). PCR was performed as follows:

1. The emulsion was transferred in 50-100 µL amounts into approximately 10 separate PCR tubes or a 96-well plate using a single pipette tip. For this step, the water-in-oil emulsion was highly viscous.

2. The plate was sealed, or the PCR tube lids were closed, and the containers were placed into in a MJ thermocycler with or without a 96-well plate adaptor.

3. The PCR thermocycler was programmed to run the following program:

1 cycle (4 minutes at 94° C.)—Hotstart Initiation;

40 cycles (30 seconds at 94° C., 30 seconds at 58° C., 90 seconds at 68° C.);

25 cycles (30 seconds at 94° C., 6 minutes at 58° C.); and Storage at 14° C.

4. After completion of the PCR reaction, the amplified material was removed in order to proceed with breaking the emulsion and bead recovery.

Example 7

Breaking the Emulsion and Bead Recovery

This example describes how to break the emulsion and recover the beads with amplified template thereon. Preferably, the post-PCR emulsion should remain intact. The lower phase of the emulsion should, by visual inspection, remain a milky white suspension. If the solution is clear, the emulsion may have partially resolved into its aqueous and oil phases, and it is likely that many of the beads will have a mixture of templates. If the emulsion has broken in one or two of the tubes, these samples should not be combined with the others. If the emulsion has broken in all of the tubes, the procedure should not be continued.

1. All PCR reactions from the original 600 µl sample were combined into a single 1.5 ml microfuge tube using a single pipette tip. As indicated above, the emulsion was quite viscous. In some cases, pipetting was repeated several times for each tube. As much material as possible was transferred to the 1.5 ml tube.

2. The remaining emulsified material was recovered from each PCR tube by adding 50 µl of Sigma Mineral Oil into each sample. Using a single pipette tip, each tube was pipetted up and down a few times to resuspend the remaining material.

3. This material was added to the 1.5 ml tube containing the bulk of the emulsified material.

4. The sample was vortexed for 30 seconds.

5. The sample was spun for 20 minutes in the tabletop microfuge tube at 13.2 K rpm in the Eppendorf microcentrifuge.

6. The emulsion separated into two phases with a large white interface. As much of the top, clear oil phase as possible was removed. The cloudy material was left in the tube. Often a white layer separated the oil and aqueous layers. Beads were often observed pelleted at the bottom of the tube.

7. The aqueous layer above the beads was removed and saved for analysis (gel analysis, Agilent 2100, and Taqman). If an interface of white material persisted above the aqueous layer, 20 microliters of the underlying aqueous layer was removed. This was performed by penetrating the interface material with a pipette tip and withdrawing the solution from underneath.

8. In the PTP Fabrication and Surface Chemistry Room Fume Hood, 1 ml of Hexanes was added to the remainder of the emulsion.

9. The sample was vortexed for 1 minute and spun at full speed for 1 minute.

10. In the PTP Fabrication and Surface Chemistry Room Fume Hood, the top, oil/hexane phase was removed and placed into the organic waste container.

11. 1 ml of 1× Annealing Buffer was added in 80% Ethanol to the remaining aqueous. phase, interface, and beads.

12. The sample was vortexed for 1 minute or until the white substance dissolved.

13. The sample was centrifuged for 1 minute at high speed. The tube was rotated 180 degrees, and spun again for 1 minute. The supernatant was removed without disturbing the bead pellet.

14. The beads were washed with 1 ml of 1× Annealing Buffer containing 0.1% Tween 20 and this step was repeated.

Example 8

Single Strand Removal and Primer Annealing

If the beads are to be used in a pyrophosphate-based sequencing reaction, then it is necessary to remove the second strand of the PCR product and anneal a sequencing primer to the single stranded template that is bound to the bead. This example describes a protocol for accomplishing that.

1. The beads were washed with 1 ml of water, and spun twice for 1 minute. The tube was rotated 180° between spins. After spinning, the aqueous phase was removed.

2. The beads were washed with 1 ml of 1 mM EDTA. The tube was spun as in step 1 and the aqueous phase was removed.

3. 1 ml of 0.125 M NaOH was added and the sample was incubated for 8 minutes.

4. The sample was vortexed briefly and placed in a microcentrifuge.

5. After 6 minutes, the beads were pelleted as in step 1 and as much solution as possible was removed.

6. At the completion of the 8 minute NaOH incubation, 1 ml of 1× Annealing Buffer was added.

7. The sample was briefly vortexed, and the beads were pelleted as in step 1. As much supernatant as possible was removed, and another 1 ml of 1× Annealing buffer was added.

8. The sample was briefly vortexed, the beads were pelleted as in step 1, and 800 µl of 1× Annealing Buffer was removed.

9. The beads were transferred to a 0.2 ml PCR tube.

10. The beads were transferred and as much Annealing Buffer as possible was removed, without disturbing the beads.

11. 100 µl of 1× Annealing Buffer was added.

12. 4 µl of 100 µM sequencing primer was added. The sample was vortexed just prior to annealing.

13. Annealing was performed in a MJ thermocycler using the "80Anneal" program.

14. The beads were washed three times with 200 µl of 1× Annealing Buffer and resuspended with 100 µl of 1× Annealing Buffer.

15. The beads were counted in a Hausser Hemacytometer. Typically, 300,000 to 500,000 beads were recovered (3,000-5,000 beads/µL).

16. Beads were stored at 4° C. and could be used for sequencing for 1 week.

Example 9

Optional Enrichment Step

The beads may be enriched for amplicon containing bead using the following procedure. Enrichment is not necessary but it could be used to make subsequent molecular biology techniques, such as DNA sequencing, more efficient.

Fifty microliters of 10 µM (total 500 pmoles) of biotin-sequencing primer was added to the Sepharose beads containing amplicons from Example 5. The beads were placed in a thermocycler. The primer was annealed to the DNA on the bead by the thermocycler annealing program of Example 2.

After annealing, the sepharose beads were washed three times with Annealing Buffer containing 0.1% Tween 20. The beads, now containing ssDNA fragments annealed with biotin-sequencing primers, were concentrated by centrifugation and resuspended in 200 µl of BST binding buffer. Ten microliters of 50,000 unit/ml Bst-polymerase was added to the resuspended beads and the vessel holding the beads was placed on a rotator for five minutes. Two microliters of 10 mM dNTP mixture (i.e., 2.5 µl each of 10 mM dATP, dGTP, dCTP and dTTP) was added and the mixture was incubated for an additional 10 minutes at room temperature. The beads were washed three times with annealing buffer containing 0.1% Tween 20 and resuspended in the original volume of annealing buffer.

Fifty microliters of Dynal Streptavidin beads (Dynal Biotech Inc., Lake Success, N.Y.; M270 or MyOne™ beads at 10 mg/ml) was washed three times with Annealing Buffer containing 0.1% Tween 20 and resuspended in the original volume in Annealing Buffer containing 0.1% Tween 20. Then the Dynal bead mixture was added to the resuspended sepharose beads. The mixture was vortexed and placed in a rotator for 10 minutes at room temperature.

The beads were collected on the bottom of the test tube by centrifugation at 2300 g (500 rpm for Eppendorf Centrifuge 5415D). The beads were resuspended in the original volume of Annealing Buffer containing 0.1% Tween 20. The mixture, in a test tube, was placed in a magnetic separator (Dynal). The beads were washed three times with Annealing Buffer containing 0.1% Tween 20 and resuspended in the original volume in the same buffer. The beads without amplicons were removed by wash steps, as previously described. Only Sepharose beads containing the appropriated DNA fragments were retained.

The magnetic beads were separated from the sepharose beads by addition of 500 µl of 0.125 M NaOH. The mixture was vortexed and the magnetic beads were removed by magnetic separation. The Sepharose beads remaining in solution was transferred to another tube and washed with 400 µl of 50 mM Tris Acetate until the pH was stabilized at 7.6.

Example 10

Nucleic Acid Sequencing using Bead Emulsion PCR

The following experiment was performed to test the efficacy of the bead emulsion PCR. For this protocol, 600,000 Sepharose beads, with an average diameter of 25-35 µm (as supplied my the manufacturer) were covalently attached to capture primers at a ratio of 30-50 million copies per bead. The beads with covalently attached capture primers were mixed with 1.2 million copies of single stranded Adenovirus Library. The library constructs included a sequence that was complimentary to the capture primer on the beads.

The adenovirus library was annealed to the beads using the procedure described in Example 1. Then, the beads were resuspended in complete PCR solution. The PCR Solution and beads were emulsified in 2 volumes of spinning emulsification oil using the same procedure described in Example 2. The emulsified (encapsulated) beads were subjected to amplification by PCR as outlined in Example 3. The emulsion was broken as outlined in Example 4. DNA on beads was rendered single stranded, sequencing primer was annealed using the procedure of Example 5.

Next, 70,000 beads were sequenced simultaneously by pyrophosphate sequencing using a pyrophosphate sequencer from 454 Life Sciences (New Haven, Conn.) (see co-pending application of Lohman et al., filed concurrently herewith entitled "Methods of Amplifying and Sequencing Nucleic Acids" U.S. Ser. No. 60/476,592 filed Jun. 6, 2003). Multiple batches of 70,000 beads were sequenced and the data were listed in Table 6, below.

TABLE 6

| Alignment Error Tolerance | Alignments | | | | | Inferred Read Error |
|---|---|---|---|---|---|---|
| | None | Single | Multiple | Unique | Coverage | |
| 0% | 47916 | 1560 | | 1110 | 54.98% | 0.00% |
| 5% | 46026 | 3450 | | 2357 | 83.16% | 1.88% |
| 10% | 43474 | 6001 | 1 | 3742 | 95.64% | 4.36% |

This table shows the results obtained from BLAST analysis comparing the sequences obtained from the pyrophosphate sequencer against Adenovirus sequence. The first column shows the error tolerance used in the BLAST program. The last column shows the real error as determined by direct comparison to the known sequence.

Bead Emulsion PCR for Double Ended Sequencing

Example 11

Template Quality Control

As indicated previously, the success of the Emulsion PCR reaction was found to be related to the quality of the single stranded template species. Accordingly, the quality of the template material was assessed with two separate quality controls before initiating the Emulsion PCR protocol. First, an aliquot of the single-stranded template was run on the 2100 BioAnalyzer (Agilent). An RNA Pico Chip was used to verify that the sample included a heterogeneous population of fragments, ranging in size from approximately 200 to 500 bases. Second, the library was quantitated using the RiboGreen fluorescence assay on a Bio-Tek FL600 plate fluorometer. Samples determined to have DNA concentrations below 5 ng/µl were deemed too dilute for use.

Example 12

DNA Capture Bead Synthesis

Packed beads from a 1 mL N-hydroxysuccinimide ester (NHS)-activated Sepharose HP affinity column (Amersham Biosciences, Piscataway, N.J.) were removed from the column. The 30-25 µm size beads were selected by serial passage through 30 and 25 µm pore filter mesh sections (Sefar America, Depew, N.Y., USA). Beads that passed through the first filter, but were retained by the second were collected and activated as described in the product literature (Amersham Pharmacia Protocol # 71700600AP). Two different amine-labeled HEG (hexaethyleneglycol) long capture primers were obtained, corresponding to the 5' end of the sense and anti-sense strand of the template to be amplified, (5'-Amine-3 HEG spacers gcttacctgaccgacctctgcctatccctgttgcgtgtc-3'; SEQ ID NO:12; and 5'-Amine-3 HEG spacers ccattcccagctcgtcttgccatctgttccctccctgtc-3'; SEQ ID NO:13) (IDT Technologies, Coralville, Iowa, USA). The primers were designed to capture of both strands of the amplification products to allow double ended sequencing, i.e., sequencing the first and second strands of the amplification products. The capture primers were dissolved in 20 mM phosphate buffer, pH 8.0, to obtain a final concentration of 1 mM. Three microliters of each primer were bound to the sieved 30-25 µm beads. The beads were then stored in a bead storage buffer (50 mM Tris, 0.02% Tween and 0.02% sodium azide, pH 8). The beads were quantitated with a hemacytometer (Hausser Scientific, Horsham, Pa., USA) and stored at 4° C. until needed.

Example 13

PCR Reaction Mix Preparation and Formulation

As with any single molecule amplification technique, contamination of the reactions with foreign or residual amplicon from other experiments could interfere with a sequencing run. To reduce the possibility of contamination, the PCR reaction mix was prepared in a in a UV-treated laminar flow hood located in a PCR clean room. For each 600,000 bead emulsion PCR reaction, the following reagents were mixed in a 1.5 ml tube: 225 µl of reaction mixture (1× Platinum HiFi Buffer (Invitrogen)), 1 mM dNTPs, 2.5 mM MgSO$_4$ (Invitrogen), 0.1% BSA, 0.01% Tween, 0.003 U/µl thermostable PPi-ase (NEB), 0.125 µM forward primer (5'-gcttacctgaccgacctctg-3'; SEQ ID NO:14) and 0.125 µM reverse primer (5'-ccattcccagctcgtcttg-3'; SEQ ID NO:15) (IDT Technologies, Coralville, Iowa, USA) and 0.2 U/µl Platinum Hi-Fi Taq Polymerase (Invitrogen). Twenty-five microliters of the reaction mixture was removed and stored in an individual 200 µl PCR tube for use as a negative control. Both the reaction mixture and negative controls were stored on ice until needed.

Example 14

Binding Template Species to DNA Capture Beads

Successful clonal DNA amplification for sequencing relates to the delivery of a controlled number of template species to each bead. For the experiments described herein below, the typical target template concentration was determined to be 0.5 template copies per capture bead. At this concentration, Poisson distribution dictates that 61% of the beads have no associated template, 30% have one species of template, and 9% have two or more template species. Delivery of excess species can result in the binding and subsequent amplification of a mixed population (2 or more species) on a single bead, preventing the generation of meaningful sequence data. However, delivery of too few species will result in fewer wells containing template (one species per bead), reducing the extent of sequencing coverage. Consequently, it was deemed that the single-stranded library template concentration was important.

Template nucleic acid molecules were annealed to complimentary primers on the DNA capture beads by the following method, conducted in a UV-treated laminar flow hood. Six hundred thousand DNA capture beads suspended in bead storage buffer (see Example 9, above) were transferred to a 200 µl PCR tube. The tube was centrifuged in a benchtop mini centrifuge for 10 seconds, rotated 180°, and spun for an additional 10 seconds to ensure even pellet formation. The supernatant was removed, and the beads were washed with 200 µl of Annealing Buffer (20 mM Tris, pH 7.5 and 5 mM magnesium acetate). The tube was vortexed for 5 seconds to resuspend the beads, and the beads were pelleted as before. All but approximately 10 µl of the supernatant above the beads was removed, and an additional 200 µl of Annealing Buffer was added. The beads were again vortexed for 5 seconds, allowed to sit for 1 minute, and then pelleted as before. All but 10 µl of supernatant was discarded.

Next, 1.5 µl of 300,000 molecules/µl template library was added to the beads. The tube was vortexed for 5 seconds to mix the contents, and the templates were annealed to the beads in a controlled denaturation/annealing program preformed in an MJ thermocycler. The program allowed incubation for 5 minutes at 80° C., followed by a decrease by 0.1° C./sec to 70° C., incubation for 1 minute at 70° C., decrease by 0.1° C./sec to 60° C., hold at 60° C. for 1 minute, decrease by 0.1° C./sec to 50° C., hold at 50° C. for 1 minute, decrease by 0.1° C./sec to 20° C., hold at 20° C. Following completion of the annealing process, the beads were removed from the thermocycler, centrifuged as before, and the Annealing Buffer was carefully decanted. The capture beads included on average 0.5 copy of single stranded template DNA bound to each bead, and were stored on ice until needed.

Example 15

Emulsification

The emulsification process creates a heat-stable water-in-oil emulsion containing 10,000 discrete PCR microreactors per microliter. This serves as a matrix for single molecule, clonal amplification of the individual molecules of the target library. The reaction mixture and DNA capture beads for a single reaction were emulsified in the following manner. In a UV-treated laminar flow hood, 200 µl of PCR solution (from Example 10) was added to the tube containing the 600,000 DNA capture beads (from Example 11). The beads were resuspended through repeated pipetting. After this, the PCR-bead mixture was incubated at room temperature for at least 2 minutes, allowing the beads to equilibrate with the PCR solution. At the same time, 450 µl of Emulsion Oil (4.5% (w:w) Span 80, 1% (w:w) Atlox 4912 (Uniqema, Delaware) in light mineral oil (Sigma)) was aliquotted into a flat-topped 2 ml centrifuge tube (Dot Scientific) containing a sterile ¼ inch magnetic stir bar (Fischer). This tube was then placed in a custom-made plastic tube holding jig, which was then centered on a Fisher Isotemp digital stirring hotplate (Fisher Scientific) set to 450 RPM.

Figure 30:
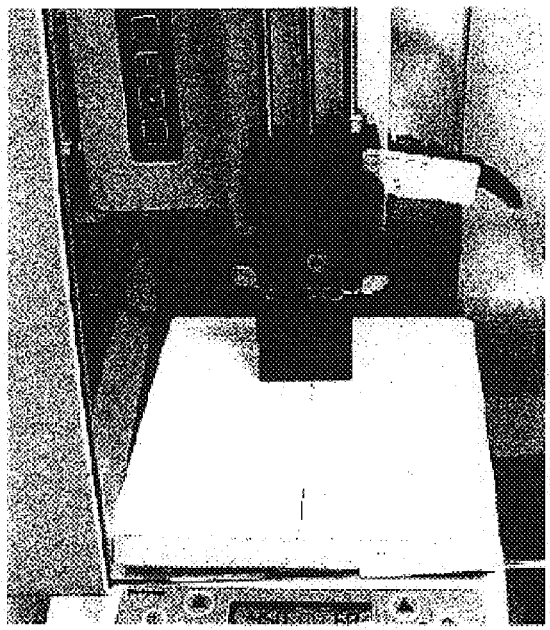
FIG. 30 depiction of jig used to hold tubes on the stir plate below vertical syringe pump. The jig was modified to hold three sets of bead emulsion amplification reaction mixtures. The syringe was loaded with the PCR reaction mixture and beads.
Figure 31:
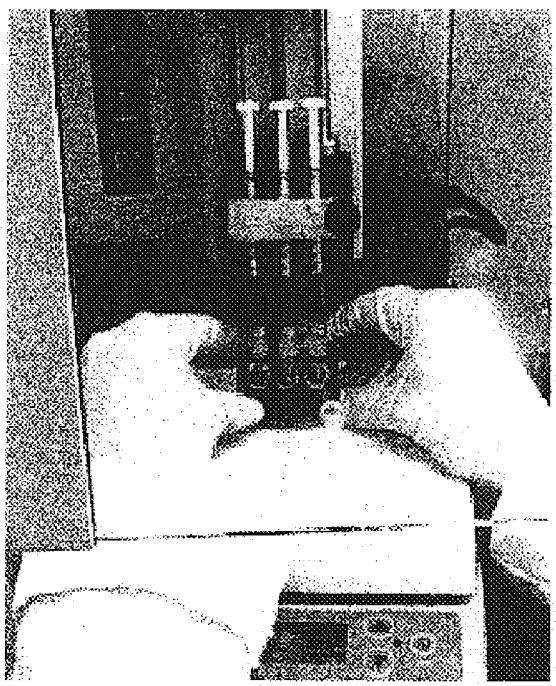
FIG. 31 depiction of optimal placement of syringes in vertical syringe pump and orientation of emulsion tubes below syringe outlets.
Figure 32:
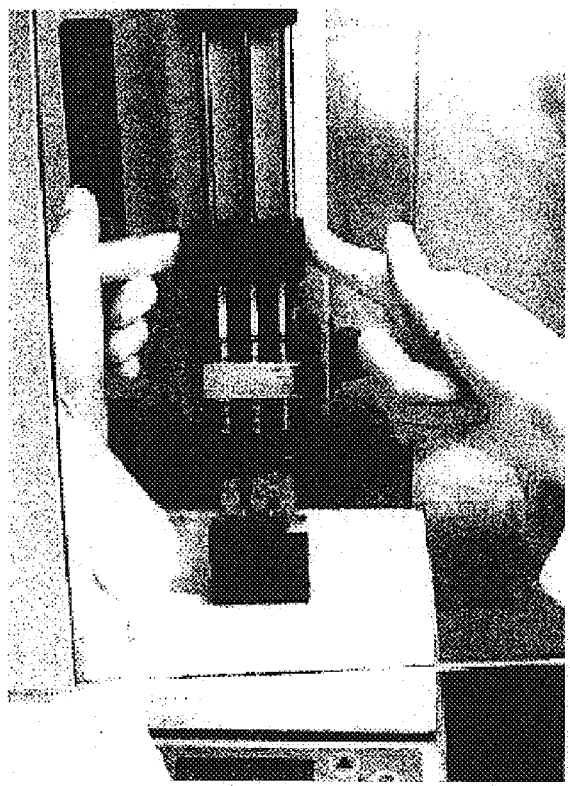
FIG. 32 depiction of optimal placement of syringe pump pusher block against syringe plungers, and optimal orientation of jig on the stir plate. Using this arrangement, the syringe contents were expelled into the agitated emulsion oil.

The PCR-bead solution was vortexed for 15 seconds to resuspend the beads. The solution was then drawn into a 1 ml disposable plastic syringe (Benton-Dickenson) affixed with a plastic safety syringe needle (Henry Schein). The syringe was placed into a syringe pump (Cole-Parmer) modified with an aluminum base unit orienting the pump vertically rather than horizontally (FIG. 30). The tube with the emulsion oil was aligned on the stir plate so that it was centered below the plastic syringe needle and the magnetic stir bar was spinning properly. The syringe pump was set to dispense 0.6 ml at 5.5 ml/hr. The PCR-bead solution was added to the emulsion oil in a dropwise fashion. Care was taken to ensure that the droplets did not contact the side of the tube as they fell into the spinning oil.

Once the emulsion was formed, great care was taken to minimize agitation of the emulsion during both the emulsification process and the post-emulsification aliquotting steps. It was found that vortexing, rapid pipetting, or excessive mixing could cause the emulsion to break, destroying the discrete microreactors. In forming the emulsion, the two solutions turned into a homogeneous milky white mixture with the viscosity of mayonnaise. The contents of the syringe were emptied into the spinning oil. Then, the emulsion tube was removed from the holding jig, and gently flicked with a forefinger until any residual oil layer at the top of the emulsion disappeared. The tube was replaced in the holding jig, and stirred with the magnetic stir bar for an additional minute. The stir bar was removed from the emulsion by running a magnetic retrieval tool along the outside of the tube, and the stir bar was discarded.

Figure 33:
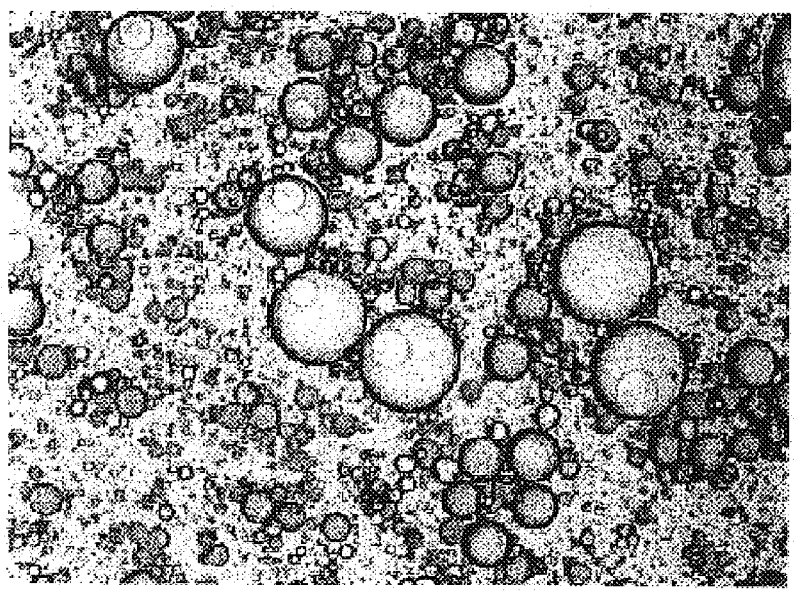
FIG. 33 depiction of beads (see arrows) suspended in individual microreactors according to the methods of the invention.
Figure 35A:
FIG. 35 illustrates the encapsulation of a bead comprising two oligonucleotide sequences for double stranded sequencing.
Figure 35B:
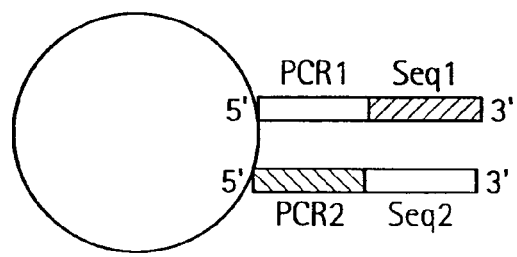
Figure 35C:
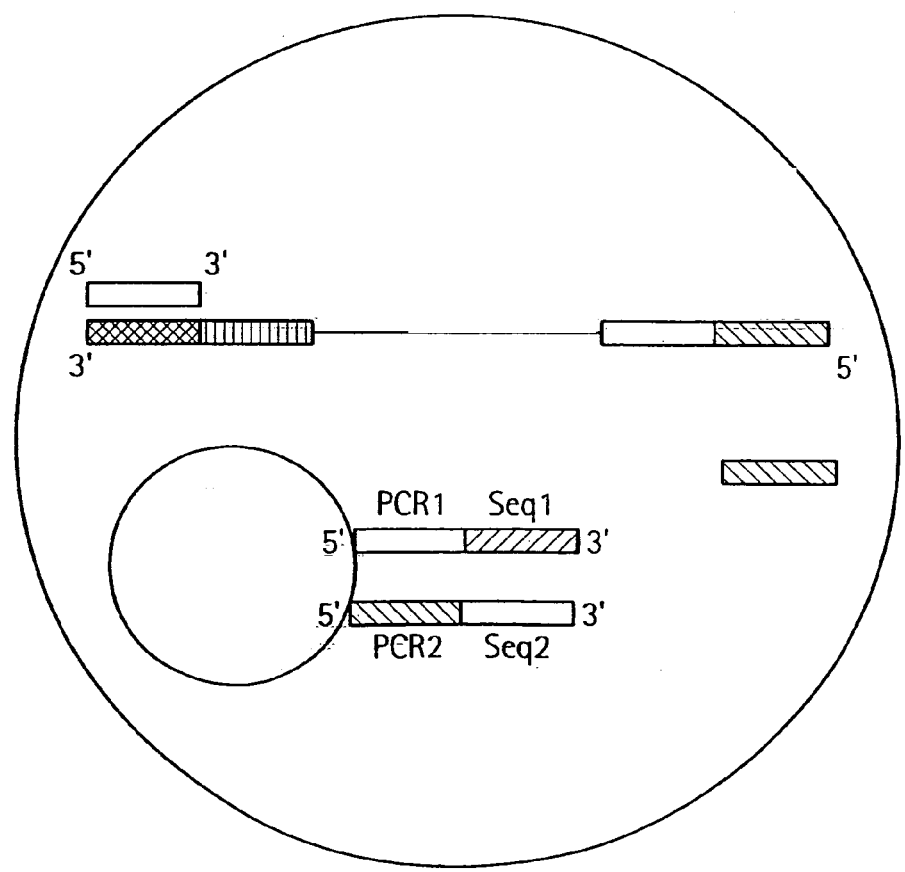
Figure 36:
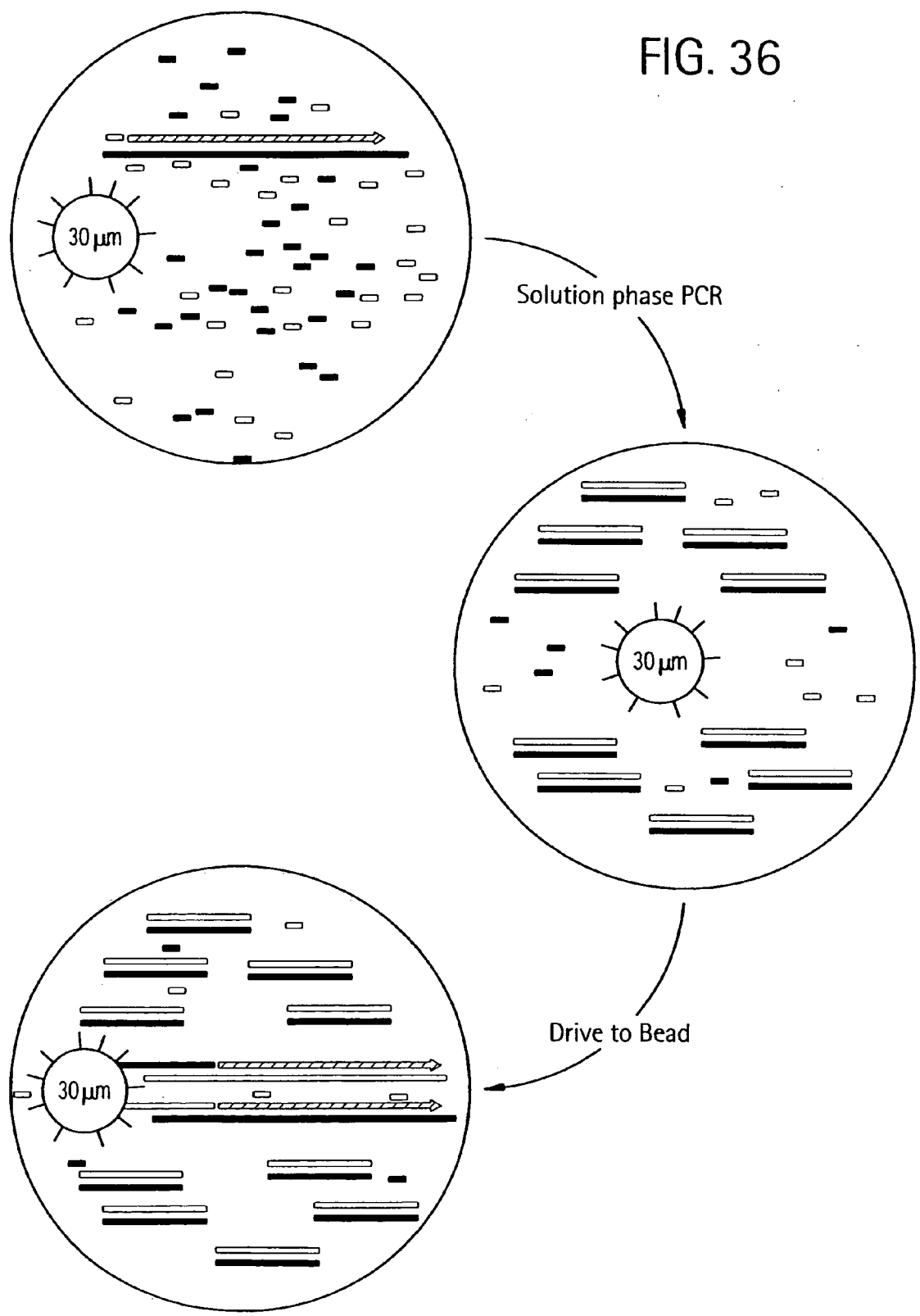
FIG. 36 illustrates solution phase PCR and drive to bead procedure—a step in a preferred embodiment of double ended sequencing.
Figure 37A:
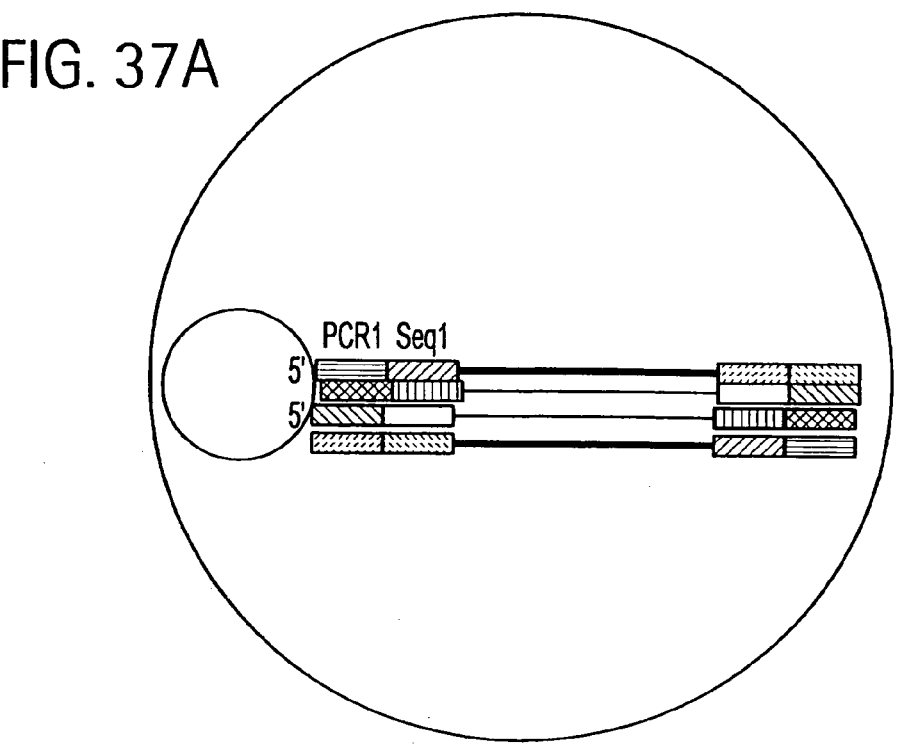
FIG. 37 illustrates emulsion breaking and recovery of amplified template DNA on a bead—a step in a preferred embodiment of double ended sequencing.
Figure 37B:
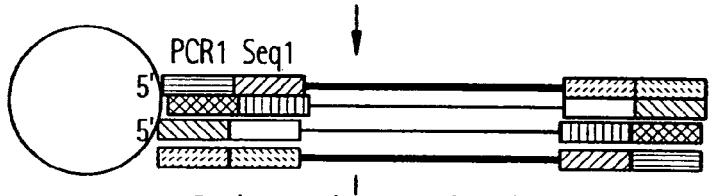
Figure 37C:
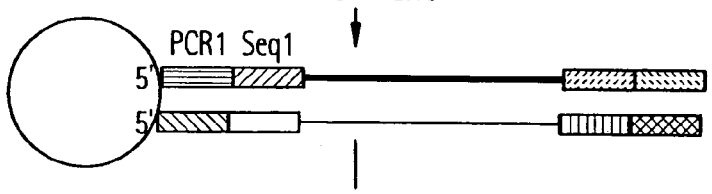
Figure 37D:
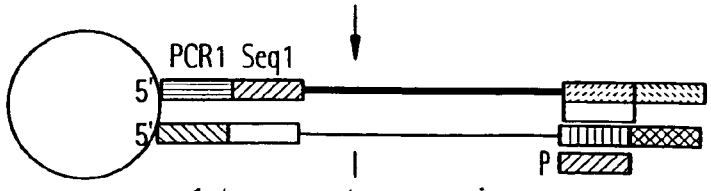
Figure 37E:
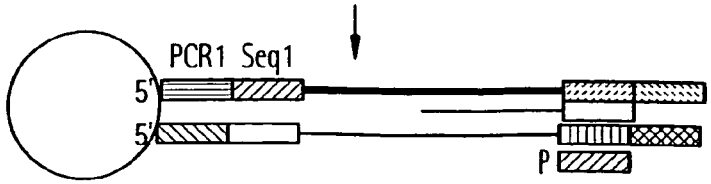

Twenty microliters of the emulsion was taken from the middle of the tube using a P100 pipettor and placed on a microscope slide. The larger pipette tips were used to minimize shear forces. The emulsion was inspected at 50× magnification to ensure that it was comprised predominantly of single beads in 30 to 150 micron diameter microreactors of PCR solution in oil (FIG. 33). After visual examination, the emulsions were immediately amplified.

Example 16

Amplification

The emulsion was aliquotted into 7-8 separate PCR tubes. Each tube included approximately 75 µl of the emulsion. The tubes were sealed and placed in a MJ thermocycler along with the 25 µl negative control described above. The following cycle times were used: 1 cycle of incubation for 4 minutes at 94° C. (Hotstart Initiation), 30 cycles of incubation for 30 seconds at 94° C., and 150 seconds at 68° C. (Amplification), and 40 cycles of incubation for 30 seconds at 94° C., and 360 seconds at 68° C. (Hybridization and Extension). After completion of the PCR program, the tubes were removed and the emulsions were broken immediately or the reactions were stored at 10° C. for up to 16 hours prior to initiating the breaking process.

Example 17

Breaking the Emulsion and Bead Recovery

Following amplification, the emulsifications were examined for breakage (separation of the oil and water phases). Unbroken emulsions were combined into a single 1.5 ml microcentrifuge tube, while the occasional broken emulsion was discarded. As the emulsion samples were quite viscous, significant amounts remained in each PCR tube. The emulsion remaining in the tubes was recovered by adding 75 µl of mineral oil into each PCR tube and pipetting the mixture. This mixture was added to the 1.5 ml tube containing the bulk of the emulsified material. The 1.5 ml tube was then vortexed for 30 seconds. After this, the tube was centrifuged for 20 minutes in the benchtop microcentrifuge at 13.2 K rpm (full speed).

After centrifugation, the emulsion separated into two phases with a large white interface. The clear, upper oil phase was discarded, while the cloudy interface material was left in the tube. In a chemical fume hood, 1 ml hexanes was added to the lower phase and interface layer. The mixture was vortexed for 1 minute and centrifuged at full speed for 1 minute in a benchtop microcentrifuge. The top, oil/hexane phase was removed and discarded. After this, 1 ml of 80% Ethanol/10× Annealing Buffer was added to the remaining aqueous phase, interface, and beads. This mixture was vortexed for 1 minute or until the white material from the interface was dissolved. The sample was then centrifuged in a benchtop microcentrifuge for 1 minute at full speed. The tube was rotated 180 degrees, and spun again for an additional minute. The supernatant was then carefully removed without disturbing the bead pellet.

The white bead pellet was washed twice with 1 ml Annealing Buffer containing 0.1% Tween 20. The wash solution was discarded and the beads were pelleted after each wash as described above. The pellet was washed with 1 ml Picopure water. The beads were pelleted with the centrifuge-rotate-centrifuge method used previously. The aqueous phase was carefully removed. The beads were then washed with 1 ml of 1 mM EDTA as before, except that the beads were briefly vortexed at a medium setting for 2 seconds prior to pelleting and supernatant removal.

Amplified DNA, immobilized on the capture beads, was treated to obtain single stranded DNA. The second strand was removed by incubation in a basic melt solution. One ml of Melt Solution (0.125 M NaOH, 0.2 M NaCl) was subsequently added to the beads. The pellet was resuspended by vortexing at a medium setting for 2 seconds, and the tube placed in a Thermolyne LabQuake tube roller for 3 minutes. The beads were then pelleted as above, and the supernatant was carefully removed and discarded. The residual Melt solution was neutralized by the addition of 1 ml Annealing Buffer. After this, the beads were vortexed at medium speed for 2 seconds. The beads were pelleted, and the supernatant was removed as before. The Annealing Buffer wash was repeated, except that only 800 µl of the Annealing Buffer was removed after centrifugation. The beads and remaining Annealing Buffer were transferred to a 0.2 ml PCR tube. The beads were used immediately or stored at 4° C. for up to 48 hours before continuing on to the enrichment process.

Example 18

Optional Bead Enrichment

The bead mass included beads with amplified, immobilized DNA strands, and empty or null beads. As mentioned previously, it was calculated that 61% of the beads lacked template DNA during the amplification process. Enrichment was used to selectively isolate beads with template DNA, thereby maximizing sequencing efficiency. The enrichment process is described in detail below.

The single stranded beads from Example 14 were pelleted with the centrifuge-rotate-centrifuge method, and as much supernatant as possible was removed without disturbing the beads. Fifteen microliters of Annealing Buffer were added to the beads, followed by 2 µl of 100 µM biotinylated, 40 base enrichment primer (5'-Biotin-tetra-ethyleneglycol spacers ccattccccagctcgtcttgccatctgttccctccctgtctcag-3'; SEQ ID NO:16). The primer was complimentary to the combined amplification and sequencing sites (each 20 bases in length) on the 3' end of the bead-immobilized template. The solution was mixed by vortexing at a medium setting for 2 seconds, and the enrichment primers were annealed to the immobilized DNA strands using a controlled denaturation/annealing program in an MJ thermocycler. The program consisted of the following cycle times and temperatures: incubation for 30 seconds at 65° C., decrease by 0.1° C./sec to 58° C., incubation for 90 seconds at 58° C., and hold at 10° C.

While the primers were annealing, Dynal MyOne™ streptavidin beads were resuspend by gentle swirling. Next, 20 µl of the MyOne™ beads were added to a 1.5 ml microcentrifuge tube containing 1 ml of Enhancing fluid (2 M NaCl, 10 mM Tris-HCl, 1 mM EDTA, pH 7.5). The MyOne bead mixture was vortexed for 5 seconds, and the tube was placed in a Dynal MPC-S magnet. The paramagnetic beads were pelleted against the side of the microcentrifuge tube. The supernatant was carefully removed and discarded without disturbing the MyOne™ beads. The tube was removed from the magnet, and 100 µl of enhancing fluid was added. The tube was vortexed for 3 seconds to resuspend the beads, and stored on ice until needed.

Upon completion of the annealing program, 100 µl of annealing buffer was added to the PCR tube containing the DNA capture beads and enrichment primer. The tube vortexed for 5 seconds, and the contents were transferred to a fresh 1.5 ml microcentrifuge tube. The PCR tube in which the enrichment primer was annealed to the capture beads was washed once with 200 µl of annealing buffer, and the wash solution was added to the 1.5 ml tube. The beads were washed three times with 1 ml of annealing buffer, vortexed for 2 seconds, and pelleted as before. The supernatant was carefully removed. After the third wash, the beads were washed twice with 1 ml of ice cold Enhancing fluid. The beads were vortexed, pelleted, and the supernatant was removed as before. The beads were resuspended in 150 µl ice cold Enhancing fluid and the bead solution was added to the washed MyOne™ beads.

The bead mixture was vortexed for 3 seconds and incubated at room temperature for 3 minutes on a LabQuake tube roller. The streptavidin-coated MyOne™ beads were bound to the biotinylated enrichment primers annealed to immobilized templates on the DNA capture beads. The beads were then centrifuged at 2,000 RPM for 3 minutes, after which the beads were vortexed with 2 second pulses until resuspended.

The resuspended beads were placed on ice for 5 minutes. Following this, 500 µl of cold Enhancing fluid was added to the beads and the tube was inserted into a Dynal MPC-S magnet. The beads were left undisturbed for 60 seconds to allow pelleting against the magnet. After this, the supernatant with excess MyOne™ and null DNA capture beads was carefully removed and discarded.

The tube was removed from the MPC-S magnet, and 1 ml of cold enhancing fluid added to the beads. The beads were resuspended with gentle finger flicking. It was important not to vortex the beads at this time, as forceful mixing could break the link between the MyOne™ and DNA capture beads. The beads were returned to the magnet, and the supernatant removed. This wash was repeated three additional times to ensure removal of all null capture beads. To remove the annealed enrichment primers and MyOne™ beads, the DNA capture beads were resuspended in 400 µl of melting solution, vortexed for 5 seconds, and pelleted with the magnet. The supernatant with the enriched beads was transferred to a separate 1.5 ml microcentrifuge tube. For maximum recovery of the enriched beads, a second 400 µl aliquot of melting solution was added to the tube containing the MyOne™ beads. The beads were vortexed and pelleted as before. The supernatant from the second wash was removed and combined with the first bolus of enriched beads. The tube of spent MyOne™ beads was discarded.

The microcentrifuge tube of enriched DNA capture beads was placed on the Dynal MPC-S magnet to pellet any residual MyOne™ beads. The enriched beads in the supernatant were transferred to a second 1.5 ml microcentrifuge tube and centrifuged. The supernatant was removed, and the beads were washed 3 times with 1 ml of annealing buffer to neutralize the residual melting solution. After the third wash, 800 µl of the supernatant was removed, and the remaining beads and solution were transferred to a 0.2 ml PCR tube. The enriched beads were centrifuged at 2,000 RPM for 3 minutes and the supernatant decanted. Next, 20 µl of annealing buffer and 3 µl of two different 100 µM sequencing primers (5'-ccatctgttc-cctccctgtc-3'; SEQ ID NO:17; and 5'-cctatccctgttgcgtgtc-3' phosphate; SEQ ID NO:18) were added. The tube was vortexed for 5 seconds, and placed in an MJ thermocycler for the following 4-stage annealing program: incubation for 5 minutes at 65° C., decrease by 0.1° C./sec to 50° C., incubation for 1 minute at 50° C., decrease by 0.1° C./sec to 40° C., hold at 40° C. for 1 minute, decrease by 0.1° C./sec to 15° C., and hold at 15° C.

Upon completion of the annealing program, the beads were removed from thermocycler and pelleted by centrifugation for 10 seconds. The tube was rotated 180°, and spun for an additional 10 seconds. The supernatant was decanted and discarded, and 200 µl of annealing buffer was added to the tube. The beads were resuspended with a 5 second vortex, and pelleted as before. The supernatant was removed, and the beads resuspended in 100 µl annealing buffer. At this point, the beads were quantitated with a Multisizer 3 Coulter Counter (Beckman Coulter). Beads were stored at 4° C. and were stable for at least 1 week.

Example 19

Double Strand Sequencing

Figure 38:
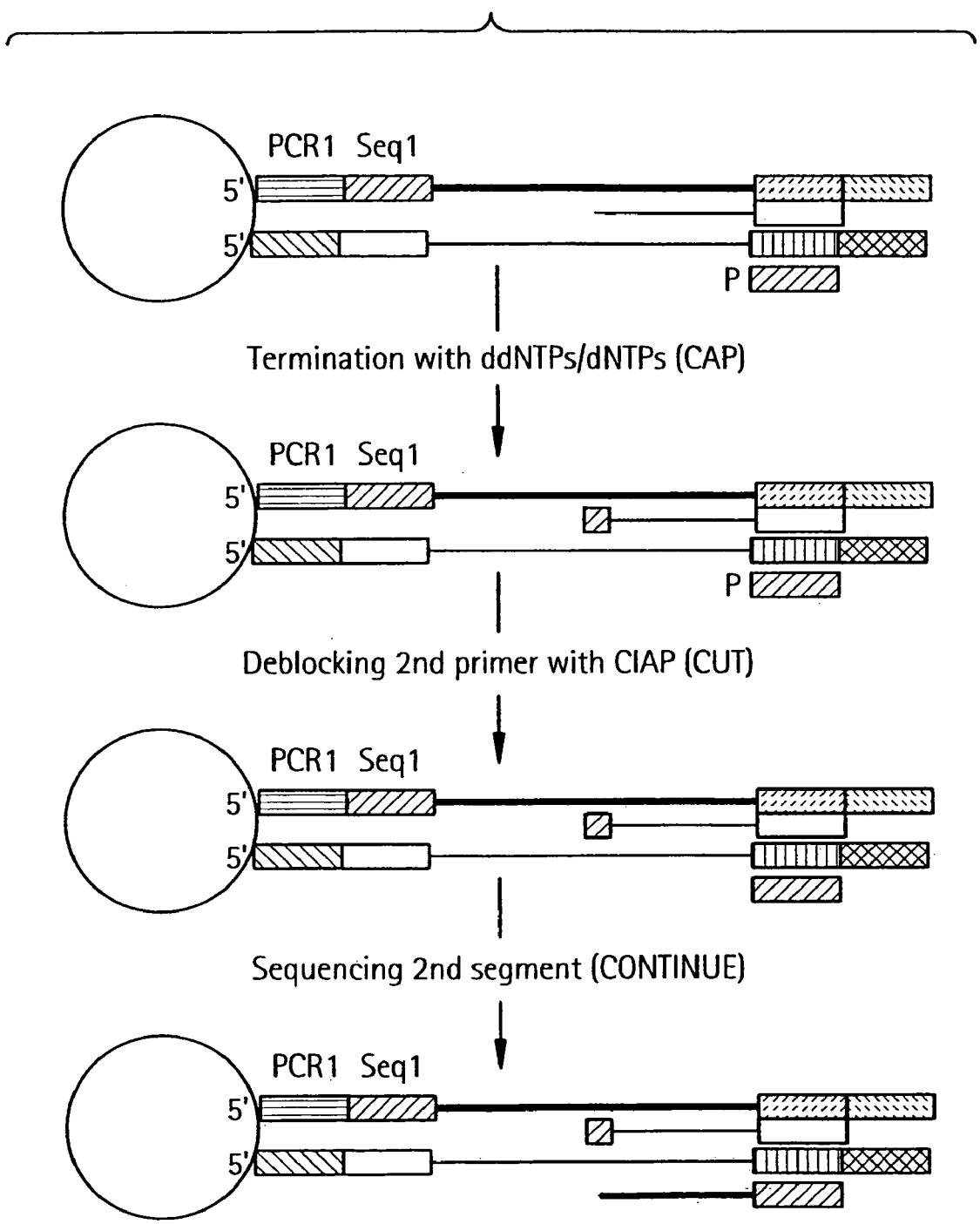
FIG. 38 depicts a schematic representation of a preferred method of double stranded sequencing.

For double strand sequencing, two different sequencing primers are used; an unmodified primer MMP7A and a 3' phosphorylated primer MMP2Bp. There are multiple steps in the process. This process is shown schematically in FIG. 38.

1. First Strand Sequencing. Sequencing of the first strand involves extension of the unmodified primer by a DNA polymerase through sequential addition of nucleotides for a predetermined number of cycles.

2. CAPPING: The first strand sequencing was terminated by flowing a Capping Buffer containing 25 mM Tricine, 5 mM Mangesium acetate, 1 mM DTT, 0.4 mg/ml PVP, 0.1 mg/ml BSA, 0.01% Tween and 2 µM of each dideoxynucleotides and 2 µM of each deoxynucleotide.

3. CLEAN: The residual deoxynucleotides and dideoxynucleotides was removed by flowing in Apyrase Buffer containing 25 mM Tricine, 5 mM Magnesium acetate, 1 mM DTT, 0.4 mg/ml PVP, 0.1 mg/ml BSA, 0.01% Tween and 8.5 units/L of Apyrase.

4. CUTTING: The second blocked primer was unblocked by removing the phosphate group from the 3' end of the modified 3' phosphorylated primer by flowing a Cutting buffer containing 5 units/ml of Calf intestinal phosphatases.

5. CONTINUE: The second unblocked primer was activated by addition of polymerase by flowing 1000 units/ml of DNA polymerases to capture all the available primer sites.

6. Second Strand Sequencing: Sequencing of the second strand by a DNA polymerase through sequential addition of nucleotides for a predetermined number of cycles.

Using the methods described above, the genomic DNA of *Staphylococcus aureus* was sequenced. The results are presented in FIG. 39. A total of 31,785 reads were obtained based on 15770 reads of the first strand and 16015 reads of the second strand. Of these, a total of 11,799 reads were paired and 8187 reads were unpaired obtaining a total coverage of 38%.

Read lengths ranged from 60 to 130 with an average of 95+/−9 bases (FIG. 40). The distribution of genome span and the number of wells of each genome span is shown in FIG. 41. Representative alignment strings, from this genomic sequencing, are shown in FIG. 42.

Example 20

Template PCR 30 micron NHS Sepharose beads were coupled with 1 mM of each of the following primers:

```
MMP1A:     cgtttcccctgtgtgcctttg       (SEQ ID NO:19)

MMP1B:     ccatctgttgcgtgcgtgtc        (SEQ ID NO:20)
```

Drive-to-bead PCR was performed in a tube on the MJ thermocycler by adding 50 µl of washed primer-coupled beads to a PCR master mix at a one-to-one volume-to-volume ratio. The PCR master mixture included:

1× PCR buffer;
1 mM of each dNTP;
0.625 µM primer MMP1A;
0.625 µM primer MMP1B;
1 µl of 1 unit/µl Hi Fi Taq (Invitrogen, San Diego, Calif.); and
~5-10 ng Template DNA (the DNA to be sequenced).

The PCR reaction was performed by programming the MJ thermocycler for the following: incubation at 94° C. for 3 minutes; 39 cycles of incubation at 94° C. for 30 seconds, 58° C. for 30 seconds, 68° C. for 30 seconds; followed by incubation at 94° C. for 30 seconds and 58° C. for 10 minutes; 10 cycles of incubation at 94° C. for 30 seconds, 58° C. for 30 seconds, 68° C. for 30 seconds; and storage at 10° C.

Example 21

Template DNA Preparation and Annealing Sequencing Primer

The beads from Example 1 were washed two times with distilled water; washed once with 1 mM EDTA, and incubated with 0.125 M NaOH for 5 minutes. This removed the DNA strands not linked to the beads. Then, the beads were washed once with 50 mM Tris Acetate buffer, and twice with Annealing Buffer: 200 mM Tris-Acetate, 50 mM Mg Acetate, pH 7.5. Next, 500 pmoles of Sequencing Primer MMP7A (ccatctgttccctccctgtc; SEQ ID NO:21) and MMP2B-phos (cctatccctgttgcgtgtc; SEQ ID NO:22) were added to the beads. The primers were annealed with the following program on the MJ thermocycler: incubation at 60° C. for 5 minutes; temperature drop of 0.1 degree per second to 50° C.; incubation at 50° C. for 5 minutes; temperature drop of 0.1 degree per second to 4° C.; incubation at 40° C. for 5 minutes; temperature drop of 0.1 degree per second to 10° C. The template was then sequenced using standard pyrophosphate sequencing.

Example 22

Sequencing and Stopping of the First Strand

The beads were spun into a 55 μm PicoTiter plate (PTP) at 3000 rpm for 10 minutes. The PTP was placed on a rig and run using de novo sequencing for a predetermined number of cycles. The sequencing was stopped by capping the first strand. The first strand was capped by adding 100 μl of 1×AB (50 mM Mg Acetate, 250 mM Tricine), 1000 unit/ml BST polymerase, 0.4 mg/ml single strand DNA binding protein, 1 mM DTT, 0.4 mg/ml PVP (Polyvinyl Pyrolidone), 10 μM of each ddNTP, and 2.5 μM of each dNTP. Apyrase was then flowed over in order to remove excess nucleotides by adding 1× AB, 0.4 mg/ml PVP, 1 mM DTT, 0.1 mg/ml BSA, 0.125 units/ml apyrase, incubated for 20 minutes.

Example 23

Preparation of Second Strand for Sequencing

The second strand was unblocked by adding 100 μl of 1× AB, 0.1 unit per ml poly nucleotide kinase, 5 mM DTT. The resultant template was sequenced using standard pyrophosphate sequencing (described, e.g., in U.S. Pat. Nos. 6,274,320, 6258,568 and 6,210,891, incorporated herein by reference). The results of the sequencing method can be seen in FIG. 10F where a fragment of 174 bp was sequenced on both ends using pyrophosphate sequencing and the methods described in these examples.

Example 24

Sequence Analysis of Nucleic Acid on a Picotiter Plate

The picotiter plate containing amplified nucleic acids as described in Example 2 is placed in a perfusion chamber. Then sulfurylase, apyrase, and luciferase are delivered to the picotiter plate.

The sequencing primer primes DNA synthesis extending into the insert suspected of having a polymorphism, as shown in FIGS. 11A-11D. The sequencing primer is first extended by delivering into the perfusion chamber, in succession, a wash solution, a DNA polymerase, and one of dTTP, dGTP, dCTP, or α thio dATP (a dATP analog). The sulfurylase, luciferase, and apyrase, attached to the termini convert any PPi liberated as part of the sequencing reaction to detectable light. The apyrase present degrades any unreacted dNTP. Light is typically allowed to collect for 3 seconds (although 1-100, e.g., 2-10 seconds is also suitable) by a CCD camera linked to the fiber imaging bundle, after which additional wash solution is added to the perfusion chamber to remove excess nucleotides and byproducts. The next nucleotide is then added, along with polymerase, thereby repeating the cycle.

During the wash the collected light image is transferred from the CCD camera to a computer. Light emission is analyzed by the computer and used to determine whether the corresponding dNTP has been incorporated into the extended sequence primer. Addition of dNTPs and pyrophosphate sequencing reagents is repeated until the sequence of the insert region containing the suspected polymorphism is obtained.

Example 25

On Picotiter Plate PCR Amplification

Picotiter Plate Preparation:
In a further embodiment, the single stranded library attached to beads are distributed directly onto the picotiter plate and then the nucleic acid template on each bead is amplified (using PCR or other known amplification technology) to generate sufficient copy number of the template that will generate detectable signal in the pyrophosphate-based sequencing methods disclosed herein.

Example 26

Sequence Analysis of Nucleic Acid on a PTP

Reagents used for sequence analysis and as controls were the four nucleotides and 0.1 μM Pyrophosphate (PPi) were made in substrate solution. Substrate solution refers to a mixture of 300 μM Luciferin and 4 μM adenosine 5'-phosphosulfate, APS, which are the substrates for the cascade of reactions involving PPi, Luciferase and Sulfurylase. The substrate was made in assay buffer. The concentration of PPi used to test the enzymes and determine the background levels of reagents passing through the chamber was 0.1 μM. The concentration of the nucleotides, dTTP, dGTP, dCTP was 6.5 μM and that of αdATP was 50 μM. Each of the nucleotides was mixed with DNA polymerase, Klenow at a concentration of 100 U/mL.

The PTP was placed in the flow chamber of the embodied instrument, and the flow chamber was attached to the faceplate of the CCD camera. The PTP was washed by flowing substrate (3 ml per min, 2 min) through the chamber. After this, a sequence of reagents was flown through the chamber by the pump connected to an actuator, which was programmed to switch positions, which had tubes inserted in the different reagents. The sequence of reagents, flow rates, and flow times were determined. The camera was set up in a fast acquisition mode, with exposure time=2.5 s.

The signal output from the pad was determined as the average of counts on all the pixels within the pad. The frame number was equivalent to the time passed during the experiment. Graphing was used to represent the flow of the different reagents.

Example 27

Plate-Based Platform for Picoliterscale PCR Reactions

Materials and Methods

Unless otherwise indicated, all common laboratory chemicals were purchased either from Sigma (Sigma-Aldrich Corporation, St. Louis, Mo.) or Fisher (Fisher Scientific, Pittsburgh, Pa.).

The PicoTiterPlates™ (25×75×2 mm) were manufactured by anisotropic etching of fiber optic faceplates in a manner similar to that previously described (Pantano, P. and Walt, D. R., *Chemistry of Materials* 1996, 8, 2832-2835). Plates were etched in three different microwell depths, 26, 50 and 76 µm. Microwell center-to-center pitch was 50 µm, and well diameters ranged between 39 and 44 µm (See FIG. 14), with a calculated well density of 480 wells/mm$^2$.

Solid-Phase Immobilization of Oligonucleotide Primers: Packed beads from a 1 ml NHS-activated Sepharose HP affinity column (Amersham Biosciences, Piscataway, N.J.) were removed from the column and activated according to the manufacturer's instructions (Amersham Pharmacia Protocol # 71700600AP). Twenty-five microliters of a 1 mM amine-labeled HEG capture primer (5'-Amine-3 hexaethyleneglycol spacers ccatctgttgcgtgcgtgtc-3'; SEQ ID NO:23) (IDT Technologies, Coralville, Iowa) in 20 mM phosphate buffer pH 8.0 were bound to the beads. After this, 36 to 25 µm beads were selected by serial passage through 36 and 25 µm pore filter mesh sections (Sefar America, Depew, N.Y.). DNA capture beads that passed through the first filter, but were retained by the second were collected in bead storage buffer (50 mM Tris, 0.02% Tween, 0.02% Sodium Azide, pH 8), quantitated with a hemacytometer (Hausser Scientific, Horsham, Pa.) and stored at 4° C. until needed.

Generation of Test DNA Fragments: Amplification test fragments were derived from a commercially available adenovirus serotype 5 vector, pAdEasy (Stratagene, La Jolla, Calif.). Fragments were amplified using bipartite PCR primers, the 5' end of which contained a 20 base amplification region, and a 20 base 3' section, complementary to a specific region of the adenovirus genome. Using these primers, two fragments were amplified from the 12933-13070 and 5659-5767 position of the adenovirus genome and assigned labels Fragment A and Fragment B, respectively.

The sequences for the forward and reverse primers for Fragment A was as follows. A slash (/) denotes the separation between the two regions of the primer: forward (5'-cgtttcccct-gtgtgccttg/catcttgtccactaggctct-3'; SEQ ID NO:24-SEQ ID NO:25), and reverse (5'-ccatctgttgcgtgcgtgtc/accagcactcg-caccacc-3'; SEQ ID NO:26-SEQ ID NO:27). The primers for the Fragment B included: forward (5'-cgtttcccctgtgtgccttg/tacctctccgcgctaggcg-3'; SEQ ID NO:28-SEQ ID NO:29), and reverse (5'-ccatctgttgcgtgcgtgtc/ccccggacgagacgcag-3'; SEQ ID NO:30-SEQ ID NO:31).

Reaction conditions included 50 mM KCl, 10 mM Tris-HCl (pH 9.0), 0.1% Triton X-100, 2.5 mM MgCl$_2$, 0.2 mM dNTP, 1 µM each forward and reverse primer, 0.1 U/µl Taq (Promega, Madison, Wis.) and 50 nmol template DNA. Both templates were amplified with a PCR program that include 35 cycles of incubation at 94° C. for 30 seconds, 56° C. for 30 seconds, and 72° C. for 90 seconds. With PCR primers, the total length of the amplified fragments was 178 bp for Fragment A and 148 bp for Fragment B.

To generate fluorescent probes, biotinylated double stranded fluorescent probes were prepared by PCR amplification from the pAdEasy vector as described above. However, the primer sequences were changed to prevent hybridization between the test fragment and probe primer regions. In addition, the reverse primers for both fragments utilized a 5' biotin followed by 3× hexaethyleneglycol spacers to permit product immobilization to beads prior to elution of the single stranded probe.

The sequence for the forward primer for the fluorescent Fragment A probe was as follows. A slash (/) denotes the separation between the two regions of the primer (5'-atctct-gcctactaaccatgaag/catcttgtccactaggctct-3'; SEQ ID NO:32-SEQ ID NO:33). The sequence for the reverse primer was 5'-biotin-3× hexaethyleneglycol spacers-gtttctctccagcctct-caccga/accagcactcgcaccacc-3'; SEQ ID NO:34-SEQ ID NO:35. The primers for the Fragment B were as follows: forward (5'-atctctgcctactaaccatgaag/tacctctccgcgtaggcg-3'; SEQ ID NO:36-SEQ ID NO:37), and reverse (5'-biotin-3× hexaethyleneglycol spacers-gtttctctccagcctctcaccga/ccccg-gacgagacgcag-3'; SEQ ID NO:38-SEQ ID NO:39).

Fluorescent moieties were incorporated through the nucleotide mixture. This included 0.2 mM dATP/dGTP/dCTP, 0.15 mM TTP and 0.05 mM Alexa Fluor 488-dUTP (Molecular Probes, Eugene, Oreg.) for Fragment A. Alternately, 0.2 mM dATP/dGTP/TTP, 0.15 mM dCTP and 0.05 mM Alexa Fluor 647-dCTP (Molecular Probes, Eugene, Oreg.) was used for amplifying Fragment B. The fluorescent products were purified with a QIAquick PCR Purification Kit (Qiagen, Valencia, Calif.). The biotinylated DNA was subsequently bound to 100 µl (approximately 8.1 million) Streptavidin Sepharose High Performance beads (Amersham Biosciences) in 1× binding wash (5 mM Tris HCl pH 7.5, 1 M NaCl, 0.5 mM EDTA, 0.05% Tween-20) for 2 hours at room temperature. After incubation, the beads were washed three times in TE buffer (10 mM Tris, 1 mM EDTA, pH 8.0) and incubated with 250 µl melt solution (0.125 N NaOH/0.1 M NaCl) for 2 minutes, releasing the single stranded probe from the beads.

Beads were pelleted with brief centrifugation in a benchtop centrifuge and the supernatant was neutralized in 1.25 ml buffer PB (Qiagen) with 1.9 µl glacial acetic acid. This mixture was repurified on a QiaQuick column (Qiagen), and the concentration of the purified probe was determined by Taq-Man quantification using the BioRad iCycler (BioRad, Hercules, Calif.).

Solution-phase PTPCR was performed as follows. The PCR reaction mixture was loaded into individual wells of a single 14 mm×43 mm PicoTiterPlate™. For this, 500 µl of PCR reaction mixture (1× Platinum HiFi Buffer (Invitrogen, Carlsbad, Calif.), 2.5 mM MgSO$_4$, 0.5% BSA, 1 mM dNTPs (MBI Fermentas, Hanover, Md.), 1 µM forward (5'-cgtttc-ccctgtgtgccttg-3'; SEQ ID NO:40) and reverse (5'-ccatctgt-tgcgtgcgtgtc-3'; SEQ ID NO:41) primers, 0.05% Tween-80, 1 U/µl Platinum High Fidelity DNA Polymerase (Invitrogen), 0.003 U/µl Thermostable Pyrophosphatase (USB, Cleveland, Ohio), and a calculated 5 copies of Fragment B template per well) were combined in a 1.5 ml microcentrifuge tube. The tube was vortexed thoroughly and stored on ice until the PicoTiterPlate™ loading cartridge was assembled.

Figure 20:
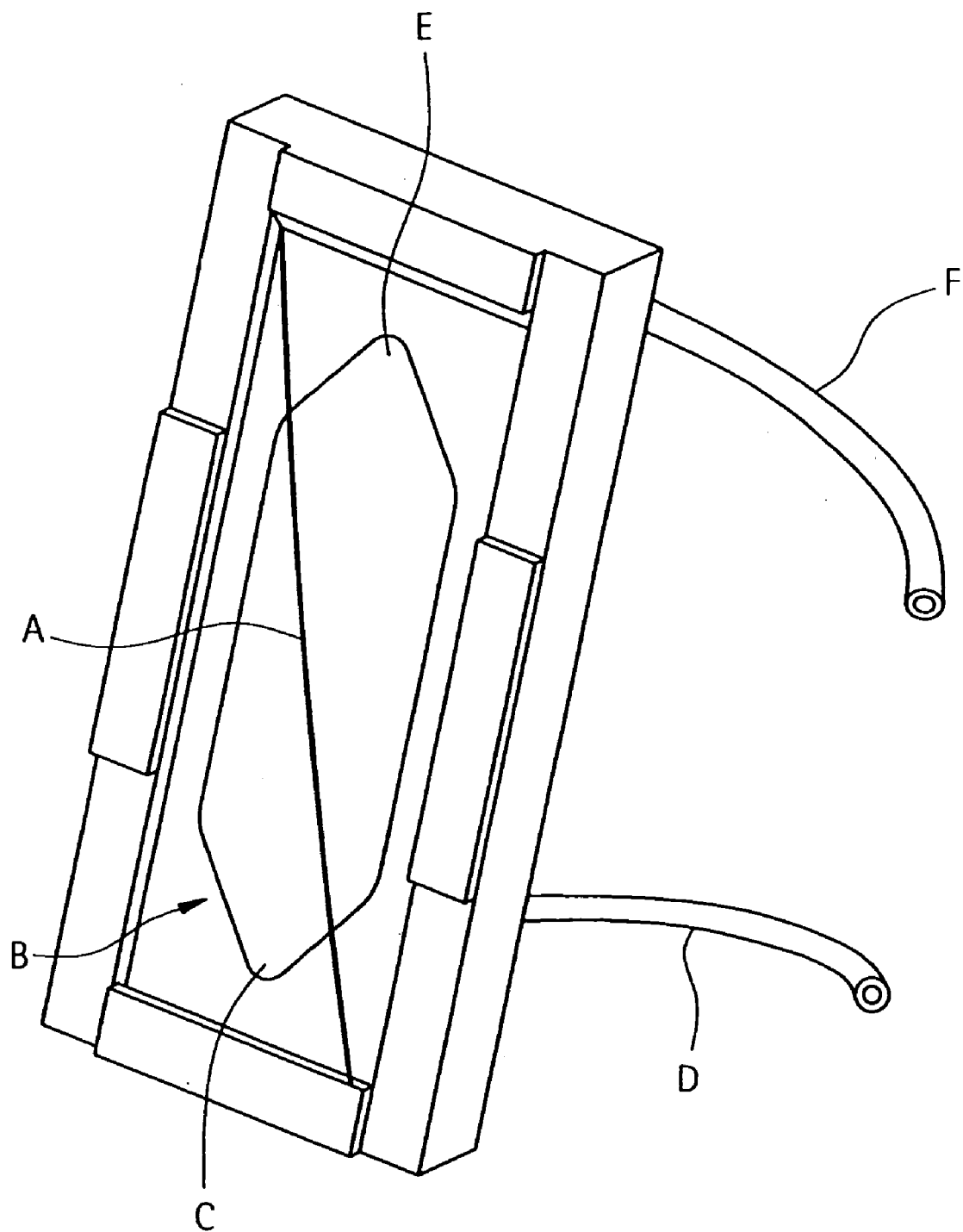
FIG. 20 depicts a PicoTiterPlate™ loading cartridge. "A" refers to a PicoTiterPlate™ with microwells facing into the cartridge, the distance between the open sides of the PicoTiterPlate™ wells and the wall of the loading cartridge is 0.3 mm; "B" refers to a silicon sealing gasket; "C" refers to an inlet port; "D" refers to an inlet loading tube; "E" refers to an outlet port and "F" refers to an outlet tube. The PicoTiterPlate™ is held in the cartridge with plastic clamps. The liquid is filled via the inlet loading tube D and enters the space between the open sides of the PicoTiterPlate™ wells and the wall of the loading cartridge through the inlet port C. The area defined by the silicon sealing gasket B is filled and excess liquid leaves the cartridge via the outlet port E and the outlet tubing F.

The in-house PicoTiterPlate™ loading cartridge was attached to the PicoTiterPlate™ with two plastic clips, seating the silicon cartridge gasket firmly on the PicoTiterPlate™ surface (see FIG. 20). The PCR reaction mix was drawn into a 1 ml disposable syringe, and the mouth of the syringe inserted into the input tube of the loading cartridge. The loading cartridge was placed on end, so that the input port was oriented at the bottom of cartridge, and the PCR mix was slowly loaded into the chamber. While loading, inspected through the transparent back of the PicoTiterPlate™ to ensure even, bubble-free delivery.

Figure 21:
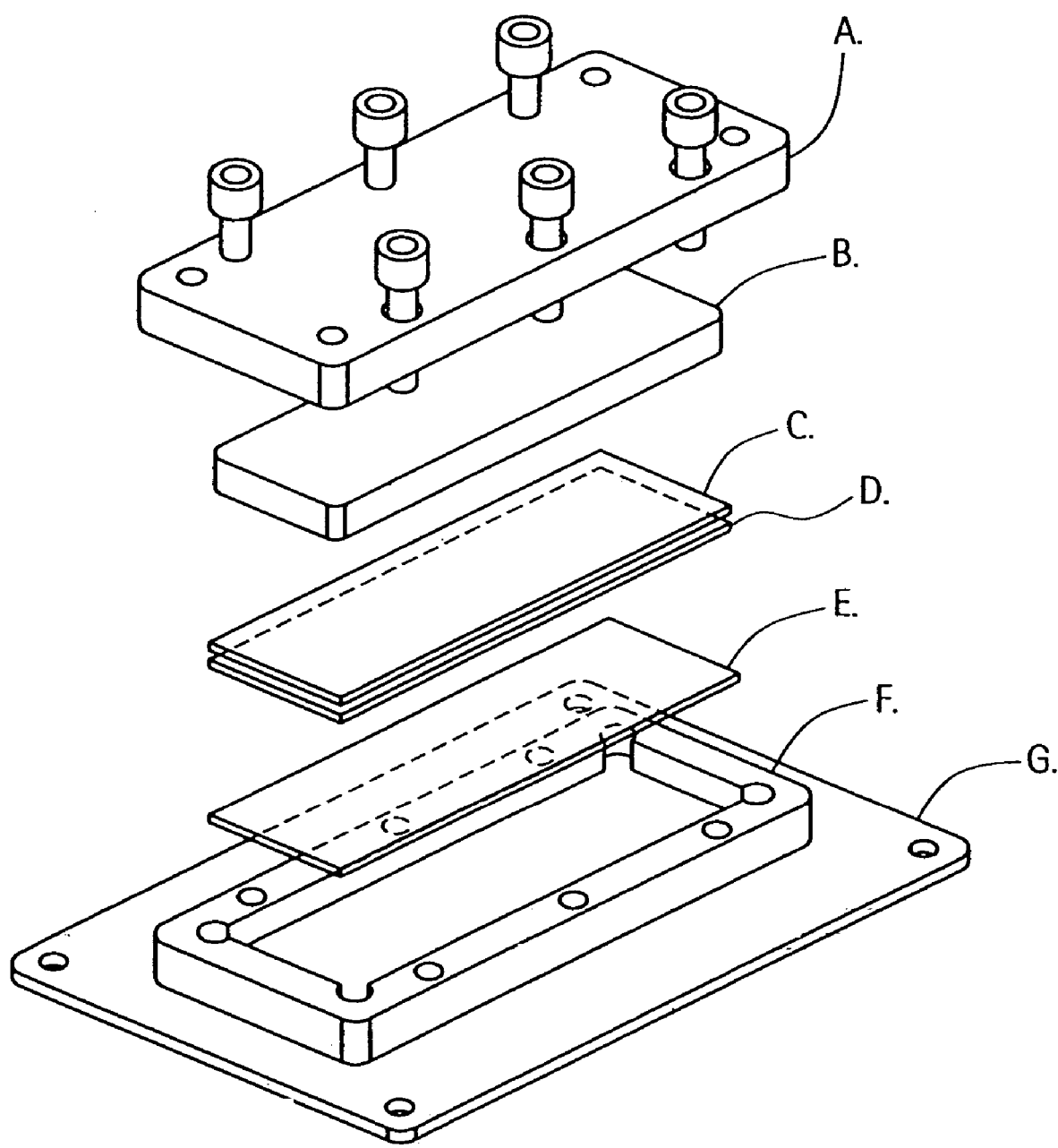
FIG. 21 depicts a PicoTiterPlate™ amplification chamber in exploded view. "A" refers to an amplification chamber lid with six retaining bolts; "B" refers to a closed cell foam insulation pad; "C" refers to a 25 mm by 75 mm standard glass microscope slide; "D" refers to a 0.25 mm thick silicon sheet; "E" refers to a PicoTiterPlate™; "F" refers to an amplification chamber base; "G" refers to a second 0.25 mm thick silicon sheet.

After loading, the PCR mixture was allowed to incubate for 5 minutes, at which time the reaction mixture was withdrawn from the PicoTiterPlate™ loading cartridge. The PicoTiterPlate™ was removed from the loading cartridge, and immediately placed in the amplification chamber (see FIG. 21). The PicoTiterPlate™ surface was covered with a 0.25 mm thick Silpad A-2000 silicon sheet (The Bergquist Company, Chanhassen, Minn.). On top of this was placed a 25 mm×75 mm standard glass microscope slide (Fisher). A closed cell foam insulation pad (Wicks Aircraft Supply, Highland, Ill.) was placed on top of the microscope slide. An aluminum lid was attached to the base of the chamber by six 25 mm bolts sealed the amplification chamber.

Once sealed, the amplification chamber was placed on a Thermocycler MJ PTC 225 Tetrad (MJ Research, Waltham, Mass.) equipped with Flat Block Alpha Units. The amplification program included incubation for 3 minutes at 94° C. (Hotstart Initiation) followed by 40 cycles of incubation for 12 seconds at 94° C., 12 seconds at 58° C., 12 seconds at 68° C., with a 10° C. final hold. After completion of the PCR program, the PicoTiterPlate™ was removed from the amplification chamber, and the loading cartridge was reattached. A disposable syringe was used to fill the cartridge chamber with 1 ml of $H_2O$, and allowed to incubate for 20 minutes 10° C. at room temperature.

After the incubation was completed, the recovery solution was withdrawn from the loading cartridge and transferred to a 1.5 ml microcentrifuge tube. PCR product was quantitated using an iCycler RealTime PCR unit (BioRad) and FAM-labeled reporter probes (Epoch Biosciences, Bothell, Wash.). The TaqMan Universal PCR MasterMix (Applied Biosystems, Foster City, Calif.) was combined with 0.3 µM forward and reverse primers, 0.15 µM FAM-labeled probe, and 27 µl of the reaction mix added to each well of a 96 well PCR plate.

Purified fragments were used to create a standard curve (six standards ranging from $1\times10^9$ to $1\times10^4$ molecules per well), which was run in triplicate. The PCR amplification was run with the following parameters: incubation for 5 minutes at 94° C. (hotstart initiation), 60 cycles of incubation for 15 seconds at 94° C., 45 seconds at 68° C., with a final hold at 4° C. Data was analyzed using the iCycler Optical Systems Software Version 2.3 (BioRad), and the PCR yield was quantitated using the iCycler data and Microsoft Excel (Microsoft, Redmond, Wash.).

Solid-phase PTPCR was performed similarly to solution phase PTPCR, except that DNA capture beads were loaded into the PicoTiterPlate™ wells prior to amplification by centrifugation as described below. In addition, the PCR mixture was loaded into the microwells after the bead deposition was completed. To facilitate retention of the capture beads during wash steps, the solid phase experiments utilized 50 µm deep PicoTiterPlate™s. The PicoTiterPlate™ was placed in an in-house built plexiglass bead loading jig. This was similar to the PicoTiterPlate™ loading jig described in FIG. 20, except that the PicoTiterPlate™ was sandwiched between a bottom Plexiglas plate and a jig top plate, containing inlet and outlet ports, and sealed via a silicon gasket with plastic screws.

Template DNA was preannealed to the DNA capture beads at 5 template copies per bead by incubation at 80° C. for 3 minutes, after which beads were allowed to cool to room temperature for 15 minutes. The beads were then spun into the PicoTiterPlate™ wells prior to loading the PCR reaction mixture. Bead Loading Buffer (450 µl; 1× Platinum HiFi PCR buffer (Invitrogen), 0.02% Tween-80) containing one hundred thousand Sepharose DNA capture beads (approximately 1 bead per 3 PicoTiterPlate™ wells) were injected by pipette into the jig through one of the inlet ports. Each inlet hole was then sealed with a circular adhesive pad (3M VHS, St. Paul, Minn.). The jig held the PicoTiterPlate™ with its wells facing up and covered with the bead suspension. This was centrifuged at 2000 rpm for 5 minutes at room temperature in an Allegra 6 centrifuge (Beckman Coulter, Fullerton, Calif.) using a Microtiter Rotor.

After centrifugation, the PicoTiterPlate™ was removed from the jig. The PCR reaction mix was loaded onto the PicoTiterPlate™ as described for solution phase PCR. However, the solid-phase PCR mixture omitted template since the template was preannealed to the DNA capture beads. The solid-phase PCR amplification program included additional hybridization/extension cycles to compensate for the slower kinetics of the immobilized primer. The program included incubation for 3 minutes at 94° C. for hotstart initiation, 40 cycles of incubation for 12 seconds at 94° C., 12 seconds at 58° C., 12 seconds at 68° C., followed by 10 cycles of incubation for 12 seconds at 94° C., 10 minutes at 68° C. for hybridization and extension, with a 10° C. final hold.

Upon completion of the PCR program, the PicoTiterPlate™ was removed from the amplification chamber, and washed with 1 ml $H_2O$ as described for solution phase PCR. The PicoTiterPlate™ was then prepared for hybridization detection of immobilized PCR product.

Hybridization was performed with fluorescently labeled probes as follows. After PTPCR was complete, the strand complementary to the immobilized strand was removed. For this, the whole PicoTiterPlate™ was incubated in 0.125 M NaOH for 8 minutes at room temperature. This solution was neutralized by two 5 minute washes in 50 ml of 20 mM Tris-acetate pH 7.5. The PicoTiterPlate™ was then placed in a custom-made 800 µl hybridization chamber, and blocked with hybridization buffer (3.5× SSC, 3.0% SDS, 20× SSC buffer is 3 M NaCl; 0.3 M $Na_3$-citrate) at 65° C. for 30 minutes. The contents of the chamber were replaced with fresh hybridization buffer containing the probes: 20 nM fluorescent Fragment A (Alexa-488) and Fragment B (Alexa-647). The probes were allowed to hybridize to their targets. Incubation was carried out at 65° C. for 4 hours while shaking at 200 RPM on an orbital shaker (Bamstead International, Dubuque, Iowa).

After hybridization, the PicoTiterPlate™ was washed with 2× SSC, 0.1% SDS for 15 minutes at 37° C., followed by a 15 minute wash in 1× SSC at 37° C., with two final 15 minute washes in 0.2× SSC at 37° C. Following post-hybridization washing, the PicoTiterPlates™ were air dried and placed in a FLA-8000 Fluorescent Image Analyzer (Fujifilm Medical Systems USA, Stamford, Conn.) and scanned at the 635 and 473 nm wavelength. The resulting 16-bit tiff images were imported into Genepix 4.0 (Axon Instruments, Union City, Calif.). A block of 100 analysis features was drawn over the area of interest and the 635 and 473 fluorescence intensities were recorded for each feature. Data was then exported to Microsoft Excel for further analysis.

Control beads were prepared as follows. Biotinylated test templates A and B were prepared by PCR amplification from the pAdEasy vector, purified, immobilized on Streptavidin Sepharose High Performance beads and strand separated as described under "Preparation of Fluorescent Probes". However, fluorescently labeled dNTPs were omitted in the PCR reaction. Pelleted beads were washed 3 times with TE buffer and stored at 4° C. in TE until deposition onto the PicoTiterPlate™.

Results

Solution-phase amplification was demonstrated by loading PicoTiterPlates with PCR master mix containing a calculated 5 template copies per PicoTiterPlate™ well. Reactions were run in duplicate in PicoTiterPlates with 26, 50 and 76 μm deep wells. Forty cycles of PTPCR amplification were performed as described in Material and Methods. Additives were incorporated to prevent the deleterious surface effects routinely reported with silica reaction vessels (Kalinina, O., et al., *Nucleic Acids Res.* 1997, 25, 1999-2004; Wittwer, C. T. and Garling, D. J., *Biotechniques* 1991, 10, 76-83; Taylor, T. B., et al., *Nucleic Acids Res.* 1997, 25, 3164-3168).

The inclusion of 0.5% BSA and 0.05% Tween-80 in the reaction mix was not only effective at reducing surface effects, it also facilitated amplification. Reducing the relative concentrations of either reagent had a negative effect on amplification. In addition, due to the polymerase-inactivating properties of silica surfaces (Taylor, T. B., et al., *Nucleic Acids Res.* 1997, 25, 3164-3168; Shoffner, M. A., Cheng, J., Hvichia, G. E., Kricka, L. J. and Wilding, P., *Nucleic Acids Res.* 1996, 24, 375-379), elevated Taq concentrations proved beneficial. Concentrations above 1 U/μl were optimum for enhancing amplicon yield.

Following PTPCR, the solution from each PicoTiterPlate™ was recovered and triplicate samples of each solution were quantified by TaqMan assay. A standard curve of diluted template (linear from $1 \times 10^9$ to $10^4$ molecules, $r^2=0.995$) was used to determine the concentration of the amplified product. The number of molecules amplified per well was obtained by dividing the amount of amplified product by the total number of wells in a PicoTiterPlate™ (372,380). The amount of amplification per well was calculated by dividing this number by the initial template concentration per well. PTPCR amplification was successful in all of the PicoTiterPlate™, with yields ranging from $2.36 \times 10^6$ fold in the 39.5 pl wells to $1.28 \times 10^9$ fold in the 50 pl wells (See Table below).

| PicoTiterPlate Depth [μm] | Well Volume [pl] | Average Fold Amplification N = 6 | Fold Amplification SD | Final Product Conc. [M] |
|---|---|---|---|---|
| 26 | 39.5 | 2.36E+06 | 1.02E+06 | 4.96E-07 |
| 50 | 76.0 | 1.28E+09 | 1.03E+09 | 1.40E-04 |
| 76 | 115.6 | 9.10E+08 | 4.95E+08 | 6.54E-05 |

The table shows PicoTiterPlate™ PCR amplification as determined by TaqMan Assay. Values reflect triplicate measurements taken from duplicate PicoTiterPlates. (N=6); SD=standard deviation.

Yield was influenced by well volume. The concentration of final product obtained for the 50 μm deep wells ($1.4 \times 10^{-4}$ M) was significantly greater (p value for ANOVA=0.023) than that obtained in the 76 μm ($6.54 \times 10^{-5}$ M) deep wells, both were two orders of magnitude greater than the yield achieved in the 26 μm deep wells ($4.96 \times 10^{-7}$ M). The 50 μm deep microwell yield represented the optimal balancing of the costs and benefits associated with low-volume PCR. In this case, maximum elevation of the effective concentrations and low thermal mass of the reagents were obtained, but the surface to volume ratio was still low enough to prevent detrimental surface effects from significantly reducing amplification efficiency.

The final concentration of PTPCR product obtained in each of the different well depths ($4.96 \times 10^{-7}$ to $1.4 \times 10^{-4}$ M) exceeded the $10^{-8}$ M concentration typically reported as the maximum achievable before the PCR plateau effect occurs (Sardelli, A., *Amplifications* 1993, 9, 1-5). The higher effective concentration of primers and template molecules resulting from the low microwell volume increased the overall reaction efficiency and postponed the onset of the plateau phase until a higher molar yield was achieved. Alternatively, this effect was caused by the high concentration of Taq used in the PTPCR reactions, as elevated polymerase concentration has also been shown effective in delaying the plateau effect (Kainz, P., *Biochim. Biophys. Acta* 2000, 1494, 23-27; Collins, F. S., et al., *Science* 2003, 300, 286-290). The amplification efficiency over 40 cycles was 44.3, 68.9 and 67.5% for the 26, 50 and 76 μm deep wells respectively, providing a high final concentration of amplicons. The greatest yield was observed in the 50 μm deep wells. It should be recognized, however, that cycle number optimization was not conducted; similar amplification yields could likely have been achieved with far fewer cycles, thereby increasing the efficiency of the PTPCR amplification.

Figure 22:
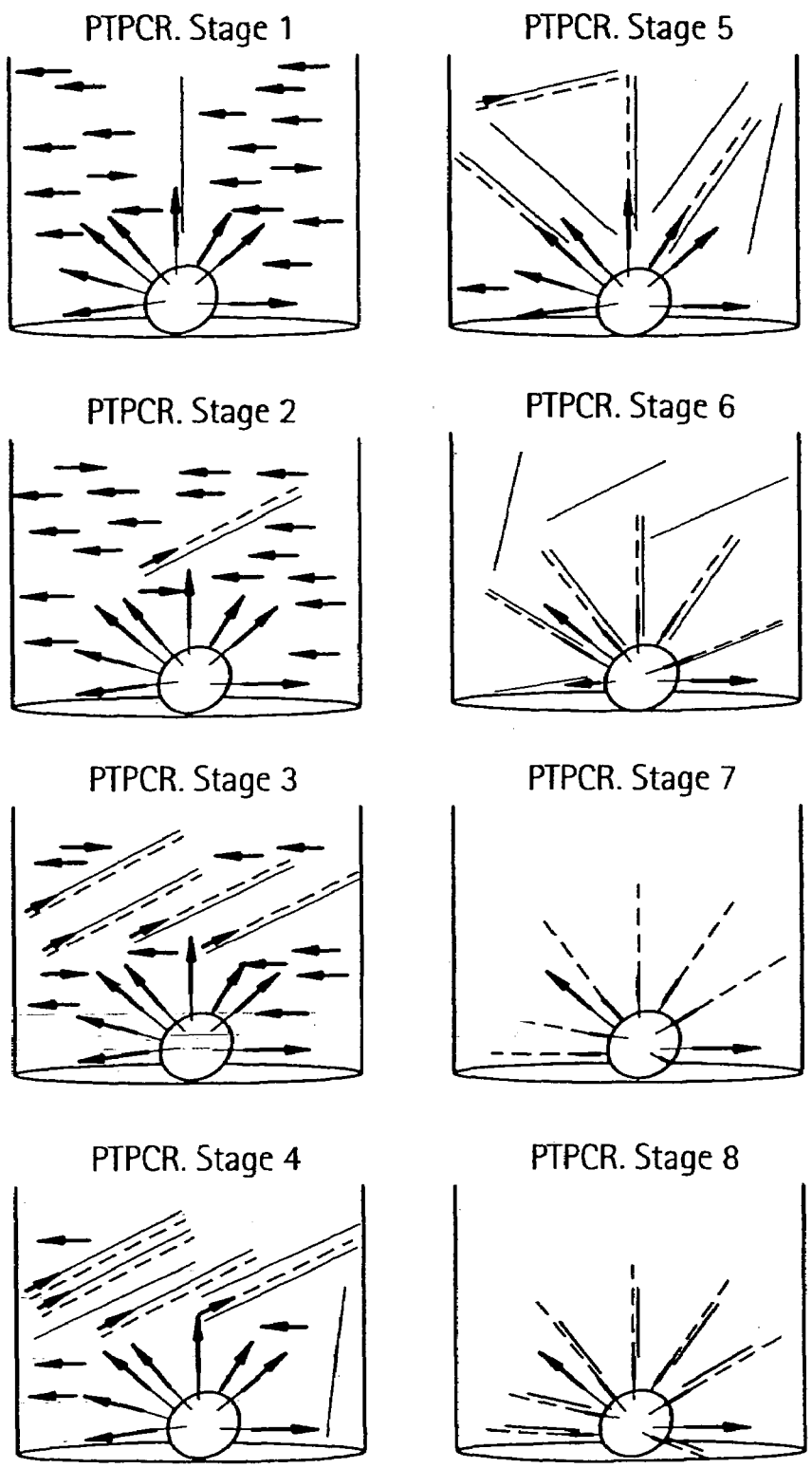
FIG. 22 depicts a schematic diagram of solid phase PicoTiterPlate™ PCR. The cylindrical structures symbolize individual PicoTiterPlate™ wells. Gray spheres symbolize beads with immobilized primers. Forward "F" (red) and Reverse "R" (blue) primers are shown in 5' to 3' orientation as indicated by arrows. Synthesized sequence complementary to the Forward and Reverse primers are shown as dark red (F complement) and dark blue (R complement) bars. Single stranded template DNA is shown as solid gray line, newly synthesized DNA strands as dashed gray lines. Fluorescently labeled hybridization probes are shown as green bars.

The experimental strategy for clonal solid phase PTPCR, starting with a single effective copy of a single stranded DNA fragment, and finishing with a specific bead-immobilized DNA amplicon detected by fluorescent probe hybridization, is depicted in FIG. 22 and described in detail below:

Stage 1: Each PicoTiterPlate™ well contains PCR reaction mix consisting of a single stranded template molecule (either single stranded and annealed to the DNA capture beads, as shown here, or free-floating in solution), Forward "F" (red) and Reverse "R" (blue) primers in solution, as well as R primers attached to a DNA capture bead. Solution phase primers are present in an 8:1 molar ratio, with the F primer in excess. Arrows indicate the 5'->3' DNA orientation.

Stage 2: The initial thermal cycle denatures the DNA template, allowing R primers in solution to bind to the complementary region on the template molecule. Thermostable polymerases initiate elongation at the primer site (dashed line), and in subsequent cycles, solution-phase exponential amplification ensues. Bead immobilized primers are not assumed to be major contributors to the amplification at this stage.

Stage 3: Early Phase PCR. During early exponential amplification (1 to 10 cycles) both F and R primers amplify the template equally, despite an excess of F primers in solution.

Stage 4: Mid Phase PCR. Between cycles 10 and the R primers are depleted, halting exponential amplification. The reaction then enters an asymmetric amplification phase, and the amplicon population becomes increasingly dominated by F strands.

Stage 5: Late Phase PCR. After 30 to 40 cycles, asymmetric amplification continues to increase the concentration of F strands in solution. Excess F strands, without R strand complements, begin to anneal to bead-immobilized R primers. Thermostable polymerases utilize the F strand as a template to synthesize an immobilized R strand of the amplicon.

Stage 6: Final Phase PCR. Continued thermal cycling forces additional annealing to bead-bound primers. Solution phase amplification may be minimal at this stage, but concentration of immobilized R strands continues to increase.

Stage 7: The non-immobilized, F strand, complementary to the immobilized R strand, is removed by alkali denaturation. The DNA capture beads are now populated by single stranded R strands of the amplicon.

Stage 8: Fluorescently labeled probes (green bars) complementary to the R strand are annealed to the immobilized strand. Probes specific for particular strand sequences are labeled with unique fluorophores, resulting in a range of homogenous and heterogeneous fluorescent signals depending on the number of discrete templates amplified within a given PicoTiterPlate™ well.

Figure 23A:
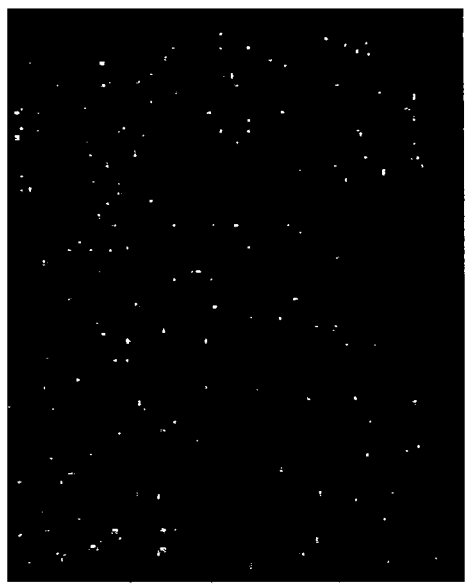
FIGS. 23A-C depict fluorescent probes hybridization to bead-immobilized test DNA fragments.
Figure 23B:

Initially, fluorescently labeled probe specificity was confirmed by binding biotinylated Fragment A or Fragment B test DNA fragments to streptavidin Sepharose beads, loading the beads into a 50 µm deep PicoTiterPlate™ by centrifugation and hybridizing a mixed population of fluorescently labeled probes for the Fragment A and Fragment B fragments. No mixed signals or nonspecific hybridizations were observed; the beads with the Fragment A product displayed the 488 nm signal, while the Fragment B beads exhibited the 635 nm signal (See FIGS. 23A and 23B). Close examination of FIGS. 23A and 23B reveals a few Fragment A beads in the Fragment B pad and vice versa. Given the purity of the signal displayed by these nomadic beads, it is likely that they are either the product of some cross contamination during the loading process, or were washed from one pad to the other during subsequent wash steps.

Figure 23C:
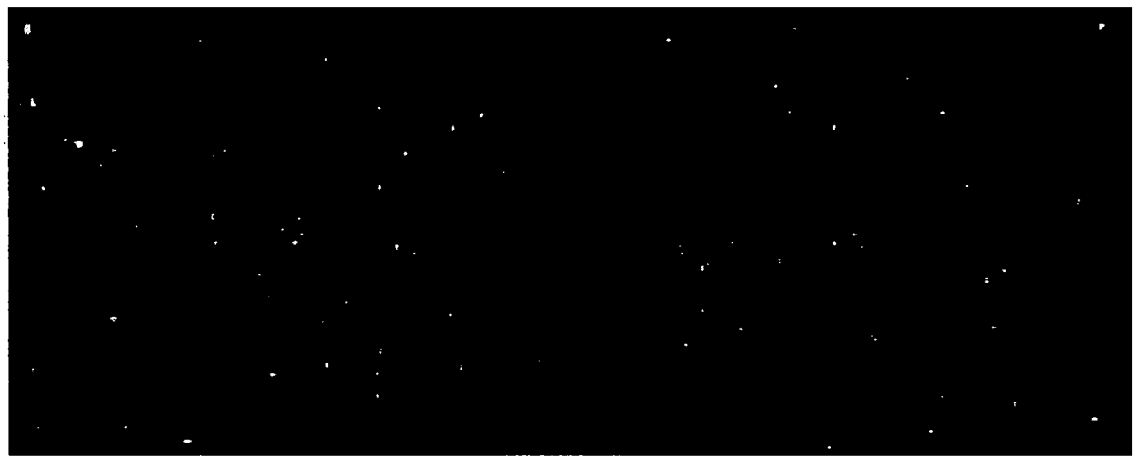

As indicated in FIG. 23C, the fluorescent probes detected successful solid phase PTPCR amplification of both Fragment A and Fragment B templates. The signals generated by the hybridized probe depended on the relative efficiency of dye incorporation within the probes, the sensitivity of the reactions to unequal amounts of template DNA, as well as the total and relative amounts of amplified product present on each bead. In addition, it is likely that the amount of template generated and retained on the DNA capture beads varied from well to well, and the number of capture primers bound to each bead is also likely to vary due to bead size distribution. As a result, the non-normalized ratios generated by the probe hybridization should be seen as semi-qualitative rather than quantitative data. Nevertheless, the fluorescent signals generated by the hybridized probes ranged from a homogeneous Fragment B signal (red) to an equally homogenous Fragment A signal (green), with heterogeneous mixes of the two signals (degrees of yellow) evident as well.

Due to the probe specificity displayed by the controls, as well as the sizeable number of homogenous red and green beads on the PicoTiterPlate™, it is unlikely that nonspecific probe hybridization caused the heterogeneous signals. The close proximity of homogenous beads of either template suggests it is unlikely that the heterogeneous beads resulted from amplicon leakage between wells during amplification; if intra-well cross-talk were responsible, one would expect to see heterogeneous beads located between homogenous beads of either template, and a generally patchy distribution of homogenous signals. Rather, it is likely that template molecules disassociated from their original bead and reannealed to new beads in the PicoTiterPlate™ loading mix prior to being spun into the microwells, or were washed from one bead to another as the PCR mix was applied to the PicoTiterPlate™. Regardless of the cause of the mixed template beads, the hybridization results show that PCR amplification in the PicoTiterPlate™ microwells can drive sufficient product to the DNA capture beads to enable fluorescent probe hybridization and detection.

Discussion

The results in this example demonstrate that PicoTiterPlate™-based PCR alleviates many factors associated with the DNA amplification process, such as high costs of reagents, large numbers of reactions, and lengthy reaction times, delivering another "evolutionary jump" in PCR technology. The microwells on a single PicoTiterPlate™ can function as up to 370,000 discrete reaction vessels achieving high yield ($2.3 \times 10^6$ to $1.2 \times 10^9$ fold) amplification even at reaction volumes as low as 39.5 picoliters. As a result, throughput is increased, and the total reagent cost for PTPCR is reduced; the reaction volume contained in an entire 26 or 76 µm deep PicoTiterPlate™ is 15.3 and 43 µl, respectively. Increases in the size of the PicoTiterPlate™ can further increase the maximal throughput. For example, increasing the PicoTiterPlate™ dimensions to 40 mm×75 mm provides approximately $1.4 \times 10^6$ discrete reaction vessels, and a PicoTiterPlate™ possessing the same perimeter dimensions as a commercially available 96-well PCR plate (85.47 mm×127.81 mm) could contain as many as $5.24 \times 10^6$ wells.

Solution phase PCR amplifications, regardless of the number and volume in which they are conducted, are of limited utility unless the product can be recovered easily and efficiently. Previous efforts in parallel PCR (Nagai, H., et al., *Anal. Chem.* 2001, 73, 1043-1047) required evaporation of the liquid reaction mixture, leaving the amplicon dried to the walls of the microreactor, after which it could be recovered for further manipulations. The methodology disclosed herein avoids the problems of product recovery by including solid phase amplification, immobilizing the PCR product to a DNA capture bead. Thus, the product of a PicoTiterPlate™ microwell reaction is not 370,000 wells containing solution-phase PCR product, but up to 370,000 beads bound with immobilized PCR product. These PCR products are suitable for numerous solid-phase methods of nucleic acid interrogation including the potential capacity to support a massively parallel approach to sequencing whole genomes containing up to hundreds of millions of bases. The simplicity of the disclosed method would drastically reduce costs for sequencing and other applications now requiring robotics to maintain large-scale cloning and PCR.

The disclosures of one or more embodiments of the invention are set forth in the accompanying description. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated by reference.

Example 28

Rig Sequencing Method

Step 1: Preparation of pAdEasy PCR DNA Beads

This procedure was used for a 384-well plate PCR of Adenovirus clones. Streptavidin-Sepharose beads (12 mls) were prepared for binding PCR fragments by washing once with 2 M NaCl solution and resuspending in 288 mls of 2 M NaCl. The washed beads were transferred to fifteen 96-well plates at 200 µl of bead suspension/well. The PCR products (25 µl) were transferred to a 384-deep-well plate using a Tecan TeMo robot. To bind DNA to solid supports, 25 µl of bead suspension (15,000 beads) were added to each well of every 384-deep well plate using a Tecan TeMo robot and mixed. The final concentration of NaCl in the binding reaction was 1 M. The binding reaction was incubated with shaking at room temperature for 3 hr on a shaker. The contents of the microtiter plates were pooled by inverting the 384-well plates on to a reservoir and centrifuging at 1000 g in a Beckman Allegra benchtop centrifuge. The pooled beads were transferred into a 50 ml Falcon tube, centrifuged at 1000 g, and the supernatant was removed.

Approximately a million beads (mobile solid support) were washed once with 100 µl of 2 M NaCl followed by two washes with distilled water (100 µl each). The washed beads were incubated in 300 µl melting reagent (0.1 M NaCl and 0.125 M NaOH) for 10 minutes in a rotator to remove the non-biotinylated DNA strand. The tube was centrifuged at maximum speed to pellet the beads and the melt solution was removed and discarded. The beads were washed with 100 µl of melt solution followed by three more washes with 1× Annealing buffer. After the washes, the beads were resuspended in 25 µl of 1× Annealing buffer.

Primer P2 (500 pmoles) was added to the bead mixture and mixed. The bead mixture, in tubes, was placed into an automated incubator (PCR thermocycler in this case) with the following temperature profiles: incubation at 60° C. for 5 minutes, decrease 0.1° C./second down to 50° C., incubation at 50° C. for 5 minutes, decrease 0.1° C./second down to 40° C., incubation at 40° C. for 5 minutes, decrease 0.1° C./second down to 4° C., incubation at 4° C. forever.

After annealing, the beads were washed carefully and resuspended in 200 µl of Bst DNA polymerase binding solution. Then, 10 µl aliquots (50,000 beads) of the bead suspension were processed for sequencing on the instrument described below.

Step 2: Preparation of Control DNA Beads

Six control DNA sequences TF 2, 7, 9, 10, 12 and 15 were cloned into pBluescript II KS+vector and plasmid DNA was used as template for PCR with one biotinylated primer for solid-phase immobilization of the amplicons.

The following reagents were added to a 1.7 ml tube to create a PCR mix.

| | |
|---|---|
| 10X HIFI buffer | 100 µl |
| 10 mM dNTP mix | 100 µl |
| 50 mM MgSO$_4$ | 60 µl |
| 5'-Bio-3HEG-MMP1B | 10 µl |
| MMP1A | 10 µl |
| HIFI Taq Polymerase | 10 µl |
| Mol. Bio. Grade Water | 690 µl |

Twenty microliters of plasmid template DNA was added and the mix was aliquoted by 50 µl into 0.2 ml PCR tubes. The following program was used for thermocycling: incubation at 94° C. for 4 minutes; 39 cycles of incubation at 94° C. for 15 seconds, 58° C. for 30 seconds, 68° C. for 90 seconds, and 68° C. for 120 seconds; hold at 10° C.

Amplified DNA for each test fragment was purified using the Qiagen MinElute PCR Clean-Up Kit as per manufacturer's instructions. The purity and yield of each of the test fragments DNA was assessed using the Agilent 2100 Bioanalyzer and DNA 500 reagent kit and chip. Biotinylated PCR products were immobilized onto Sepharose streptavidin beads at 10 million DNA copies/bead.

Beads were washed once with 2 M NaCl solution. This was done by adding 100 µl, vortexing briefly to resuspend the beads, centrifuging for 1 minute at maximum speed to pellet the beads, and then removing the supernatant. This was followed by a second wash with 2 M NaCl. The beads were then resuspended in 30 µl of 2 M NaCl. PCR product was added to beads. The mixture was vortexed to resuspend the beads in solution and then placed in a rack, on a titer plate shaker, at speed 7, for 1 hour at room temperature.

The non-biotinylated second strand was removed by incubation with the alkaline melt solution (0.1 M NaOH/0.15 M NaCl) for 10 minutes in an overhead rotator at room temperature. This was followed by washing the beads once with 100 µl of melt solution and three times with 100 µl of 1× annealing buffer (50 mM Tris-Acetate, pH 7.5; 5 mM MgCl$_2$). Sequencing primer was annealed to the immobilized single-stranded DNA by centrifugation for one minute at maximum speed. The supernatant was removed and the beads were resuspended in 25 µl of 1× annealing buffer. Next, 5 µl of sequencing primer MMP7A (100 pmol/µl) was added to the bead suspension and the following temperature profile was used to hybridize the sequencing primer:

Incubation at 60° C. for 5 minutes;
Decrease 0.1° C./second down to 50° C.;
Incubation 50° C. for 5 minutes;
Decrease 0.1° C./second down to 40° C.;
Incubation at 40° C. for 5 minutes;
Decrease 0.1° C./second down to 4° C.; and
Hold at 4° C.

Beads were washed twice with 100 µl of 1× annealing buffer and then resuspended to a final volume of 200 µl with 1× annealing buffer and stored in 10 µl aliquots in labeled tube strips in a 4° C. refrigerator.

Step 3: Sequencing Chemistry

Sepharose beads with immobilized single stranded DNA templates and annealed sequencing primer were incubated with *E. coli* single strand binding protein (Amersham Biosciences) (5 µl of 2.5 µg/µl ssb stock solution per 50,000 beads) and 500 U (10 µl of 50 U/µl) of Bst DNA polymerase (NEB) in 200 µl of Bst polymerase binding solution (25 mM Tricine pH 7.8; 5 mM magnesium acetate; 1 mM DTT; 0.4 mg/ml PVP MW 360,000) for 30 minutes at room temperature on a rotator. After this, the DNA beads were mixed with the SL beads and deposited into the wells of the PicoTiter Plate as follows. Reagents required for a sequencing run on a 454 instrument included 1) substrate wash solution; 2) apyrase containing wash solution; 3) 100 nM inorganic pyrophosphate calibration standard; 4) individual nucleotide triphosphate solutions.

All solutions were prepared in the sulfurylase-luciferase assay buffer with enzyme substrates (25 mM Tricine pH 7.8; 5 mM magnesium acetate; 0.4 mg/ml PVP MW 360,000; 0.01% Tween 20; 300 µM D-luciferin; 4 µM APS). The substrate wash solution was identical to the luciferase assay buffer. The apyrase containing wash solution was based on the luciferase assay buffer, except no enzyme substrates (APS and D-luciferin) were added and this wash contained apyrase (Sigma St. Louis, Mo.; Pyrosequencing AB, Pyrosequencing, Inc. Westborough, Mass.) in the final concentration of 8.5 U/1.

Sodium pyrophosphate (PP$_i$) standard was prepared by adding sodium pyrophosphate tetrabasic decahydrate (Sigma, St. Louis, Mo.) to the luciferase assay buffer to a final concentration 100 nM. Nucleotide triphosphates (dCTP, dGTP, TTP; minimum diphosphate grade) (Amersham Biosciences AB, Uppsala, Sweden) were diluted to final concentration of 6.5 µM in the luciferase assay buffer. Deoxyadenosine triphosphate analog, 2'-Deoxyadenosine-5'-O-(1-thiotriphosphate), Sp-isomer (Sp-dATP-α-S, Biolog Life Science Institute, Bremen, Germany) was diluted to final concentration of 50 μM in the luciferase assay buffer.

Step 4: Cloning His6-BCCP-sulfurylase and His6-BCCP-luciferase

Bacillus stearothermophilus (Bst) ATP sulfurylase (E.C. 2.7.7.4) and firefly (Photinus pyralis) luciferase (E.C. 1.13.12.7) were cloned into Nhe I-BamH I digested pRSET-A vector (Invitrogen). The coding sequence of the BCCP (biotin carboxyl carrier protein) gene (Alix, J. H., DNA 8 (10), 779-789 (1989); Muramatsu, S. and Mizuno, T., Nucleic Acids Res. 17 (10), 3982 (1989), Jackowski, S. and Alix, J. H., J. Bacteriol. 172 (7), 3842-3848 (1990); Li, S. J. and Cronan, J. E. Jr., J. Biol. Chem. 267 (2), 855-863 (1992), Genbank accession number M80458) was used to design PCR primers to amplify the fragment corresponding to amino acids 87-165 of the BCCP protein. The forward primer was 5'-ctagctag-catggaagcgccagcagca-3'; SEQ ID NO:42 and the reverse primer was 5'-ccgggatccctcgatgacgaccagcggc-3'; SEQ ID NO:43. The PCR cocktail was prepared as Mix 1 and Mix 2, 25 μl each. Mix 1 included 75 pmoles of primers, 100 ng of E. coli genomic DNA and 5 μmoles of dNTPs. Mix 2 included 1 unit of Fidelity Expand DNA polymerase (Boehringer Mannheim/Roche Diagnostics Corporation, Indianapolis, Ind., Cat. No. 1 732 641) and 5 μl of 10× Fidelity Expand buffer (Boehringer Mannheim/Roche Diagnostics Corporation, Indianapolis, Ind.). To allow PCR hot-start, Mix 1 and Mix 2 were heated separately for 20 seconds at 96° C. before they were pooled. The pooled reaction was cycled as follows: incubation at 96° C. for 3 min, 10 cycles of incubation at 96° C. for 30 sec, 55° C. for 1 min, and 68° C. for 2 min, then 20 cycles of incubation at 96° C. for 30 sec, 60° C. for 1 min, and 68° C. for 2 min, followed by a polishing step of incubation at 72° C. for 7 min. After PCR, a single 250 bp fragment was obtained. The BCCP fragment was digested with Nhe I and BamH I and subcloned into Nhe I-BamH I digested pRSET-A.

Step 5: Expression of Sulfurylase and Luciferase.

The Bst ATP sulfurylase and P. pyralis luciferase open reading frames were amplified by PCR with primers that contain Pst I/Hind III and BamH I/Xho I sites (the first enzyme was at the 5' end and the second enzyme was at the 3' end), respectively. This produced an N-terminal fusion of 6× His and BCCP domain to ATP sulfurylase and luciferase. The enzymes were expressed in E. coli using biotin-supplemented growth media to allow for in-vivo biotinylation via the BCCP domain. The enzymes were purified to near homogeneity using a combination of IMAC and a size-exclusion column chromatography. Purification was assessed by electrophoresis using the Agilent 2100 Bioanalyzer on Protein 200 Plus chips.

Step 6: Solid Phase Immobilization of Luciferase and Sulfurylase

The enzymes were immobilized onto Dynal M-280 streptavidin coated magnetic microparticles (Dynal, Oslo, Norway) and Bangs microspheres (300 nm) by incubation of 1:3 mixture of ATP sulfurylase and luciferase, respectively. The binding was performed by mixing 50 μg of ATP sulfurylase and 150 μg of luciferase with 1 mg of Dynal M-280 beads or 0.6 mg of Bangs microspheres in TAGE buffer (25 mM Tris-Acetate pH 7.8, 200 mM ammonium sulfate, 15% v/v glycerol and 30% v/v ethylene glycol). The mixture was incubated for 1 hour at 4° C. on a rotator. After binding, the beads could be stored at −20° C. in the enzyme solution for 3 months. Before use, beads were washed thoroughly in luciferase assay buffer containing 0.1 mg/ml bovine serum albumin (Sigma, St Louis, Mo.). Immobilized enzyme activity was assayed using a luminometer (Turner, Sunnyvale, Calif.). Washed beads were stored on ice until deposition onto a PTP slide.

Step 7: PicoTiterPlates™ (PTPs)

The PicoTiterPlates™ (25×75×2 mm) were manufactured by anisotropic etching of fiber optic face plates in a manner similar to that described in literature. Plates were etched in three different microwell depths, 26, 50 and 76 mm. Microwell center-to-center pitch was 50 μm, and well diameters ranged between 39 and 44 μm with a calculated well density of 480 wells/mm$^2$.

Step 8: PTP Loading

Sepharose beads carrying DNA templates and Dynal M-280/Bangs 0.3 μm bead mixture with immobilized sulfurylase and luciferase enzymes were deposited into individual wells of a PicoTiter plate using a centrifugation-based method. The procedure employed an in-house polycarbonate fixture (jig) which included a bottom plate (with slide positioning pegs), an elastomer sealing gasket, and a top plate with two loading ports. The PTP slide was placed onto the bottom plate with the etched side facing up and the top plate with sealing gasket in place was clamped on top of the PTP slide. The whole assembly was tightened with four plastic screws in order to provide a water-tight seal. The sealing gasket was designed to form a mask for bead deposition, resulting in one hexagonal area (14×43 mm) covering roughly 270,000 PTP wells.

Beads were deposited in ordered layers. The PTP was removed from incubating in Bead Wash Buffer. Layer 1, a mix of DNA and enzyme beads, was deposited. After centrifuging, Layer 1 supernatant was aspirated off the PTP and Layer 2, Dynal enzyme beads, was deposited.

A bead suspension was prepared by mixing 150,000 DNA carrying Sepharose beads in 120 μl of the ssb/Bst pol binding mix (see above) with 270 μl of Dynal-SL and Bangs-SL beads (both at 10 mg/ml) in a total volume of 500 μl of the luciferase assay buffer containing 0.1 mg/ml bovine serum albumin. The bead slurry was vortexed and flowed into the bead deposition jig through pipetting ports. Care was taken to avoid introducing air bubbles. The jig/PTP assembly was centrifuged at 2000 rpm for 8 minutes in a Beckman Allegra 6 centrifuge equipped with a 4-position plate swing-out rotor. After centrifugation, the supernatant was carefully removed from the jig chamber using a pipette. A second layer of only Dynal-SL beads was deposited. This layer included 125 μl of Dynal-SL (at 10 mg/ml) and 375 μl Bead Wash Buffer in a 1.5 ml tube (2.5 mg/ml Dynal beads). The Dynal bead mixture was pipetted into the PTP main active area and centrifuged for 8 minutes at 2000 rpm. Layer 2 mixture was aspirated and the PTP was placed back into Bead Wash Buffer (luciferase assay buffer with 0.1 mg/ml bovine serum albumin and 8.5 U/l apyrase) until ready to load onto the Sequencer.

Step 9: Sequencing Instrument

The in-house sequencing instrument included three major assemblies: a fluidics subsystem, a PTP cartridge/flow chamber, and an imaging subsystem. The fluidics subsystem included reagent reservoirs, reagents inlet lines, a multi-valve manifold, and a peristaltic pump. It allowed for reagent delivery into the flow chamber, one reagent at a time, at a pre-programmed flow rate and duration. The PTP cartridge/flow chamber was designed in such a way that after attaching a PTP, there would be 300 μm space between the PTP top (etched side) and the chamber ceiling. It included means for temperature control of the reagents and PTP, as well as a light-tight housing. The polished side of a PTP was exposed at the back side of the PTP cartridge and was placed directly in contact with the imaging system. The imaging system comprised a CCD camera with a 1-1 imaging fiber bundle, as well as cryogenic cooling system for the camera, and camera control electronics. The camera used was a Spectral Instruments (Tucson, Ariz.) series 600 camera with a Fairchild Imaging LM485 CCD (16 million pixels, 15 μm pixel size). This was bonded directly to the imaging fiber bundle with 6 μm fiber pitch. The camera was cooled to −70° C. and operated in a frame transfer mode. In this way, the center portion of the CCD was used for imaging while the outer portion of the CCD was used for image storage and read-out. The read-out occurred through 4 ports at each corner of the CCD. The data acquisition rate was set to 1 frame per 30 seconds. The frame-transfer shift time was approximately 0.25 seconds. All camera images were stored in a UTIFF 16 format on a computer hard drive (IBM eServer xSeries 335, IBM, White Plains, N.Y.).

Step 10: Sequencing Run Conditions

The cyclical delivery of sequencing reagents into the PTP wells and washing of the sequencing reaction byproducts from the wells was achieved by a pre-programmed operation of the fluidics system. The program was written in a form of a Microsoft Excel script, specifying the reagent name (Wash, dATPαS, dCTP, dGTP, dTTP, $PP_i$ standard), flow rate and duration of each script step. Flow rate was set at 3 ml/min for all reagents and the linear velocity within the flow chamber was approximately. An initial wash step (5 minutes) was followed by a $PP_i$ standard flow (2 min), followed by 21 or 42 cycles of (Wash—C—Wash—A—Wash—G—Wash—T), where each nucleotide flow was 0.5 minute and wash steps were 2 minutes. After all cycles of nucleotide additions and washes, a second $PP_i$ standard flow (2 min) was delivered, followed by a final 5 minutes wash step. The total run time was 4 hours. Reagent volumes required to complete this run script were as follows: 300 ml each wash solution, 50 ml of each nucleotide solution, 20 ml of $PP_i$ standard solution. During the run, all reagents were kept at room temperature. Because the flow chamber and flow chamber inlet tubing were maintained at 3° C., all reagents entering the flow chamber were at 30° C.

Example 29

Genome Sequencing in Open Microfabricated High Density Picoliter Reactors

We describe a scalable, highly parallel sequencing system with raw throughput significantly greater than that of state-of-the-art capillary electrophoresis instruments. The apparatus uses a novel 60×60 mm² fibreoptic slide containing 1,600,000 individual wells and is able to sequence 25 million bases, at 99% or better accuracy (phred 20), in a 4 hour run. To provide sequencing templates, we clonally amplify DNA fragments on beads in the droplets of an emulsion. The template-carrying beads are loaded into the wells to convert each into a picoliter-scale sequencing reactor. We perform sequencing by synthesis using a pyrosequencing protocol optimized for solid support and the small dimension of the open reactors. Here we show the utility, throughput, accuracy and robustness of this system by shotgun sequencing and de novo assembling the *Mycoplasma genitalium* genome with 96% coverage at 99.96% accuracy in one run of the machine.

DNA sequencing has dramatically changed the nature of biomedical research and medicine. Reductions in the cost, complexity and time required to sequence large amount of DNA, including improvements in the ability to sequence bacterial and eukaryotic genomes will have significant scientific, economic and cultural impact. Large scale sequencing projects, including whole genome sequencing, have usually required the cloning of DNA fragments into bacterial vectors, amplification and purification of individual templates, followed by Sanger sequencing[1] using fluorescent chain-terminating nucleotide analogues and either slab gel or capillary electrophoresis. Current estimates put the cost of sequencing a human genome between $10 and $25 million[3]. Alternative sequencing methods have been described[4, 5, 6, 7, 8] however, no technology has displaced the use of bacterial vectors and Sanger sequencing as the main generators of sequence information.

In this paper we describe an integrated system whose throughput routinely enables applications requiring millions of bases of sequence information, including whole genome sequencing Our focus has been on the co-development of an emulsion-based method[9, 10, 11] to isolate and amplify DNA fragments in vitro, and of a fabricated substrate and instrument that performs pyrophosphate-based sequencing ("pyrosequencing"[5, 12]) in picoliter-sized wells.

In a typical run we generate over 25 million bases with a phred 20 or better quality score (predicted to have an accuracy of 99% or higher). While this phred 20 quality throughput is significantly higher than that of Sanger sequencing by capillary electrophoresis, it is currently at the cost of substantially shorter reads and lower average individual read accuracy[13]. We further characterize the performance of the system, and demonstrate that it is possible to assemble bacterial genomes de novo from relatively short reads, by sequencing a known bacterial genome, *Mycoplasma genitalium* (580 kbp), and comparing our shotgun sequencing and de novo assembly with the results originally obtained for this genome[14]. The results of shotgun sequencing and de novo assembly of a larger bacterial genome, *Streptococcus pneumoniae*[15] (2.1 Mbp), are presented in Supplementary Table 4.

Emulsion Based Sample Preparation

We generate random libraries of DNA fragments by shearing an entire genome and isolating single DNA molecules by limiting dilution (Supplementary Methods: Library Preparation). Specifically, we randomly fragment the entire genome, add specialized common adapters to the fragments, capture the individual fragments on their own beads and, within the droplets of an emulsion, clonally amplify the individual fragment (FIGS. 43A and 43B). Unlike in current sequencing technology, our approach does not require subcloning in bacteria or the handling of individual clones; the templates are handled in bulk within the emulsions[9, 10, 11].

Sequencing in Fabricated Picoliter Sized Reaction Vessels

Figure 44:
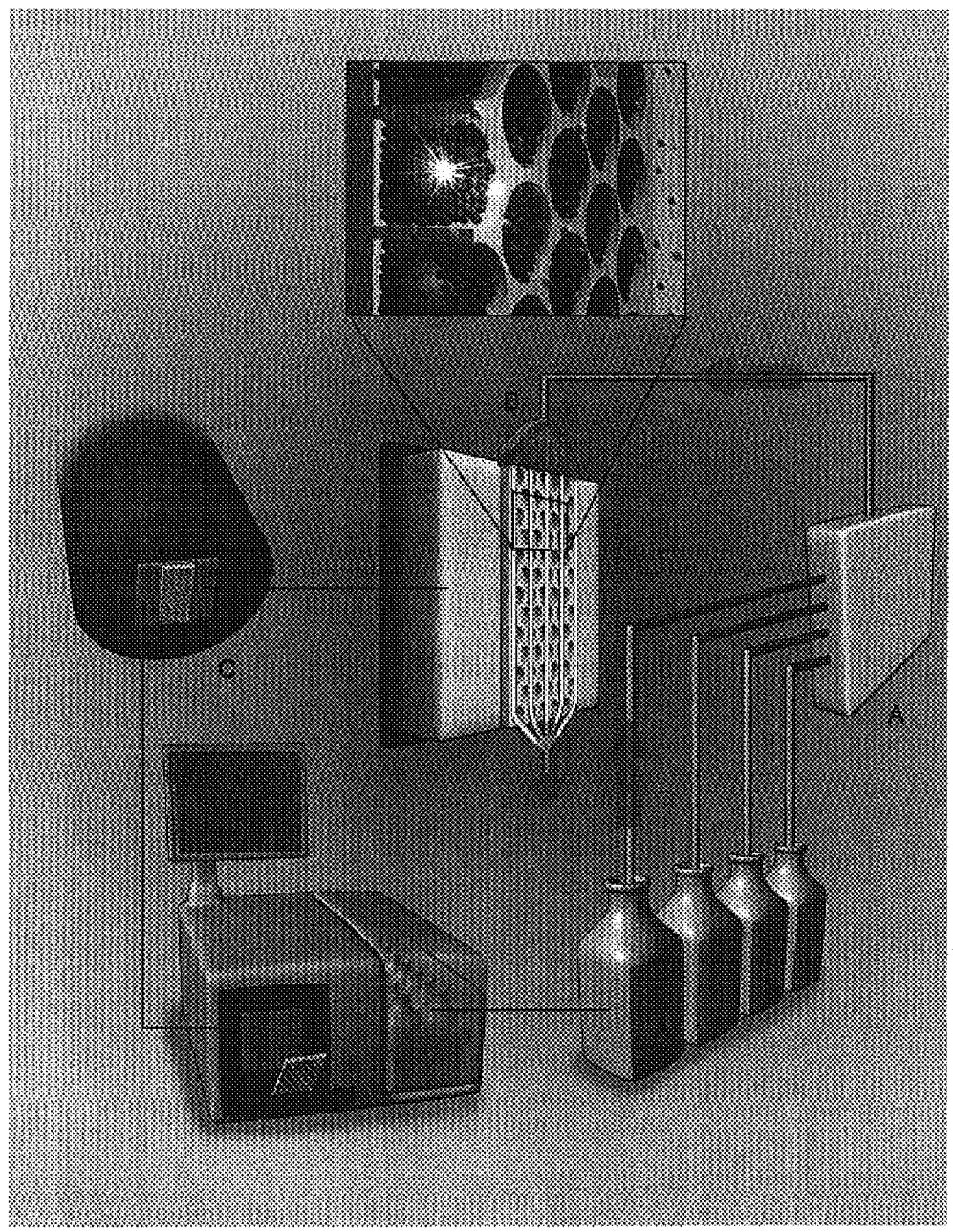
FIG. 44 Sequencing Instrument. The sequencing instrument consists of the following major subsystems: a fluidic assembly (A), a flow chamber that includes the well-containing fibre optic slide (B), a CCD camera-based imaging assembly (C) and a computer that provides the necessary user interface and instrument control.

We perform sequencing by synthesis simultaneously in open wells of a fibreoptic slide using a modified pyrosequencing protocol that is designed to take advantage of the small scale of the wells. The fibreoptic slides are manufactured by slicing of a fibreoptic block that is obtained by repeated drawing and fusing of optic fibres. At each iteration, the diameters of the individual fibres decrease as they are hexagonally packed into bundles of increasing cross-sectional sizes. Each fibreoptic core is 44 μm in diameter and surrounded by 2-3 μm of cladding; etching of each core creates reaction wells approximately 55 μm in depth with a centre-to-centre distance of 50 μm (FIG. 43C), resulting in a calculated well size of 75 pL and a well density of 480 wells/mm². The slide, containing approximately 1.6 million wells[16], is loaded with beads and mounted in a flow chamber designed to create a 300 µm high channel, above the well openings, through which the sequencing reagents flow (FIG. 44, A and B). The unetched base of the slide is in optical contact with a second fibreoptic imaging bundle bonded to a CCD sensor, allowing the capture of emitted photons from the bottom of each individual well (FIG. 44, C, and Supplementary Methods: Imaging System).

We developed a three-bead system, and optimized the components to achieve high efficiency on solid support. The combination of picoliter-sized wells, enzyme loading uniformity allowed by the small beads and enhanced solid support chemistry enabled us to develop a method that extends the useful read length of sequencing-by-synthesis to 100 bp (Supplementary Methods: Sequencing).

In the flow-chamber cyclically delivered reagents flow perpendicularly to the wells. This configuration allows simultaneous extension reactions on template carrying beads within the open wells and relies on convective and diffusive transport to control the addition or removal of reagents and by-products. The time scale for diffusion into and out of the wells is on the order of 10 seconds in the current configuration and is dependent on well depth and flow channel height. The time scales for the signal-generating enzymatic reactions are on the order of 0.02-1.5 seconds (Supplementary Methods: Interwell Diffusion). The current reaction is dominated by mass transport effects and improvements based on faster delivery of reagents are possible. Well depth was selected based on a number of competing requirements: (i) wells need to be deep enough for the DNA-carrying beads to remain in the wells in the presence of convective transport past the wells, (ii) they must be sufficiently deep to provide adequate isolation against diffusion of by-products from a well in which incorporation is taking place to a well where no incorporation is occurring, and (iii) they must be shallow enough to allow rapid diffusion of nucleotides into the wells, and rapid washing out of remaining nucleotides at the end of each flow cycle to enable high sequencing throughput and reduced reagent use. Following the flow of each nucleotide, a wash containing a nuclease is used to ensure that nucleotides do not remain in any well prior to the next nucleotide being introduced.

Base Calling of Individual Reads

Figure 45:
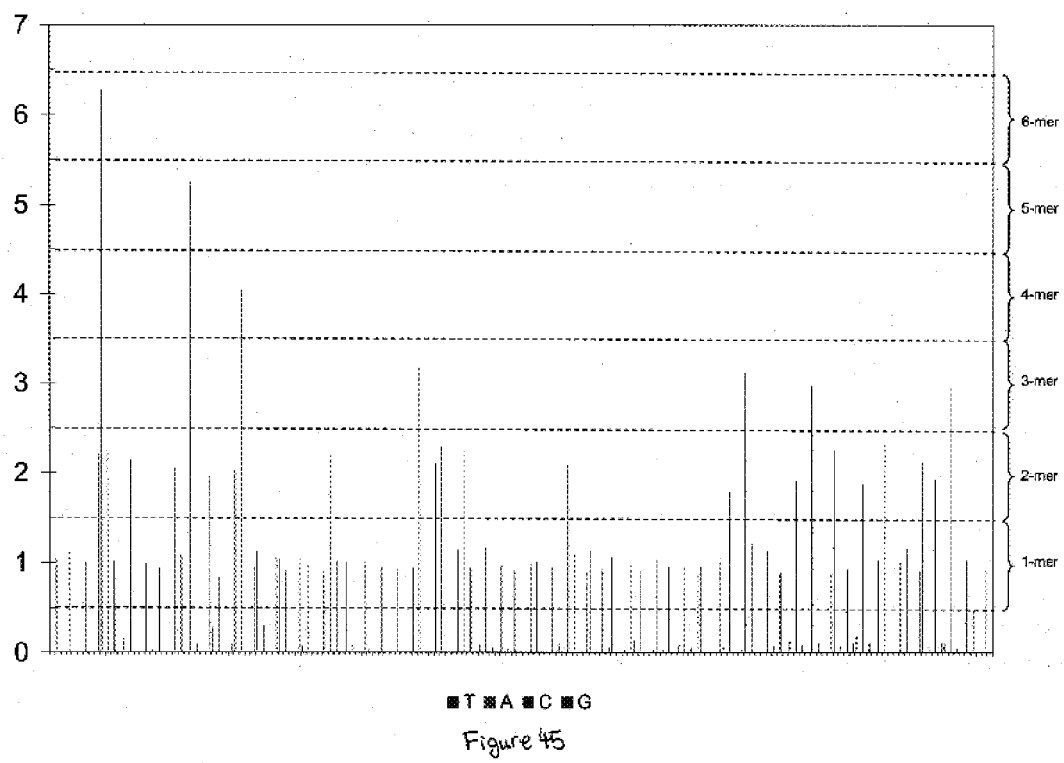
FIG. 45 Flowgram of a 113 base read from an *M. genitalium* run. Nucleotides are flowed in the order T, A, C, G. The sequence is shown above the flowgram. The signal value intervals corresponding to the various homopolymers are indicated on the right. The first four bases (in red, above the flowgram) constitute the "key" sequence, used to identify wells containing a DNA-carrying bead.
Figure 52:
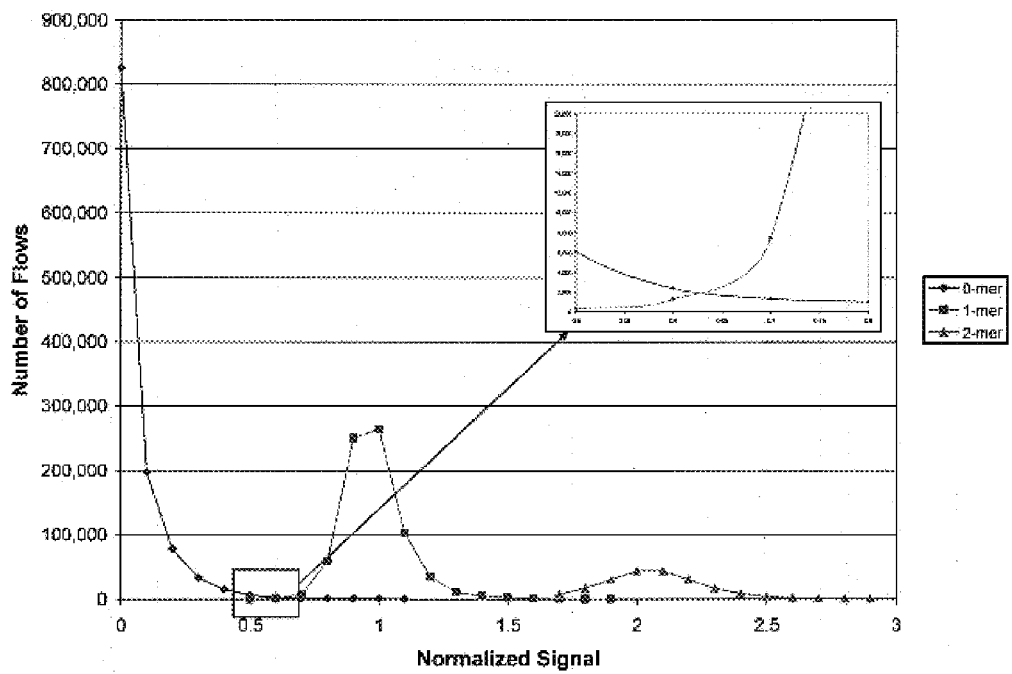
FIG. 52 Typical histogram of signal intensities for negative and positive flows.

Nucleotide incorporation is detected by the associated release of inorganic pyrophosphate (PPi) and the generation of photons[5, 12]. Wells containing template-carrying beads are identified by detecting a known four-nucleotide "key" sequence at the beginning of the read (Supplementary Methods: Image Processing). Raw signals are background-subtracted, normalized and corrected. The normalized signal intensity at each nucleotide flow, for a particular well, indicates the number of nucleotides, if any, that were incorporated. This linearity in signal is preserved to at least homopolymers of length 8 (FIG. 52). In sequencing by synthesis a very small number of templates on each bead lose synchronism (i.e. either get ahead of, or fall behind, all other templates in sequence[17]). The effect is primarily due to left-over nucleotides in a well (creating "carry forward") or to incomplete extension. Typically, we observe a carry forward rate of 1-2% and an incomplete extension rate of 0.1-0.3%. Correction of these shifts is essential because the loss of synchronism is a cumulative effect that degrades the quality of sequencing at longer read lengths. We have developed algorithms, based on detailed models of the underlying physical phenomena, that allow us to determine, and correct for, the amounts of carry forward and incomplete extension occurring in individual wells (Supplementary Methods: Signal Processing). FIG. 45 shows the processed result, a 113 bp long read generated in the *M. genitalium* run discussed below. To assess sequencing performance and the effectiveness of the correction algorithms, independently of artifacts introduced during the emulsion-based sample preparation, we created test fragments with difficult-to-sequence stretches of identical bases of increasing length (homopolymers) (Supplementary Methods: Test Fragments and FIG. 46). Using these test fragments, we have verified that at the individual read level we achieve base call accuracy of approximately 99.4%, at read lengths in excess of 100 bp (Table 29.1).

High Quality Reads and Consensus Accuracy.

Figure 51:
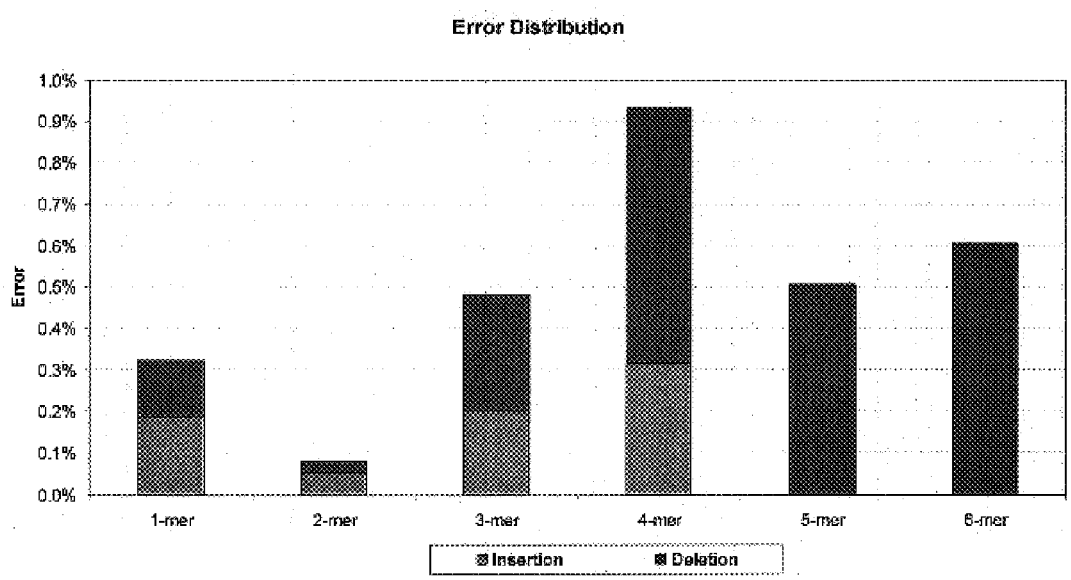
FIG. 51 Detailed error rates in sequencing a mixture of 6 test fragments, as a function of homopolymer length. Single base error rates are referenced to the total number of single bases sequenced. For each homopolymer, the error rate is referenced to the total number of bases sequenced that belong to homopolymers of that length.

Prior to base calling or aligning reads, we select high quality reads without relying on a priori knowledge of the genome or template being sequenced (Supplementary Methods: High Quality Reads). This selection is based on the observation that poor quality reads have a high proportion of signals that do not allow a clear distinction between a flow during which no nucleotide was incorporated and a flow during which one or more nucleotide was incorporated. When base calling individual reads, errors can occur because of signals that have ambiguous values (FIG. 51). To improve the usability of our reads, we also developed a metric which allows us to estimate ab initio the quality (or probability of correct base call) of each base of a read, analogous to the phred score[18] used by current Sanger sequencers (Supplementary Methods: Quality Scores and FIG. 54).

Higher quality sequence can be achieved by taking advantage of the high oversampling that our system affords and building a consensus sequence. Sequences are aligned to one another using the signal strengths at each nucleotide flow, rather than individual base calls, to determine optimal alignment (Supplementary Methods: Flow-space Mapping, Consensus Accuracy and Genome Coverage). The corresponding signals are then averaged, after which base calling is performed. This approach greatly improves the accuracy of the sequence (FIG. 53), and provides an estimate of the quality of the consensus base. We refer to that quality measure as the Z-score; it is a measure of the spread of signals in all the reads at one location and the distance between the average signal and the closest base calling threshold value. In both re-sequencing and de novo sequencing, as the minimum Z-score is raised the consensus accuracy increases, while coverage decreases; approximately half of the excluded bases, as the Z-score is increased, belong to homopolymers of length 4 and larger. Sanger sequencers usually require a depth of coverage at any base of three or more in order to achieve a consensus accuracy of 99.99%. To achieve a minimum of three fold coverage of 95% of the unique portions of a typical genome requires approximately 7 to 8 fold oversampling. Due to our higher error rate, we have observed that comparable consensus accuracies, over a similar fraction of a genome, are achieved with a depth of coverage of 4 or more, requiring approximately 10-12× oversampling.

*Mycoplasma genitalium* (580,069 bp).

Figure 46A:
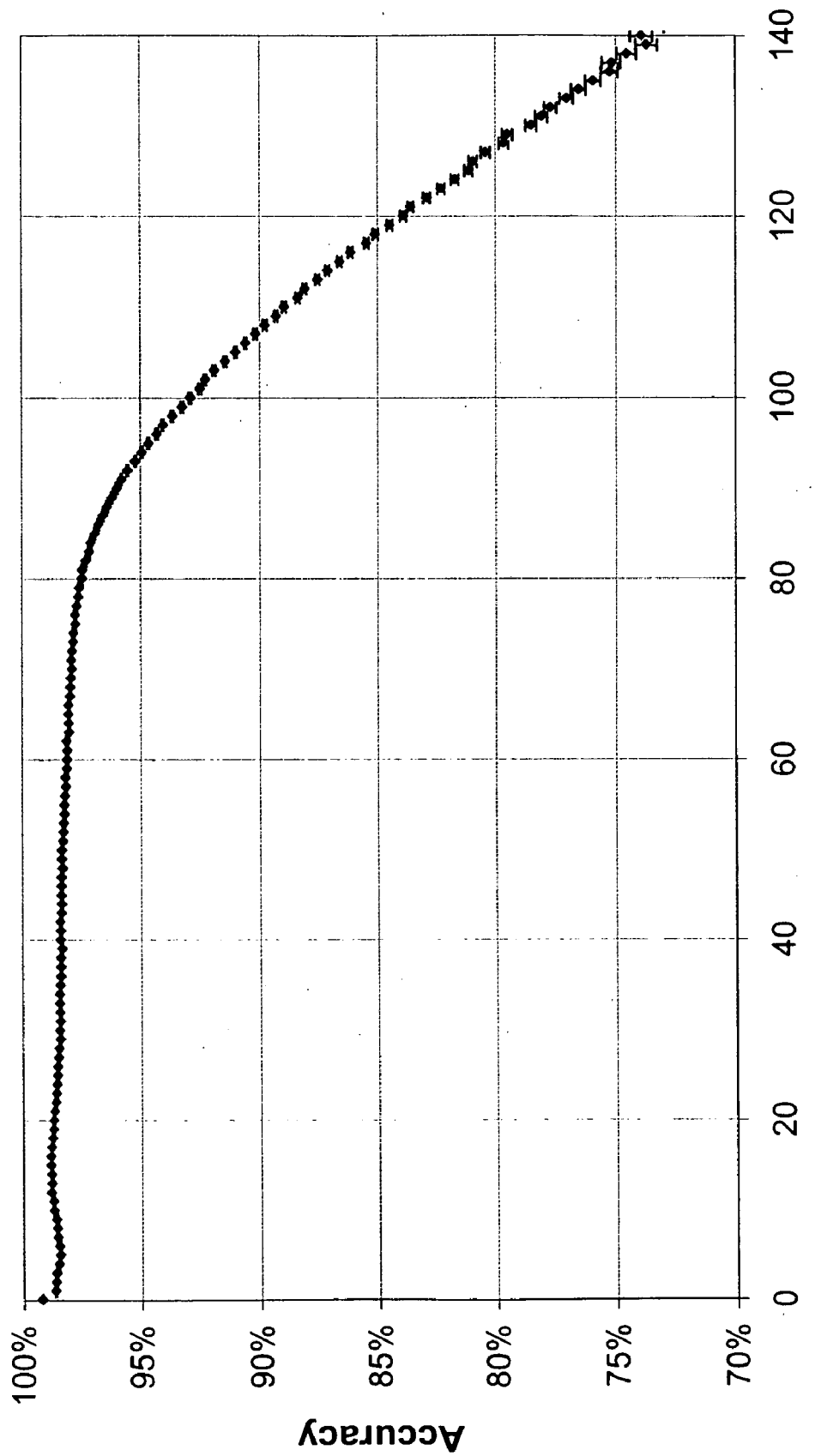
FIG. 46 *M. genitalium* Data. (A) Read length distribution for the 306,178 High Quality Reads of the *M. genitalium* sequencing run. This distribution reflects the base composition of individual sequencing templates. (B) Average read accuracy, at the single read level, as a function of base position for the 238,066 mapped reads of the same run.
Figure 46B:
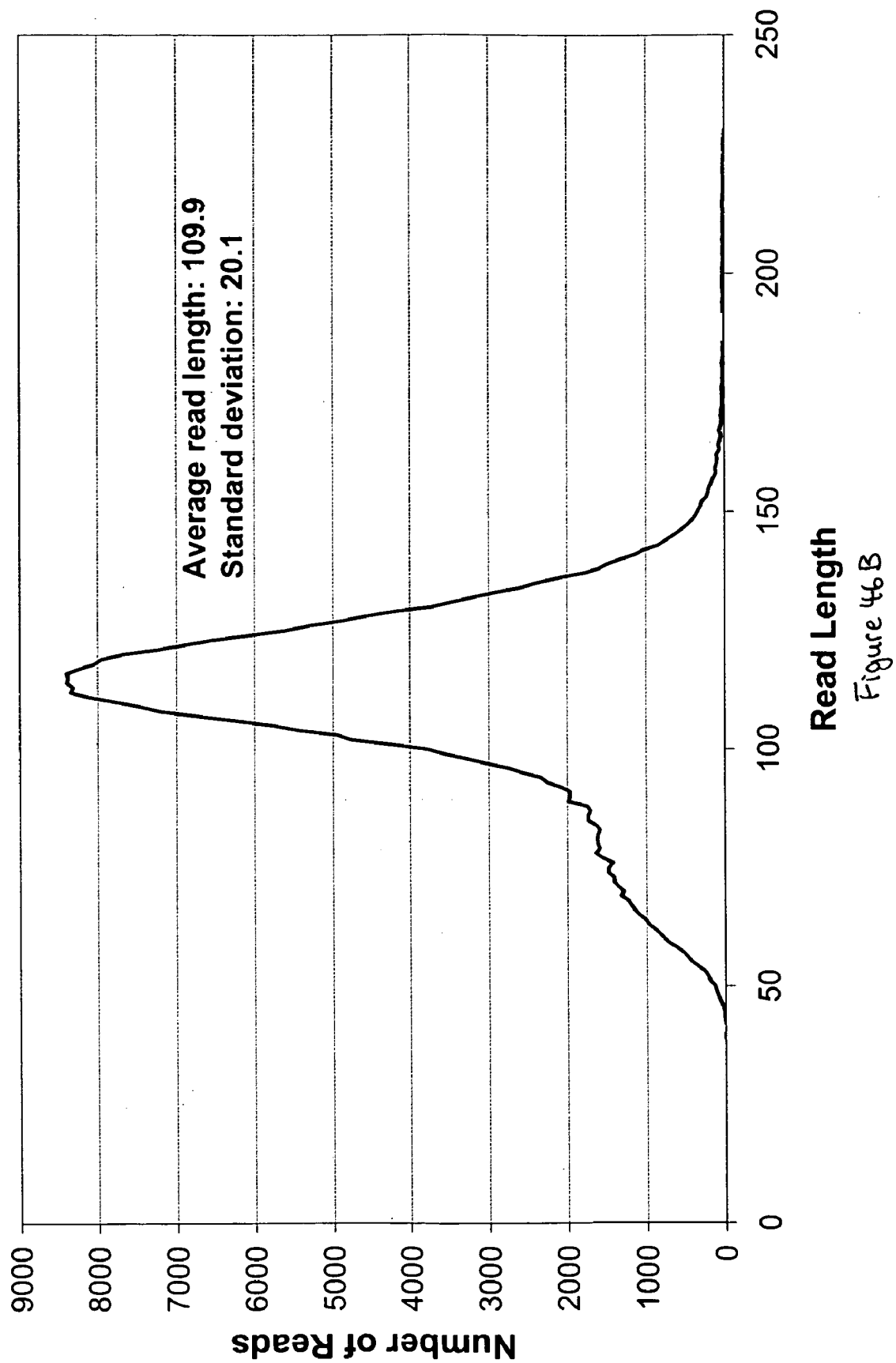
Figure 53:
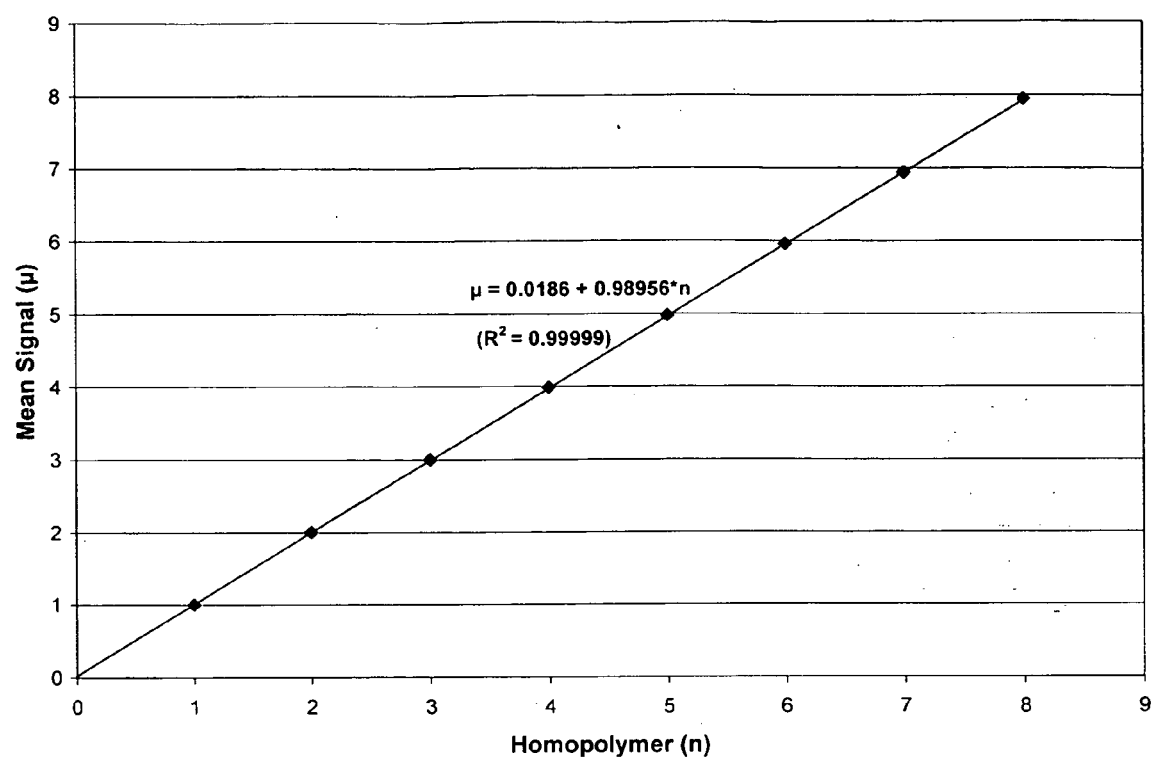
FIG. 53 Average of the flow signals ascribed to various homopolymers for the mapped reads of the *M. genitalium* run discussed in the paper.
Figure 54:
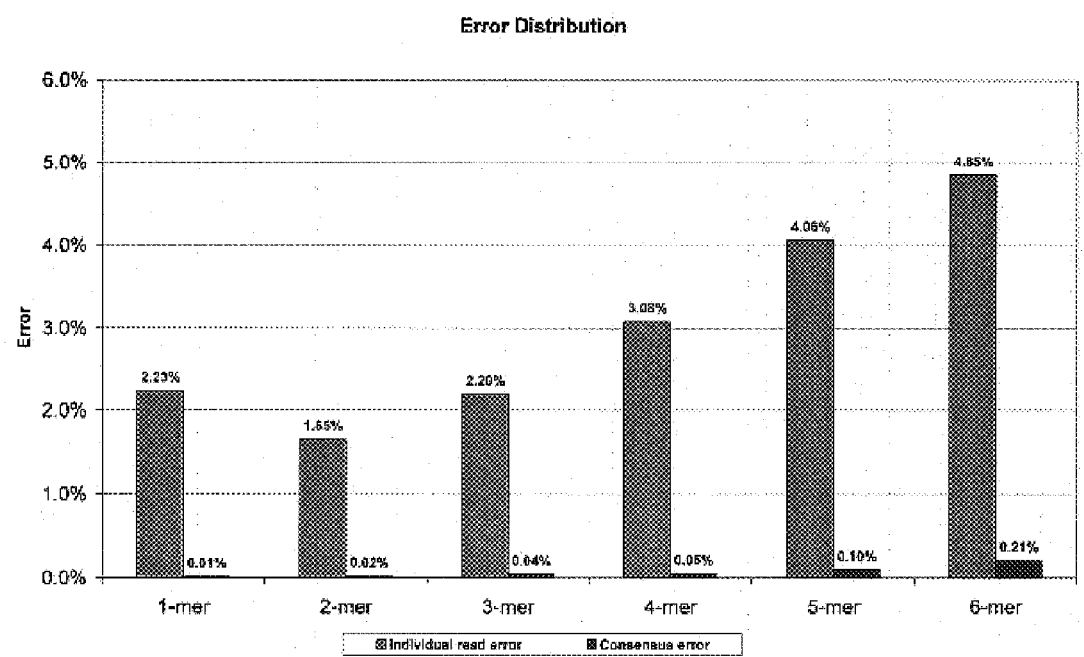
FIG. 54 Detailed error rates in sequencing an *M. genitalium* library, as a function of homopolymer length. As for test fragments, single base error rates are referenced to the total number of single bases sequenced; for homopolymers, the error rate is referenced to the total number of bases sequenced that belong to homopolymers of each length. The error rates are shown for individual reads and after the consensus sequence was formed using all reads, without Z-score restriction.
Figure 55:
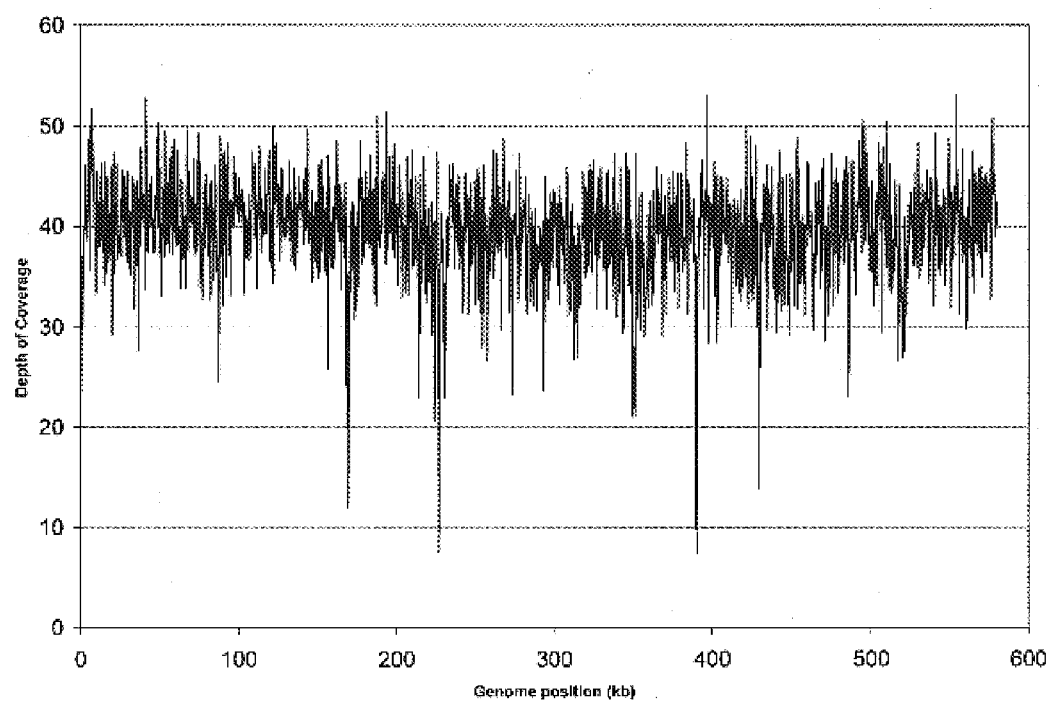
FIG. 55 Depth of coverage as a function of genome position for the *M. genitalium* run. Slightly lower coverage in isolated regions is due to the presence of repeat regions excluded in the mapping.

*Mycoplasma* genomic DNA was fragmented and prepared into a sequencing library as described above. (This was accomplished by a single individual in 4 hours.) Following emulsion PCR and bead deposition onto a 60×60 mm$^2$ fibre-optic slide, a process which took one individual 6 hours, 42 cycles of 4 nucleotides were flowed through the sequencing system in an automated 4 hour run of the instrument. The results are summarized in Table 29.2. In order to measure the quality of individual reads, we aligned each High Quality Read to the reference genome at 70% stringency, using flow-space mapping and criteria similar to those used previously in assessing the accuracy of other base callers[18]. When assessing sequencing quality, only reads that mapped to unique locations in the reference genome were included. Since this process excludes repeat regions (parts of the genome whose corresponding flowgrams are 70% similar to one another), the selected reads did not cover the genome completely. FIG. 46A illustrates the distribution of read lengths for this run. The average read length was 110 bp, the resulting oversample 40 fold, and 84,011 reads (27.4%) were perfect. FIG. 46B summarizes the average error as a function of base position. Coverage of non-repeat regions was consistent with the sample preparation and emulsion not being biased (FIG. 54). At the individual read level, we observe an insertion and deletion error rate of approximately 3.3%; substitution errors have a much lower rate, on the order of 0.5%. When using these reads without any Z-score restriction, we covered 99.94% of the genome in 10 contiguous regions with a consensus accuracy of 99.97%. The error rate in homopolymers is significantly reduced in the consensus sequence (FIG. 53). Of the bases not covered by this consensus sequence (366 bp), all belonged to excluded repeat regions. Setting a minimum Z-score equal to 4, coverage was reduced to 98.1% of the genome, while consensus accuracy increased to 99.996%. We further demonstrated the reproducibility of the system by repeating the whole genome sequencing of M. genitalium an additional 8 times, achieving a 40 fold coverage of the genome in each of the 8 separate instrument runs (Supplementary Table 3).

We assembled the M. genitalium reads from a single run into 25 contigs with an average length of 22.4 kbp. One of these contigs was misassembled due to a collapsed tandem repeat region of 60 bp, and was corrected by hand. The original sequencing of M. genitalium resulted in 28 contigs prior to directed sequencing used for finishing the sequence [14]. Our assembly covered 96.54% of the genome and attained a consensus accuracy of 99.96%. Non-resolvable repeat regions amount to 3% of the genome: we therefore covered 99.5% of the unique portions of the genome. Sixteen of the breaks between contigs were due to non-resolvable repeat regions, 2 were due to missed overlapping reads (our read filter and trimmer are not perfect and the algorithms we use to perform the pattern matching of flowgrams occasionally misses valid overlaps), and the remainder to thin read coverage. Setting a minimum Z-score of 4, coverage was reduced to 95.27% of the genome (98.2% of the resolvable part of the genome) with the consensus accuracy increasing to 99.994%.

Discussion

We have demonstrated in this paper the simultaneous acquisition of hundreds of thousands of sequence reads, 80-120 bases long, at 96% average accuracy, in a single run of the instrument using a newly developed in vitro sample preparation methodology, and sequencing technology. With phred 20 as a cutoff, we show that our instrument is able to produce over 47 million bases from test fragments and 25 million bases from genomic libraries. We used test fragments to decouple our sample preparation methodology from our sequencing technology. The decrease in single read accuracy from 99.4% for test fragments to 96% for genomic libraries is primarily due to a lack of clonality in a fraction of the genomic templates in the emulsion, and is not an inherent limitation of the sequencing technology. Most of the remaining errors result from a broadening of signal distributions, particularly for large homopolymers (7 or more), leading to ambiguous base calls. Recent work on the sequencing chemistry and algorithms that correct for crosstalk between wells suggests that the signal distributions will narrow, with an attendant reduction in errors and increase in read lengths. In preliminary experiments with genomic libraries that also includes improvements in the emulsion protocol, we are able to achieve, using 84 cycles, read lengths of 200 bp with accuracies similar to those demonstrated here for 100 bp. On occasion, at 168 cycles, we have generated individual reads which are 100% accurate over greater then 400 bp.

Using M. genitalium, we demonstrate that short fragments a priori do not prohibit the de novo assembly of bacterial genomes. In fact, the larger oversampling afforded by the throughput of our system resulted in a draft sequence having fewer contigs than with Sanger reads, with substantially less effort. By taking advantage of the oversampling, consensus accuracies greater then 99.96% were achieved for this genome. Further quality filtering the assembly, a consensus sequence can be selected with accuracy exceeding 99.99%, while incurring only a minor loss of genome coverage. Comparable results were seen when we shotgun sequenced and de novo assembled the 2.1 Mbp genome of Streptococcus pneumoniae[15] (Supplementary Table 4). The de novo assembly of genomes more complex than bacteria, including mammalian genomes, may require the development of methods, similar to those developed for Sanger sequencing, to prepare and sequence paired end libraries that can span repeats in these genome. To facilitate the use of paired end libraries we have developed methods to sequence, in an individual well, from both ends of genomic template, and plan to add paired end read capabilities to our assembler (Supplementary Methods: Double Ended Sequencing).

Future increases in throughput, and a concomitant reductions in cost per base, may come from the continued miniaturization of the fibreoptic reactors, allowing more sequence to be produced per unit area—a scaling characteristic similar to that which enabled the prediction of significant improvements in the integrated circuit at the start of its development cycle[19].

Methods

Emulsion Based Clonal Amplification. The simultaneous amplification of fragments is achieved by isolating individual DNA-carrying beads in separate ~100 μm aqueous droplets (on the order of $2 \times 10^6$/mL) made through the creation of a PCR-reaction-mixture-in-oil emulsion. (FIG. 43B and Supplementary Methods: Preparation of DNA Capture Beads, Binding Template Species to DNA Capture Beads, PCR Reaction Mix Preparation and Formulation, Emulsification and Amplification). The droplets act as separate microreactors in which parallel DNA amplifications are performed, yielding approximately $10^7$ copies of a template per bead; 800 μl of emulsion containing 1.5 million beads are prepared in a standard 2 mL tube. Each emulsion is aliquoted into 8 PCR tubes for amplification. After PCR, the emulsion is broken to release the beads, which include beads with amplified, immobilized DNA template, and empty beads (Supplementary Methods: Breaking the Emulsion and Recovery of Beads). We then enrich for template-carrying beads (Supplementary Methods: Enrichment of Beads). Typically, about 30% percent of the beads will have DNA, producing 450,000 template-carrying beads per emulsion reaction. The number of emulsions prepared depends on the size of the genome and the expected number of runs required to achieve adequate oversampling. The 580 kbp M. genitalium genome, sequenced on one 60×60 mm² fibreoptic slide, required 1.6 mL of emulsion. A human genome, oversampled 10 times, would require approximately 3000 mL of emulsion.

Bead Loading into Picoliter Wells. The enriched template-carrying beads are deposited by centrifugation into open wells (FIG. 43C), arranged along one face of a 60×60 mm² fibreoptic slide. The beads (diameter ~28 μm) are sized to ensure that no more than one bead fits in most wells (we observed that 2-5% of filled wells contain more than one bead). Loading 450,000 beads (from one emulsion preparation) onto each half of a 60×60 mm² plate was experimentally found to limit bead occupancy to approximately 35% of all wells, thereby reducing chemical and optical crosstalk between wells. A mixture of smaller beads that carry immobilized ATP sulfurylase and luciferase necessary to generate light from free pyrophosphate are also loaded into the wells to create the individual sequencing reactors (Supplementary Methods: Bead Deposition, Preparation of Enzyme Beads and Micro-particle Fillers).

Image Capture. A bead carrying 10 million copies of a template yields approximately 10,000 photons at the CCD sensor, per incorporated nucleotide. The generated light is transmitted through the base of the fibreoptic slide and detected by a large format CCD (4095×4096 pixels). The images are processed to yield sequence information simultaneously for all bead-template carrying wells. The imaging system was designed to accommodate a large number of small wells and the large number of optical signals being generated from individual wells during each nucleotide flow. Once mounted, the fibreoptic slide's position does not shift; this makes it possible for the image analysis software to determine the location of each well (whether or not it contains a DNA-carrying bead), based on light generation during the flow of a pyrophosphate solution which precedes each sequencing run. A single well is imaged by approximately nine 15 μm pixels. For each nucleotide flow, the light intensities collected by the pixels covering a particular well are summed to generate a signal for that particular well at that particular nucleotide flow. Each image captured by the CCD produces 32 megabytes of data. In order to perform all the necessary signal processing in real time, the control computer is fitted with an accessory board (Supplementary Methods: Field Programmable Arrays), hosting a 6 million gate FPGA[20, 21].

De novo Shotgun Sequence Assembler. A de novo flow-space assembler was developed to capture all of the information contained in the original flow-based signal trace. It also addresses the fact that existing assemblers are not optimized for 80 to 120 bp reads, particularly with respect to memory management due to the increased number of sequencing reads needed to achieve equivalent genome coverage. (A completely random genome covered with 100 bp reads requires approximately 50% more reads to yield the same number of contiguous regions (contigs) as achieved with 700 bp reads, assuming the need for a 30 bp overlap between reads.)[22]. This assembler consists of a series of modules: the Overlapper, which finds and creates overlaps between reads, the Unitigger, which constructs larger contigs of overlapping sequence reads, and the Multialigner, which generates consensus calls and quality scores for the bases within each contig (Supplementary Methods: De novo Sequence Assembler). (The names of the software modules are based on those performing related functions in other assemblers developed by Myers[23].)

TABLE 29.1

Summary of sequencing statistics for test fragments

| | |
|---|---|
| Size of fibre optic slide | 60 × 60 mm²<sup>Sy</sup> |
| Run Time/Number of Cycles | 243 min/42 |
| Test Fragment Reads | 497,893 |
| Average read length | 108 |
| Number of bases in test fragments | 53,705,267 |
| Phred 20 and above bases | 47,181,792 |
| Individual read insertion error rate | 0.44% |
| Individual read deletion error rate | 0.15% |
| Individual read substitution error rate | 0.004% |
| All errors | 0.60% |

TABLE 29.2

Summary statistics for *M. genitalium*

| | M. gen. 1 |
|---|---|
| Sequencing Summary | |
| Number of Instrument Runs | 1 |
| Size of fibre optic slide | 60 × 60 mm² |
| Run Time/Number of cycles | 243 min/42 |
| High Quality Reads | 306,178 |
| Average read length | 110 b |
| Number of bases in High Quality Reads | 33,655,553 |
| Phred 20 and above bases | 26,753,540 |
| Resequencing | |
| Reads mapped to single locations | 238,066 |
| Number of bases in mapped reads | 27,687,747 |
| Individual read insertion error rate | 1.67% |
| Individual read deletion error rate | 1.60% |
| Individual read substitution error rate | 0.68% |
| Resequencing Consensus | |
| Average oversampling | 40× |
| Coverage, all (Z ≥ 4) | 99.9% (98.2%) |
| Consensus accuracy, all (Z ≥ 4) | 99.97% (99.996%) |
| Consensus insertion error rate, all (Z ≥ 4) | 0.02% (0.003%) |
| Consensus deletion error rate, all (Z ≥ 4) | 0.01% (0.002%) |
| Consensus substitution error rate, all (Z ≥ 4) | 0.001% (0.0003%) |
| Number of contigs | 10 |
| De novo Assembly | |
| Coverage, all (Z ≥ 4) | 96.54% (95.27%) |
| Consensus accuracy, all (Z ≥ 4) | 99.96% (99.994%) |
| Number of contigs. | 25 |
| Average contig size | 22.4 kb |

The individual read error rates are referenced to the total number of bases in mapped reads.

1. Sanger, F., Nicklen, S., Coulson, A. R., DNA sequencing with chain-terminating inhibitors. *Proc. Natl. Acad. Sci. USA* 74, 5463 (1977).
2. Prober, J. M. et al., A system for rapid DNA sequencing with fluorescent chain-terminating dideoxynucleotides. *Science* 238, 336 (1987).
3. NIH News Release, Oct. 14, 2004, http://www.genome.gov/12513210.
4. Nyren, P., Pettersson, B., Uhlen, M., Solid phase DNA minisequencing by an enzymatic luminometric inorganic pyrophosphate detection assay. *Anal. Biochem.* 208, 171 (1993).
5. Ronaghi, M. et al., Real-time DNA sequencing using detection of pyrophosphate release. *Anal. Biochem.* 242, 84 (1996).
6. Jacobson, K. B. et al., Applications of mass spectrometry to DNA sequencing. *GATA* 8, 223 (1991).
7. Bains, W. and Smith, G. C., A novel method for nucleic acid sequence determination. *J. Theor. Biol.* 135, 303 (1988).

8. Jett, J. H. et al., High-speed DNA sequencing: an approach based upon fluorescence detection of single molecules. *Biomol. Struct. Dynamics* 7, 301 (1989).
9. Tawfik, D. S., Griffiths, A. D., Man-made cell-like compartments for molecular evolution. *Nat. Biotechnology* 16, 652 (1998).
10. Ghadessy, F. J., Ong, J. L., Holliger, P., Directed evolution of polymerase function by compartmentalized self-replication. *Proc. Nat. Acad. Sci. USA* 98, 4552 (2001).
11. Dressman, D., Yan, H., Traverso, G., Kinzler, K. W., Vogelstein, B., Transforming single DNA molecules into fluorescent magnetic particles for detection and enumeration of genetic variations. *Proc. Nat. Acad. Sci. USA* 100, 8817 (2003).
12. Ronaghi, M., Uhlen, M., Nyren, P., A sequencing method based on real-time pyrophosphate. *Science* 281, 363 (1998).
13. Current Sanger-based capillary electrophoresis sequencing systems produce up to 700 bp of sequence information from each of 96 DNA templates at an average read accuracy of 99.4% in one hour, or 67 thousand bases per hour, with substantially all of the bases having phred 20 or better quality. (Applied Biosystems 3730xl DNA Analyzer Specification Sheet, 2004.)
14. Fraser, C. M. et al., The minimal gene complement of *Mycoplasma genitalium*. *Science* 270, 397 (1995).
15. Tettelin, H. et al., Complete genome sequence of a virulent isolate of *Streptococcus pneumoniae*. *Science* 293, 498 (2001).
16. Leamon, J. H. et al., A massively parallel PicoTiterPlate based platform for discrete picoliter-scale polymerase chain reactions. *Electrophoresis* 24, 3769 (2003).
17. Ronaghi, M., Pyrosequencing sheds light on DNA sequencing. *Genome Research* 11, 3 (2001).
18. Ewing, B., Hillier, L., Wendl, M. C., Green, P., Basecalling of automated sequencer traces using phred. I. Accuracy assessment. *Genome Research* 8, 175 (1998).
19. Moore, G. E., Cramming more components onto integrated circuits. *Electronics* 38, Number 8, April 19, (1965).
20. Mehta, K., Rajesh, V. A., Veeraswamy, S., FPGA implementation of VXIbus interface hardware. *Biomed Sci Instrum.* 29, 507 (1993).
21. Fagin, B., Watt, J. G., Gross, R., A special-purpose processor for gene sequence analysis. *Comput Appl Biosci.* 9, 221 (1996).
22. Lander, E. S., Waterman, M. S., Genomic mapping by fingerprinting random clones: a mathematical analysis. *Genomics* 2, 231 (1988).
23. Myers, E. W., Toward simplifying and accurately formulating fragment assembly. *J Comput Biol.* 2, 275 1(1995).
24. Hamilton, S. C., J. W. Farchaus and M. C. Davis. 2001. DNA polymerases as engines for biotechnology. *BioTechniques* 31:370.
25. QiaQuick Spin Handbook (QIAGEN, 2001): hypertext transfer protocol://world wide web.qiagen.com/literature/handbooks/qqspin/1016893HBQQSpin_PCR_mc_prot.pdf
26. Quick Ligation Kit (NEB): hypertext transfer protocol://world wide web.neb.com/neb/products/mod_enzymes/M2200.html.
27. MinElute kit (QIAGEN): hypertext transfer protocol://world wide web.qiagen.com/literature/handbooks/minelute/1016839_HBMinElute_Prot_Gel.pdf.
28. Biomagnetic Techniques in Molecular Biology, Technical Handbook, 3rd edition (Dynal, 1998): hypertext transfer protocol://world wide web.dynal.no/kunder/dynal/DynalPub36.nsf/cb927fbab127a0ad4125683b004b011c/4908f5b1a665858a41256adf005779f2/$FILE/Dynabeads M-280 Streptavidin.pdf.
29. Bio Analyzer User Manual (Agilent): hypertext transfer protocol://world wide web.chem.agilent.com/temp/rad31B29/00033620.pdf
30. BioAnalyzer DNA and RNA LabChip Usage (Agilent): hypertext transfer protocol://world wide web.agilent.com/chem/labonachip
31. BioAnalyzer RNA 6000 Ladder (Ambion): hypertext transfer protocol://world wide web.ambion.com/techlib/spec/sp_7152.pdf Example 30

Supplementary Materials and Methods

Figure 47:
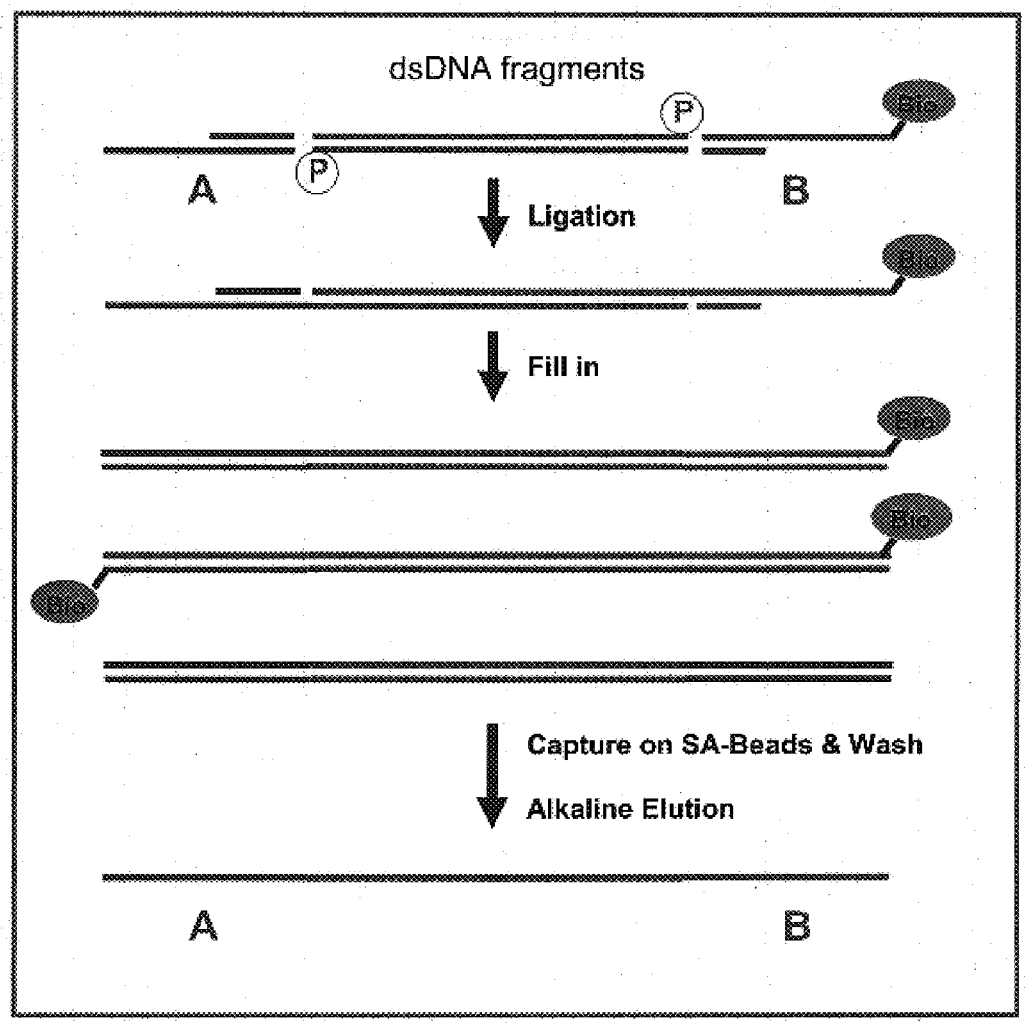
FIG. 47 Non-phosphorylated A and B adaptors are ligated to the ends of phosphorylated, polished, double-stranded genomic DNA fragments. The A and B adaptors differ in both nucleotide sequence and the presence of a 5' biotin tag on the B adaptor. Nicks are present at the 3'-junctions of each of the adaptors and the library fragment are filled in by the strand-displacement activity of Bst DNA polymerase. Streptavidin-biotin interactions are used to remove fragments flanked by homozygous adaptor sets (A/A and B/B) and to generate single stranded library templates. Fragments are bound to Streptavidin beads; unbound material (composed of homozygous A/A adaptor sets, which lack biotin) is washed away. The immobilized fragments are then denatured; both strands of the B/B fragments remain immobilized through the biotinylated B adaptor, while A/B fragments are washed free and used in subsequent sequencing steps. Replicate library preparations were observed to yield coverage of the genome and oversample with CV's of 5% or less.

Library Preparation (FIG. 47)

DNA Fragmentation. Genomic DNA samples were obtained from different sources, ranging from bacterial colonies to lyophilized samples received from commercial vendors. Upon receipt, using an OD260/280 ratio of 1.8 to 2.0, the concentration (>300 µg/mL) was verified. Fifteen micrograms of genomic DNA were diluted to a final volume of 100 µL in 1×TE buffer (10 mM Tris, 1 mM EDTA, pH 7.6) in a 2.0 mL tube. The sample was further diluted by the addition of 1.6 mL of ice-cold Nebulization Buffer (53.1% Glycerol, 37 mM Tris-HCl, 5.5 mM EDTA, pH 7.5) and gently mixed by repeated reciprocal pipette action.

The DNA solution was fragmented using an Aeromist Nebulizer (Alliance Medical, Russleville, Mo.), which had been modified as described below, inside a PCR hood (Labconco, Kansas City, Mo., USA) that was vented outside the laboratory. Briefly, a cap from a 15 mL snap cap Falcon tube was placed over the top of the nebulizer. To reduce loss caused by sample spray during nebulization, a nebulizer condensing tube consisting of a 0.50" OD×0.31" ID×1.5" long section of silicone tubing was affixed over the existing nebulizer feed tube. The DNA sample mixture was transferred to the bottom of the nebulizer chamber, and the top of the nebulizer tightly threaded onto the chamber. A loose-fitting, custom-built, delrin cap was designed to cover the top of the nebulizer and provide a lateral groove on the outside of the nebulizer for securing a pair of size #34 buna-N O-rings that held the cap in place. The entire nebulizer assembly was then wrapped tightly in parafilm (American Nat'l Can, Menasha, Wis.). The nebulizer was then connected to a nitrogen tank with the supplied tube, and the tube connections wrapped in parafilm.

The assembled nebulizer was placed upright in an ice bucket, with the bottom half of the unit submerged in the ice. The nitrogen gas was applied for 5 minutes at 50 psi; condensation on the walls of the nebulizer was knocked to the bottom of the chamber with occasional tapping. The gas was turned off, and the pressure allowed to normalize for 30 seconds before the tubing was removed from the nebulizer. The nebulizer was carefully dissembled, and the sample transferred to a 1.5 mL microcentrifuge tube. The recovered volume typically exceeded 900 µL.

Figure 48:
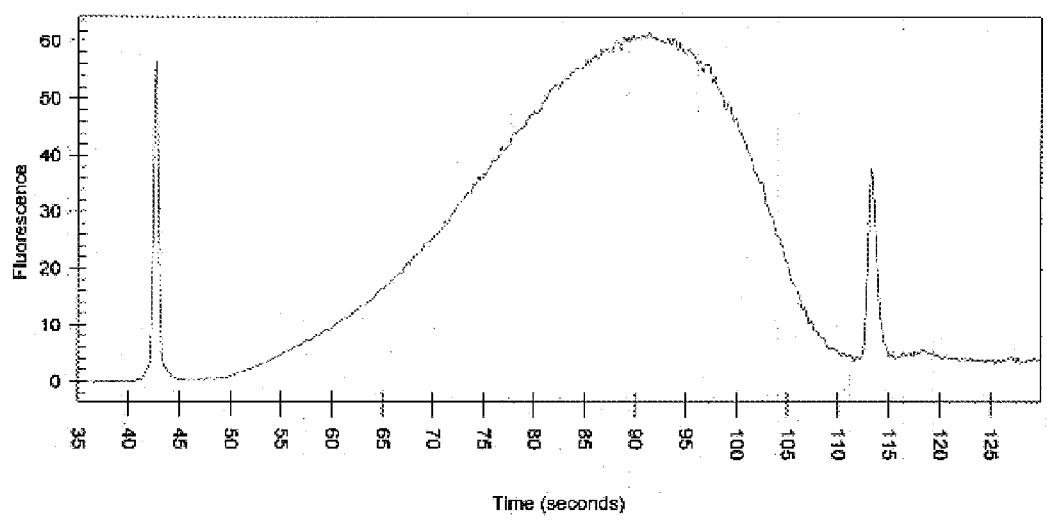
FIG. 48 Size distribution of nebulized DNA sample. Sharp flanking peaks are upper and lower reference markers.

The nebulized DNA was purified by centrifugation through a Qiaquick PCR Purification column (Qiagen, Valencia, Calif.), according to the manufacturer's instructions. Due to the large volume, the DNA sample was loaded and purified in several aliquots over the same column. The purified DNA was eluted with 30 µL of 55° C. Buffer EB (supplied in the Qiagen kit). The size distribution of the nebulized fragments was determined by resolving a 2 µL aliquot of the nebulized material on an Agilent 2100 BioAnalyzer (Agilent, Palo Alto, Calif.) using a DNA 1000 LabChip. (See FIG. 48 for a representative trace). The recovered material exhibited a size range of 50 to 900 bp with a mean fragment size of 325±50 bp.

Enzymatic Polishing. DNA nebulization generates fragments with a preponderance of frayed ends (1, 2). Fragments were blunt-ended and phosphorylated through the activity of three enzymes: T4 DNA polymerase, E. coli DNA polymerase (Klenow fragment) (New England Biolabs, Beverly, Mass.), and T4 polynucleotide kinase (New England Biolabs).

In a 0.2 mL tube, the remaining 28 μL of purified, nebulized DNA fragments were combined with 5 μL Molecular Biology Grade water (Eppendorf, Hamburg, Germany), 5 μL 10× NEBuffer 2 (New England Biolabs), 5 μL 1 mg/mL BSA (New England Biolabs), 2 μL 10 mM dNTPs (Pierce, Rockford, Ill.), and 5 μL 3 u/μL T4 DNA polymerase (New England Biolabs). The polishing reaction was thoroughly mixed and incubated in a thermocycler (MJ Research, Waltham, Mass.) for 10 minutes at 25° C. Following incubation, 1.25 μL of 5u/μL E. coli DNA polymerase (Klenow fragment) (New England Biolabs) were added, the reaction mixed well and incubated for an additional 10 minutes at 25° C. followed by 2 hours at 16° C.

The polishing reaction was then purified over a Qiaquick PCR Purification column, eluted with 30 μL of 55° C. Buffer EB, and transferred to a 0.2 mL tube for phosphorylation. The DNA was diluted to 50 μL through the addition of 5 μL Molecular Biology Grade water, 5 μL 10× T4 PNK buffer (New England Biolabs), 5 μL 10 mM ATP (Pierce), and 5 μL of 10 u/μL T4 PNK (New England Biolabs). The reaction was mixed and incubated for 30 minutes at 37° C., followed by a 20 minute incubation at 65° C. The phosphorylated fragments were then purified over a Qiaquick PCR Purification column as before, and eluted in 30 μL of 55° C. Buffer EB. The DNA concentration in a 2 μL aliquot was quantitated by fluorometry using a Turner TBS-380 Mini-Fluorometer (Turner Biosystems, Sunnyvale, Calif.).

Following fragmentation and polishing of the genomic DNA library, primer sequences were added to the each end of the DNA fragments. The 44-base primer sequences, (hereafter referred to as "adaptors") were double-stranded oligonucleotides comprised of a 5' 20 base PCR amplification primer followed by a 20 base sequencing primer, and a 3', 4 base, nonpalindromic sequencing "key" comprised of one of each deoxyribonucleotide (e.g. AGTC). Two classes of adaptors, termed "adaptor A" and "adaptor B", were used in each reaction. The A and B adaptors differed in both nucleotide sequence and the presence of a 5' biotin tag on the B adaptor. The adaptor pairs were designed to allow directional ligation to the blunt-ended, fragmented genomic DNA (Adaptor A: CCATCTCATCCCTGCGTGTCCCATCTGT-TCCCTCCCTGTCTCAG SEQ ID NO:61. Adaptor B: /5BioTEG/CCTATCCCTGTGTGCCTTGCCTATC-CCCTGTTGCGTGTCTCAG SEQ ID NO:62). For each adaptor pair, the PCR priming region contained a 5' four-base overhang and a blunt-ended 3' key region. Directionality was achieved as the 3' blunt-end side of the adaptor ligated to the blunt-ended genomic DNA fragment while the 5' overhang prevented ligation to the PCR primer region of the adaptor.

The remaining 28 μL of nebulized, polished DNA were transferred to a 0.2 mL tube and combined with 20.6 μL Molecular Biology Grade water, 60 μL 2× Quick Ligase Reaction Buffer (New England Biolabs), 1.8 μL of an equimolar mix of adaptor A and B (200 pmol of each adaptor/ μL), 9.6 μL of 2000 U/μL Quick Ligase (New England Biolabs). The tube contents were thoroughly mixed, incubated for 20 minutes at 25° C., purified twice over a Qiaquick PCR Purification column, and eluted in 30 μL of 55° C. Buffer EB after each centrifugation.

Gel Purification. A 2% agarose (Invitrogen, Carlsbad, Calif.)/TBE slab gel was prepared with 4.5 μL of a 10 mg/mL stock of Ethidium Bromide (Fisher Scientific, Pittsburgh, Pa.) added to the molten agarose solution. Three microliters of 10× Ready-Load Dye (Invitrogen) were added to 30 μL of ligated DNA library, and the dye/ligation reaction loaded into two adjacent wells in the gel (approximately 16.5 μL per lane). Ten microliters (1 g) of a 100-bp ladder (Invitrogen) were loaded into flanking wells on either side of the library samples, with two empty lanes separating the library and ladder samples. The gel was run at 100V for 3 hours, after which the gel was transferred to a GelDoc (BioRad, Hercules, Calif.) UV box which had been draped with plastic wrap to reduce the chance of contamination. A sterile, single-use scalpel was used to excise the region of each library sample migrating between the 250 and 500 base pair markers in the DNA ladders, and the gel slices were then placed in a 15 mL Falcon tube. The library was extracted from the each agarose plug with 2 columns from a MinElute Gel Extraction Kit (Qiagen), one per sample. The process was conducted according to the manufacturer's instructions, with the following modifications. Due to the large volume of dissolved agarose, each library was broken into several aliquots and serially processed through the respective column. Also, the duration of the dry spin after the Buffer PE spin was extended to 2 minutes (rather than 1 minute) to ensure complete removal of the ethanol, and the eluates from each column were pooled to achieve a final library volume of 20 μL. One microliter of the isolated library was analyzed on a BioAnalyzer DNA 1000 LabChip to verify that the size distribution of the library population fell between 250 and 500 bp.

Nick Repair. The two nicks at the 3'-junctions were repaired by the strand-displacement activity of Bst DNA polymerase, Large Fragment. The remaining 19 μL of the size fractionated library were combined with 40 μL of Molecular Biology Grade water, 8 μL 10× ThermoPol Reaction Buffer (New England Biolabs), 8 μL of 1 mg/mL BSA (New England Biolabs), 2 μL 10 mM dNTPs (Pierce), and 3 μL of 8 U/μL Bst DNA polymerase, Large Fragment (New England Biolabs), and incubated for 30 minutes at 65° C. for 30 minutes.

Isolation of the Single-Stranded AB Adapted Library. One hundred microliters of stock M-270 Streptavidin beads (Dynal, Oslo, Norway) were washed twice in a 1.5 mL microcentrifuge tube with 200 μL of 1× B&W Buffer (5 mM Tris-HCl (pH 7.5), 0.5 mM EDTA, 1 M NaCl) by vortexing the beads in the wash solution, immobilizing the beads with the Magnetic Particle Concentrator (MPC) (Dynal), drawing the solution off from the immobilized beads and repeating. After the second wash, the beads were resuspended in 100 μL of 2× B&W Buffer (10 mM Tris-HCl (pH 7.5), 1 mM EDTA, 2 M NaCl), to which the entire 80 μL of the Bst polymerase-treated library and 20 μL of Molecular Biology Grade water were then added. The sample was then mixed by vortexing and placed on a horizontal tube rotator for 20 minutes at room temperature. The bead mixture was then washed twice with 200 μL of 1× B&W Buffer, then twice with 200 μL of Molecular Biology Grade water.

The final water wash was removed from the bead pack using the MPC, and 250 μL of Melt Solution (100 mM NaCl, and 125 mM NaOH) were added. The beads were resuspended with thorough mixing in the melt solution and the bead suspension incubated for 10 minutes at room temperature on a tube rotator.

In a separate 1.5 mL centrifuge tube, 1250 µL of buffer PB (from the QiaQuick PCR Purification Kit) were neutralized through the addition of 9 µL of 20% aqueous acetic acid. Using the Dynal MPC, the beads in the melt solution were pelleted; the 250 µL of supernatant (containing the now single-stranded library) were carefully decanted and transferred to the tube of freshly-prepared neutralized buffer PB.

The 1500 µL of neutralized, single-stranded library were concentrated over a single column from a MinElute PCR Purification Kit (Qiagen), warmed to room temperature prior to use. Due to volume constraints, the sample was loaded and concentrated in two 750 µL aliquots. Concentration of each aliquot was conducted according to the manufacturer's instructions for spin columns using a microcentrifuge, with the following modifications: the dry spin after the Buffer PE spin was extended to 2 minutes (rather than 1 minute) to ensure complete removal of the ethanol, and the single-stranded library sample was eluted in 15 µL of Buffer EB (Qiagen) at 55° C.

Library Quantitation and Quality Assessment. The quantity and quality of the resultant single-stranded DNA library was assessed with the Agilent 2100 and a fluorescent plate reader. As the library consisted of single stranded DNA, an RNA Pico 6000 LabChip for the Agilent 2100 was used and prepared according to the manufacturer's guidelines. Triplicate 1 µL aliquots were analyzed, and the mean value reported by the Agilent analysis software wad used to estimate the DNA concentration. The final library concentration was typically in excess of $10^8$ molecules/µL. The library samples were stored in concentrated form at −20° C. until needed.

Preparation of DNA Capture Beads

Packed beads from a 1 mL N-hydroxysuccinimide ester (NHS)-activated Sepharose HP affinity column (Amersham Biosciences, Piscataway, N.J.) were removed from the column and activated as described in the product literature (Amersham Pharmacia Protocol # 71700600AP). Twenty-five microliters of a 1 mM amine-labeled HEG capture primer (5'-Amine-3 sequential 18-atom hexa-ethyleneglycol spacers CCATCTGTTGCGTGCGTGTC-3' SEQ ID NO:63) (IDT Technologies, Coralville, Iowa, USA) in 20 mM phosphate buffer, pH 8.0, were bound to the beads, after which 25-36 µm beads were selected by serial passage through 36 and 25 µm pore filter mesh sections (Sefar America, Depew, N.Y., USA). DNA capture beads that passed through the first filter, but were retained by the second were collected in bead storage buffer (50 mM Tris, 0.02% Tween, 0.02% sodium azide, pH 8), quantitated with a Multisizer 3 Coulter Counter (Beckman Coulter, Fullerton, Calif., USA) and stored at 4° C. until needed.

Binding Template Species to DNA Capture Beads

Template molecules were annealed to complementary primers on the DNA Capture beads in a UV-treated laminar flow hood. One and one half million DNA capture beads suspended in bead storage buffer were transferred to a 200 µL PCR tube, centrifuged in a benchtop mini centrifuge for 10 seconds, the tube rotated 180° and spun for an additional 10 seconds to ensure even pellet formation. The supernatant was then removed, and the beads washed with 200 µL of Annealing Buffer (20 mM Tris, pH 7.5 and 5 mM magnesium acetate), vortexed for 5 seconds to resuspend the beads, and pelleted as above. All but approximately 10 µL of the supernatant above the beads were removed, and an additional 200 µL of Annealing Buffer were added. The beads were vortexed again for 5 seconds, allowed to sit for 1 minute, then pelleted as above. All but 10 µL of supernatant were discarded, and 1.2 µL of $2\times10^7$ molecules per µL template library were added to the beads. The tube was vortexed for 5 seconds to mix the contents, after which the templates were annealed to the beads in a controlled denaturation/annealing program preformed in an MJ thermocycler (5 minutes at 80° C., followed by a decrease by 0.1° C./sec to 70° C., 1 minute at 70° C., decrease by 0.1° C./sec to 60° C., hold at 60° C. for 1 minute, decrease by 0.1° C./sec to 50° C., hold at 50° C. for 1 minute, decrease by 0.1° C./sec to 20° C., hold at 20° C.). Upon completion of the annealing process the beads were stored on ice until needed.

PCR Reaction Mix Preparation and Formulation

To reduce the possibility of contamination, the PCR reaction mix was prepared in a UV-treated laminar flow hood located in a PCR clean room. For each 1,500,000 bead emulsion PCR reaction, 225 µL of reaction mix (1× Platinum HiFi Buffer (Invitrogen), 1 mM dNTPs (Pierce), 2.5 mM $MgSO_4$ (Invitrogen), 0.1% Acetylated, molecular biology grade BSA (Sigma, St. Louis, Mo.), 0.01% Tween-80 (Acros Organics, Morris Plains, N.J.), 0.003 U/µL thermostable pyrophosphatase (NEB), 0.625 µM forward (5'-CGTTTCCCCTGT-GTGCCTTG-3' SEQ ID NO:64) and 0.039 µM reverse primers (5'-CCATCTGTTGCGTGCGTGTC-3' SEQ ID NO:65) (IDT Technologies) and 0.15 U/µL Platinum Hi-Fi Taq Polymerase (Invitrogen)) were prepared in a 1.5 mL tube. Twenty-five microliters of the reaction mix were removed and stored in an individual 200 µL PCR tube for use as a negative control. Both the reaction mix and negative controls were stored on ice until needed. Additionally, 240 µL of mock amplification mix (1× Platinum HiFi Buffer (Invitrogen), 2.5 mM $MgSO_4$ (Invitrogen), 0.1% BSA, 0.01% Tween) for every emulsion were prepared in a 1.5 mL tube, and similarly stored at room temperature until needed.

Emulsification and Amplification

The emulsification process creates a heat-stable water-in-oil emulsion with approximately 1,000 discrete PCR microreactors per microliter which serve as a matrix for single molecule, clonal amplification of the individual molecules of the target library. The reaction mixture and DNA capture beads for a single reaction were emulsified in the following manner: in a UV-treated laminar flow hood, 160 µL of PCR solution were added to the tube containing the 1,500,000 DNA capture beads. The beads were resuspended through repeated pipette action, after which the PCR-bead mixture was permitted to sit at room temperature for at least 2 minutes, allowing the beads to equilibrate with the PCR solution. Meanwhile, 400 µL of Emulsion Oil (60% (w/w) DC 5225C Formulation Aid (Dow Chemical Co., Midland, Mich.), 30% (w/w) DC 749 Fluid (Dow Chemical Co.), and 30% (w/w) Ar20 Silicone Oil (Sigma)) were aliquotted into a flat-topped 2 mL centrifuge tube (Dot Scientific, Burton, Mich.). The 240 µL of mock amplification mix were then added to 400 µL of emulsion oil, the tube capped securely and placed in a 24 well TissueLyser Adaptor (Qiagen) of a TissueLyser MM300 (Retsch GmbH & Co. KG, Haan, Germany). The emulsion was homogenized for 5 minutes at 25 oscillations/sec to generate the extremely small emulsions, or "microfines", that confer additional stability to the reaction.

The combined beads and PCR reaction mix were briefly vortexed and allowed to equilibrate for 2 minutes. After the microfines had been formed, the amplification mix, templates and DNA capture beads were added to the emulsified material. The TissueLyser speed was reduced to 15 oscillations/sec and the reaction mix homogenized for 5 minutes. The lower homogenization speed created water droplets in the oil mix with an average diameter of 100 to 150 µm, sufficiently large to contain DNA capture beads and amplification mix.

The total volume of the emulsion is approximately 800 µL contained in one 2 mL flat-topped centrifuge tube. The emulsion was aliquotted into 7-8 separate PCR tubes each containing roughly 100 µL. The tubes were sealed and placed in a MJ thermocycler along with the 25 µl negative control made previously. The following cycle times were used: 1× (4 minutes @ 94° C.)—Hotstart Initiation, 40× (30 seconds @ 94° C., 60 seconds @ 58° C., 90 seconds @ 68° C.)—Amplification, 13× (30 seconds @ 94° C., 360 seconds at 58° C.)—Hybridization Extension. After completion of the PCR program, the reactions were removed and the emulsions either broken immediately (as described below) or the reactions stored at 10° C. for up to 16 hours prior to initiating the breaking process.

Breaking the Emulsion and Recovery of Beads

Fifty microliters of isopropyl alcohol (Fisher) were added to each PCR tube containing the emulsion of amplified material, and vortexed for 10 seconds to lower the viscosity of the emulsion. The tubes were centrifuged for several seconds in a microcentrifuge to remove any emulsified material trapped in the tube cap. The emulsion-isopropyl alcohol mix was withdrawn from each tube into a 10 mL BD-Disposable Syringe (Fisher Scientific) fitted with a blunt 16 gauge blunt needle (Brico Medical Supplies, Metuchen, N.J.). An additional 50 µL of isopropyl alcohol were added to each PCR tube, vortexed, centrifuged as before, and added to the contents of the syringe. The volume inside the syringe was increased to 9 mL with isopropyl alcohol, after which the syringe was inverted and 1 mL of air was drawn into the syringe to facilitate mixing the isopropanol and emulsion. The blunt needle was removed, a 25 mm Swinlock filter holder (Whatman, Middlesex, United Kingdom) containing 15 µm pore Nitex Sieving Fabric (Sefar America, Depew, N.Y., USA) attached to the syringe luer, and the blunt needle affixed to the opposite side of the Swinlock unit.

The contents of the syringe were gently but completely expelled through the Swinlock filter unit and needle into a waste container with bleach. Six milliliters of fresh isopropyl alcohol were drawn back into the syringe through the blunt needle and Swinlock filter unit, and the syringe inverted 10 times to mix the isopropyl alcohol, beads and remaining emulsion components. The contents of the syringe were again expelled into a waste container, and the wash process repeated twice with 6 mL of additional isopropyl alcohol in each wash. The wash step was repeated with 6 mL of 80% Ethanol/1× Annealing Buffer (80% Ethanol, 20 mM Tris-HCl, pH 7.6, 5 mM Magnesium Acetate). The beads were then washed with 6 mL of 1× Annealing Buffer with 0.1% Tween (0.1% Tween-20, 20 mM Tris-HCl, pH 7.6, 5 mM Magnesium Acetate), followed by a 6 mL wash with picopure water.

After expelling the final wash into the waste container, 1.5 mL of 1 mM EDTA were drawn into the syringe, and the Swinlock filter unit removed and set aside. The contents of the syringe were serially transferred into a 1.5 mL centrifuge tube. The tube was periodically centrifuged for 20 seconds in a minifuge to pellet the beads and the supernatant removed, after which the remaining contents of the syringe were added to the centrifuge tube. The Swinlock unit was reattached to the filter and 1.5 mL of EDTA drawn into the syringe. The Swinlock filter was removed for the final time, and the beads and EDTA added to the centrifuge tube, pelletting the beads and removing the supernatant as necessary.

Second-Strand Removal

Amplified DNA, immobilized on the capture beads, was rendered single stranded by removal of the secondary strand through incubation in a basic melt solution. One mL of freshly prepared Melting Solution (0.125 M NaOH, 0.2 M NaCl) was added to the beads, the pellet resuspended by vortexing at a medium setting for 2 seconds, and the tube placed in a Thermolyne LabQuake tube roller for 3 minutes. The beads were then pelleted as above, and the supernatant carefully removed and discarded. The residual melt solution was then diluted by the addition of 1 mL Annealing Buffer (20 mM Tris-Acetate, pH 7.6, 5 mM Magnesium Acetate), after which the beads were vortexed at medium speed for 2 seconds, and the beads pelleted, and supernatant removed as before. The Annealing Buffer wash was repeated, except that only 800 µL of the Annealing Buffer were removed after centrifugation. The beads and remaining Annealing Buffer were transferred to a 0.2 mL PCR tube, and either used immediately or stored at 4° C. for up to 48 hours before continuing with the subsequent enrichment process.

Enrichment of Beads

Up to this point the bead mass was comprised of both beads with amplified, immobilized DNA strands, and null beads with no amplified product. The enrichment process was utilized to selectively capture beads with sequenceable amounts of template DNA while rejecting the null beads.

The single stranded beads from the previous step were pelleted by 10 second centrifugation in a benchtop mini centrifuge, after which the tube was rotated 180° and spun for an additional 10 seconds to ensure even pellet formation. As much supernatant as possible was then removed without disturbing the beads. Fifteen microliters of Annealing Buffer were added to the beads, followed by 2 µL of 100 µM biotinylated, 40 base HEG enrichment primer (5' Biotin-18-atom hexa-ethyleneglycol spacer-CGTTTCCCCTGTGTGCCT-TGCCATCTGTTCCCTCCCTGTC-3', IDT Technologies SEQ ID NO:66), complementary to the combined amplification and sequencing sites (each 20 bases in length) on the 3'-end of the bead-immobilized template. The solution was mixed by vortexing at a medium setting for 2 seconds, and the enrichment primers annealed to the immobilized DNA strands using a controlled denaturation/annealing program in an MJ thermocycler. (30 seconds @ 65° C., decrease by 0.1° C./sec to 58° C., 90 seconds@ 58° C., and a 10° C. hold.)

While the primers were annealing, a stock solution of SeraMag-30 magnetic streptavidin beads (Seradyn, Indianapolis, Ind., USA) was resuspended by gentle swirling, and 20 µL of SeraMag beads were added to a 1.5 mL microcentrifuge tube containing 1 mL of Enhancing Fluid (2 M NaCl, 10 mM Tris-HCl, 1 mM EDTA, pH 7.5). The SeraMag bead mix was vortexed for 5 seconds, and the tube placed in a Dynal MPC-S magnet, pelletting the paramagnetic beads against the side of the microcentrifuge tube. The supernatant was carefully removed and discarded without disturbing the SeraMag beads, the tube removed from the magnet, and 100 µL of enhancing fluid were added. The tube was vortexed for 3 seconds to resuspend the beads, and the tube stored on ice until needed.

Upon completion of the annealing program, 100 µL of Annealing Buffer were added to the PCR tube containing the DNA Capture beads and enrichment primer, the tube vortexed for 5 seconds, and the contents transferred to a fresh 1.5 mL microcentrifuge tube. The PCR tube in which the enrichment primer was annealed to the capture beads was washed once with 200 µL of annealing buffer, and the wash solution added to the 1.5 mL tube. The beads were washed three times with 1 mL of annealing buffer, vortexed for 2 seconds, pelleted as before, and the supernatant carefully removed. After the third wash, the beads were washed twice with 1 mL of ice cold enhancing fluid, vortexed, pelleted, and the supernatant removed as before. The beads were then resuspended in 150 µL ice cold enhancing fluid and the bead solution added to the washed SeraMag beads.

The bead mixture was vortexed for 3 seconds and incubated at room temperature for 3 minutes on a LabQuake tube roller, while the streptavidin-coated SeraMag beads bound to the biotinylated enrichment primers annealed to immobilized templates on the DNA capture beads. The beads were then centrifuged at 2,000 RPM for 3 minutes, after which the beads were gently "flicked" until the beads were resuspended. The resuspended beads were then placed on ice for 5 minutes. Following the incubation on ice, cold Enhancing Fluid was added to the beads to a final volume of 1.5 mL. The tube inserted into a Dynal MPC-S magnet, and the beads were left undisturbed for 120 seconds to allow the beads to pellet against the magnet, after which the supernatant (containing excess SeraMag and null DNA capture beads) was carefully removed and discarded.

The tube was removed from the MPC-S magnet, 1 mL of cold enhancing fluid added to the beads, and the beads resuspended with gentle flicking. It was essential not to vortex the beads, as vortexing may break the link between the SeraMag and DNA capture beads. The beads were returned to the magnet, and the supernatant removed. This wash was repeated three additional times to ensure removal of all null capture beads. To remove the annealed enrichment primers and SeraMag beads from the DNA capture beads, the beads were resuspended in 1 mL of melting solution, vortexed for 5 seconds, and pelleted with the magnet. The supernatant, containing the enriched beads, was transferred to a separate 1.5 mL microcentrifuge tube, the beads pelleted and the supernatant discarded. The enriched beads were then resuspended in 1× Annealing Buffer with 0.1% Tween-20. The beads were pelleted on the MPC again, and the supernatant transferred to a fresh 1.5 mL tube, ensuring maximal removal of remaining SeraMag beads. The beads were centrifuged, after which the supernatant was removed, and the beads washed 3 times with 1 mL of 1× Annealing Buffer. After the third wash, 800 µL of the supernatant were removed, and the remaining beads and solution transferred to a 0.2 mL PCR tube. The average yield for the enrichment process was 30% of the original beads added to the emulsion, or approximately 450,000 enriched beads per emulsified reaction. As a 60×60 mm$^2$ slide requires 900,000 enriched beads, two 1,500,000 bead emulsions were processed as described above.

Sequencing Primer Annealing

The enriched beads were centrifuged at 2,000 RPM for 3 minutes and the supernatant decanted, after which 15 µL of annealing buffer and 3 µL of 100 mM sequencing primer (5'-CCATCTGTTCCCTCCCTGTC-3', IDT Technologies SEQ ID NO:67), were added. The tube was then vortexed for 5 seconds, and placed in an MJ thermocycler for the following 4 stage annealing program: 5 minutes @ 65° C., decrease by 0.1° C./sec to 50° C., 1 minute @ 50° C., decrease by 0.1° C./sec to 40° C., hold at 40° C. for 1 minute, decrease by 0.1° C./sec to 15° C., hold at 15° C.

Upon completion of the annealing program, the beads were removed from thermocycler and pelleted by centrifugation for 10 seconds, rotating the tube 180°, and spun for an additional 10 seconds. The supernatant was discarded, and 200 µL of annealing buffer were added. The beads were resuspended with a 5 second vortex, and the beads pelleted as before. The supernatant was removed, and the beads resuspended in 100 µL annealing buffer, at which point the beads were quantitated with a Multisizer 3 Coulter Counter. Beads were stored at 4° C. and were stable for at least one week.

Incubation of DNA Beads with Bst DNA Polymerase, Large Fragment and SSB Protein

Bead wash buffer (100 ml) was prepared by the addition of apyrase (Biotage, Uppsala Sweden) (final activity 8.5 units/liter) to 1× assay buffer containing 0.1% BSA. The fibreoptic slide was removed from picopure water and incubated in bead wash buffer. Nine hundred thousand of the previously prepared DNA beads were centrifuged and the supernatant was carefully removed. The beads were then incubated in 1290 µl of bead wash buffer containing 0.4 mg/mL polyvinyl pyrrolidone (MW 360,000), 1 mM DTT, 175 µg of *E. coli* single strand binding protein (SSB) (United States Biochemicals Cleveland, Ohio.) and 7000 units of Bst DNA polymerase, Large Fragment (New England Biolabs). The beads were incubated at room temperature on a rotator for 30 minutes.

Preparation of Enzyme Beads and Micro-Particle Fillers

UltraGlow Luciferase (Promega Madison Wis.) and Bst ATP sulfurylase were prepared in house as biotin carboxyl carrier protein (BCCP) fusions. The 87-aminoacid BCCP region contains a lysine residue to which a biotin is covalently linked during the in vivo expression of the fusion proteins in *E. coli*. The biotinylated luciferase (1.2 mg) and sulfurylase (0.4 mg) were premixed and bound at 4° C. to 2.0 mL of Dynal M280 paramagnetic beads (10 mg/mL, Dynal SA) according to the manufacturer's instructions. The enzyme bound beads were washed 3 times in 2000 µL of bead wash buffer and resuspended in 2000 µL of bead wash buffer.

Seradyn microparticles (Powerbind SA, 0.8 µm, 10 mg/mL, Seradyn Inc, Indianapolis, Ind.) were prepared as follows: 1050 µL of the stock were washed with 1000 µL of 1× assay buffer containing 0.1% BSA. The microparticles were centrifuged at 9300 g for 10 minutes and the supernatant removed. The wash was repeated 2 more times and the microparticles were resuspended in 1050 µL of 1× assay buffer containing 0.1% BSA. The beads and microparticles were stored on ice until use.

Bead Deposition

The Dynal enzyme beads and Seradyn microparticles were vortexed for one minute and 1000 µL of each were mixed in a fresh microcentrifuge tube, vortexed briefly and stored on ice. The enzyme/Seradyn beads (1920 µl) were mixed with the DNA beads (1300 µl) and the final volume was adjusted to 3460 µL with bead wash buffer. Beads were deposited in ordered layers. The fibreoptic slide was removed from the bead wash buffer and Layer 1, a mix of DNA and enzyme/Seradyn beads, was deposited. After centrifuging, Layer 1 supernatant was aspirated off the fibreoptic slide and Layer 2, Dynal enzyme beads, was deposited. This section describes in detail how the different layers were centrifuged.

Layer 1. A gasket that creates two 30×60 mm$^2$ active areas over the surface of a 60×60 mm$^2$ fibreoptic slide was carefully fitted to the assigned stainless steel dowels on the jig top. The fibreoptic slide was placed in the jig with the smooth unetched side of the slide down and the jig top/gasket was fitted onto the etched side of the slide. The jig top was then properly secured with the screws provided, by tightening opposite ends such that they are finger tight. The DNA-enzyme bead mixture was loaded on the fibreoptic slide through two inlet ports provided on the jig top. Extreme care was taken to minimize bubbles during loading of the bead mixture. Each deposition was completed with one gentle continuous thrust of the pipette plunger. The entire assembly was centrifuged at 2800 rpm in a Beckman Coulter Allegra 6 centrifuge with GH 3.8-A rotor for 10 minutes. After centrifugation the supernatant was removed with a pipette.

Layer 2. Dynal enzyme beads (920 µL) were mixed with 2760 µL of bead wash buffer and 3400 µL of enzyme-bead suspension was loaded on the fibreoptic slide as described previously. The slide assembly was centrifuged at 2800 rpm for 10 min and the supernatant decanted. The fibreoptic slide was removed from the jig and stored in bead wash buffer until ready to be loaded on the instrument.

Sequencing on the 454 Instrument

All flow reagents were prepared in 1× assay buffer with 0.4 mg/mL polyvinyl pyrrolidone (MW 360,000), 1 mM DTT and 0.1% Tween 20. Substrate (300 µM D-luciferin (Regis, Morton Grove, Ill.) and 2.5 µM adenosine phophosulfate (Sigma)) was prepared in 1× assay buffer with 0.4 mg/mL polyvinyl pyrrolidone (MW 360,000), 1 mM DTT and 0.1% Tween 20. Apyrase wash is prepared by the addition of apyrase to a final activity of 8.5 units per liter in 1× assay buffer with 0.4 mg/mL polyvinyl pyrrolidone (MW 360,000), 1 mM DTT and 0.1% Tween 20. Deoxynucleotides dCTP, dGTP and dTTP (GE Biosciences Buckinghamshire, United Kingdom) were prepared to a final concentration of 6.5 µM, α-thio deoxyadenosine triphosphate (dATPαS, Biolog, Hayward, Calif.) and sodium pyrophosphate (Sigma) were prepared to a final concentration of 50 µM and 0.1 µM, respectively, in the substrate buffer.

The 454 sequencing instrument consists of three major assemblies: a fluidics subsystem, a fibreoptic slide cartridge/flow chamber, and an imaging subsystem. Reagents inlet lines, a multi-valve manifold, and a peristaltic pump form part of the fluidics subsystem. The individual reagents are connected to the appropriate reagent inlet lines, which allows for reagent delivery into the flow chamber, one reagent at a time, at a pre-programmed flow rate and duration. The fibreoptic slide cartridge/flow chamber has a 300 µm space between the slide's etched side and the flow chamber ceiling. The flow chamber also included means for temperature control of the reagents and fibreoptic slide, as well as a light-tight housing. The polished (unetched) side of the slide was placed directly in contact with the imaging system.

The cyclical delivery of sequencing reagents into the fibreoptic slide wells and washing of the sequencing reaction byproducts from the wells was achieved by a pre-programmed operation of the fluidics system. The program was written in the form of an Interface Control Language (ICL) script, specifying the reagent name (Wash, dATPαS, dCTP, dGTP, dTTP, and PPi standard), flow rate and duration of each script step. Flow rate was set at 4 mL/min for all reagents and the linear velocity within the flow chamber was approximately ~1 cm/s. The flow order of the sequencing reagents were organized into kernels where the first kernel consisted of a PPi flow (21 seconds), followed by 14 seconds of substrate flow, 28 seconds of apyrase wash and 21 seconds of substrate flow. The first PPi flow was followed by 21 cycles of dNTP flows (dC-substrate-apyrase wash-substrate dA-substrate-apyrase wash-substrate-dG-substrate-apyrase wash-substrate-dT-substrate-apyrase wash-substrate), where each dNTP flow was composed of 4 individual kernels. Each kernel is 84 seconds long (dNTP—21 seconds, substrate flow—14 seconds, apyrase wash—28 seconds, substrate flow—21 seconds); an image is captured after 21 seconds and after 63 seconds. After 21 cycles of dNTP flow, a PPi kernel is introduced, and then followed by another 21 cycles of dNTP flow. The end of the sequencing run is followed by a third PPi kernel. The total run time was 244 minutes. Reagent volumes required to complete this run are as follows: 500 mL of each wash solution, 100 mL of each nucleotide solution. During the run, all reagents were kept at room temperature. The temperature of the flow chamber and flow chamber inlet tubing is controlled at 30° C. and all reagents entering the flow chamber are pre-heated to 30° C.

Imaging System

The camera is a Spectral Instruments (Tucson, Ariz.) Series 600 camera with a Fairchild Imaging LM485 CCD (4096×4096 15 µm pixels), directly bonded to a 1-1 imaging fibre bundle. The camera, cooled to −20° C., can be operated in either of two modes: (i) frame transfer mode, in which the center portion of the CCD is used for imaging while the outer portion of the CCD is used for image storage and slow read-out (this mode is used for the smaller fibreoptic slides) or (ii) full frame mode, in which the entire CCD is used for imaging and read-out occurs during the wash (i.e. dark) portion of each flow cycle (this mode is used for the 60×60 mm² slide). The data is read out through 4 ports, one at each corner of the CCD. Signal integration was set at 28 seconds per frame, with a frame shift time of approximately 0.25 second in the frame transfer mode; in the full frame mode, signal integration (frame duration) was set at 21 seconds (wash capture frame) and 63 seconds (nucleotide capture frame). All camera images were stored in UTIFF 16 format on a computer hard drive (IBM eServer Series 337, IBM, White Plains, N.Y.).

Interwell Diffusion

To assess the sensitivity of our system to reaction by-products diffusing from one well into a neighboring one, we developed a simplified one-dimensional model of interwell diffusion behavior. We have found that at the current well-to-well distance of 50 µm, diffusion of ATP will induce a background signal on the order of 10% or less in an immediately neighboring well. We developed correction computer algorithms to suppress this source of noise.

We created a one-dimensional model of the fibreoptic faceplate (i.e. modeled a linear array of wells) in which the wells are represented as lumped chemical reactors that produce pyrophosphate and ATP during the sequencing reaction. Within each well the generation of reaction by-products can be modeled by a set of coupled kinetic equations as follows:

$$\frac{d}{dt}\begin{bmatrix} DNA_n \\ dNTP \\ PPI \\ ATP \end{bmatrix}_{(1)} = \begin{bmatrix} -R_{bst(1)} \\ -R_{bst(1)} - k_c([dNTP]_{(1)} - [dNTP]_{(0)}) \\ R_{bst(1)} - R_{sulf(1)} + R_{luc(1)} - k_c[PPI]_{(1)} \\ R_{sulf(1)} - R_{luc(1)} - k_c[ATP]_{(1)} \end{bmatrix}$$

Figure 49:
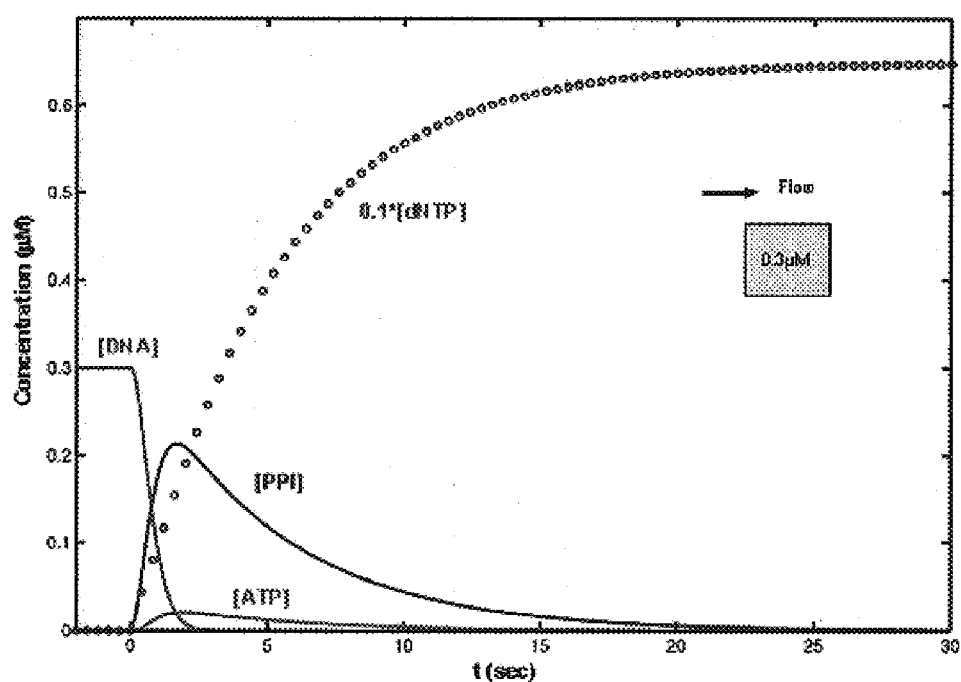
FIG. 49 Kinetic modeling of single well. Assumption: 10 million DNA copies per bead, [DNA]=0.3 µM.

Numerical solution of this set of equations is shown in FIG. 49.

When considering two adjacent wells, the following set of equations must be added:

$$\frac{d}{dt}\begin{bmatrix} DNA_n \\ dNTP \\ PPI \\ ATP \end{bmatrix}_{(2)} = \begin{bmatrix} -R_{bst(2)} \\ -R_{bst(2)} - k_c([dNTP]_{(2)} - [dNTP]_{(0)}) \\ R_{bst(2)} - R_{sulf(2)} + R_{luc(2)} - k_c([PPI]_{(2)} - \theta[PPI]_{(1)}) \\ R_{sulf(2)} - R_{luc(2)} - k_c([ATP]_{(2)} - \theta\,[ATP]_{(1)}) \end{bmatrix}$$

Figure 50:
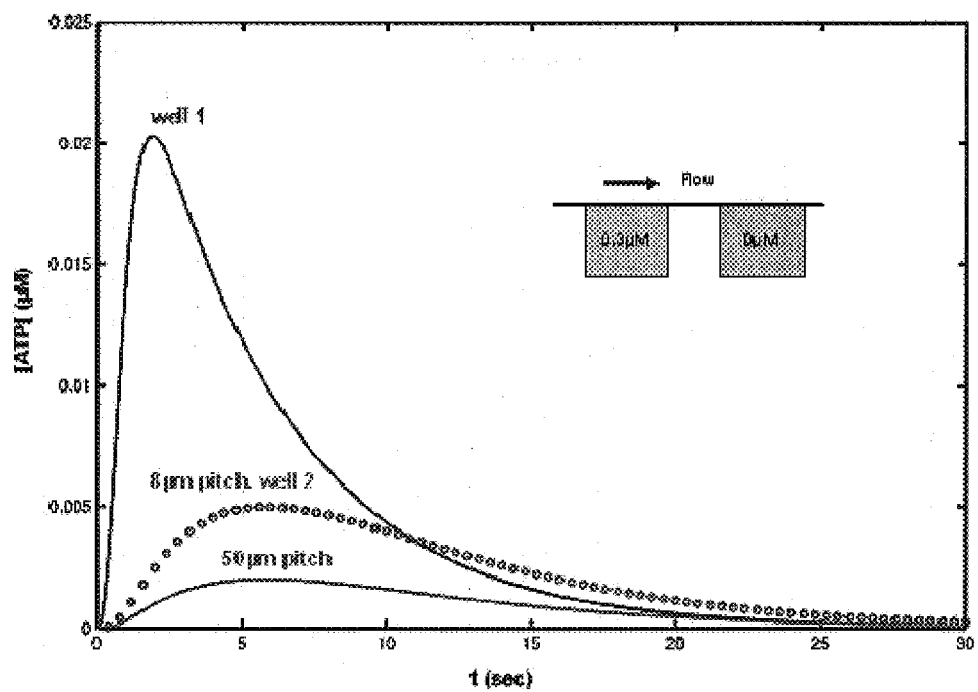
FIG. 50 Chemical cross-talk modeling. At t=0, $[DNA]_{well\,1}$=0.3 µM, $[DNA]_{well\,2}$=0.

The cross-talk between wells is characterized by a mass transfer coefficient $k_c$ and a mixing ratio $\theta$, determined by the flow conditions and the well geometry. The parameters ($k_c$, $\theta$) are obtained by solving a complete three-dimensional two-well problem, using a finite-element method; their values are then extended to the multi-well modeling for similar flows and well geometries. This separation of transport and chemical reactions phenomena allows us to simulate sequencing at high fibreoptic faceplate occupation numbers, and to probe the effects of chemical contamination between neighboring wells. Numerical solution of the equations shows that inter-well effects remain low, even at a significantly reduced pitch (8 µm) (FIG. 50).

Field Programmable Gate Arrays (FPGA)

The on-board computer is fitted with an accessory RC2000 PCI board (Celoxica, Abingdon, UK) hosting a 6 million gate Virtex II FPGA (Field Programmable Gate Array) chip (Xilinx, San Jose, Calif.). We have developed software to download to the FPGA binary modules that encode in hardware the algorithms to perform the successive image processing steps. Handel-C (Celoxica, Abingdon, UK) was used to design FPGA hardware logic. At the conclusion of a sequencing run all of the data is available to the on-board computer to execute final signal adjustments and to align the fragments to a specified genome or to perform shotgun assembly. Without FPGA, image processing for the sequencing runs described here takes an additional 6 hours on the on-board computer.

Image Processing

Once applied to the imaging system, the fibreoptic slide's position does not shift; this makes it possible for the image analysis software to determine the location (in CCD pixel coordinates) of each well, based on light generation during a PPi standard flow which precedes each sequencing run. In operation, the entire slide is simultaneously imaged by the camera. A single well is imaged by approximately 9 pixels. The first step in processing data is to perform background subtraction for each acquired image at the pixel level, using an "erosion-dilation" algorithm that automatically determines the local background for each pixel. Then, for each nucleotide flow, the light intensities collected, over the entire duration of the flow by the pixels covering a particular well, are summed to generate a signal for that particular well at that particular flow. We correct the acquired images to eliminate cross-talk between wells due to optical bleed (the fibreoptic cladding is not completely opaque and transmits a small fraction of the light generated within a well into an adjacent well) and to diffusion of ATP or PPi (generated during synthesis) from one well to another one further downstream. To perform this correction, we empirically determined the extent of crosstalk under low occupancy conditions and derived deconvolution matrices to remove from each well's signal the contribution coming from neighboring wells. In order to account for variability in the number of enzyme-carrying beads in each well and variability in the number of template copies bound to each bead, two types of normalization are carried out: (i) raw signals are first normalized by reference to the pre- and post-sequencing run PPi standard flows, (ii) these signals are further normalized by reference to the signals measured during incorporation of the first three bases of the known "key" sequence included in each template.

Signal Processing

We correct the signals measured at each flow and in each well to account for carry forward and incomplete extension. It is straightforward to calculate the extent of synchronism loss for any known sequence, assuming given levels of carry forward and incomplete extension. Supplementary Table 1, the result of model calculation, illustrates the impact of these effects on sequencing accuracy; it shows the extent of incomplete extension and carry forward that can be tolerated, assuming that no correction is performed, in order to achieve a read accuracy of approximately 99% at various read lengths. Alternatively, higher levels of accuracy can be achieved with similar values of incomplete extension and carry forward by using an inverse transformation to correct the raw signals for loss of synchronism, or, higher levels of incomplete extension and carry forward can be accommodated at the same level of accuracy by correcting signals. Since the amount of carry forward and incomplete extension, as well as the underlying sequence, is unknown a priori, our approach is based on an iterative technique and two-dimensional minimization to achieve a least squares fit between the measured signals and the model's output. The impact of carry forward and incomplete extension is felt particularly towards the end of reads due to the cumulative effect of theses errors.

Test Fragments

We created difficult-to-sequence fragments that include ascending and descending stretches of identical bases (homopolymers) of increasing length (2N, 3N, 4N, 5N, 6N, 5N, 4N, 3N, 2N), interspersed with single nucleotides, to investigate the sequencing performance of the instrument. These fragments allow us to eliminate from our assessment any sample preparation or emulsion PCR artifacts that may cause additional errors. Overall sequencing accuracy is shown in Table 1 and further broken down by homopolymer in FIG. 51.

Purification of Test Fragment Plasmid DNA. Individual test fragments were cloned into the pBluescript II KS+vector (Stratagene, La Jolla, Calif.), transfected into $E.$ $coli$ cultures and stored at −80° C. in glycerol until needed. Individual vials of the $E.$ $coli$ cultures, each containing one of the 6 individual test fragments, were plated and grown on LB Amp/X-gal Agar Petri plates. The plasmid containing colonies were selected by blue/white screening and grown to saturation overnight at 37° C. in liquid LB broth with ampicillin. The plasmids were harvested and purified from 25 mL of the culture using the QiaFilter Midi plasmid purification kit (Qiagen), following the manufacturer's instructions. Purified plasmids were diluted to 10 ng/µL in 1× TE (10 mM Tris, 1 mM EDTA, pH 7.5) and stored at −20° C.

PCR Amplification of Test Fragments. The test fragments were biotinylated by amplifying them with a pair of PCR primers, one of which contained 5' biotin. Nine hundred eighty microliters of PCR master mix (1× Platinum HiFi Buffer (Invitrogen), 1 mM dNTPs (Pierce), 2.5 mM MgSO4 (Invitrogen), 1 µM forward (5'-CGTTTCCCCTGTGTGC-CTTG-3' SEQ ID NO:68) and 1 µM biotinylated reverse primers (5'-Biotin-3 sequential 18-atom hexa-ethyleneglycol spacers CCATCTGTTGCGTGCGTGTC-3' SEQ ID NO:69) (IDT Technologies) and 0.02 U/µL Platinum Hi-Fi Taq Polymerase (Invitrogen) were prepared in a 1.5 mL tube, thoroughly mixed via vortexing, and a 50 µL negative control removed. Twenty microliters of a given test fragment were added to the remainder, the solution mixed and dispensed in 50 µL aliquots into 0.2 mL PCR tubes. The process was repeated for each of the 5 remaining test fragments. The PCR reactions and corresponding negative controls were placed in a MJ thermocycler and amplified under the following conditions: 4 minute hot start initiation @ 94° C., followed by 39 amplification cycles comprised of 15 seconds @ 94° C., 30 seconds @ 58° C., 90 seconds @ 68° C., and a single extension at 68° C. for 120 seconds. The amplification ended with an infinite hold at 10° C. The biotinylated PCR fragments were purified by processing them with a MinElute PCR Clean-Up Kit (Qiagen) according to the manufacturer's instructions, except that each 950 µL of PCR reaction generated for each test fragment were split over 6 MinElute columns, and pooled after the final step. The quantity and quality of PCR product was assessed with the Agilent 2100 BioAnalyzer, using a DNA 500 LabChip prepared according to the manufacturer's guidelines. Triplicate 1 µL aliquots were analyzed; the concentration of the purified PCR product typically fell between 1 and 3 pmol/µl.

Binding the Biotinylated PCR Product to Streptavidin Beads, Biotinylated PCR products were immobilized onto sieved Sepharose Streptavidin-coated particles (Amersham) at 10 million DNA copies/bead as follows. Five 50 mL bottles of Sepharose streptavidin particles were sieved through a 28 µm N/28/17/65 nylon mesh (Sefar America, Depew, N.Y., USA) to exclude the large beads. The beads that passed through this filter were then passed through a N25/19/55 nylon mesh (Sefar America) with a 25 µm pore size. The beads retained by the filter, exhibiting a size range between 27 and 32 µm diameter, were then quantitated on a Multisizer 3 Coulter Counter (Beckman) and subsequently used to bind the biotinylated test fragments. An aliquot of 700,000 of the sieved beads were washed once with 100 µL of 2 M NaCl solution, vortexed briefly to resuspend them, then centrifuged for 1 minute at maximum speed in a Minifuge to pellet the beads. The supernatant was then removed, after which the beads were washed again with 2M NaCl and resuspended in 30 µL of 2 M NaCl. A total of 11.6 pmoles of biotinylated PCR product was added to beads, vortexed to resuspend the beads in solution and allowed to bind to the streptavidin beads for 1 hour at room temperature on a titer plate shaker, at speed 7. The non-biotinylated second strand was removed by incubation in an alkaline melt solution (0.1 M NaOH/0.15 M NaCl) for 10 minutes at room temperature in a horizontal tube rotator. The supernatant, containing the denatured, non-biotinylated strand was discarded, and the beads washed once with 100 µL of melt solution and three times with 100 µL of 1× annealing buffer (50 mM Tris-Acetate, pH 7.5; 5 mM $MgCl_2$). The beads were then centrifuged for one minute at maximum speed on a Minifuge, the supernatant discarded, and the beads resuspended in 25 µL of 1× annealing buffer. Five microliters of 100 µM sequencing primer (5'-CCATCTGTTCCCTCCCTGTC-3', IDT Technologies SEQ ID NO:70) were added to the bead suspension. The bead/primer mix was then vortexed for 5 seconds, and placed in an MJ thermocycler for the following 4 stage annealing program: 5 minutes @ 60° C., decrease by 0.1° C./sec to 50° C., 1 minute @ 50° C., decrease by 0.1° C./sec to 40° C., hold at 40° C. for 1 minute, decrease by 0.1° C./sec to 15° C., hold at 15° C. Following the annealing step, the beads were washed twice with 100 µL of 1× annealing buffer (20 mM Tris, pH 7.5 and 5 mM magnesium acetate) and resuspended in a final volume of 200 µL with 1× annealing buffer. The beads were stored in 10 µL aliquots in labeled tube strips, in a 4° C. refrigerator until needed.

High Quality Reads

Each flow, in each well, results in no incorporation, or incorporation of one, or two, or three, etc. nucleotides. For any sequencing run, a histogram of signal intensities for each of these groups can be compiled (when dealing with a known sequence). As illustrated in FIG. 52, the signal strengths of the various groups overlap slightly. Generally, good reads (i.e. those that map to a reference genome with few errors) have most of their signals close to integral values equal to the number of incorporated nucleotides. FIG. 53 shows that the average of all measured signals for homopolymers of successive lengths increases linearly with homopolymer length, to a very high degree of accuracy. We have found that those reads in which a substantial number of signals fall in the overlap region between a negative flow (one in which no nucleotide is incorporated) and a positive flow (one in which at least one nucleotides is incorporated) (0.5<signal<0.7) are of poor quality (i.e. do not map anywhere in the genome or do so with a large number of errors), mostly because such reads originate from beads that carry copies of two or more templates. This allowed us to develop an a priori filter for selecting "High Quality Reads": for each read, we count the number of flows that fall in the overlap region and select only those reads whose number of such flows is less than 5% of the total number of flows. For reads that do not meet this criterion, we progressively trim the read by eliminating flows, starting from the end of the read, until the criterion is either satisfied (number of flows in indeterminate region<5% of remaining flows) or the number of flows has been reduced to less than 84 (21 cycles), at which point the read is considered to have been filtered out of the pool of High Quality Reads.

Base Calling

In principle, the intensity of an observed signal directly indicates the number of incorporated nucleotides. However, as illustrated in FIG. 52, the distributions of signal strengths of the various homopolymers overlap slightly. Were it not for this overlap, it would be possible to base call unambiguously any given sequence of signals. In pyrophosphate-based sequencing the two types of direct errors are overcalls (calling one more base than actually present in the genome) or undercalls (calling one less base than actually present in the genome). The identity of a base is not in question since it is determined by the addition of one known nucleotide at a time. Substitution errors (miscalling one base for another) result from the occurrence of two consecutive errors (undercall followed by overcall or vice-versa) and are therefore significantly rarer. We observed that the average error rate, at the single read level, is higher for library reads than for test fragments (compare FIG. 51 and FIG. 54). We developed computer models of the expected signals to verify that our measurements, and higher error rates, are consistent with the hypothesis that, when sequencing libraries, some beads carry copies of more than one template. Most of these reads get filtered out by the selection process described above. Those, however, for which the admixture significantly favors one template, may not be filtered out and contribute heavily to the overall error rate.

At the individual read level, Tables 1 and 2 report error rates that are referred to the total number of bases aligned. These numbers are analogous to error rates reported by current sequencers; however, they do not best characterize the intrinsic performance of the instrument since errors also can occur during negative flows. Each flow, whether negative or positive, can be assigned an error rate. For instance, for the 238,066 *M. genitalium* reads analyzed in Table 2, the insertion rate referenced to the total number of flows is 1.53% (compared to 2.01% when referenced to the number of bases aligned); similarly the deletion error rate referenced to the total number of flows is 1.48% (compared to 1.94% when referenced to the number of bases aligned).

Quality Scores

The confidence in (or "quality" of) any particular base call associated with a given signal value is a function of where that signal falls in the distribution of signals, for a given homopolymer length. Based on a large number of runs in which we sequenced various known genomes (*Adenovirus, S. aureus, M. genitalium*), as well as test fragments, and mapped the resulting reads, we determined that negative flows follow a lognormal distribution, while all positive flows are normally distributed with mean (FIG. 53) and standard deviation proportional to the underlying homopolymer length; furthermore these distributions remain remarkably invariant across different genomes and test fragments. This observation allows the calculation of a quality score for each individual base called. To estimate a quality score for a particular base call, the probability must be determined that the measured signal originates from a homopolymer of length at least equal to the called length. For instance, if two A's are called for a particular signal, the quality score for the second A is given by the probability that the observed signal came from a homopolymer of length two or greater. Since the probability of measuring a signal, given a homopolymer length, was empirically established, Bayes' Theorem can be used to determine the probability that a particular homopolymer length produced the observed signal, as follows:

$$P(n|s) = \frac{P(s|n)P(n)}{\sum_j P(s|j)P(j)}$$

where s is the observed signal and n is the length of the homopolymer that produced the signal. As described above, the probability $P(s|n)$ of measuring signal s given a homopolymer of length n follows a Gaussian distribution. For a random nucleotide sequence, the probability $P(n)$ of encountering a homopolymer of length n is simply $\frac{1}{4}^n$ (ignoring a multiplicative normalization constant). The quality score assigned to each base called for each fragment can then be reported as a phred-equivalent using the following transformation:

$$Q = -10 \log_{10}[P(\geq n|s)]$$

Figure 56:
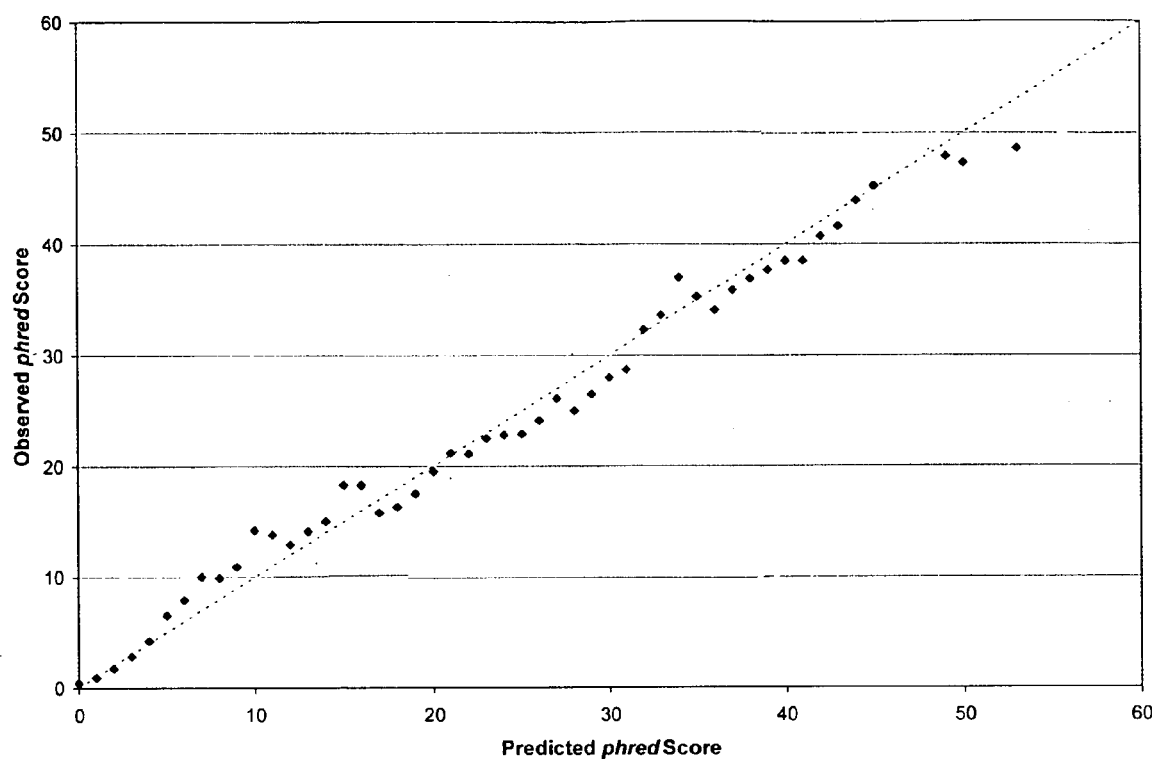
FIG. 56 Correlation between predicted and observed quality scores for a sequencing run of *C. jejuni* (data not shown).

We verified the validity of this approach by correlating calculated phred scores and observed phred scores, sequencing known genomes other than those used to establish the distribution of signals (FIG. 56). Our correlation shows excellent correspondence up to phred 50 and compares favorably to that established for Sanger sequencing and capillary eletrophoresis[3].

Flow-Space Mapping, Consensus Accuracy and Genome Coverage

Given the order in which nucleotides are flowed, a given reference genome implies a known succession of ideal signal values. This ideal flowgram is divided into contiguous, overlapping, sub-flowgrams of a particular length (default length is 24 flows) which are indexed so as to allow very rapid searching (each sub-flowgram starts at a positive flow). To map the query flowgram to the target, we divide the query flowgram into sliding sub-flowgrams having the length that was used in the indexing step and search the space of indexed ideal sub-flowgrams. A perfect match anchors the query flowgram against the reference genome. The alignment of the read is then assessed beginning at the 5' end, moving down the entire length of the read. The longest segment that meets a user-specified total mismatch threshold is selected, at which point the alignment is terminated and the read is trimmed. The reads are aligned to the reference at a very low level of stringency in order to detect mutations or other genomic variations. Once such alignments have been performed, all the flow signals from the various reads that correspond to the same location in the target are arithmetically averaged, after which individual base-calling is performed. As illustrated in FIG. 54, this procedure is extremely effective in reducing error rates; it is equally applicable whether re-sequencing or consensus base calling a de novo assembly. We estimate the quality of the average signal (without relying on knowledge of the underlying sequence) by measuring the absolute value of its distance from the closest signal threshold for the corresponding homopolymer, and dividing it by the normalized standard deviation of all the signals measured at that particular genome location. We call this ratio the Z-score. To enhance the reliability of observed variations, the consensus sequence is filtered by imposing a minimum Z-score to give rise to a high quality consensus sequence. By using an exactly known sequence, we determine the number of errors which yields an estimate of the quality of the consensus calls and the correlation between minimum Z-score and consensus accuracy. We report genome coverage based on regions with consensus sequence accuracy of 99.99% or better, which typically is achieved by selecting a minimum Z-score equal to 4. Without Z-score restriction, we naturally achieve larger coverage at slightly lower consensus accuracy.

De Novo Sequence Assembler

We select high quality reads (as described above) to ensure that the flowgrams to be processed consist most likely of sequence data from the original sample. The Overlapper performs a complete all-against-all fragment comparison to identify all possible overlaps between fragments. To assemble the read fragments produced by the instrument, the Overlapper assesses read similarity by directly comparing the flowgrams of each read; we currently use a scalar product to assess similarity between flowgrams:

$$\text{Score} = \Sigma_i S_{1i} \cdot S_{2i}$$

where $S_{1i}$ and $S_{2i}$ are the signal intensities (normalized such that the length of each "vector" is equal to 1) and the sum is carried out over the putative overlap region. We have found that a threshold value of 0.85-0.90 provides optimum predictivity and selectivity. If the observed overlap score between two flowgram regions exceeds the selected minimum stringency value, an overlap flag is set for this read pair. (The overlap determination takes into account the possibility of reverse complement reads as well.) To increase efficiency, Overlapper uses a hashing indexing method to quickly identify fragments that might be considered as potential overlap candidates. Given the set of all pair-wise overlaps between reads determined by the Overlapper, the Unitigger module groups these reads into unitigs. A unitig is a collection of reads whose overlaps between each other are consistent and uncontested by reads external to the unitig. A unitig's ends represent entries or exits from repeat regions in the genome being assembled or from completely unsequenced regions. Unitigs are constructed from consistent chains of maximal depth overlaps (i.e. pair wise reads whose maximal overlaps are with each other). Finally, Multialigner takes all the reads that make up the unitigs and aligns all the read signals. It performs a consensus call by first averaging the signals for a given location to obtain a single average signal which is used to perform the actual base call.

The unitigs generated by the Multialigner are then sent to through a contig optimization process, in which breaks caused by deficiencies in the overlap detection or the use of chains of maximal depth overlaps are repaired. The Multi-aligner unitigs have the property that their ends stretch into repeat regions or into regions "fractured" into multiple contigs by one or more errant reads that may break the chain of maximal overlaps. The contig optimization process involves three steps. The first step performs an all-against-all unitig comparison and joins any overlaps detected between the unitigs. This comparison, performed in nucleotide space, is followed by a branch-point analysis which identifies repeat region boundaries based on where contig sequences diverge from a common region. Contigs are broken at those boundaries, and any non-repeat contig larger than 500 bases is output.

The second step of the contig optimization process takes the contigs from the first step and performs a "restitching", in which any read that spans two contig ends is used to join those contigs. As with the first step, this is performed in nucleotide space and the branch-point analyzer is used to identify any repeat-region joins. The final step is a quality control step, where all of the reads are mapped to the resulting contig sequences, contigs are broken wherever there are less than 4 spanning reads, and only contigs larger than 500 bases are output.

Finally, a consensus regeneration step is performed to calculate the final contig consensi. This step uses the same flow-space mapping and consensus generation procedure described in the previous section, except that an iterative procedure is performed, where new consensi are reused as input to the procedure until no bases with a Z-score of 4 or more change. The resulting contigs and consensus sequences are then output by the assembler process.

Double Ended Sequencing

Figure 57:
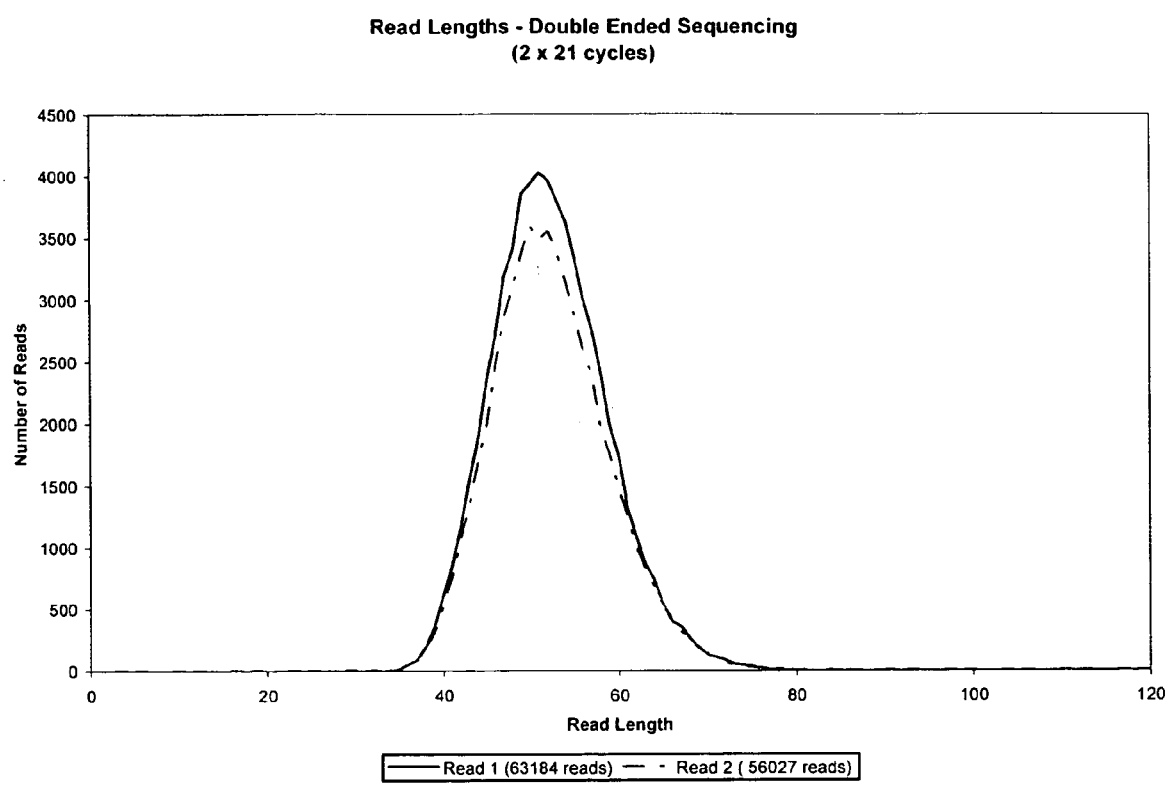
FIG. 57 Read lengths of paired end reads. Note this was for a 21 cycle run so the average length is commensurate with the lower number of cycles.

In order to perform sequencing from both ends of a single template within an individual well ("double ended sequencing"), the emulsion PCR procedure is altered, with two oligonucleotide primers (one in each direction) attached to the Sepharose DNA capture bead. The adaptor sequences used in the ssDNA library preparations are constructed such that two unique sequencing primers are incorporated into the library fragments (one for each strand). In double ended sequencing, two sequencing primers are used, with the second sequencing primer protected by a 3'-phosphate. Sequencing is performed in one direction as with single ended sequencing. The first strand sequencing is terminated by flowing a Capping Buffer containing 25 mM Tricine, 5 mM Magnesium acetate, 1 mM DTT, 0.4 mg/mL PVP, 0.1 mg/mL BSA, 0.01% Tween and 2 µM of each dideoxynucleotide and 2 µM of each deoxynucleotide. The residual deoxynucleotides and dideoxynucleotides are removed by flowing Apyrase Buffer containing 25 mM Tricine, 5 mM Magnesium acetate, 1 mM DTT, 0.4 mg/mL PVP, 0.1 mg/mL BSA, 0.01% Tween and 8.5 units/L of Apyrase. The second blocked primer is unblocked by removing the phosphate group from the 3' end of the modified 3' phosphorylated primer by flowing a cutting buffer containing 5 units/mL of Calf intestinal alkaline phosphatase in 25 mM Tricine, 5 mM Magnesium acetate, 1 mM DTT, 0.4 mg/mL PVP, 0.1 mg/mL BSA, 0.01% Tween. The second unblocked primer is activated by addition of polymerase by flowing 1000 units/mL of Bst DNA polymerase, Large Fragment, to capture all the available primer sites. Sequencing of the second strand by Bst DNA polymerase, Large Fragment, proceeds through sequential addition of nucleotides for a predetermined number of cycles just as in single ended sequencing. In proof-of-concept experiments we have demonstrated that double ended sequencing does produce paired-end reads with no significant loss in sequencing quality for the second strand. FIG. 57 shows the read lengths of mapped paired reads from amplified fragments in a double ended sequencing run of S. aureus COL[4] (21 cycles followed by 21 cycles); Supplementary Table 2 summarizes sequencing statistics, at the individual read level, for both reads.

SUPPLEMENTARY TABLE 1

Predicted sequencing accuracy as a function of incomplete extension and carry forward at different read lengths

| Read Length | 100 | 100 | 200 | 200 | 400 | 400 |
|---|---|---|---|---|---|---|
| Incomplete Extension | 0.0 | 0.0025 | 0.0 | 0.0013 | 0.0 | 0.0007 |
| Carry Forward | 0.01 | 0.0 | 0.005 | 0.0 | 0.003 | 0.00 |
| Predicted Accuracy | ~99% | ~99% | ~99% | ~99% | ~99% | ~99% |

SUPPLEMENTARY TABLE 2

Sequencing statistics for doubled ended sequencing run of S. aureus

|  | S. aureus Read 1 | S. aureus Read 2 |
|---|---|---|
| Sequencing Run Summary | | |
| Size of fiber optic slide | 30 × 60 mm² | 30 × 60 mm² |
| Run Time/Number of cycles | 126 min/21 | 126 min/21 |
| High Quality Reads | 162,261 | 148,187 |
| Average read length | 44 b | 44 b |
| Number of bases in High Quality Reads | 7,115,310 | 6,575,545 |
| Individual Reads | | |
| Reads mapped to single locations | 63,184 | 56,027 |
| Individual read insertion error rate | 0.98% | 1.49% |
| Individual read deletion error rate | 2.57% | 4.41% |
| Individual read substitution error rate | 0.23% | 0.47% |

SUPPLEMENTARY TABLE 3

Summary statistics for eight additional independent sequencing runs of *M. genitalium*

| | M. gen. 2 | M. gen. 3 | M. gen. 4 | M. gen. 5 | M. gen. 6 | M. gen. 7 | M. gen. 8 | M. gen. 9 |
|---|---|---|---|---|---|---|---|---|
| Sequencing Run Summary | | | | | | | | |
| High Quality Reads | 294,529 | 301,482 | 285,905 | 302,193 | 287,364 | 294,451 | 288,613 | 287,506 |
| Average read length | 111 b | 111 b | 111 b | 112 b | 111 b | 112 b | 111 b | 112 b |
| Number of bases in High Quality Reads | 32,633,064 | 33,426,447 | 31,683,321 | 33,930,424 | 31,927,352 | 32,176,323 | 32,125,411 | 32,131,739 |
| Phred 20 and above bases | 25,576,988 | 26,492,794 | 24,201,381 | 26,632,816 | 24,608,146 | 24,982,885 | 24,696,409 | 25,181,881 |
| Resequencing | | | | | | | | |
| Reads mapped to single locations | 228,420 | 235,770 | 221,401 | 234,679 | 221,025 | 222,527 | 224,651 | 224,478 |
| Number of bases in mapped reads | 26,553,470 | 27,423,465 | 25,734,641 | 27,191,266 | 25,720,866 | 25,845,112 | 26,139,994 | 26,103,403 |
| Insertion error rate | 1.85% | 1.64% | 2.07% | 2.41% | 1.85% | 2.00% | 1.91% | 1.76% |
| Deletion error rate | 1.65% | 1.59% | 1.73% | 2.12% | 1.66% | 1.74% | 1.63% | 1.65% |
| Substitution error rate | 0.69% | 0.69% | 0.70% | 0.73% | 0.68% | 0.68% | 0.68% | 0.67% |
| Resequencing Consensus | | | | | | | | |
| Average oversampling (unique reads) | 38x | 39x | 37x | 38x | 37x | 37x | 38x | 37x |
| Genome coverage ($Z \geq 4$) | 98.1% | 98.3% | 98.1% | 98.2% | 98.1% | 98.1% | 98.1% | 98.2% |
| Consensus accuracy ($Z \geq 4$) | 99.996% | 99.996% | 99.998% | 99.996% | 99.994% | 99.998% | 99.996% | 99.996% |
| Consensus insertion error rate ($Z \geq 4$) | 0.003% | 0.003% | 0.001% | 0.002% | 0.005% | 0.000% | 0.002% | 0.002% |
| (Number of inserted bases) | (17 b) | (17 b) | (6 b) | (12 b) | (27 b) | (3 b) | (13 b) | (12 b) |
| Consensus deletion error rate ($Z \geq 4$) | 0.001% | 0.001% | 0.001% | 0.002% | 0.001% | 0.002% | 0.002% | 0.002% |
| (Number of deleted bases) | (8 b) | (8 b) | (8 b) | (9 b) | (6 b) | (11 b) | (9 b) | (10 b) |

All runs (42 cycles) were performed on 60 × 60 mm² fiber optic slides. For clarity only statistics for the consensus sequence with $Z \geq 4$ are shown. Starting from a single source of fragmented and adapter-linked genomic DNA, we created 2 bead emulsions per run. The 8 sequencing runs produced on average 292,755 High Quality Reads (CV = 2.2%), resulting in an average of 32,504,260 bases (CV = 2.4%) of which an average of 25,296,663 (CV = 3.5%) were of phred 20 or better quality. On average 226,619 reads (CV = 2.56%) mapped to a single location, yielding an average of 26,339,027 mapped bases (CV = 2.5%). Setting a minimum Z-score equal to 4, the average coverage was 98.15% (CV = 0.08%) with an average consensus accuracy of 99.996% (CV = 0.001%).

SUPPLEMENTARY TABLE 4

Summary statistics for *S. pneumoniae* (2 runs)

| | |
|---|---|
| Sequencing Summary | |
| Size of fibre optic slide | 60 × 60 mm² |
| Run Time/Number of cycles | 243 min/42 |
| High Quality Reads | 529,077 |
| Average read length | 100 b |
| Number of bases in High Quality Reads | 52,692,071 |
| Phred 20 and above bases | 40,014,199 |
| Resequencing | |
| Reads mapped to single locations | 382,829 |
| Number of bases in mapped reads | 43,129,894 |
| Individual read insertion error rate | 1.17% |
| Individual read deletion error rate | 2.50% |
| Individual read substitution error rate | 0.83% |
| Resequencing Consensus | |
| Average oversampling | 17× |
| Coverage, all ($Z \geq 4$) | 96.3% (91.2%) |
| Consensus accuracy, all ($Z \geq 4$) | 99.85% (99.981%) |
| Consensus insertion error rate, all ($Z \geq 4$) | 0.11% (0.018%) |
| Consensus deletion error rate, all ($Z \geq 4$) | 0.04% (0.001%) |
| Consensus substitution error rate, all ($Z \geq 4$) | 0.003% (0.0009%) |
| Number of contigs | 184 |
| De novo Assembly | |
| Coverage, all ($Z \geq 4$) | 92.0% (90.44%) |
| Consensus accuracy, all ($Z \geq 4$) | 99.97% (99.992%) |
| Number of contigs | 255 |
| Average contig size | 7.8 kb |

The first run had 110,516 perfect reads (40.8%) and the second 88,068 perfect reads (34.1%). The individual read error rates are referenced to the total number of bases in mapped reads. There were 12 misassembled contigs (3 due to collapsed tandem repeats and 9 misjoins of separate genome regions); these were corrected by hand prior to assessing the assembly results. As with *M. genitalium*, the majority (88%) of the non-covered bases belonged to non-resolvable repeat regions of the genome which cover 7% of this genome. When we selected bases with a minimum Z-score of 4, 90.44% of the genome was covered with a consensus accuracy of 99.992%. In comparison, the original sequencing of *S. pneumoniae* generated 390 contigs larger than 1.5 kbp[15].

1. Pan, H. et al., The complete nucleotide sequences of the SacBII Kan domain of the P1 pAD10-SacBII cloning vector and three cosmid cloning vectors: pTCF, svPHEP, and LAWRIST16. GATA 11, 181 (1994).
2. Bankier, A. T., Weston, K. M. and Barrell, B. G., Random cloning and sequencing by the M13/dideoxynucleotide chain termination method. Meth. Enzymol. 155, 51 (1987).
3. Li, M., Nordbord, M. and Li, L. M., Adjust quality scores from alignment and improve sequencing accuracy. Nucleic Acids Research 32, 5183 (2004).
4. de Lencastre, H., Tomasz, A., Reassessment of the number of auxiliary genes essential for expression of high-level methicillin resistance in *Staphylococcus aureus*. Antimicrob Agents Chemother. 38, 2590 (1994).

What is claimed is:

1. A method of sequencing a target nucleic acid, comprising:
   a) converting a reference nucleic acid sequence into a reference number sequence comprising a plurality of reference numbers each representing an ideal signal from a nucleotide triphosphate, wherein the reference number sequence further comprises an organization that represents an order of sequential introduction of a plurality of the nucleotide triphosphates;
   b) detecting signals when a plurality of the nucleotide triphosphates are introduced in the sequential order over one or more copies of a fragment of the target nucleic acid, each signal corresponding to a query number of a query number sequence indicative of a nucleic acid sequence of said fragment, wherein the query number sequence comprises the order that represents the sequential introduction of the plurality of the nucleotide triphosphates;
   c) matching the query number sequence to a contiguous subset of the reference number sequence at one or more positions;
   d) comparing the similarity of the query number sequence to the reference number sequence to generate a quality score, wherein the quality score is indicative of the quality of the match between the query number sequence and the contiguous subset of the reference number sequence;
   e) repeating steps b) through d) for a plurality of different fragments of the target nucleic acid;
   f) anchoring the query number sequences from a plurality of the fragments at the positions on the reference number sequence corresponding to the match with the highest quality score;
   g) averaging the query numbers of one or more of the query number sequences at each sequence position of the reference number sequence that is covered by the one or more query number sequences, thereby generating a consensus number sequence; and
   h) converting the consensus number sequence into a nucleic acid sequence.

2. The method of claim 1, further comprising dividing the reference number sequence into overlapping, ideal sub reference number sequences of a predetermined length, and indexing the ideal sub reference number sequences.

3. The method of claim 2, further comprising dividing each query number sequence into a plurality of query sub number sequences, each having a length corresponding to the predetermined length of the ideal sub reference number sequences.

4. The method of claim 3, further comprising searching the indexed ideal sub reference number sequences to determine a position for matching the query sub number sequences to the reference number sequence.

5. A method of sequencing a target nucleic acid, comprising:
   a) detecting signals when a plurality of nucleotide triphosphates are introduced in a sequential order over one or more copies of a fragment of the target nucleic acid;
   b) associating each signal to a query number of a query number sequence indicative of the nucleic acid sequence of the fragment;
   c) repeating steps a) and b) to produce a plurality of the query number sequences for a plurality of different fragments;
   d) comparing the plurality of query number sequences to one another to identify a plurality of overlapping regions between the plurality of query number sequences;
   e) matching the plurality of the query number sequences at the overlapping regions;
   f) generating a quality score based on the matching, wherein the quality score is indicative of the quality of the match;
   g) identifying a plurality of pair-wise overlapping query number sequences by determining matches having a quality score meeting a predetermined threshold;
   h) grouping the pair-wise overlapping query number sequences into one or more unitigs;
   i) averaging the sequence numbers of the query number sequences at each of one or more matching positions within each unitig, thereby generating a consensus number sequence which comprises a unitig consensus number sequence; and
   j) converting each unitig consensus number sequence into a unitig consensus nucleic acid sequence.

6. The method of claim 5, wherein the one or more unitigs in step h) comprise consistent chains of maximal overlap of the query number sequences.

7. The method of claim 5, further comprising the steps of:
   k) comparing unitig consensus nucleic acid sequences to each other to identify sequence overlaps; and
   l) joining unitig consensus having common overlapping sequences, thereby forming one or more contigs comprising contig nucleic acid sequences.

8. The method of claim 7, further comprising the steps of:
   m) identifying boundaries within each contig, wherein a boundary is a region where unitig sequences diverge from a common region; and
   n) breaking contigs at boundaries identified in step m).

9. The method of claim 8, further comprising the step of:
   o) joining any two contigs whose ends are overlapped by the same fragment nucleic acid sequence, wherein optionally the contigs thus joined are broken if a boundary is identified.

10. The method of claim 9, further comprising the steps of:
    p) identifying all matches between fragment nucleic acid sequences and the contigs; wherein optionally the contigs are broken at any position where fewer than 4 fragment nucleic acid sequences are matched;
    q) calculating contig consensus number sequences by averaging the sequence numbers of the query number sequences associated with the fragment nucleic acid sequences aligned to contigs in step p); and
    r) converting the contig consensus number sequences into contig consensus nucleic acid sequences.

11. The method of claim 10, further comprising repeating steps p) through r) with the contig consensus nucleic acid sequences until substantially no consensus base calls change, thereby calculating a final contig consensus sequence.

* * * * *